United States Patent
Liu et al.

(10) Patent No.: US 6,720,319 B2
(45) Date of Patent: Apr. 13, 2004

(54) COMPOUNDS USEFUL AS REVERSIBLE INHIBITORS OF CYSTEINE PROTEASES

(75) Inventors: Weimin Liu, Sandy Hook, CT (US); Denice M. Spero, West Redding, CT (US); David S. Thomson, Ridgefield, CT (US); Yancey D. Ward, Sandy Hook, CT (US); Erick R. R. Young, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/261,993

(22) Filed: Oct. 1, 2002

(65) Prior Publication Data
US 2003/0216383 A1 Nov. 20, 2003

Related U.S. Application Data

(60) Division of application No. 09/808,439, filed on Mar. 14, 2001, now Pat. No. 6,525,052, which is a continuation-in-part of application No. 09/655,351, filed on Sep. 8, 2000, now Pat. No. 6,420,364.

(51) Int. Cl.$^7$ .................. A61K 31/535; C07D 413/12; C07D 265/30
(52) U.S. Cl. ................. 514/232.2; 514/235.8; 514/237.2; 514/238.5; 544/82; 544/121; 544/126; 544/129; 544/130; 544/141; 544/162; 544/163; 544/171
(58) Field of Search .................. 544/82, 121, 12, 544/126, 129, 130, 141; 514/232.2, 235

(56) References Cited

U.S. PATENT DOCUMENTS 5,776,718 A   7/1998   Klaus et al.

6,525,052 B2 * 2/2003 Bekkali et al. .......... 514/237.2

FOREIGN PATENT DOCUMENTS

| WO | PCT US/00/23584 | 1/2001 |
| WO | WO 01/19816 | 3/2001 |
| WO | PCT US/01/08084 | 10/2001 |

* cited by examiner

Primary Examiner—Joseph K. McKane
Assistant Examiner—Ebenezer Sackey
(74) Attorney, Agent, or Firm—Robert P. Raymond; Anthony P. Bottino; Timothy X. Witkowski

(57) ABSTRACT

Disclosed are novel cathepsin S, K, F, L and B reversible inhibitory compounds of the formula (Ia) and (Ib) where $R_2$, $R_3$, $R_4$, $R_5$, $R_6$, $R_7$, $R_8$, Het and X are defined herein. The compounds are useful for treating autoimmune and other diseases. Also disclosed are processes for making such novel compounds.

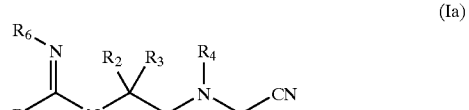

(Ia)

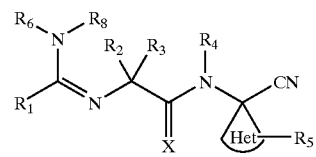

(Ib)

16 Claims, No Drawings

COMPOUNDS USEFUL AS REVERSIBLE INHIBITORS OF CYSTEINE PROTEASES

RELATED APPLICATION DATA

This application is a divisional of U.S. application Ser. No. 09/808,439 filed Mar. 14, 2001 now U.S. Pat. No. 6,525,052 which is a continuation-in-part of U.S. application Ser. No. 09/655,351 filed Sep. 8, 2000 now U.S. Pat. No. 6,420,364.

TECHNICAL FIELD OF THE INVENTION

This invention relates to amidino and guanidino peptidyl compounds active as cysteine protease inhibitors. The compounds are reversible inhibitors of the cysteine protease cathepsin S, K, F, L and B are therefore useful in the treatment of autoimmune and other diseases. The invention also relates to processes for preparing such compounds and pharmaceutical compositions comprising them.

BACKGROUND OF THE INVENTION

Cathepsin S and cathepsin K are members of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including atherosclerosis, emphysema, osteoporosis, chronic inflammation and immune disorders (H. A. Chapman et al., 1997, Ann. Rev. Physiol., 59, 63). Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et al, 1999, Immunity, 10, 207)

The specificity of the immune response relies on processing of foreign protein and presentation of antigenic peptide at the cell surface. Antigenic peptide is presented bound to MHC Class II, a heterodimeric glycoprotein expressed in certain antigen presenting cells of hematopoietic lineage, such as B cells, macrophages and dendritic cells. Presentation of antigen to effector cells, such as T-cells, is a fundamental step in recognition of non-self and thus initiation of the immune response.

Recently MHC Class II heterodimers were shown to associate intracellularly with a third molecule designated invariant chain. Invariant chain facilitates Class II transport to the endosomal compartment and stabilizes the Class II protein prior to loading with antigen. Invariant chain interacts directly with Class II dimers in the antigen-binding groove and therefore must be proteolyzed and removed or antigen cannot be loaded or presented. Current research suggests that invariant chain is selectively proteolyzed by cathepsin S, which is compartmentalized with MHC Class II complexes within the cell. Cathepsin S degrades invariant chain to a small peptide, termed CLIP, which occupies the antigen-binding groove. CLIP is released from MHC Class II by the interaction of MHC Class II with HLA-DM, a MHC-like molecule thus freeing MHC Class II to associate with antigenic peptides. MHC Class II-antigen complexes are then transported to the cell surface for presentation to T-cells, and initiation of the immune response.

Cathepsin S, through proteolytic degradation of invariant chain to CLIP, provides a fundamental step in generation of an immune response. It follows that inhibition of antigen presentation via prevention of invariant chain degradation by cathepsin S could provide a mechanism for immuno-regulation. Control of antigen-specific immune responses has long been desirable as a useful and safe therapy for autoimmune diseases. Such diseases include Crohn's disease and arthritis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87), atherosclerosis (G. K. Sukhova et al., 1998, J. Clin. Invest., 102, 576) and endometriosis (WO 9963115, 1999).

A cathepsin S inhibitor has been found to block the rise in IgE titers and eosinophil infiltration in the lung in a mouse model of pulmonary hypersensitivity, suggesting that cathepsin S may be involved in asthma (R. J. Riese et al., J. Clin. Investigation, 1998, 101, 2351).

Another cysteine protease, cathepsin F has been found in macrophages and is also involved in antigen processing. It has been postulated that cathepsin F in stimulated lung macrophages and possibly other antigen presenting cells could play a role in airway inflammation (G. -P. Shi et al., J. Exp. Med., 2000, 191, 1177).

Cathepsin K, another cysteine protease has been found to be highly expressed in osteoclasts and to degrade bone collagen and other bone matrix proteins. Inhibitors of cathepsin K have been shown to inhibit bone resorption in mice. Therefore, cathepsin K may play a role in osteoclastic bone resorption and cathepsin K inhibitors may be useful in the treatment of diseases involving bone resorption such as osteoporosis (F. Lazner et al., Human Molecular Genetics, 1999, 8, 1839).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R.

P. Hanzlik et al., 1991, Biochim. Biophys. Acta., 1073, 33), which are non-selective, inhibiting both cysteine and serine proteases as well as other nucleophiles. Peptidyl nitriles (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Examples of cathepsin S inhibitors have been reported. J. L. Klaus et al. (WO 9640737) described reversible inhibitors of cysteine proteases including cathepsin S, containing an ethylene diamine. In U.S. Pat. No. 5,776,718 to Palmer et al. there is disclosed in it's broadest generic aspect a protease inhibitor comprising a targeting group linked through a two carbon atom chain to an electron withdrawing group (EWG). The compounds of the present application are structurally distinct and thus excluded from the U.S. Pat. No. 5,776,718 patent with particular embodiments possessing unexpectedly greater activity than the closest compounds of the prior art. Other examples of cathepsin S inhibitors have been reported by E. T. Altmann et al, (WO 9924460, 1999) which describes dipeptide nitriles asserted to have activity as inhibitors of Cathepsins B, K, L and S. The WO publication does not disclose any compounds possessing a guanidino or amidino structure at the P3 position.

Additional peptidyl nitriles have been reported as protease inhibitors. For example, both nitriles and ketoheterocycles are described by B. A. Rowe et al. (U.S. Pat. No. 5,714,471) as protease inhibitors useful in the treatment of neurodegenerative diseases. Peptidyl nitrites are reported by B. Malcolm et al. (WO 9222570) as inhibitors of picornavirus protease. B. J. Gour-Salin (Can. J. Chem., 1991, 69, 1288) and T. C. Liang (Arch. Biochim. Biophys., 1987, 252, 626) described peptidyl nitrites as inhibitors of papain A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

In light of the above, there is a clear need for compounds which reversibly and selectively inhibit cysteine proteases such as cathepsin S and cathepsin K for indications in which these proteases exacerbate disease.

BRIEF DESCRIPTION OF THE INVENTION

It is therefore an object of this invention to provide novel compounds according to the formulas (Ia) and (Ib) as desrcribed herein which reversibly inhibit the cysteine proteases cathepsin S, K, F, L and B. It is a further object of the invention to provide methods for treating diseases and pathological conditions exacerbated by these cysteine proteases such as, but not limited, to rheumatoid arthritis, multiple sclerosis, asthma and osteoporosis. It is yet a further object of the invention to provide novel processes for preparation of the above-mentioned novel compounds.

DETAILED DESCRIPTION OF THE INVENTION

A proposed mechanism of action of the cysteine protease inhibitors of this invention is that the inhibitors contain a functionality that can react (reversibly or irreversibly) with the active site cysteine. The reactive functionality is attached to a peptide or peptide mimic that can be recognized and accommodated by the region of the protease surrounding the active site. The nature of both the reactive functionality and the remaining portion of the inhibitor determine the degree of selectivity and potency toward a particular protease.

Given the similarity of the active sites in cysteine proteases, it may be anticipated that a given class of inhibitors might have activity against more that one cysteine protease. It may also be expected that due to structural differences between individual cysteine proteases, different compounds of the invention may have different inhibitory potencies against different cysteine proteases. Thus some of the compounds of the invention may also be expected to be most effective in treating diseases mediated by cysteine proteases that they inhibit most potently. The activity of particular compounds disclosed herein against cysteine proteases such as cathepsin S, K, F, L and B may be determined by the screens described in the section entitled "Assessment of Biological Properties."

Accordingly, in a first generic aspect of the invention, there are provided compounds of formula (Ia) and (Ib):

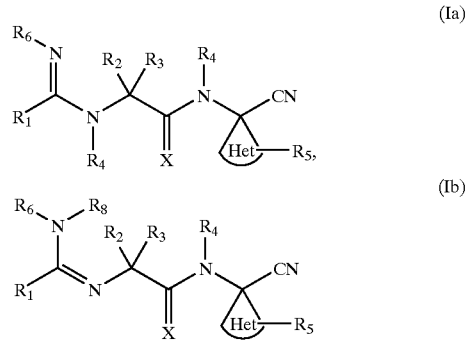

wherein:

Het is
azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydrooxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydro-quinolinyl, decahydro-isoquinolinyl, 1,2,3,4-tetrahydro-quinolinyl, indolinyl, octahydro-quinolizinyl, dihydro-indolizinyl, octahydro-indolizinyl, octahydro-indolyl, decahydroquinazolinyl, decahydro-quinoxalinyl, 1,2,3,4-tetrahydroquinazolinyl or 1,2,3,4-tetrahydroquinoxalinyl;

A C6–C10 bridged bicyclo wherein one or more carbon atoms are optionally replaced by a heteroatom chosen from N, O and S;

each being optionally substituted with one or more $R_5$;

$R_1$ is a bond, hydrogen, C1–10 alkyl, C1–10 alkoxy, aryloxy, C3–8 cycloalkyl, C3–8 cycloalkyloxy, aryl, benzyl, tetrahydronaphthyl, indenyl, indanyl, C1–10alkylsulfonylC1–10alkyl, C3–8cycloalkylsulfonylC1–10alkyl, arylsulfonylC1–10alkyl, heterocyclyl selected from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzisoxazolyl, quinolinyl, tetrahydroquinolinyl, isoquinolinyl, tetrahydroisoquinolinyl, quinazolinyl, tetrahydroquinazolinyl, benzoxazolyl and quinoxalinyl, heterocyclyloxy wherein the heterocyclyl moiety is selected from those herein described in this paragraph, hydroxy or amino; wherein RI is optionally substituted by one or more $R_a$;

$R_a$ is a bond, C1–10 alkyl, C3–8 cycloalkyl, aryl, tetrahydronaphthyl, indenyl, indanyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10 alkoxy, C1–10alkanoyl, C1–10alkanoyloxy, aryloxy, benzyloxy, C1–10 alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$; with the proviso that $R_1$ and $R_a$ simultaneously cannot be a bond;

$R_b$ is a C1–6 saturated or unsaturated branched or unbranched carbon chain optionally partially or fully halogenated wherein one or more carbon atoms are optionally replaced by O, N, S(O), S(O)$_2$ or S and wherein said chain is optionally independently substituted with 1–2 oxo groups, —NH$_2$, or one or more C1–4 alkyl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl;

or $R_b$ is C3–6 cycloalkyl, aryl, aryloxy, benzyloxy, halogen, hydroxy, oxo, carboxy, cyano, nitro, mono-C1–5alkylamino, di-C1–5alkylamino, carboxamide, amidino or guanidino;

$R_2$ is hydrogen or C1–3 alkyl;

$R_3$ is a bond, hydrogen, C1–10 alkyl, C2–10alkylene, C3–8 cycloalkyl, arylC1–5alkyl or aryl wherein $R_3$ is optionally substituted by one or more $R_c$;

$R_c$ is C1–10 alkyl, C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, benzimidazolyl, benzthiazolyl, tetrahydroquinolinyl, quinolinyl, tetrahydroisoquinolinyl, isoquinolinyl, quinazolinyl, quinoxalinyl, C1–10 alkoxy, aryloxy, C1–10 alkanoyl, aroyl, C1–10 alkoxycarbonyl, aryloxycarbonyl, C1–10 alkanoyloxy, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino;

$R_2$ and $R_3$ together with the carbon they are attached optionally form a nonaromatic 5–7 membered cycloalkyl or heterocyclic ring;

each $R_4$ is independently hydrogen, hydroxy or C1–3 alkyl;

$R_5$ is a bond, hydrogen, carbonyl, C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C1–10 alkoxy, aryloxy, C3–8 cycloalkyl, aryl, benzyl, tetrahydronaphthyl, indenyl, indanyl, C3–7cycloalkylsulfonylC1–5alkyl, arylsulfonylC1–5alkyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridizinyl, tetrazolyl, triazolyl, pyrazolyl, indolyl, benzofuranyl, benzothienyl, benzimidazolyl, benzthiazolyl, quinolinyl, tetrahydroquinolinyl, isoquinolinyl, tetrahydroisoquinolinyl, quinazolinyl, tetrahydroquinazolinyl, benzoxazolyl and quinoxalinyl, heterocyclyloxy wherein the heterocyclyl moiety is selected from those herein described in this paragraph, C1–10alkanoyl, aroyl, C1–10alkanoyloxy, benzyloxy, C1–10alkoxycarbonyl, arylC1–5alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is halogen, hydroxy, oxy, oxo, carboxy, cyano, nitro, carboxamide, amidino or guanidino, $R_5$ may be further optionally substituted by one or more $R_e$;

$R_e$ is C1–10 alkyl, C1–10alkoxyC1–10alkyl, C1–10alkylaminoC1–10alkyl, C1–10alkylthioC1–10alkyl wherein the sulfur atom may be oxidized to a sulfoxide or sulfone, C1–10 alkoxy, C3–8 cycloalkyl, aryl, tetrahydronaphthyl, indenyl, indanyl, pyrrolidinyl, piperidinyl, morpholinyl, thiomorpholinyl, piperazinyl, indolinyl, thiopyranyl, tetrahydrothiopyranyl, pyranyl, tetrahydropyranyl, tetrahydrofuranyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, benzisoxazolyl, quinolinyl, isoquinolinyl, quinazolinyl, quinoxalinyl, C1–10alkanoyl, aroyl, C1–10alkanoyloxy, aryloxy, benzyloxy, C1–10 alkoxycarbonyl, arylC1–3alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further optionally substituted by one or more $R_f$;

$R_f$ is C1–5 alkyl, C3–6 cycloalkyl, tolylsulfonyl, C1–5 alkoxy, aryl, aryloxy, benzyloxy, halogen, hydroxy, oxo, carboxy, cyano, nitro, carboxamide, amidino or guanidino;

$R_6$ is
hydrogen, hydroxy, nitrile or
a C1–6 saturated or unsaturated branched or unbranched carbon chain optionally partially or fully halogenated wherein one or more C atoms are optionally replaced by O, NH, S(O), S(O)$_2$ or S and wherein said chain is optionally independently substituted with 1–2 oxo groups, —NH$_2$, one or more C$_{1-4}$ alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

wherein $R_1$ and $R_6$ in the formulas (Ia) or (Ib) optionally form a 4 to 8 membered mono- or 7–12 membered polycyclo heteroring system, each aromatic or nonaromatic, wherein each heteroring is optionally substituted by one or more $R_7$;

each $R_7$ and $R_8$ are independently:
C1–5 alkyl chain optionally interrupted by one or two N, O or S(O)$_m$ and optionally substituted by 1–2 oxo, amino, hydroxy, halogen, C1–4alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl, aryl, aryloxy, aroyl, furanyl, thienyl, pyrrolyl, imidazolyl, pyridinyl, pyrimidinyl, C1–5 alkanoyl, C1–5 alkoxycarbonyl, aryloxycarbonyl, benzyloxycarbonyl, C1–5 alkanoylamino, aroylamino, C1–5 alkylthio, arylthio C1–5 alkylsulfonylamino, arylsulfonylamino, C1–5 alkylaminosulfonyl, arylaminosulfonyl, C3–6 cycloalkyl and benzyloxy each of the aforementioned are optionally halogenated, halogen, hydroxy, oxo, carboxy, nitrile, nitro or NH$_2$C(O)—;

m is 0, 1 or 2;
X is =O, =S or =N—$R_6$ wherein $R_6$ is as defined above, and
pharmaceutically acceptable derivatives thereof.

In another embodiment of the invention, there are provided novel compounds of the formula (Ia) and formula (Ib) as described immediately above, and wherein:

Het is piperidinyl, pyrrolidinyl, tetrahydropyranyl, tetrahydrothiopyranyl, azetidinyl, azepanyl, oxepanyl, tetrahydrofuranyl, oxetanyl, hexahydropyrimidinyl, hexahydropryidazinyl, piperazinyl, 1,4,5,6-tetrahydropyrimidinyl, octahydro-indolizinyl, octahydro-quinolizinyl, decahydro-quinolinyl, 1,2,3,4-tetrahydro-quinolinyl, dihydro-oxazolyl, 1,2-thiazinanyl-1,1-dioxide, 1,2,6-thiadiazinanyl-1,1-dioxide, isothiazolidinyl-1,1-dioxide, imidazolidinyl, pyrazolidinyl or a bridged bicyclo chosen from aza-bicyclo[3.2.1]octane, aza-bicyclo[2.2.1]heptane, aza-bicyclo[2.2.2]octane, aza-bicyclo[3.2.2]nonane, aza-bicyclo[2.1.1]hexane, aza-bicyclo[3.1.1]heptane, aza-bicyclo[3.3.2]decane and 2-oxa or 2-thia-5-aza-bicyclo[2.2.1]heptane;

each ring being substituted with one or more $R_5$;
$R_1$ is a bond, hydrogen, C1–7 alkyl, C1–7 alkoxy, C3–7 cycloalkyl, aryloxy, phenyl, benzyl, naphthyl, tetrahydronaphthyl, C1–7alkylsulfonylC1–7alkyl, C3–7cycloalkylsulfonylC1–7alkyl, arylsulfonylC1–7alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein $R_1$ is optionally substituted by one or more $R_a$;

$R_a$ is a bond C1–7 alkyl, C3–6 cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, C1–7 alkoxy, C1–7alkanoyl, C1–7alkanoyloxy, aryloxy, benzyloxy, C1–7 alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_a$ is halogen, hydroxy, oxo, carboxy, cyano, nitro, carboxamide, amidino or guanidino, $R_a$ may be further optionally substituted by one or more $R_b$;

$R_b$ is C1–5 alkyl, C3–6 cycloalkyl, aryl, C1–5 alkoxy, aryloxy, benzyloxy, halogen, hydroxy, oxo, carboxy, cyano, nitro, carboxamide, amidino or guanidino;

$R_2$ is hydrogen or methyl or ethyl;

$R_3$ is a bond, hydrogen, C1–5 alkyl, C2–5alkylene, C3–7 cycloalkyl, arylC1–3alkyl or aryl wherein $R_3$ is optionally substituted by one or more $R_c$;

$R_c$ is C1–5 alkyl, C3–7 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1] pentanyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_c$ is halogen, hydroxy, oxo, carboxy, cyano, nitro, amidino or guanidino, $R_c$ may be further optionally substituted by one or more $R_d$;

$R_d$ is C1–5 alkyl, C3–6 cycloalkyl, aryl, arylC1–4 alkyl, C1–5 alkoxy, aryloxy, arylC1–5alkoxy, aroyl, halogen, hydroxy, oxo or cyano;

$R_4$ is hydrogen or methyl;

$R_5$ is a bond, hydrogen, carbonyl, C1–8 alkyl, C1–8alkoxyC1–8alkyl, C1–8alkylaminoC1–8alkyl, C1–8alkylthioC1–8alkyl wherein the sulfur atom may be oxidized to a sulfoxide or sulfone, C1–8 alkoxy, aryloxy, C3–7 cycloalkyl, aryl, benzyl, tetrahydronaphthyl, indanyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, oxazolyl, thiazolyl, imidazolyl, pyridinyl, pyrimidinyl, pyrazinyl, tetrazolyl, triazolyl, pyrazolyl, indolyl, benzofuranyl, benzothienyl, benzimidazolyl, benzthiazolyl, quinolinyl, isoquinolinyl, quinazolinyl, benzoxazolyl and quinoxalinyl, heterocyclyloxy wherein the heterocyclyl moiety is selected from those herein described in this paragraph, C1–7alkanoyl, aroyl, C1–7alkanoyloxy, benzyloxy, C1–7 alkoxycarbonyl, arylC1–4alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_5$ is halogen, hydroxy, oxy, oxo, carboxy, cyano, nitro or carboxamide, $R_5$ may be further optionally substituted by one or more $R_e$;

$R_e$ is C1–7 alkyl, C1–7alkoxyC1–7alkyl, C1–7alkylaminoC1–7alkyl, C1–7alkylthioC1–7alkyl wherein the sulfur atom may be oxidized to a sulfoxide or sulfone, C1–7 alkoxy, C3–7 cycloalkyl, aryl, tetrahydronaphthyl, indanyl, pyrrolidinyl, piperidinyl, morpholinyl, thiomorpholinyl, piperazinyl, thiopyranyl, tetrahydrothiopyranyl, tetrahydropyranyl, tetrahydrofuranyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, C1–5 alkanoyl, aroyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, or $R_e$ is halogen, hydroxy, oxo, carboxy, cyano, nitro, carboxamide, amidino or guanidino, $R_e$ may be further optionally substituted by one or more $R_f$;

$R_f$ is methyl, ethyl, t-butyl, tolylsulfonyl, C1–3 alkoxy, cyclopropyl, cyclohexyl, phenyl, naphthyl, phenoxy, benzyloxy, fluoro, chloro, bromo, hydroxy, oxo, carboxy, cyano, nitro or carboxamide;

$R_6$ is
hydrogen, hydroxy, nitrile or
a C1–6 saturated or unsaturated branched or unbranched carbon chain optionally partially or fully halogenated wherein one or more C atoms are optionally replaced by O, NH, S(O), S(O)$_2$ or S and wherein said chain is optionally independently substituted with 1–2 oxo groups, —NH$_2$, one or more C1–4 alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;

$R_1$ and $R_6$ of the formula (Ia) or formula (Ib) form a monocyclic 5, 6 or 7 membered aromatic or nonaromatic heterocyclic ring optionally substituted by $R_7$;

or a bicyclic ring having one 5, 6 or 7 membered aromatic or nonaromatic heterocyclic ring fused to a second 5–7 membered aromatic or nonaromatic heterocyclic or carbocyclic ring wherein each ring is optionally independently substituted by one or more $R_7$;

$R_7$ and $R_8$ are independently C1–5 alkyl, C3–6 cycloalkyl, aryl, C1–5 alkoxy, aryloxy, benzyloxy each of the aforementioned are optionally halogenated or $R_x$ is halogen, hydroxy, oxo, carboxy, nitrile, nitro or NH$_2$C(O)—;

m is 0, 1 or 2 and

X is O or S.

In yet another embodiment of the invention, there are provided novel compounds of the formulas (Ia) and (Ib) as described immediately above, and wherein:

Het is piperidinyl, pyrrolidinyl, azetidinyl, azepanyl, oxepanyl, tetrahydropyranyl, tetrahydrothiopyranyl, tetrahydrofuranyl, oxetanyl, octahydro-indolizinyl, octahydro-quinolizinyl or aza-bicyclo[3.2.1]octanyl, each ring being optionally substituted with one or more $R_5$;

$R_1$ is a bond, C1–5 alkyl, C1–5 alkoxy, C3–6 cycloalkyl, aryloxy, phenyl, benzyl, naphthyl, C1–3alkylsulfonylC1–3alkyl, C3–6cycloalkylsulfonylC1–3alkyl, arylsulfonylC1–3alkyl, pyrrolidinyl, piperidinyl, morpholinyl, thiomorpholinyl, piperazinyl, furanyl, thienyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclopentyl, cyclohexyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, benzthiazolyl, benzoxazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl, piperazinyl, thienyl, oxazolyl, thiazolyl, imidazolyl, pyridinyl, pyrimidinyl, benzimidazolyl or benzthiazolyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is C1–3 alkyl, C3–6 cycloalkyl, aryl, C1–3 alkoxy, aryloxy, benzyloxy, halogen, hydroxy, oxo, carboxy, cyano, nitro, carboxamide, amidino or guanidino;

$R_2$ is hydrogen or methyl;

$R_3$ is a bond, hydrogen, C1–5 alkyl, C2–5alkylene, C4–6 cycloalkyl or arylC1–2alkyl wherein $R_3$ is optionally substituted by one or more $R_c$;

$R_c$ is C1–4 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, quinoxalinyl, C1–4 alkoxy, phenoxy, naphthyloxy, C1–3 alkanoyl, benzoyl, C1–3 alkoxycarbonyl, phenoxycarbonyl, C1–3 alkanoyloxy, benzoyloxy, carbamoyl wherein the nitrogen atom may be independently mono or di-substituted by C1–5 alkyl or aryl, or $R_c$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–5 alkyl or aryl, or $R_c$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_4$ is hydrogen;

$R_5$ is a bond, hydrogen, carbonyl, C1–6 alkyl, C1–6alkoxyC1–6alkyl, C1–6alkylaminoC1–6alkyl, C1–6alkylthioC1–6alkyl wherein the sulfur atom may be oxidized to a sulfoxide or sulfone, C1–6 alkoxy, phenoxy, naphthyloxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, tetrahydrothiopyranyl, furanyl, tetrahydrofuranyl, thienyl, oxazolyl, thiazolyl, imidazolyl, pyridinyl, pyrimidinyl, pyrazolyl, benzofuranyl, benzothienyl, benzimidazolyl, benzthiazolyl, quinolinyl, isoquinolinyl and benzoxazolyl, heterocyclyloxy wherein the heterocyclyl moiety is selected from those herein described in this paragraph, C1–3 alkanoyl, benzoyl, naphthoyl, C1–4alkanoyloxy, benzyloxy, C1–4 alkoxycarbonyl, arylC1–2alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–4 alkanoylamino, aroylamino, C1–4 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, pyrazinyl, indolyl, benzofuranyl, benzothienyl, benzimidazolyl or benzthiazolyl, or $R_5$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–3 alkylaminosulfonyl, phenylaminosulfonyl, amino wherein the nitrogen atom may be independently mono or di-substituted by C1–4 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_5$ is halogen, hydroxy, oxo, carboxy, cyano, nitro or carboxamide, $R_5$ may be further optionally substituted by one or more $R_e$;

$R_e$ is C1–4 alkyl, C1–4 alkoxy, C3–7 cycloalkyl, phenyl, naphthyl, indanyl, pyrrolidinyl, piperidinyl, morpholinyl, thiomorpholinyl, piperazinyl, tetrahydrothiopyranyl, tetrahydropyranyl, tetrahydrofuranyl, thienyl, oxazolyl, thiazolyl, imidazolyl, pyridinyl, pyrimidinyl, pyrazinyl, indolyl, benzimidazolyl, benzthiazolyl, benzoxazolyl, quinolinyl, isoquinolinyl, quinazolinyl, quinoxalinyl, C1–4 alkanoyl, aroyl, C1–4alkanoyloxy, phenoxy, naphthyloxy, benzyloxy, C1–4 alkoxycarbonyl, phenoxycarbonyl, benzoyloxy, carbamoyl wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, or benzthiazolyl, or $R_e$ is C1–4 alkanoylamino, benzoylamino, C1–4 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_e$ is C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–4 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzthiazolyl, or $R_e$ is halogen, hydroxy, oxo, carboxy, cyano, nitro or carboxamide, $R_e$ may be further optionally substituted by one or more $R_f$;

$R_f$ is methyl, ethyl, t-butyl, tolylsulfonyl, methoxy, cyclopropyl, phenyl, phenoxy, benzyloxy, fluoro, chloro, bromo, hydroxy, oxo, carboxy or carboxamide.

$R_1$ and $R_6$ of the formula (Ia) or Formula (Ib) optionally form a monocyclic 5 or 6 membered aromatic or nonaromatic heterocyclic ring optionally substituted by $R_7$;

or a bicyclic ring having one 5, 6 or 7 membered aromatic or nonaromatic heterocyclic ring fused to a second 5–6 membered aromatic or nonaromatic heterocyclic or carbocyclic ring wherein each ring is optionally independently substituted by one or more $R_7$;

R₇ and R₈ are independently C1–4 alkyl, C5–6 cycloalkyl, C1–4 alkoxy, halogen, hydroxy, oxo, carboxy, nitrile, nitro or NH₂C(O)—; and X is O.

In yet still another embodiment of the invention, there are provided novel compounds of the formulas (Ia) and (Ib) as described immediately above, and wherein:

Het is piperidinyl, pyrrolidinyl, azetidinyl, azepanyl, oxepanyl, tetrahydropyranyl, oxetanyl or tetrahydrothiopyranyl each ring being optionally substituted with one or more R₅;

R₁ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein R₁ is optionally substituted by one or more R_a;

R_a is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or R_a is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or R_a is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or R_a is halogen, hydroxy, oxo, carboxy, cyano, nitro, carboxamide, amidino or guanidino, R_a may be further optionally substituted by one or more R_b;

R_b is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

R₂ is hydrogen;

R₃ is a bond, C1–3 alkyl, C2–4alkylene, C5–6 cycloalkyl, benzyl or naphthylmethyl wherein R₃ is optionally substituted by one or more R_c;

R_c is C1–3 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbamoyl wherein the nitrogen atom may be independently mono or di-substituted by C1–3 alkyl or aryl, or R_c is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or R_c is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or R_c is halogen, hydroxy, oxo, carboxy or cyano, R_c may be further optionally substituted by one or more R_d;

R_d is methyl, cyclopropyl, cyclohexyl, phenyl, benzyl, methoxy, phenoxy, benzyloxy, benzoyl, fluoro, chloro, oxo or cyano;

R₅ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–3alkanoyl, benzoyl, naphthoyl, C1–3alkanoyloxy, benzyloxy, C1–3 alkoxycarbonyl, benzyloxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or R₅ is C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofuranyl, benzothienyl, benzimidazolyl or benzthiazolyl, or R₅ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzthiazolyl, or R₅ is halogen, hydroxy, oxo, carboxy, cyano or carboxamide, R₅ may be further optionally substituted by one or more R_e;

R_e is C1–3 alkyl, C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–3 alkanoyl, aroyl, C1–3alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is halogen, hydroxy, oxo, carboxy, cyano or carboxamide, $R_e$ may be further optionally substituted by one or more $R_f$; and $R_f$ is methyl, phenyl, tolylsulfonyl, methoxy, phenoxy, benzyloxy, fluoro, chloro, bromo, hydroxy, oxo, carboxy or carboxamide;

$R_1$ and $R_6$ of the formula (Ia) or Formula (Ib) form a bicyclic ring having one 5 or 6 membered aromatic or nonaromatic heterocyclic ring fused to a second 5–6 membered heteroaryl, heterocycle or phenyl ring;

wherein each ring is optionally independently substituted by one or two $R_7$.

In yet a further embodiment of the invention, there are provided novel compounds of the formulas (Ia) and (Ib) as described immediately above, and wherein:

Het is piperidinyl, pyrrolidinyl, azetidinyl, azepanyl or tetrahydropyranyl each ring being substituted with one or more $R_5$;

$R_1$ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

$R_b$ is methyl, cyclopropyl, phenyl, methoxy, phenoxy, benzyloxy, fluoro, chloro, hydroxy, oxo, carboxy or carboxamide;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is methyl, ethyl, n-propyl, i-propyl, C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, thienyl, oxazolyl, thiazolyl, indolyl, benzofuranyl, benzothienyl, benzthiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, R, may be further optionally substituted by one or more $R_d$;

$R_d$ is methyl, cyclopropyl, phenyl, methoxy, fluoro, chloro or oxo;

$R_5$ is a bond, hydrogen, carbonyl, C1–4 alkyl, C1–4alkoxyC1–4alkyl, C1–4alkylaminoC1–4alkyl, C1–4alkylthioC1–4alkyl wherein the sulfur atom may be oxidized to a sulfoxide or sulfone, C1–4 alkoxy, phenoxy, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–2alkanoyl, benzoyl, naphthoyl, C1–2alkanoyloxy, benzyloxy, C1–2 alkoxycarbonyl, benzyloxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_5$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is fluoro, chloro, bromo, hydroxy, oxo, carboxy or carboxamide, $R_5$ may be further optionally substituted by one or more $R_e$;

$R_e$ is C1–3 alkyl, C1–2 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–2 alkanoyl, aroyl, C1–2alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, $R_e$ may be further optionally substituted by one or more $R_f$;

$R_f$ is methyl, phenyl, tolylsulfonyl, methoxy, phenoxy, benzyloxy, fluoro, chloro, hydroxy, oxo, carboxy or carboxamide and $R_1$ and $R_6$ of the formula (Ia) or Formula (Ib) form a bicyclic ring having one 5–6 membered aromatic or nonaromatic heterocyclic ring fused to a phenyl ring; wherein each ring is optionally independently substituted by one or two $R_7$.

In yet still a further embodiment of the invention, there are provided novel compounds of the formula (Ia) or formula (Ib) as described immediately above, and wherein:

Het is piperidin-4-yl, piperidin-3-yl, pyrrolidin-3-yl, azetidin-3-yl, azepan-3-yl, azepan-4-yl or tetrahydropyran-4-yl, each ring being optionally substituted with one or more $R_5$;

$R_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

$R_3$ is a bond, methyl, ethyl, n-propyl, propenyl, butenyl, i-butenyl, cyclohexyl, benzyl or naphthylmethyl wherein $R_3$ is optionally substituted by one or more $R_c$;

$R_c$ is methyl, ethyl, n-propyl, i-propyl, cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, fluoro, chloro or oxo;

$R_5$ is a bond, hydrogen, carbonyl, C1–4 alkyl, C1–2alkoxyC1–2alkyl, C1–2alkylaminoC1–2alkyl, C1–2alkylthioC1–2alkyl wherein the sulfur atom may be oxidized to a sulfoxide or sulfone, C1–2 alkoxy, phenoxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$; and $R_f$ is methyl, phenyl, tolylsulfonyl, phenoxy, benzyloxy, fluoro, chloro or oxo;

$R_1$ and $R_6$ of the formula (Ia) or Formula (Ib) form the bicyclic ring

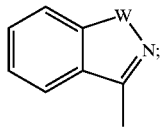

wherein W is —S(O)$_n$—, —O—C(O)— or —N—C(O)—, n is 0, 1 or 2 and wherein each ring is optionally independently substituted by one or two $R_7$.

In a further embodiment of the invention, there are provided novel compounds of the formulas (Ia) and (Ib) as described immediately above, and wherein:

Het is piperidin-4-yl, piperidin-3-yl, pyrrolidin-3-yl, azetidin-3-yl or tetrahydropyran-4-yl, each ring being substituted with one or more $R_5$;

$R_1$ is i-propyl, benzyloxy, cyclohexyl, phenyl, 4-(acetylamino)-phenyl, 4-(methanesulfonylamino)-phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

$R_3$ is ethyl, n-propyl, propenyl, butenyl, i-butenyl, benzyl or naphthylmethyl wherein $R_3$ is optionally substituted by one or more $R_c$;

$R_c$ is methyl, cyclohexyl, cyclopentyl, indanyl, 1,2,3,4-tetrahydronaphthyl, methoxy, methylthio wherein the sulfur atom may be oxidized to a sulfoxide or sulfone, fluoro or chloro;

$R_5$ is a bond, carbonyl, methyl, ethyl, n-propyl, n-butyl, t-butyl, i-propyl, i-butyl, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, $R_5$ may be further optionally substituted by one or more $R_e$;

$R_e$ is methyl, cyclopropyl, cyclopentyl, cyclohexyl, phenyl, naphthyl, indanyl, thienyl, 5-methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl; and n is 2.

In another embodiment of the invention, there are provided novel compounds of the formulas (Ia) and (Ib) as described for the broadest generic aspect above and wherein:

$R_1$ and $R_6$ remain acyclic,

Het is piperidinyl, pyrrolidinyl, azetidinyl, azepanyl, oxepanyl, tetrahydropyranyl, oxetanyl or tetrahydrothiopyranyl each ring being optionally substituted with one or more $R_5$;

$R_1$ is a bond, C1–5 alkyl, C1–5 alkoxy, C3–6 cycloalkyl, aryloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is a bond, C1–3 alkyl, cyclopropyl, cyclohexyl, phenyl, pyrrolidinyl, piperidinyl, morpholinyl, thiomorpholinyl, piperazinyl, thienyl, imidazolyl, C1–3 alkoxy, C1–3alkanoyl, C1–3alkanoyloxy, aryloxy, benzyloxy, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, n-propyl, i-propyl, cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is C1–3 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, furanyl, tetrahydropyranyl, thienyl, oxazolyl, thiazolyl, imidazolyl, pyrimidinyl, indolyl, benzofuranyl, benzothienyl, benzthiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbamoyl wherein the nitrogen atom may be independently mono or di-substituted by C1–3 alkyl or aryl, or $R_c$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or $R_c$ is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or $R_c$ is halogen, hydroxy, oxo, carboxy or cyano, $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_4$ is hydrogen;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, C3–6 cycloalkyl, phenyl, naphthyl, benzyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–3alkanoyl, benzoyl, naphthoyl, C1–3alkanoyloxy, benzyloxy, C1–3 alkoxycarbonyl, benzyloxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofuranyl, benzothienyl, benzimidazolyl or benzthiazolyl, or $R_5$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzthiazolyl, or $R_5$ is halogen, hydroxy, oxo, carboxy, cyano or carboxamide, $R_5$ may be further optionally substituted by one or more $R_e$;

$R_e$ is C1–3 alkyl, C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–3 alkanoyl, aroyl, C1–3alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_e$ is halogen, hydroxy, oxo, carboxy, cyano or carboxamide, $R_e$ may be further optionally substituted by one or more $R_f$;

$R_f$ is methyl, phenyl, tolylsulfonyl, methoxy, phenoxy, benzyloxy, fluoro, chloro, bromo, hydroxy, oxo, carboxy or carboxamide;

$R_6$ is
hydroxy, nitrile or
a C1–5 saturated or unsaturated branched or unbranched carbon chain optionally partially or fully halogenated wherein one or more C atoms are optionally replaced by O, NH, or $S(O)_2$ and wherein said chain is optionally independently substituted with 1–2 oxo groups, —$NH_2$, one or more C1–4 alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl, benzoxazolyl or quinoxalinyl;
and X is O.

In another embodiment of the invention, there are provided novel compounds of the formula (Ia) and (Ib) as described immediately above, and wherein:

$R_1$ is a bond, methyl, ethyl, i-propyl, methoxy, ethoxy, cyclopropyl, cyclopentyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is a bond, methyl, ethyl, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_a$ is fluoro, chloro, bromo, iodo, hydroxy, oxo, carboxy, cyano, nitro or carboxamide, $R_a$ may be further optionally substituted by one or more $R_b$;

$R_b$ is methyl, cyclopropyl, phenyl, methoxy, phenoxy, benzyloxy, fluoro, chloro, hydroxy, oxo, carboxy or carboxamide;

$R_3$ is a bond, C1–3 alkyl, C2–4alkylene, C5–6 cycloalkyl, benzyl or naphthylmethyl wherein $R_3$ is optionally substituted by one or more $R_c$;

$R_c$ is methyl, ethyl, n-propyl, i-propyl, C5–6 cycloalkyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, thienyl, oxazolyl, thiazolyl, indolyl, benzofuranyl, benzothienyl, benzthiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, $R_c$ may be further optionally substituted by one or more $R_d$;

$R_d$ is methyl, cyclopropyl, phenyl, methoxy, fluoro, chloro or oxo;

$R_5$ is a bond, hydrogen, carbonyl, C1–4 alkyl, C1–4alkoxyC1–4alkyl, C1–4alkylaminoC1–4alkyl, C1–4alkylthioC1–4alkyl wherein the sulfur atom may be oxidized to a sulfoxide or sulfone, C1–4 alkoxy, phenoxy, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzthiazolyl, heterocyclyloxy wherein the heterocyclyl moiety is selected from those herein described in this paragraph, C1–2alkanoyl, benzoyl, naphthoyl, C1–2alkanoyloxy, benzyloxy, C1–2 alkoxycarbonyl, benzyloxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzthiazolyl, or $R_5$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_5$ is fluoro, chloro, bromo, hydroxy, oxo, carboxy or carboxamide, $R_5$ may be further optionally substituted by one or more $R_e$;

$R_e$ is C1–3 alkyl, C1–2 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzthiazolyl, benzoxazolyl, C1–2 alkanoyl, aroyl, C1–2alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, $R_e$ may be further optionally substituted by one or more $R_f$;

$R_f$ is methyl, phenyl, tolylsulfonyl, methoxy, phenoxy, benzyloxy, fluoro, chloro, hydroxy, oxo, carboxy or carboxamide and $R_6$ is
   nitrile or
   a C1–5 saturated or unsaturated branched or unbranched carbon chain optionally partially or fully halogenated wherein one or more C atoms are optionally replaced by O, NH, or $S(O)_2$ and wherein said chain is optionally independently substituted with oxo, —$NH_2$, piperidinyl, morpholinyl, thiomorpholinyl, piperazinyl, pyridinyl, pyrimidinyl or pyrazinyl.

In yet another embodiment of the invention, there are provided novel compounds of the formula (Ia) or formula (Ib) as described immediately above, and wherein:

Het is piperidin-4-yl, piperidin-3-yl, pyrrolidin-3-yl, azetidin-3-yl, azepan-3-yl, azepan-4-yl or tetrahydropyran-4-yl, each ring being optionally substituted with one or more $R_5$;

$R_1$ is a bond, methyl, ethyl, i-propyl, methoxy, cyclopropyl, cyclohexyl, phenoxy, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl or amino; wherein $R_1$ is optionally substituted by one or more $R_a$;

$R_a$ is methyl, phenyl, thienyl, methoxy, acetyl, acetoxy, phenoxy, benzyloxy, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

$R_3$ is a bond, methyl, ethyl, n-propyl, propenyl, butenyl, i-butenyl, cyclohexyl, benzyl or naphthylmethyl wherein $R_3$ is optionally substituted by one or more $R_c$;

$R_c$ is methyl, ethyl, n-propyl, i-propyl, cyclohexyl, cyclopentyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, fluoro, chloro or oxo; and wherein the configuration at the stereocenter defined by $R_2$ and $R_3$ when they are different and the carbon they are attached to is defined as L; and $R_5$ is a bond, hydrogen, carbonyl, C1–4 alkyl, C1–2alkoxyC1–2alkyl, C1–2alkylaminoC1–2alkyl, C1–2alkylthioC1–2alkyl wherein the sulfur atom may be oxidized to a sulfoxide or sulfone, C1–2 alkoxy, phenoxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxy-carbonyl, benzoyloxy, carbamoyl wherein the nitrogen atom may be independently mono or di-substituted by methyl, ethyl or phenyl, or $R_5$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$;

$R_f$ is methyl, phenyl, tolylsulfonyl, phenoxy, benzyloxy, fluoro, chloro or oxo;

$R_6$ is
   nitrile or
   a C1–5 saturated or unsaturated branched or unbranched carbon chain optionally partially or fully halogenated wherein one or more C atoms are optionally replaced by O, NH, or $S(O)_2$ and wherein said chain is optionally independently substituted with oxo, —$NH_2$, morpholinyl or piperazinyl.

In yet still another embodiment of the invention, there are provided novel compounds of the formulas (Ia) and (Ib) as described immediately above, and wherein:

Het is piperidin-4-yl, piperidin-3-yl, pyrrolidin-3-yl, azetidin-3-yl or tetrahydropyran-4-yl, each ring being substituted with one or more $R_5$;

$R_1$ is i-propyl, benzyloxy, cyclohexyl, phenyl, 4-(acetylamino)-phenyl, 4-(methanesulfonylamino)-phenyl, 4-methoxyphenyl, 3-phenoxyphenyl, 4-chlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, 5-chlorothienyl, pyridin-4-yl, pyrazinyl, methylamino, ethylamino, dimethylamino or diethylamino;

$R_3$ is ethyl, n-propyl, propenyl, butenyl, i-butenyl, benzyl or naphthylmethyl wherein $R_3$ is optionally substituted by one or more $R_c$;

$R_c$ is methyl, cyclohexyl, cyclopentyl, indanyl, 1,2,3,4-tetrahydronaphthyl, methoxy, methylthio wherein the sulfur atom may be oxidized to a sulfoxide or sulfone, fluoro or chloro;

$R_5$ is a bond, carbonyl, methyl, ethyl, n-propyl, n-butyl, t-butyl, i-propyl, i-butyl, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, $R_5$ may be further optionally substituted by one or more $R_e$;

$R_e$ is methyl, cyclopropyl, cyclopentyl, cyclohexyl, phenyl, naphthyl, indanyl, thienyl, 5-methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl; and $R_6$ is acetyl, C1–3alkylaminocarbonyl or C1–3alkoxycarbonyl.

In yet a further embodiment of the invention, there are provided novel compounds of the formulas (Ia) and (Ib) as described immediately above, and wherein:

Het is piperidin-4-yl or pyrrolidin-3-yl;

$R_1$ is morpholin-4-yl, p-fluorophenyl or p-methoxyphenyl;

$R_5$ is methyl, propyl, n-pentyl or cyclohexyl and $R_6$ is acetyl, ethylaminocarbonyl or ethoxycarbonyl.

The activity of particular compounds disclosed herein against cathepsin K may be determined without undue experimentation by one of ordinary skill in the art in view of the art, the guidance provided throughout this specification and by the screens described in the section entitled "Assessment of Biological Properties."

The following subgeneric aspect of the compounds of the formulas (Ia) and (Ib) is postulated to possess Cathepsin K activity:

The broadest embodiment of the formula (Ia) and (Ib) as described hereinabove and wherein Het is piperidinyl, pyrrolidinyl, azetidinyl, azepanyl, oxepanyl, tetrahydropyranyl, oxetanyl or tetrahydrothiopyranyl each ring being optionally substituted with one or more $R_5$;

$R_1$ is a bond, C1–4 alkyl, C1–4 alkoxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, ethyl, propyl, i-propyl, cyclopropyl, cyclohexyl, phenyl, pyrrolidinyl, piperidinyl, morpholinyl, thiomorpholinyl, piperazinyl, thienyl, imidazolyl, methoxy, ethoxy, acetyl, acetoxy, phenoxy, naphthyloxy, benzyloxy, methoxycarbonyl, ethoxycarbonyl, phenoxycarbonyl, naphthyloxycarbonyl, benzoyloxy, carbamoyl wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is acetylamino, benzoylamino, methylthio wherein the sulfur atom may be oxidized to a sulfoxide or sulfone, ethylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl, phenyl, naphthyl, pyrrolidinyl, piperidinyl, morpholinyl, thiomorpholinyl or piperazinyl, or $R_a$ is methoxycarbonylamino, ethoxycarbonylamino, phenoxycarbonylamino, C1–2 alkylcarbamoyloxy, phenylcarbamoyloxy, naphthylcarbamoyloxy, C1–2 alkylsulfonylamino, phenylsulfonylamino, naphthylsulfonylamino, C1–2 alkylaminosulfonyl, phenylaminosulfonyl, naphthylaminosulfonyl, amino wherein the nitrogen atom may be independently mono or di-substituted by methyl, ethyl, phenyl, naphthyl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, $R_a$ may be further optionally substituted by one or more $R_b$;

$R_b$ is methyl, ethyl, cyclopropyl, cyclohexyl, phenyl, methoxy, ethoxy, phenoxy, benzyloxy, fluoro, chloro, bromo, hydroxy, oxo, carboxy, cyano, nitro or carboxamide;

$R_2$ is hydrogen or methyl;

$R_3$ is a bond, methyl, ethyl, n-propyl, i-propyl, n-butyl, i-butyl, n-pentyl, propenyl, i-butenyl, cyclohexyl, benzyl or naphthylmethyl wherein $R_3$ is optionally substituted by one or more $R_c$;

$R_c$ is methyl, ethyl, cyclohexyl, cyclopentyl, phenyl, naphthyl, bicyclo[3.1.0]hexanyl, bicyclo[1.1.1]pentanyl, cubanyl, furanyl, tetrahydropyranyl, thienyl, oxazolyl, thiazolyl, imidazolyl, pyrimidinyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl or phenyl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl or phenyl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl or phenyl, or $R_c$ is chloro, fluoro, hydroxy, oxo, carboxy or cyano;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl, piperidinyl, piperazinyl, morpholinyl or tetrahydrothiophenyl;

$R_4$ is hydrogen;

$R_5$ is a bond, hydrogen, carbonyl, C1–5 alkyl, C1–5alkoxyC1–5alkyl, C1–5alkylaminoC1–5alkyl, C1–5alkylthioC1–5alkyl wherein the sulfur atom may be oxidized to a sulfoxide or sulfone, C1–5 alkoxy, phenoxy, naphthyloxy, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, heterocyclyloxy wherein the heterocyclyl moiety is selected from those herein described in this paragraph, acetyl, benzoyl, acetyloxy, benzyloxy, methoxycarbonyl, ethoxycarbonyl, benzyloxycarbonyl, benzoyloxy, carbamoyl wherein the nitrogen atom may be independently mono or di-substituted by methyl, ethyl or phenyl, or $R_5$ is acetylamino, benzoylamino, phenylthio wherein the sulfur atom may be oxidized to a sulfoxide or sulfone, ureido wherein either nitrogen atom may be independently substituted by methyl, ethyl or phenyl, or $R_5$ is methoxycarbonylamino, ethoxycarbonylamino, phenoxycarbonylamino, methylcarbamoyloxy, phenylcarbamoyloxy, phenylsulfonylamino, phenylaminosulfonyl, amino wherein the nitrogen atom may be independently mono or di-substituted by methyl, ethyl or phenyl, or $R_5$ is fluoro, chloro, hydroxy, oxo, carboxy or carboxamide, $R_5$ may be further optionally substituted by one or more $R_e$;

$R_e$ is methyl ethyl, methoxy, ethoxy, cyclopropyl, cyclopentyl, cyclohexyl, phenyl, naphthyl, indanyl, piperidinyl, morpholinyl, indolyl, thienyl, pyridinyl, methoxy, ethoxy, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is acetylamino, benzoylamino, methylthio wherein the sulfur atom may be oxidized to a sulfoxide or sulfone, phenylthio methylthio wherein the sulfur atom may be oxidized to a sulfoxide or sulfone, ureido wherein either nitrogen atom may be independently substituted by methyl, ethyl or phenyl, or $R_e$ is methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_e$ is fluoro, chloro, hydroxy, oxo, carboxy or carboxamide, $R_e$ may be further optionally substituted by one or more $R_f$;

$R_f$ is methyl, phenyl, tolylsulfonyl, phenoxy, benzyloxy, fluoro, chloro or oxo.

Preferred cathepsin K inhibitors are those as described immediately above and wherein:

$R_1$ is a bond, methyl, ethyl, n-propyl, i-propyl, methoxy, ethoxy, benzyloxy, cyclopropyl, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, benzofuranyl, benzthienyl, benzimidazolyl, benzthiazolyl, benzoxazolyl or amino; wherein $R_1$ is optionally substituted by one or more $R_a$;

$R_a$ is methyl, cyclopropyl, phenyl, halogen, hydroxy, oxo, carboxy, cyano, nitro or carboxamide;

$R_3$ is a bond, methyl, ethyl, n-propyl, i-propyl, n-butyl, i-butyl, n-pentyl, propenyl, i-butenyl, benzyl or naphthylmethyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, carbamoyl wherein the nitrogen atom may be independently mono or di-substituted by methyl or phenyl, or $R_c$ is acetylamino, benzoylamino, methylthio, methoxycarbonylamino, methylcarbamoyloxy, methylsulfonylamino, methylaminosulfonyl, amino wherein the nitrogen atom may be independently mono or di-substituted by methyl, or $R_c$ is fluoro or oxo;

$R_2$ and $R_3$ together with the carbon they are attached optionally form a ring selected from cyclopentyl, cyclohexyl, cycloheptyl, tetrahydropyranyl, tetrahydrothiopyranyl, tetrahydrofuranyl, pyrrolidinyl or piperidinyl;

$R_5$ is methyl, ethyl, n-propyl, n-butyl, n-pentyl, 2-pentyl, 3-pentyl, phenethyl, phenpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, 2-methylbenzyl, 3-methylbenzyl, 4-methylbenzyl, 2,6-dimethylbenzyl, 2,5-dimethylbenzyl, 2,4-dimethylbenzyl, 2,3-dimethylbenzyl, 3,4-dimethylbenzyl, 3,5-dimethylbenzyl, 2,4,6-trimethylbenzyl, 2-methoxybenzyl, 3-methoxybenzyl, 4-methoxybenzyl, 2-phenoxybenzyl, 3-phenoxybenzyl, 4-phenoxybenzyl, 2-benzyloxybenzyl, 3-benzyloxybenzyl, 4-benzyloxybenzyl, 2-fluorobenzyl, 3-fluorobenzyl, 4-fluorobenzyl, 2,6-difluorobenzyl, 2,5-difluorobenzyl, 2,4-difluorobenzyl, 2,3-difluorobenzyl, 3,4-difluorobenzyl, 3,5-difluorobenzyl, 2,4,6-triflurobenzyl, 2-trifluoromethylbenzyl, 3-trifluoromethylbenzyl, 4-trifluoromethylbenzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, fluoro, oxo or carboxy.

Most preferred cathepsin K inhibitors are those as described immediately above and wherein:

$R_1$ is methoxy, benzyloxy, cyclohexyl, phenoxy, naphthyloxy, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, quinolinyl, benzofuranyl, benzthienyl, benzimidazolyl, benzthiazolyl, benzoxazolyl or amino;

wherein $R_1$ is optionally substituted by one or more $R_a$;

$R_a$ is methyl, phenyl, fluoro, chloro, hydroxy, oxo, carboxy or carboxamide;

$R_3$ is a bond, methyl, ethyl, n-propyl, i-propyl, n-butyl, i-butyl, n-pentyl, propenyl, i-butenyl or benzyl wherein $R_3$ is optionally substituted by one or more $R_c$;

$R_c$ is methyl, ethyl, cyclohexyl, cyclopentyl, phenyl, furanyl, tetrahydropyranyl, thienyl, oxazolyl, thiazolyl, methoxy, phenoxy, acetyl, benzoyl, methoxycarbonyl, acetylamino, methylthio, methylsulfonylamino or fluoro;

$R_2$ and $R_3$ together with the carbon they are attached optionally form a ring selected from cyclopentyl, cyclohexyl, cycloheptyl, tetrahydropyranyl, tetrahydrothiopyranyl or tetrahydrofuranyl;

$R_5$ is methyl, ethyl, n-propyl, n-butyl, phenethyl, phenpropyl, t-butyl, i-propyl, i-butyl, cyclopropyl, cyclohexyl, cyclopropylmethyl, cyclohexylmethyl, phenyl, benzyl, 2-methoxybenzyl, 3-methoxybenzyl, 4-methoxybenzyl 4-fluorobenzyl, 3,5-difluorobenzyl, 4-trifluoromethylbenzyl, naphthylmethyl, pyridinylmethyl, indolylmethyl, thienylmethyl, acetyl, benzoyl, ethoxycarbonyl, benzyloxycarbonyl, t-butoxycarbonyl, phenylcarbamoyl, phenylsulfonylamino or fluoro.

Most preferred cathepsin K inhibitors are those as described immediately above and wherein:

Het is pyrrolidinyl, piperidinyl or tetrahydropyranyl;

$R_1$ is benzyloxy, phenoxy, naphthyloxy, phenyl, naphthyl, pyrrolidinyl, piperidinyl, morpholinyl, thiomorpholinyl, piperazinyl, pyridinyl, indolyl, quinolinyl, benzofuranyl, benzthienyl, benzimidazolyl, benzthiazolyl, benzoxazolyl or phenylamino;

$R_3$ is n-propyl, i-butyl, propenyl, i-butenyl or 2,2-dimethylpropyl;

$R_2$ and $R_3$ together with the carbon they are attached optionally form a ring selected from cyclopentyl, cyclohexyl, or cycloheptyl;

$R_5$ is methyl, ethyl, n-propyl, phenethyl, t-butyl, i-propyl, i-butyl, cyclohexyl, cyclohexylmethyl, benzyl, 4-fluorobenzyl, naphthylmethyl, acetyl, benzoyl or benzyloxycarbonyl.

Further compounds of Formula (Ia), made up of components A, B, and C are provided in the following Table I. Any and all combinations of A, B, and C components within the structural limitations of Formula (Ia), comprise a compound of the invention, and their pharmaceutically acceptable derivatives. These compounds can be synthesized by the General schemes, methods described in the experimental section of this document and analogous methods known to those skilled in the art without undue experimentation. Preferred compounds will possess desirable inhibition activity of Cathepsin S in a cell based assay as described in Riese, R. J. et al., Immunity, 1996, 4, 357–366, incorporated herein by reference.

TABLE I

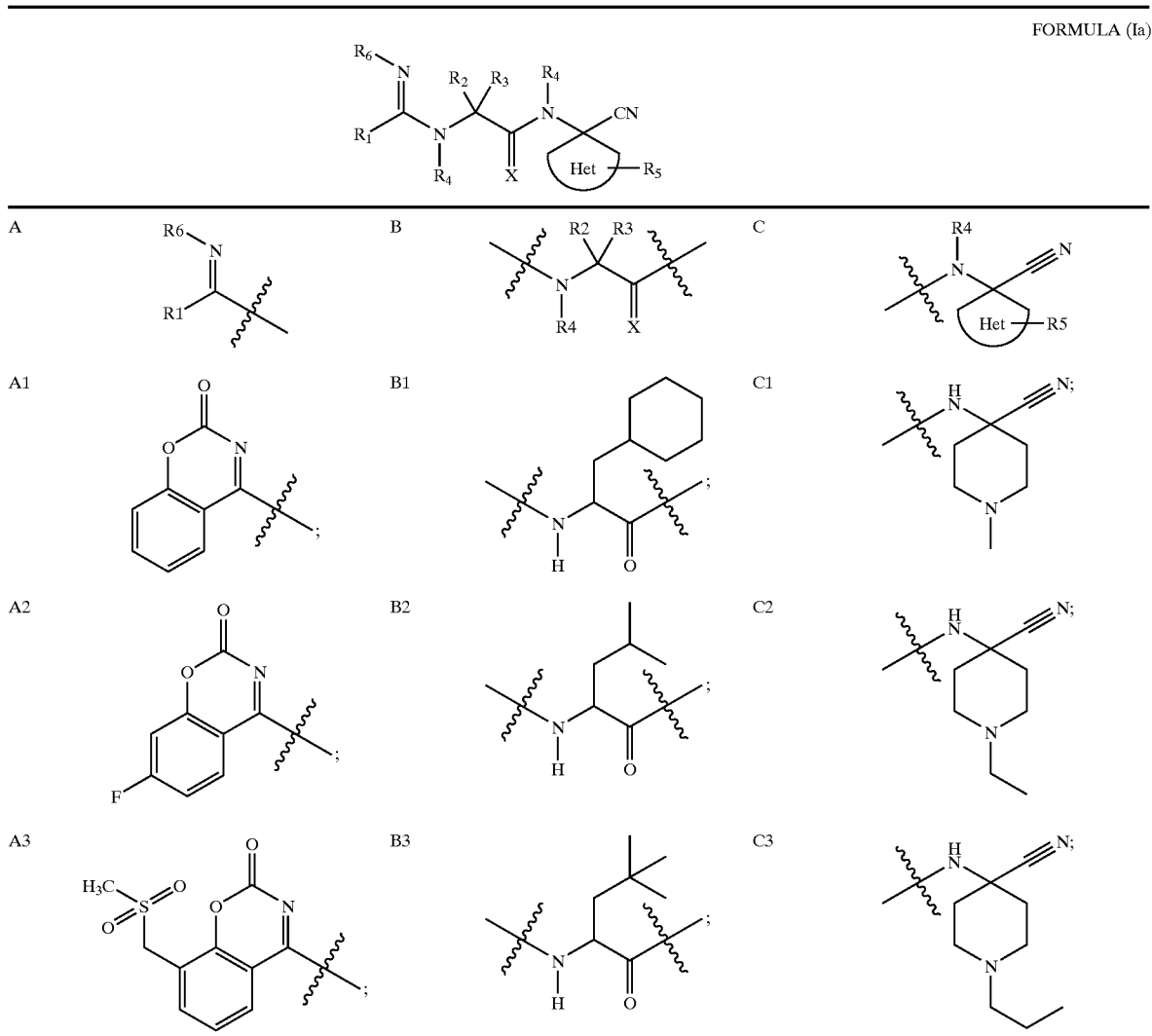

TABLE I-continued
FORMULA (Ia)
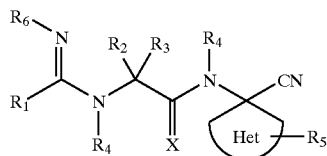
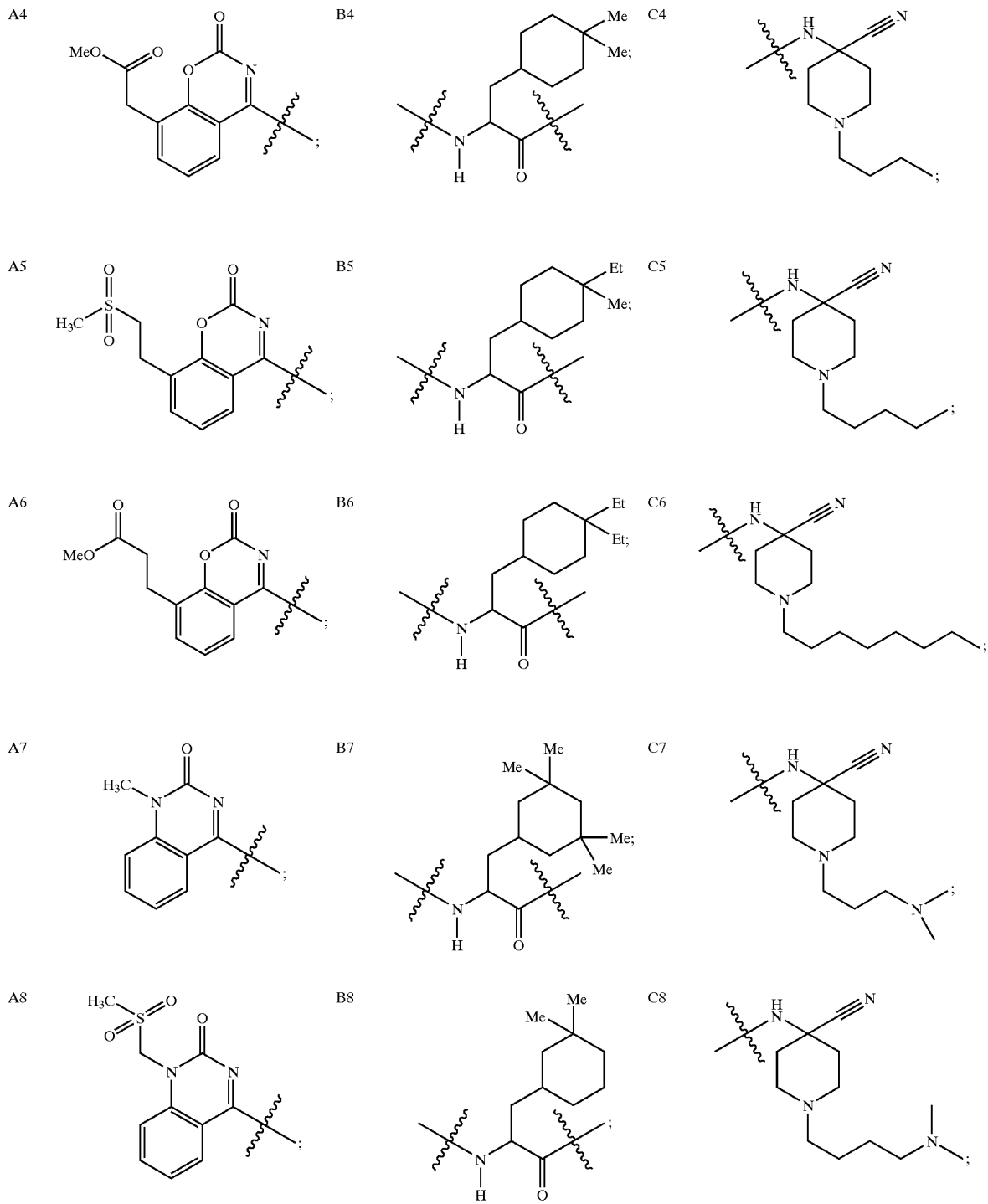

TABLE I-continued
FORMULA (Ia)
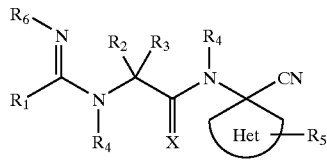
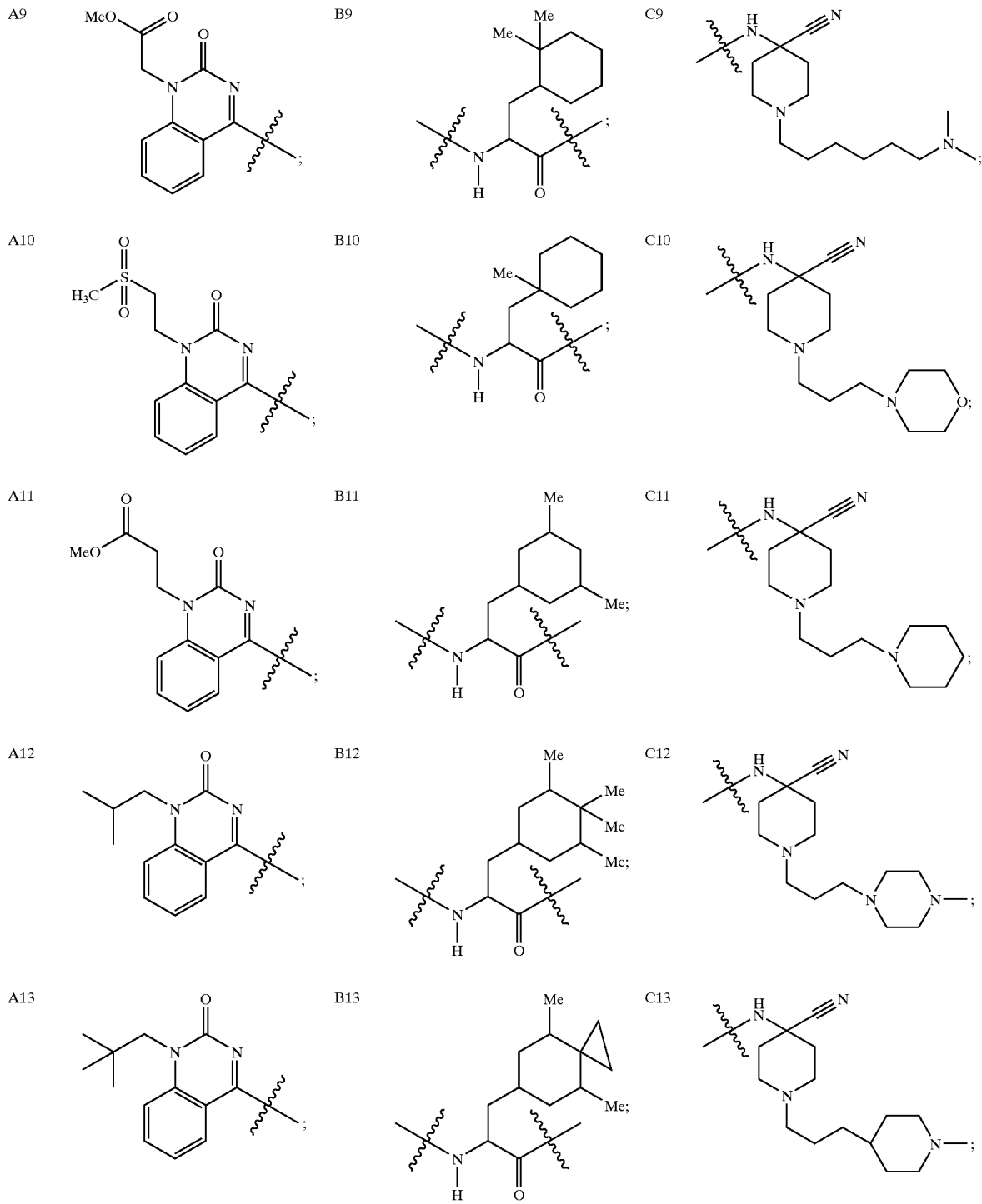

TABLE I-continued
FORMULA (Ia)
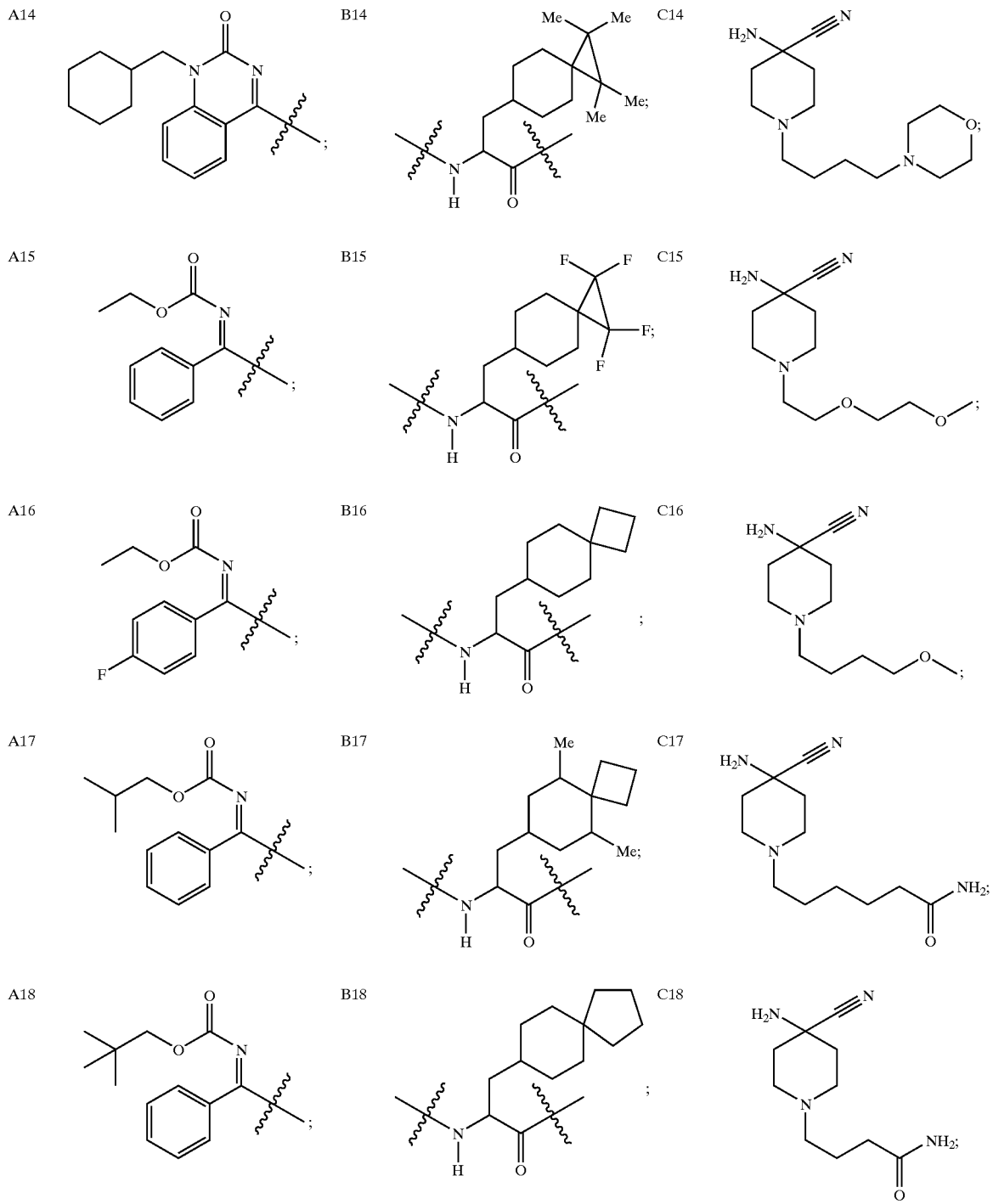

TABLE I-continued
FORMULA (Ia)
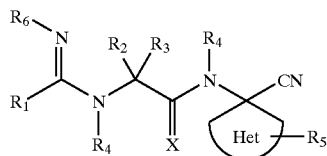
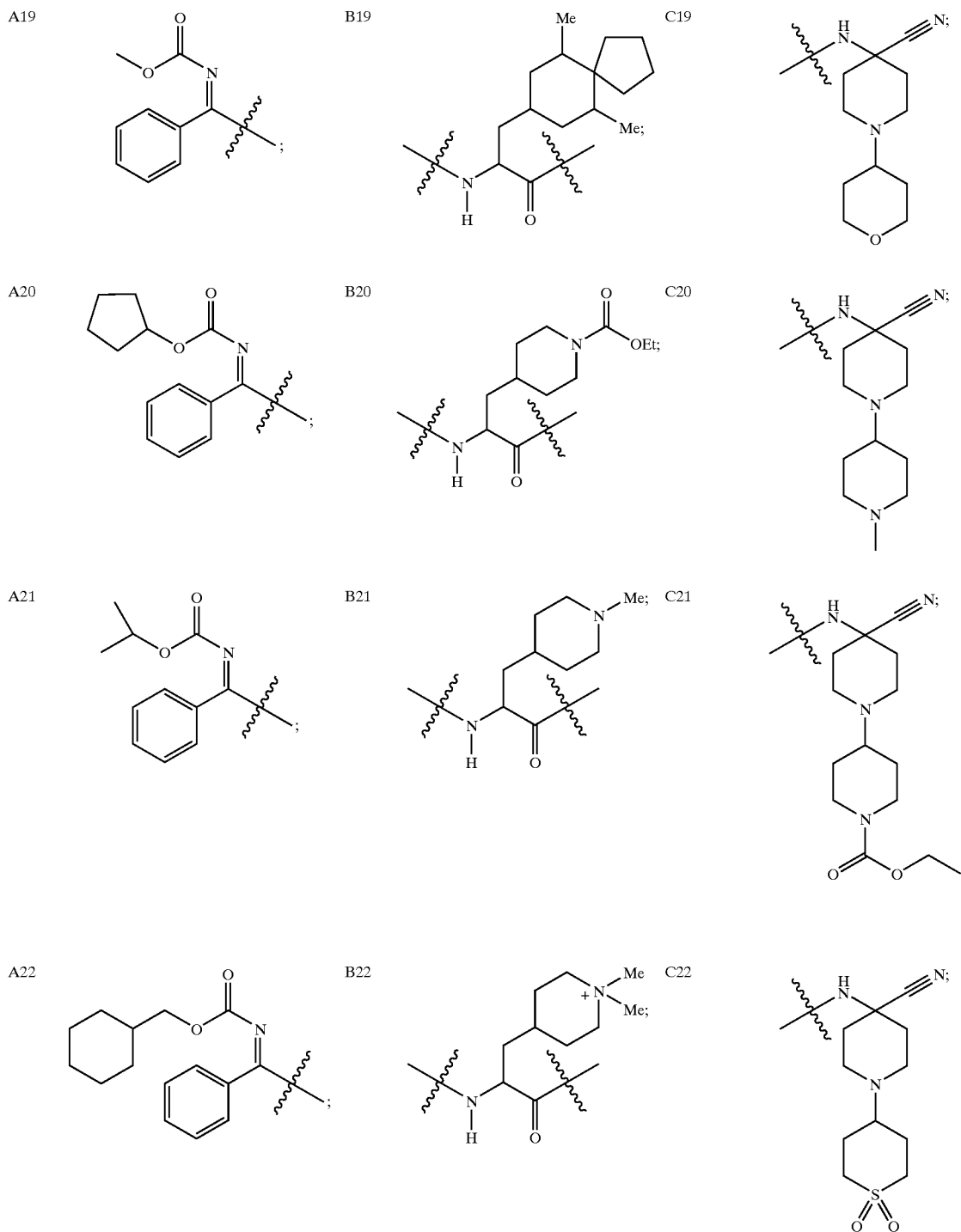

TABLE I-continued
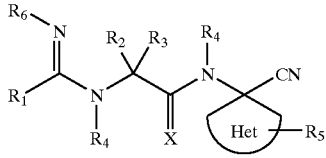

US 6,720,319 B2
TABLE I-continued
FORMULA (Ia)
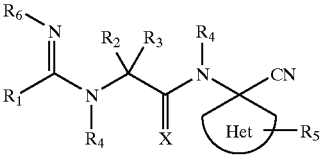
| A29 | 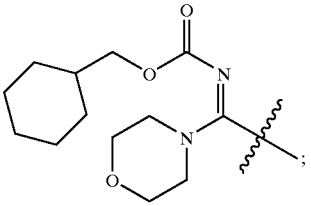 | B29 | 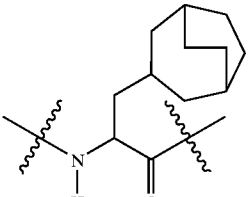 | C29 | 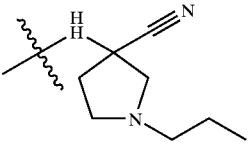 |
| A30 | 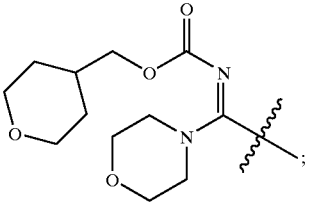 | B30 | 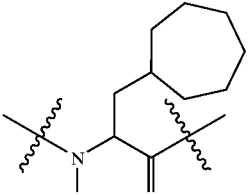 | C30 | 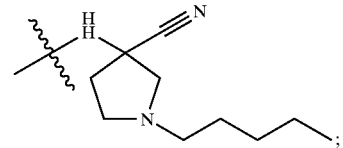 |
| A31 | 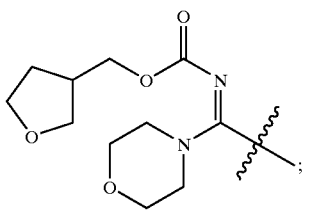 | B31 | 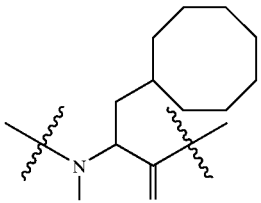 | C31 | 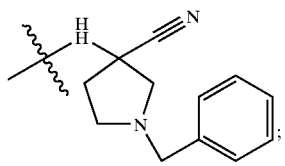 |
| A32 | 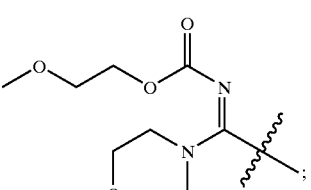 | B32 | 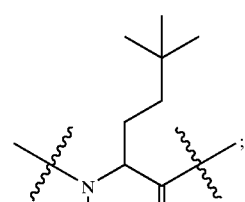 | C32 | 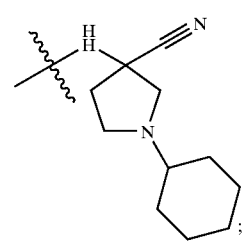 |
| A33 | 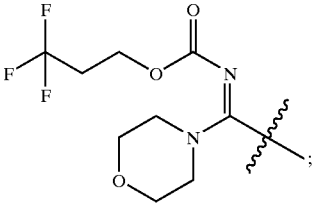 | B33 | 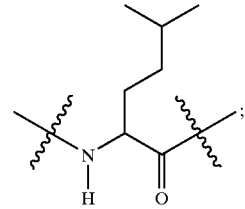 | C33 | 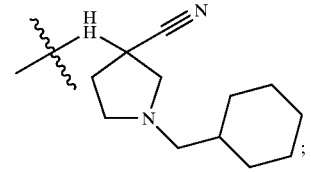 |
| A34 | 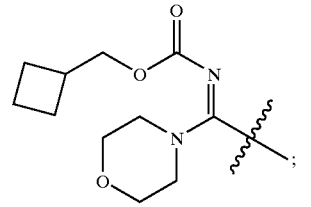 | B34 | 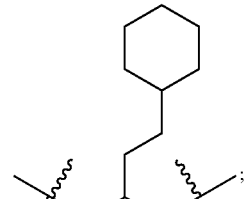 | C34 | 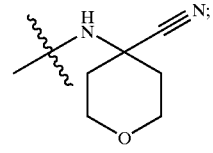 |

TABLE I-continued
FORMULA (Ia)
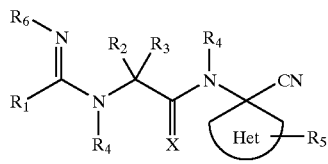
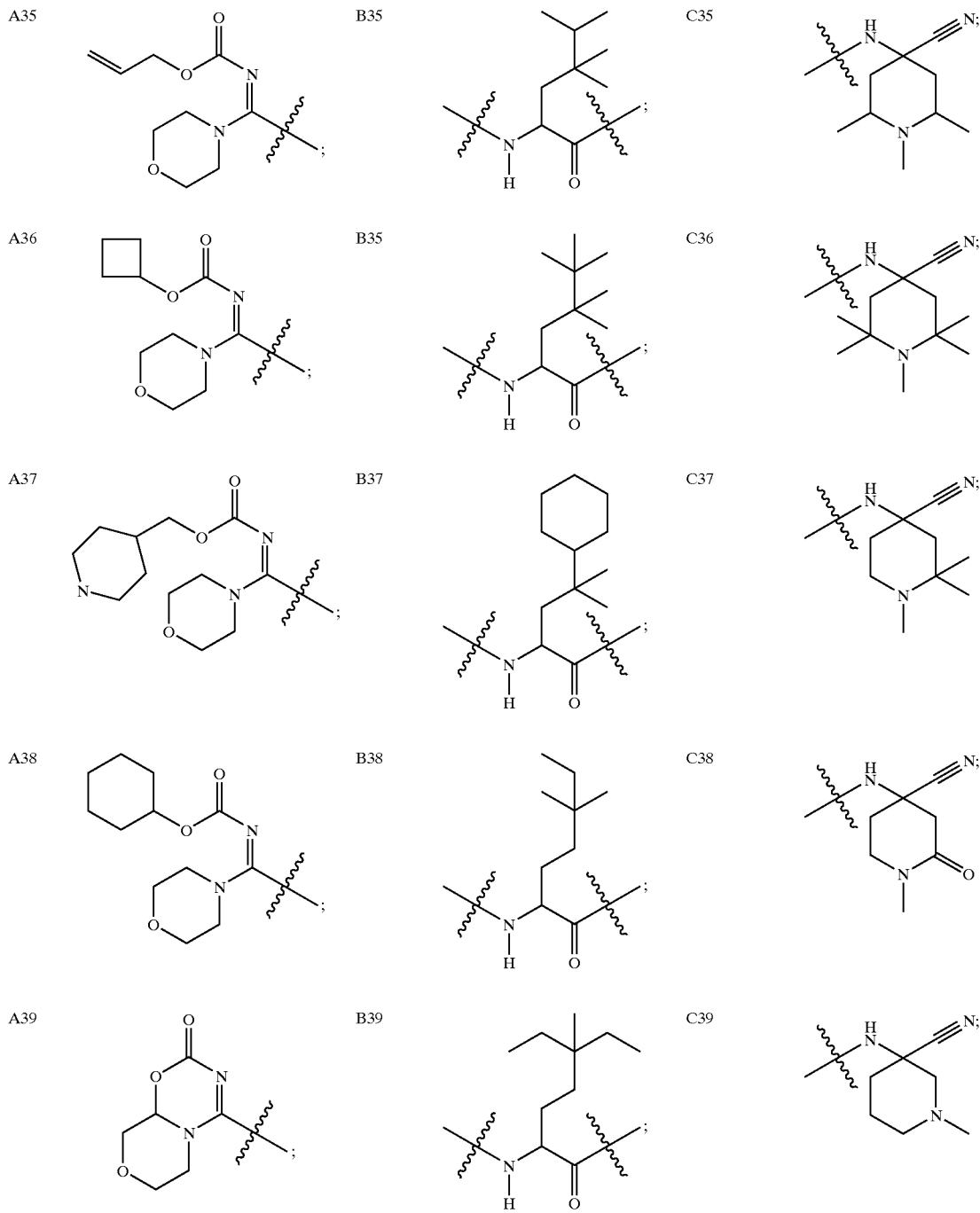

TABLE I-continued
FORMULA (Ia)
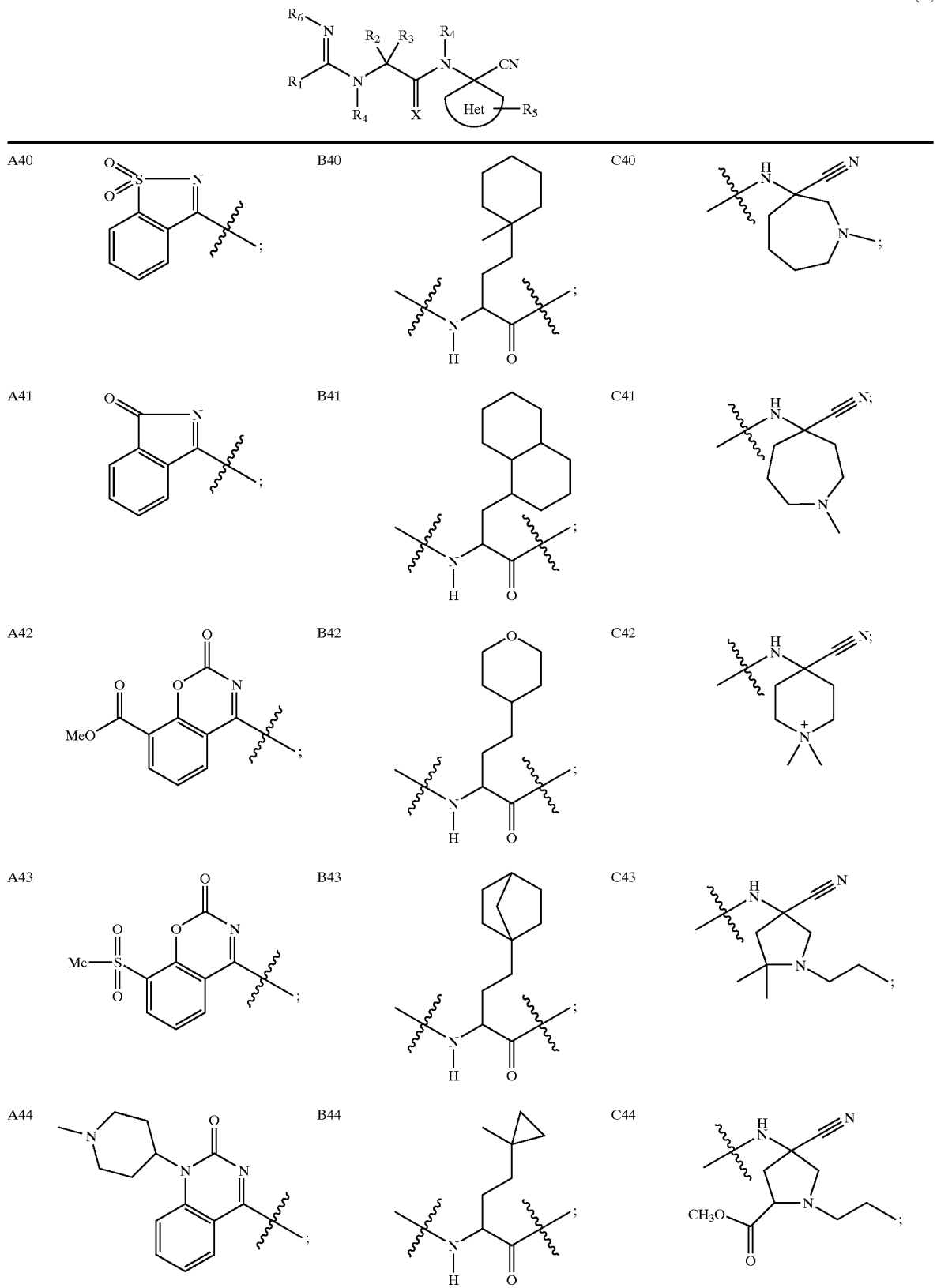

TABLE I-continued
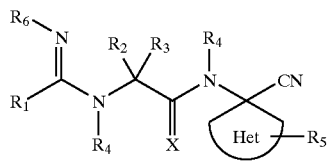
FORMULA (Ia)
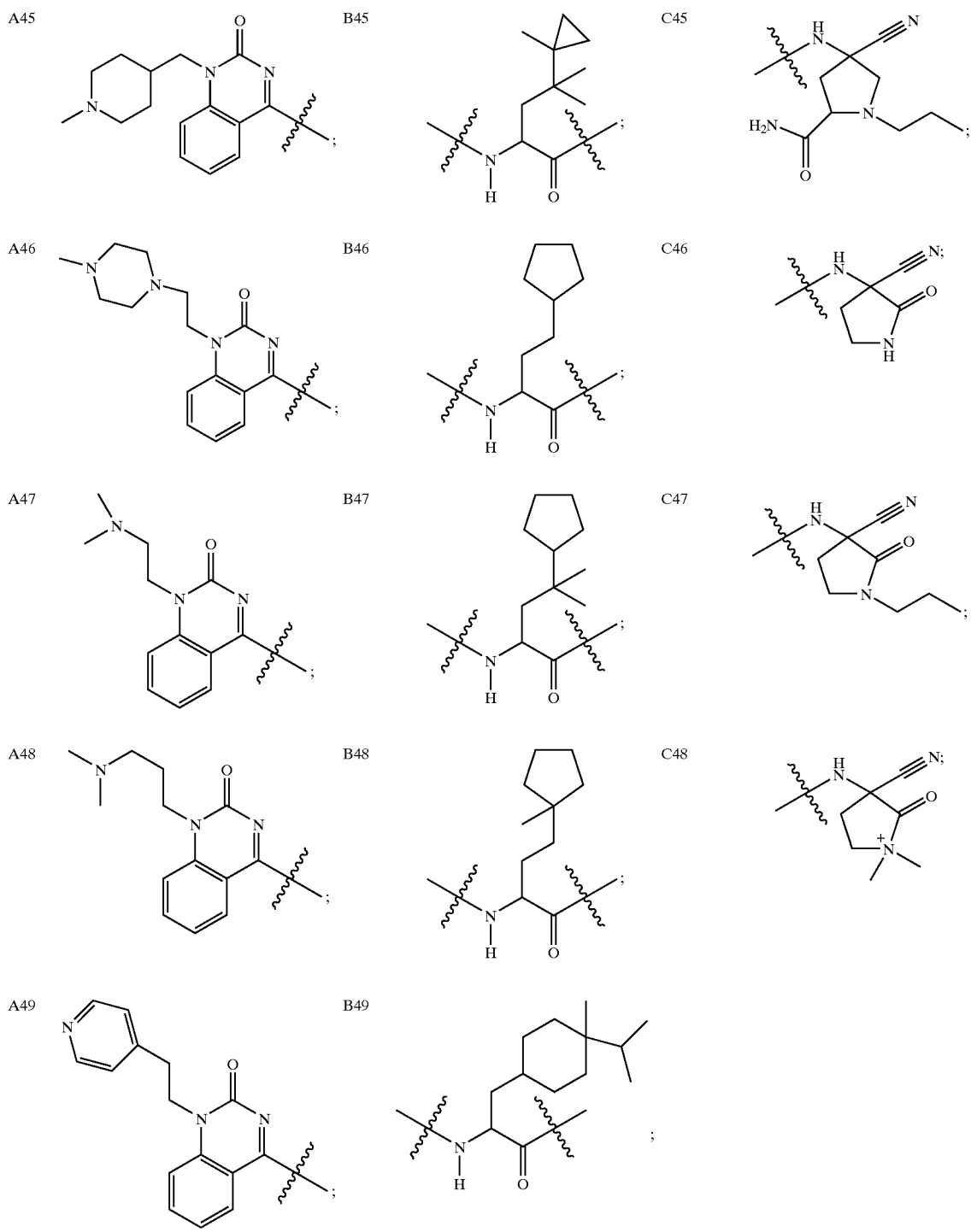

TABLE I-continued
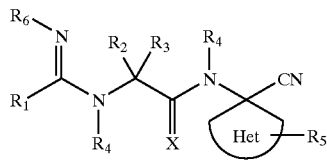
FORMULA (Ia)
A50 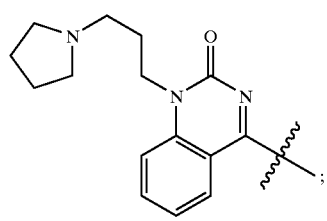 ;
A51 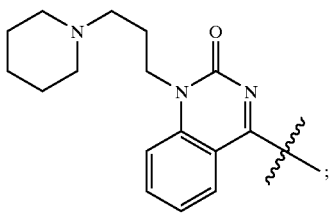 ;
A52 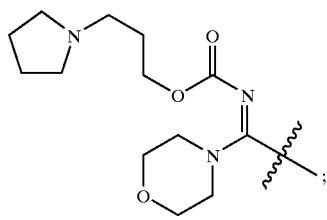 ;
A53 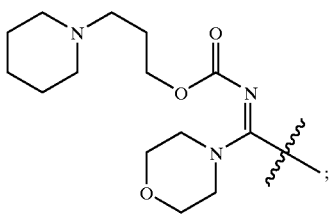 ;
A54 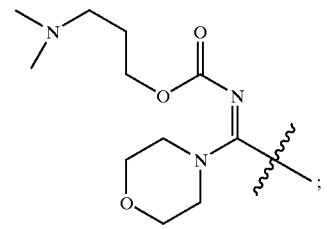 ;

TABLE I-continued

FORMULA (Ia)

A55

A56

A57 and the pharmaceutically acceptable derivates thereof.

In another embodiment of the invention there are provided the following compounds of the Formulas (Ia) and (Ib) which have been synthesized using the General schemes, methods described in the experimental section of this document and analogous methods known to those skilled in the art without undue experimentation. The compound possess desirable inhibition activity of Cathepsin S in the cell based assay referenced above.

{[1-(3-cyano-1-isobutyl-piperdin-3-yl carbamoyl)-3,3-dimethyl-butylamino]-morpholin-4-yl-methylene}-carbamic acid ethyl ester; MS: 493 (M+1)

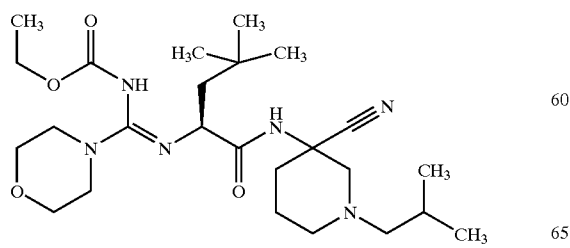

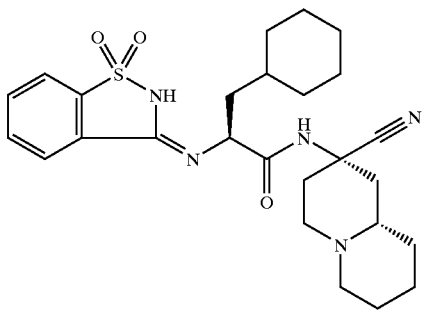

N-(2Cyano-octahydro-quinolizin-2-yl)-3-cyclohexyl-2-(1,1-dioxo-1H-1λ-benzo-3-ylamino)-propionamide; MS: 498 (M+1)

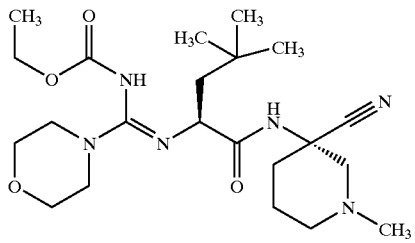

{[1-3-Cyano-1-methyl-piperidin-3-ylcarbamoyl)-3,3-dimethyl-butylamino]-morpholin-4-yl-methylene}-carbamic acid ethyl ester; MS: 451 (M+1)

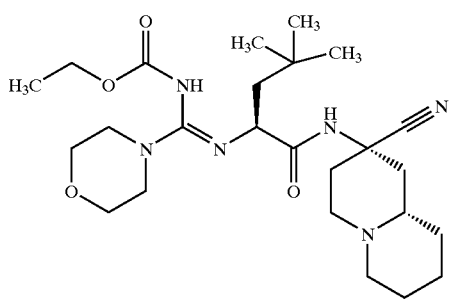

{[1-(2-cyano-octahydro-quinolizin-2-ylcarbamoyl)-3,3-dimethyl-butylamino]-morpholin-4-yl-methylene}-carbamic acid ethyl ester; MS: 491 (M+1)

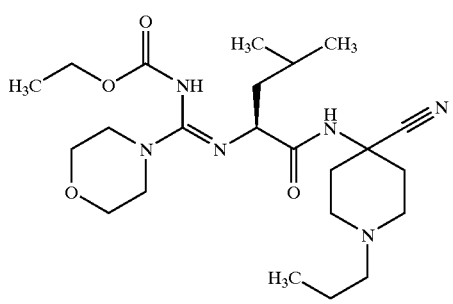

{[1-(4-Cyano-1-propyl-piperidin-4-ylcarbamoyl)-3-methyl-butylamino]-morpholin-4-yl-methylene}-carbamic acid ethyl ester; MS: 465 (M+1)

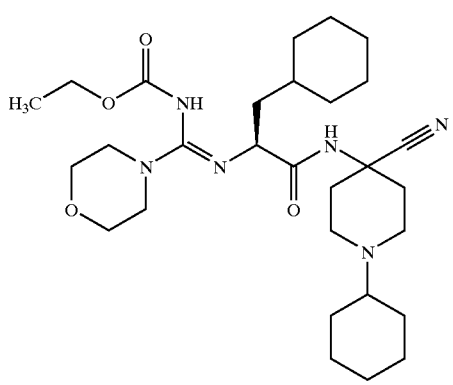

{[1-(4-cyano-1-cyclohexyl-piperidin-4-ylcarbamoyl)-2-cyclohexyl-ethylamino]-morpholin-4-yl-methylene}-carbamic acid ethyl ester; MS: 545 (M+1)

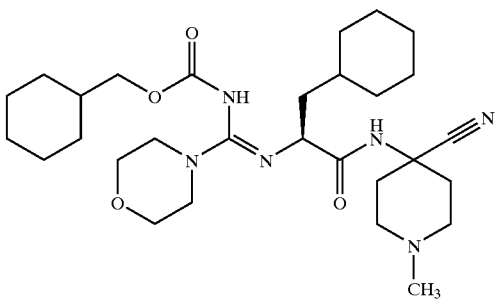

{[1-(4-cyano-1-methyl-piperidin-4-ylcarbamoyl)-2-cyclohexyl-ethylamino]-morpholin-4-yl-methylene}-carbamic acid cyclohexylmethyl ester; MS: 545 (M+1)

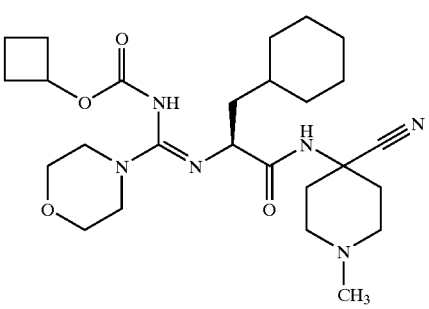

{[-1-(4-cyano-1-methyl-piperidin-4-ylcarbamoyl)-2-cyclohexyl-ethylamino]-morpholin-4-yl-methylene}-carbamic acid cyclobutyl ester; MS: 503 (M+1)

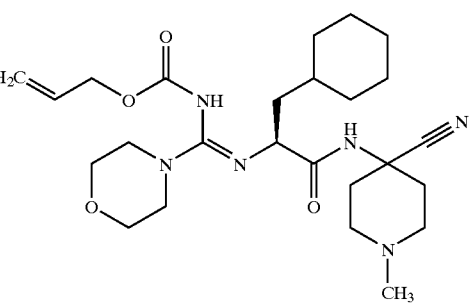

{[1-(4-cyano-1-methyl-piperidin-4-ylcarbamoyl)-2-cyclohexyl-ethylamino]-morpholin-4-yl-methylene}-carbamic acid allyl ester; MS: 489 (M+1)

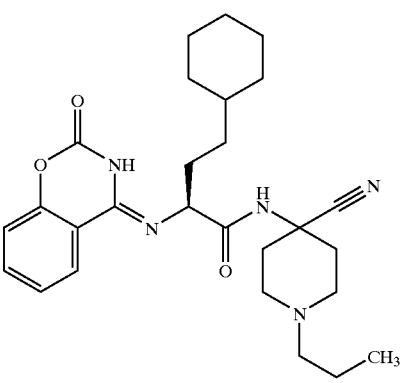

N-(4-Cyano-1-propyl-piperidin-4-yl)-4-cyclohexyl-2-(2-oxo-2,3-dihydro-benzo[e][1,3]oxazin-4-ylideneamino)-butyramide; MS: 480 (M+1)

{[1-(4-cyano-1-methy-piperidin-4-ylcarbamoyl)-2-cyclohexyl-ethyl amino]-morpholin-4-yl-methylene}-carbamic acid tetrahydro-furan-2-ylmethyl ester; MS: 533 (M+1)

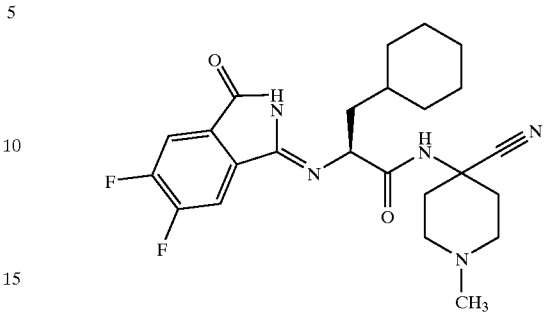

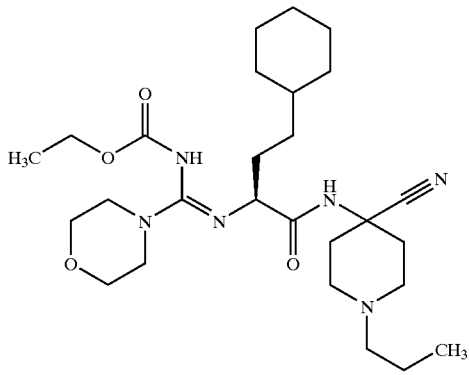

N-(4-Cyano-1-methyl-piperidin-4-yl)-3-cyclohexyl-2-(5,6-difluoro-3-oxo-2,3-dihydro-isoindol-1-ylideneamino)-propionamide; MS: 458 (M+1)

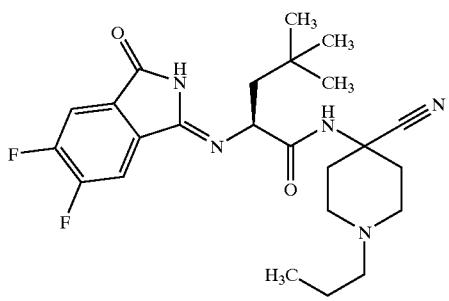

{[1-(4-cyano-1-propyl-piperidin-4-ylcarbamoyl)-3-cyclohexyl-propylamino]-morpholin-4-yl-methylene}-carbamic acid ester; MS: 519 (M+1)

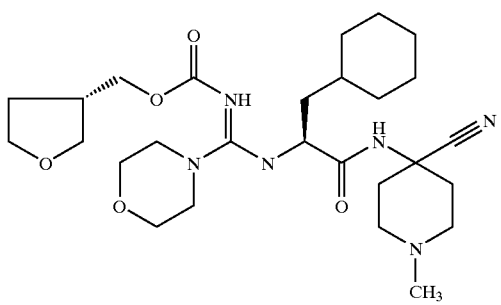

2-(5,6-Difluoro-3-oxo-2,3-dihydro-isoindol-1-ylideneamino)-4,4-dimethyl-pentanoic acid (4-cyano-1-propyl-piperidin-4-yl)-amide; MS: 460 (M+1)

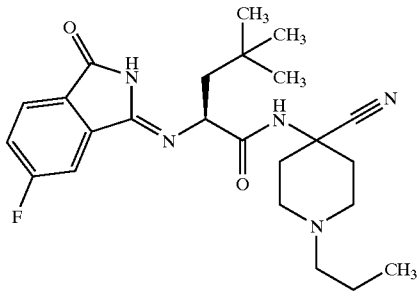

{[1-(4-cyano-1-methyl-piperidin-4-ylcarbamoyl)-2-cyclohexyl-ethylamino]-morpholin-4-yl-methylene}-carbamic acid tetrahydro-furan-3ylmethyl ester; MS: 533 (M+1)

2-(6-Fluoro-3-oxo-2,3-dihydro-isoindol-1-ylideneamino)-4,4-dimethyl-pentanoic acid (4-cyano-1-propyl-piperidin-4-yl)-amide; MS: 442 (M+1)

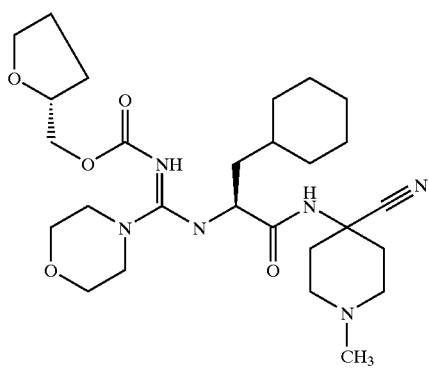

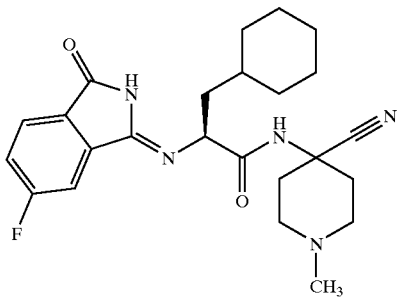

63

N-(4-Cyano-1-methyl-piperidin-4-yl)-3-cyclohexyl-2-(6-fluoro-3-oxo-2,3-dihydro-isoindol-1-ylideneamino)-propionamide; MS: 440 (M+1)

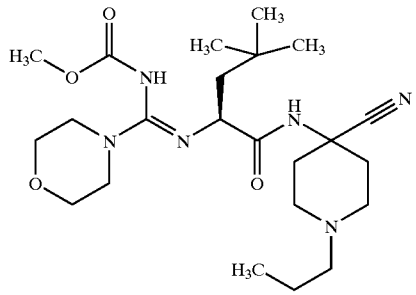

{[1-(4-Cyano-1-propyl-piperidin-4-ylcarbamoyl)-3,3-dimethyl-butylimino]-morpholin-4-yl-methyl}-carbamic acid methyl ester; MS: 465 (M+1)

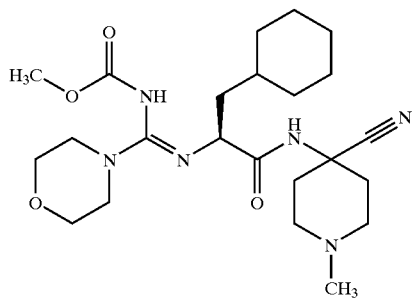

{[1-(4-Cyano-1-methyl-piperidin-4-ylcarbamoyl)-2-cyclohexyl-ethylimino]-morpholin-4-yl-methyl}-carbamic acid methyl ester; MS: 463 (M+1)

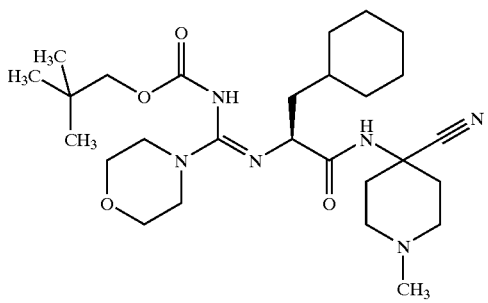

{[1-(4-Cyano-1-methyl-piperidin-4-ylcarbamoyl)-2-cyclohexyl-ethylimino]-morpholin-4-yl-methyl}-carbamic acid 2,2-dimethyl-propyl ester; MS: 519 (M+1)

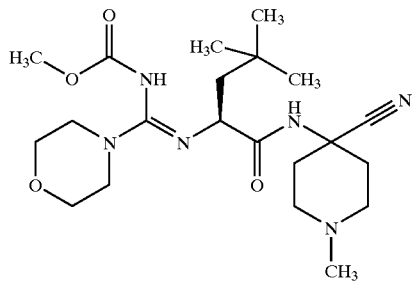

64

{[1-(4-Cyano-1-methyl-piperidin-4-ylcarbamoyl)-3,3-dimethyl-butylimino]-morpholin-4-yl-methyl}-carbamic acid methyl ester; MS: 437 (M+1)

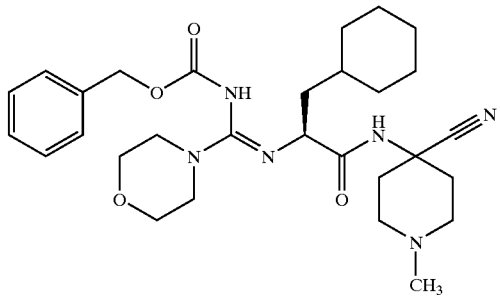

{[1-(4-Cyano-1-methyl-piperidin-4-ylcarbamoyl)-2-cyclohexyl-ethylimino]-morpholin-4-yl-methyl}-carbamic acid benzyl ester; MS: 539 (M+1)

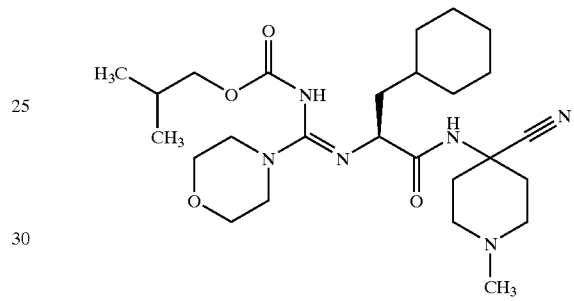

{[1-(4-Cyano-1-methyl-piperidin-4-ylcarbamoyl)-2-cyclohexyl-ethylimino]-morpholin-4-yl-methyl}-carbamic acid isobutyl ester; MS: 505 (M+1)

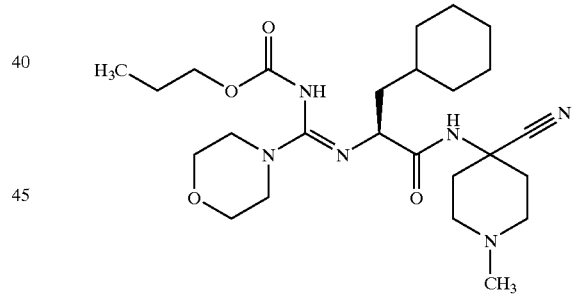

{[1-(4-Cyano-1-methyl-piperidin-4-ylcarbamoyl)-2-cyclohexyl-ethylimino]-morpholin-4-yl-methyl}-carbamic acid propyl ester; MS: 491 (M+1)

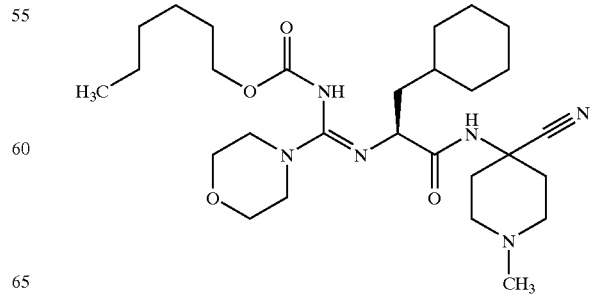

{[1-(4-Cyano-1-methyl-piperidin-4-ylcarbamoyl)-2-cyclohexyl-ethylimino]-morpholin-4-yl-methyl}-carbamic acid hexyl ester; MS: 533 (M+1)

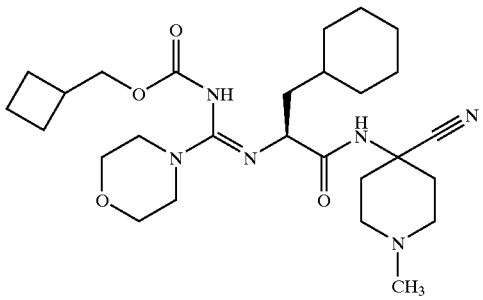

{[1-(4-Cyano-1-methyl-piperidin-4-ylcarbamoyl)-2-cyclohexyl-ethylimino]-morpholin-4-yl-methyl}-carbamic acid cyclobutylmethyl ester; MS: 517 (M+1)

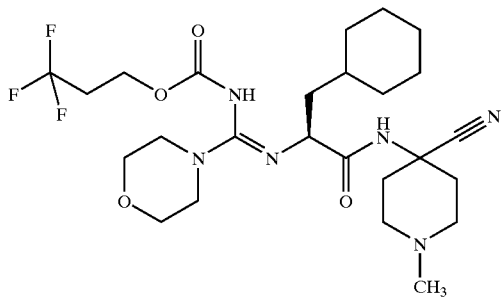

{[1-(4-Cyano-1-methyl-piperidin-4-ylcarbamoyl)-2-cyclohexyl-ethylimino]-morpholin-4-yl-methyl}-carbamic acid 3,3,3-trifluoro-propyl ester; MS: 545 (M+1)

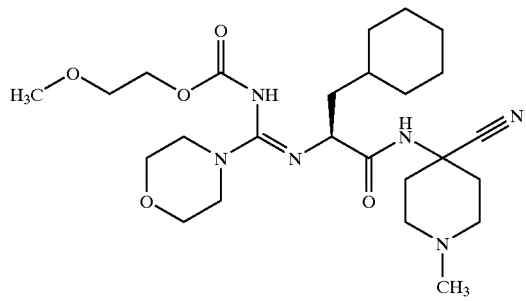

{[1-(4-Cyano-1-methyl-piperidin-4-ylcarbamoyl)-2-cyclohexyl-ethylimino]-morpholin-4-yl-methyl}-carbamic acid 2-methoxy-ethyl ester; MS: 507 (M+1)

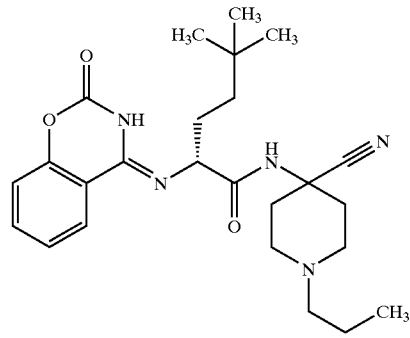

5,5-Dimethyl-2-(2-oxo-2,3-dihydro-benzo[e][1,3]oxazin-4-ylideneamino)-hexanoic acid (4-cyano-1-propyl-piperidin-4-yl)-amide; MS: 454 (M+1)

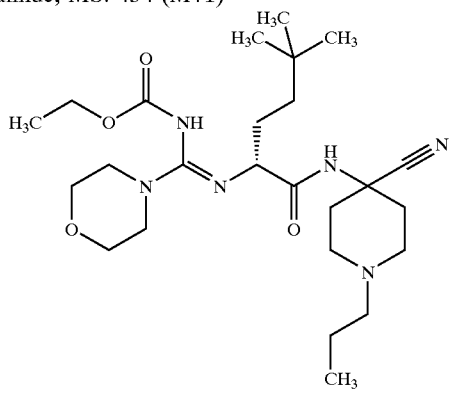

{[1-(4-Cyano-1-propyl-piperidin-4-ylcarbamoyl)-4,4-dimethyl-pentylimino]-morpholin-4-yl-methyl}-carbamic acid ethyl ester; MS: 493 (M+1)

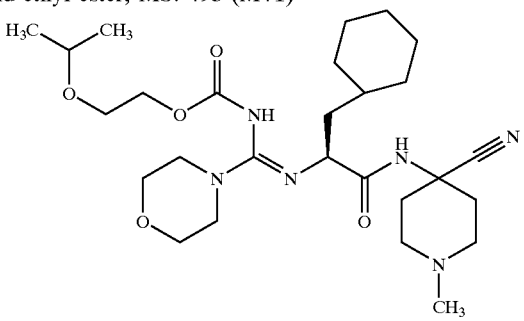

{[1-(4-Cyano-1-methyl-piperidin-4-ylcarbamoyl)-2-cyclohexyl-ethylimino]-morpholin-4-yl-methyl}-carbamic acid 2-isopropoxy-ethyl ester; MS: 534 (M+1)

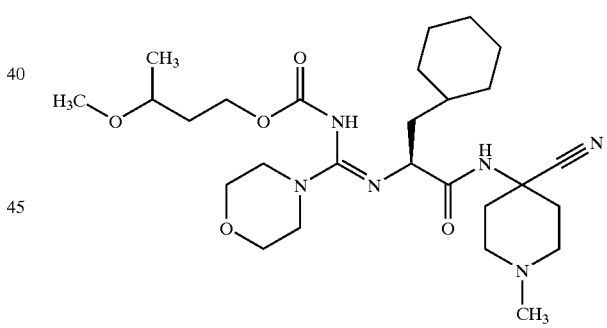

{[1-(4-Cyano-1-methyl-piperidin-4-ylcarbamoyl)-2-cyclohexyl-ethylimino]-morpholin-4-yl-methyl}-carbamic acid 3-methoxy-butyl ester; MS: 534 (M+1)

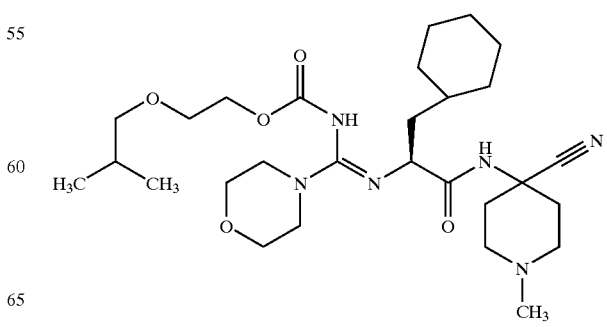

{[1-(4-Cyano-1-methyl-piperidin-4-ylcarbamoyl)-2-cyclohexyl-ethylimino]-morpholin-4-yl-methyl}-carbamic acid 2-isobutoxy-ethyl ester; MS: 549 (M+1)

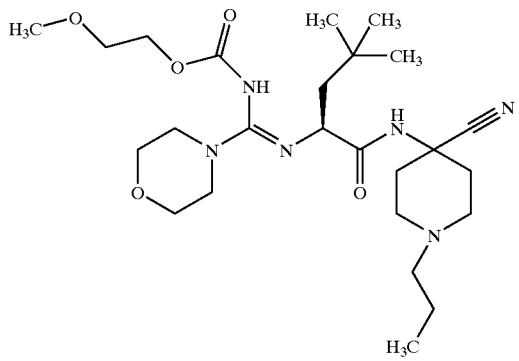

{[1-(4-Cyano-1-propyl-piperidin-4-ylcarbamoyl)-3,3-dimethyl-butylimino]-morpholin-4-yl-methyl}-carbamic acid 2-methoxy-ethyl ester; MS: 509 (M+1)

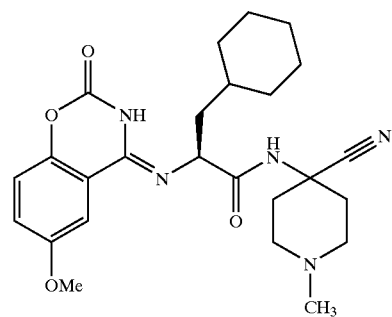

N-(4-Cyano-1-methyl-piperidin-4-yl)-4-cyclohexyl-2-(6-methoxy-2-oxo-2,3-dihydro-benzo[e][1,3]oxazin-4-ylideneamino)-butyramide; MS: 468 (M+1)

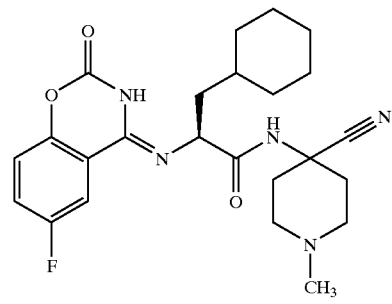

N-(4-Cyano-1-methyl-piperidin-4-yl)-4-cyclohexyl-2-(6-fluoro-2-oxo-2,3-dihydro-benzo[e][1,3]oxazin-4-ylideneamino)-butyramide; MS: 456 (M+1)

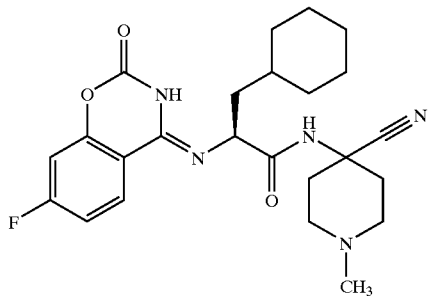

N-(4-Cyano-1-methyl-piperidin-4-yl)-4-cyclohexyl-2-(7-fluoro-2-oxo-2,3-dihydro-benzo[e][1,3]oxazin-4-ylideneamino)-butyramide; MS: 456 (M+1)

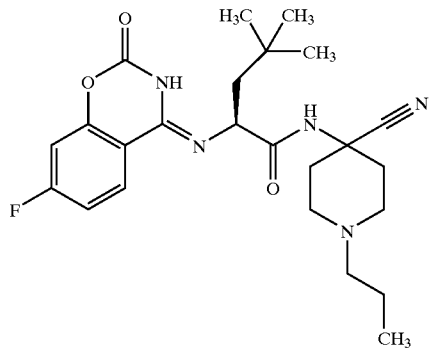

2-(7-Fluoro-2-oxo-2,3-dihydro-benzo[e][1,3]oxazin-4-ylideneamino)-5,5-dimethyl-hexanoic acid(4-cyano-1-propyl-piperidin-4-yl)-amide; MS: 458 (M+1)

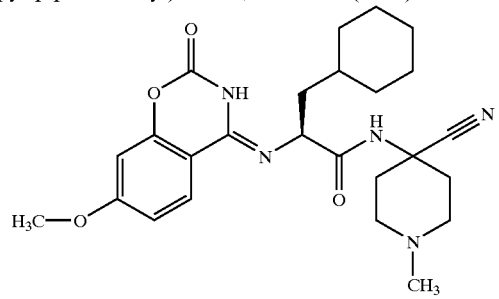

N-(4-Cyano-1-methyl-piperidin-4-yl)-4-cyclohexyl-2-(7-methoxy-2-oxo-2,3-dihydro-benzo[e][1,3]oxazin-4-ylideneamino)-butyramide; MS: 468 (M+1)

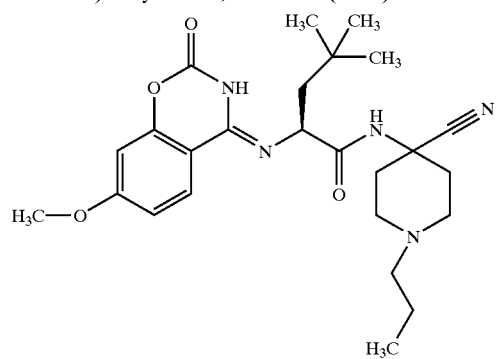

2-(7-Methoxy-2-oxo-2,3-dihydro-benzo[e][1,3]oxazin-4-ylideneamino)-5,5-dimethyl-hexanoic acid(4-cyano-1-propyl-piperidin-4-yl)-amide; MS: 470 (M+1)

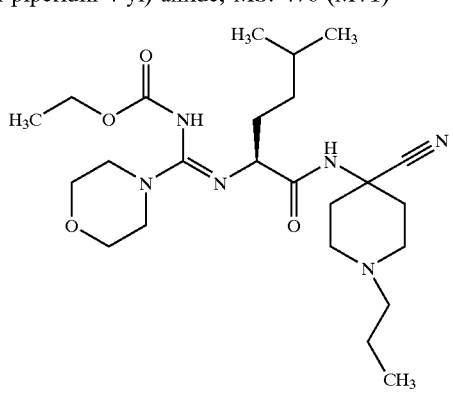

{[1-(4-Cyano-1-propyl-piperidin-4-ylcarbamoyl)-5-methyl-hexylimino]-morpholin-4-yl-methyl}-carbamic acid ethyl ester; MS: 479 (M+1)

{[1,4-Cyano-1-methyl-piperidin-4-ylcarbamoyl)-2-cyclohexyl-ethylimino]-pyrrolidin-1-yl-methyl}-carbamic acid ethyl ester; MS: 461 (M+1).

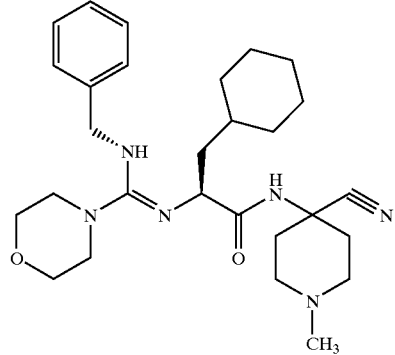

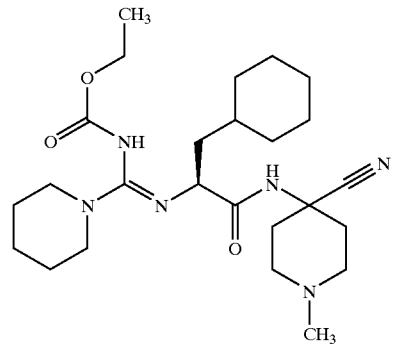

2-[(N-Benzyl-morpholine-4-carboximidoyl)-amino]-N-(4-cyano-1-methyl-piperidin-4-yl)-3-cyclohexyl-propionamide; MS: 495 (M+1).

{[1-(4-Cyano-1-methyl-piperidin-4-ylcarbamoyl)-2-cyclohexyl-ethylimino]-piperidin-1-yl-methyl}-carbamic acid ethyl ester; MS: 475 (M+1).

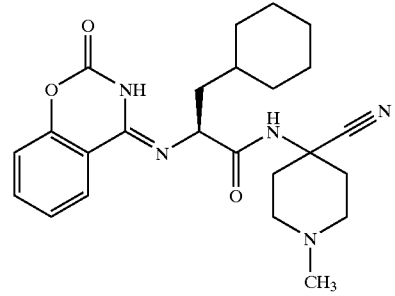

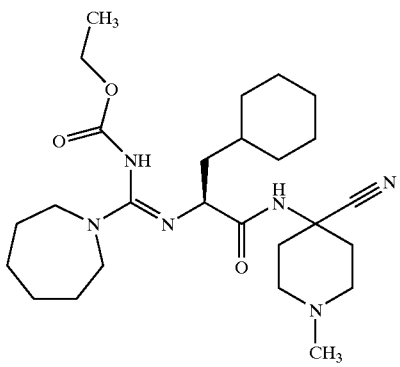

N-(4-Cyano-1-methyl-piperidin-4-yl)-3-cyclohexyl-2-(2-oxo-2,3-dihydro-benzo[e][1,3]oxazin-4-ylideneamino)-propionamide; MS: 438 (M+1).

{Azepan-1-yl-[1-(4-cyano-1-methyl-piperidin-4-ylcarbamoyl)-2-cyclohexyl-ethylimino]-methyl}-carbamic acid ethyl ester; MS: 489 (M+1).

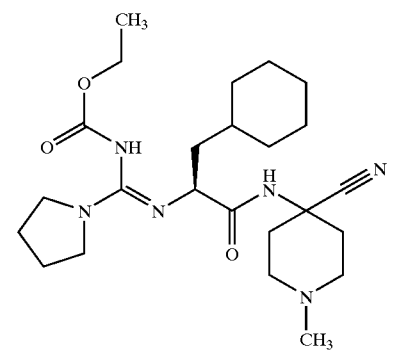

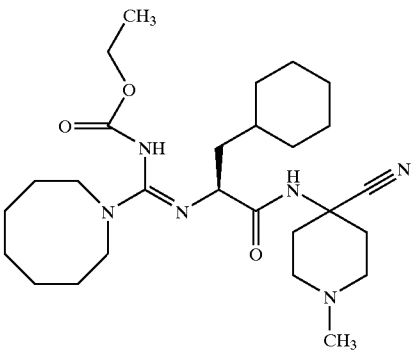

71

{Azocan-1-yl-[1-(4-cyano-1-methyl-piperidin-4-ylcarbamoyl)-2-cyclohexyl-ethylimino]-methyl}-carbamic acid ethyl ester; MS: 503 (M+1).

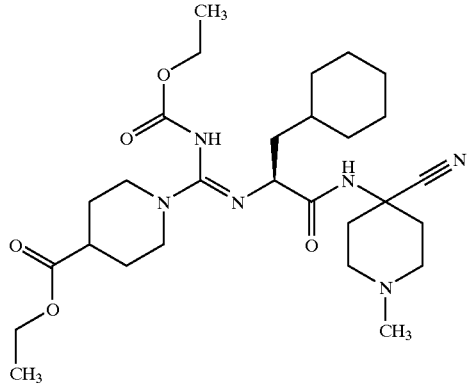

1-{[1-(4-Cyano-1-methyl-piperidin-4-ylcarbamoyl)-2-cyclohexyl-ethylimino]-ethoxycarbonylamino-methyl}-piperidine-4-carboxylic acid ethyl ester; MS: 547 (M+1).

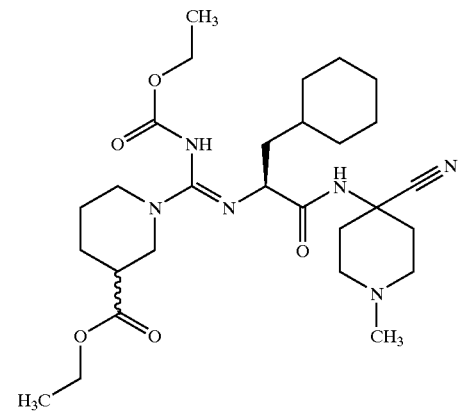

1-{[1-(4-Cyano-1-methyl-piperidin-4-ylcarbamoyl)-2-cyclohexyl-ethylimino]-ethoxycarbonylamino-methyl}-piperidine-3-carboxylic acid ethyl ester; MS: 547 (M+1).

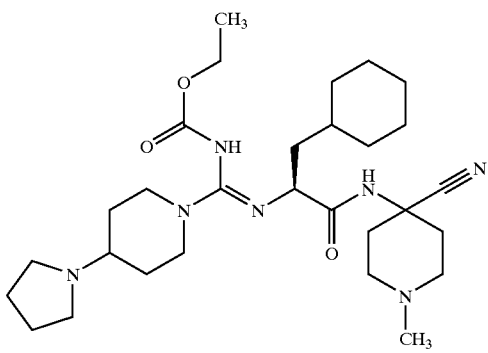

72

[[1-(4-Cyano-1-methyl-piperidin-4-ylcarbamoyl)-2-cyclohexyl-ethylimino]-(4-pyrrolidin-1-yl-piperidin-1-yl)-methyl]-carbamic acid ethyl ester; MS: 544 (M+1).

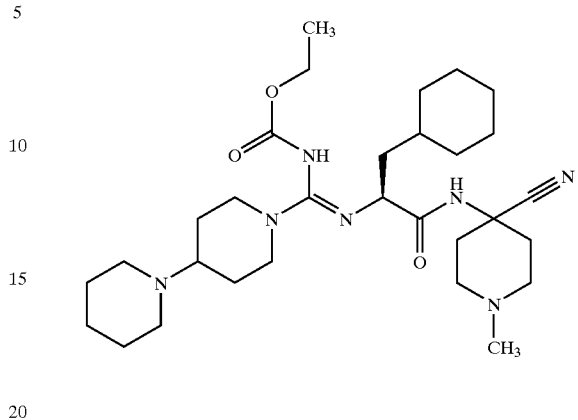

{[1,4']Bipiperidinyl-1'-yl-[1-(4-cyano-1-methyl-piperidin-4-ylcarbamoyl)-2-cyclohexyl-ethylimino]-methyl}-carbamic acid ethyl ester; MS: 558 (M+1).

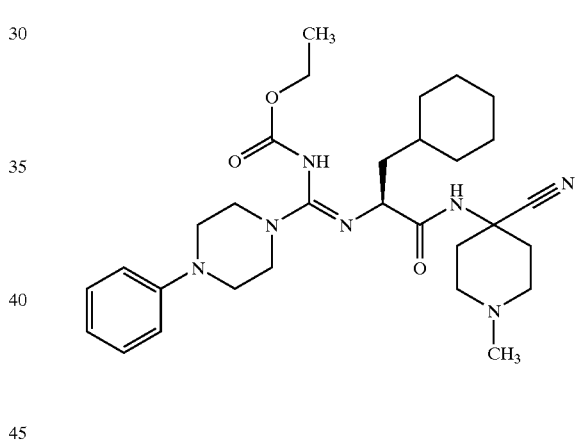

[[1-(4-Cyano-1-methyl-piperidin-4-ylcarbamoyl)-2-cyclohexyl-ethylimino]-(4-phenyl-piperazin-1-yl)-methyl]-carbamic acid ethyl ester; MS: 552 (M+1).

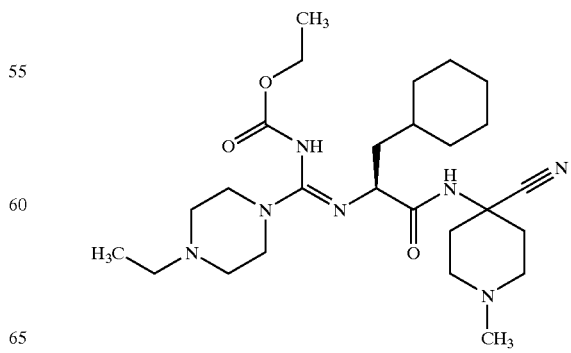

[[1-(4-Cyano-1-methyl-piperidin-4-ylcarbamoyl)-2-cyclohexyl-ethylimino]-(4-ethyl-piperazin-1-yl)-methyl]-carbamic acid ethyl ester; MS: 504 (M+1).

[[1-(4-Cyano-1-methyl-piperidin-4-ylcarbamoyl)-2-cyclohexyl-ethylimino]-(3,3,5-trimethyl-6-aza-bicyclo[3.2.1]oct-6-yl)-methyl]-carbamic acid ethyl ester; MS: 543 (M+1).

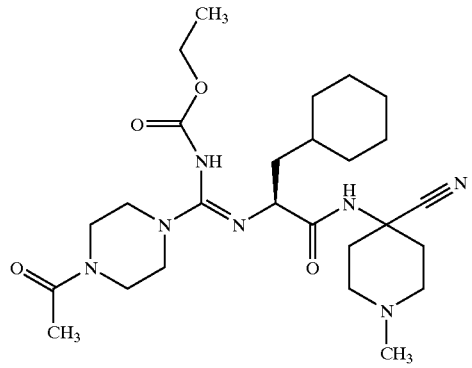

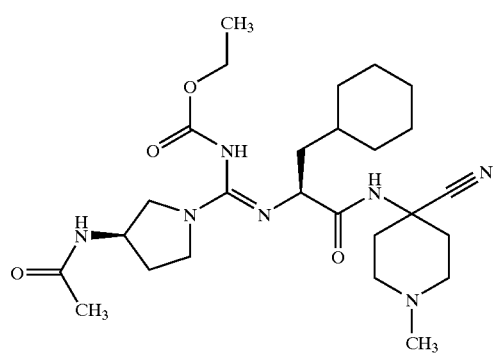

{(4-Acetyl-piperazin-1-yl)-[1-(4-cyano-1-methyl-piperidin-4-ylcarbamoyl)-2-cyclohexyl-ethylimino]-methyl}-carbamic acid ethyl ester; MS: 518 (M+1).

{(3-Acetylamino-pyrrolidin-1-yl)-[1-(4-cyano-1-methyl-piperidin-4-ylcarbamoyl)-2-cyclohexyl-ethylimino]-methyl}-carbamic acid ethyl ester; MS: 518 (M+1).

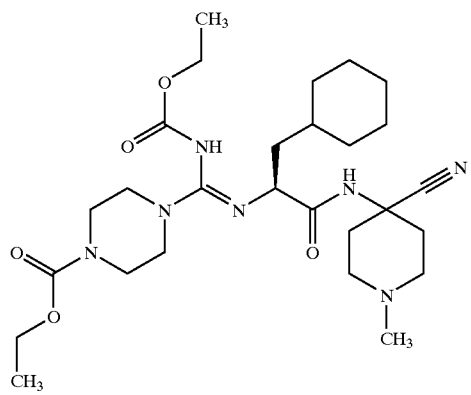

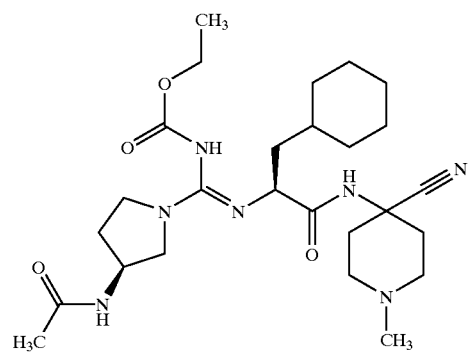

4-{[1-(4-Cyano-1-methyl-piperidin-4-ylcarbamoyl)-2-cyclohexyl-ethylimino]-ethoxycarbonylamino-methyl}-piperazine-1-carboxylic acid ethyl ester; MS: 548 (M+1).

{(3-Acetylamino-pyrrolidin-1-yl)-[1-(4-cyano-1-methyl-piperidin-4-ylcarbamoyl)-2-cyclohexyl-ethylimino]-methyl}-carbamic acid ethyl ester; MS: 518 (M+1).

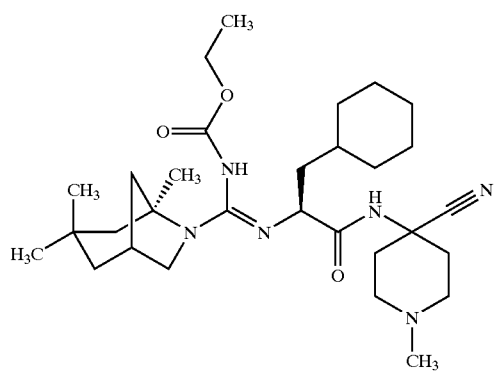

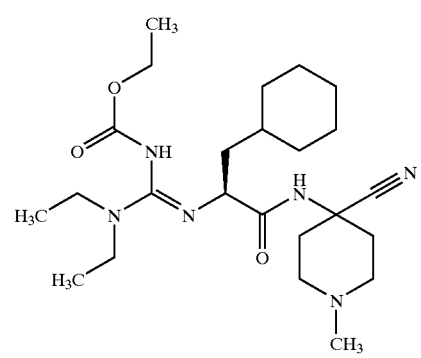

{(3-Azapent-3-yl)-[1-(4-cyano-1-methyl-piperidin-4-ylcarbamoyl)-2-cyclohexyl-ethylimino]-methyl}-carbamic acid ethyl ester; MS: 463 (M+1).

{(1,5-Dimethoxy-3-azapent-3-yl)-[1-(4-cyano-1-methyl-piperidin-4-ylcarbamoyl)-2-cyclohexyl-ethylimino]-methyl}-carbamic acid ethyl ester; MS: 523 (M+1).

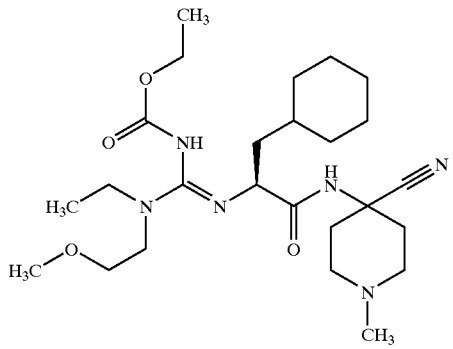

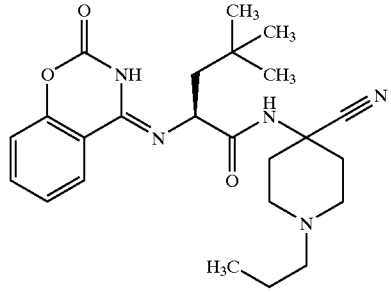

{(1-Methoxy-3-azapent-3-yl)-[1-(4-cyano-1-methyl-piperidin-4-ylcarbamoyl)-2-cyclohexyl-ethylimino]-methyl}-carbamic acid ethyl ester; MS: 493 (M+1).

4,4-Dimethyl-2-(2-oxo-2,3-dihydro-benzo[e][1,3]oxazin-4-ylideneamino)-pentanoic acid (4-cyano-1-propyl-piperidin-4-yl)-amide; MS: 440 (M+1)

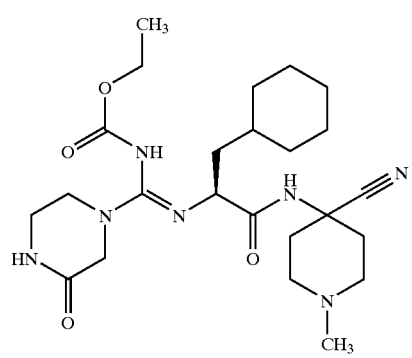

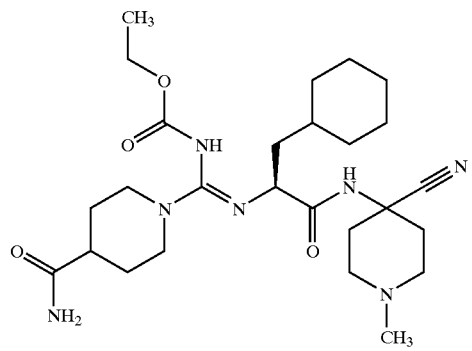

[[1-(4-Cyano-1-methyl-piperidin-4-ylcarbamoyl)-2-cyclohexyl-ethylimino]-(3-oxo-piperazin-1-yl)-methyl]-carbamic acid ethyl ester; MS: 490 (M+1).

{(4-Carbamoyl-piperidin-1-yl)-[1-(4-cyano-1-methyl-piperidin-4-ylcarbamoyl)-2-cyclohexyl-ethylimino]-methyl}-carbamic acid ethyl ester; MS: 518 (M+1)

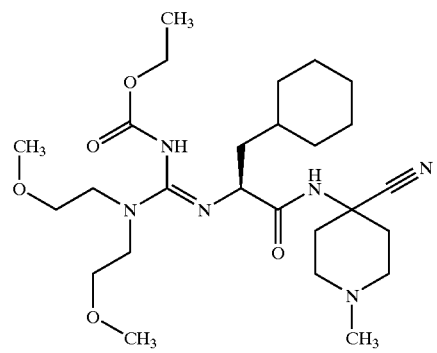

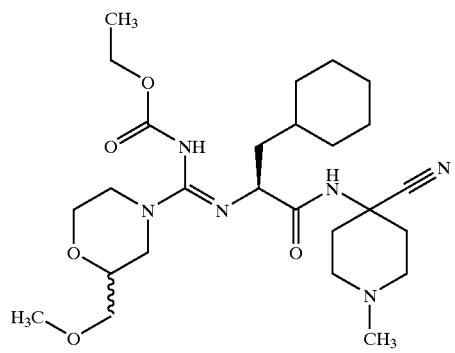

[[1-(4-Cyano-1-methyl-piperidin-4-ylcarbamoyl)-2-cyclohexyl-ethylimino]-(2-methoxymethyl-morpholin-4-yl)-methyl]-carbamic acid ethyl ester; MS: 521 (M+1)

[[1-(4-Cyano-1-methyl-piperidin-4-ylcarbamoyl)-2-cyclohexyl-ethylimino]-(2,6-dimethyl-morpholin-4-yl)-methyl]-carbamic acid ethyl ester; MS: 505 (M+1)

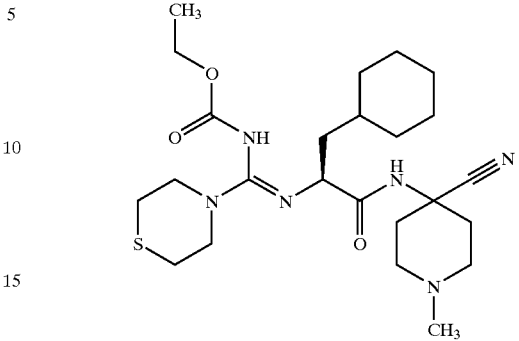

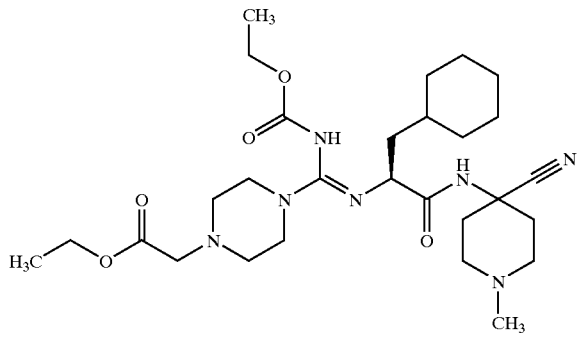

{[1-(4-Cyano-1-methyl-piperidin-4-ylcarbamoyl)-2-cyclohexyl-ethylimino]-thiomorpholin-4-yl-methyl}-carbamic acid ethyl ester; MS: 493 (M+1)

(4-{[1-(4-Cyano-1-methyl-piperidin-4-ylcarbamoyl)-2-cyclohexyl-ethylimino]-ethoxycarbonylamino-methyl}-piperazin-1-yl)-acetic acid ethyl ester; MS: 562 (M+1)

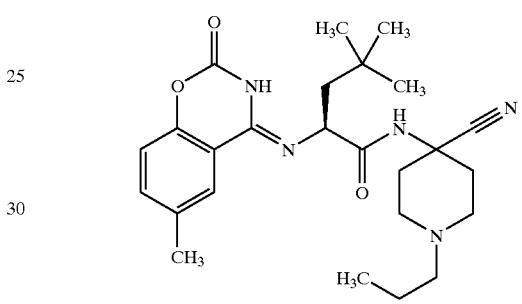

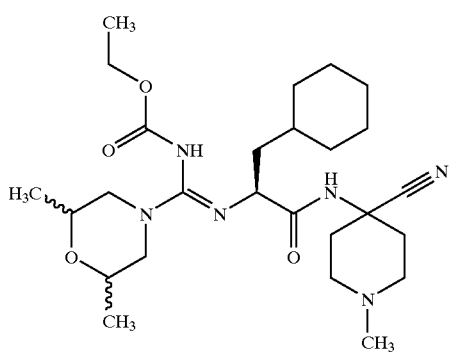

4,4-Dimethyl-2-(6-methyl-2-oxo-2,3-dihydro-benzo[e][1,3]oxazin-4-ylideneamino)-pentanoic acid (4-cyano-1-propyl-piperidin-4-yl)-amide; MS: 454 (M+1)

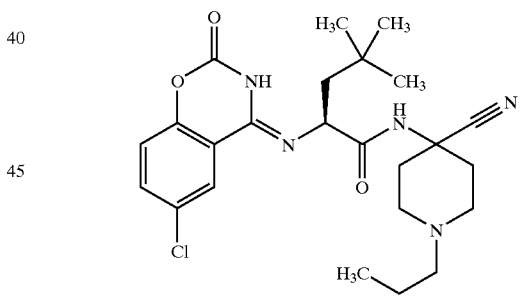

[[1-(4-Cyano-1-methyl-piperidin-4-ylcarbamoyl)-2-cyclohexyl-ethylimino]-(2,6-dimethyl-morpholin-4-yl)-methyl]-carbamic acid ethyl ester; MS: 505 (M+1)

2-(6-Chloro-2-oxo-2,3-dihydro-benzo[e][1,3]oxazin-4-ylideneamino)-4,4-dimethyl-pentanoic acid (4-cyano-1-propyl-piperidin-4-yl)-amide; MS: 475 (M+1)

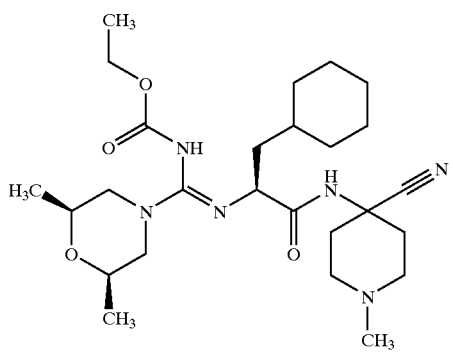

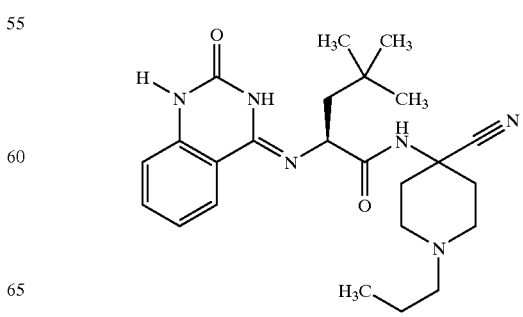

4,4-Dimethyl-2-(2-oxo-2,3-dihydro-1H-quinazolin-4-ylideneamino)-pentanoic acid (4-cyano-1-propyl-piperidin-4-yl)-amide; MS: 439 (M+1)

4,4-Dimethyl-2-(1-methyl-2-oxo-1,2-dihydro-quinazolin-4-ylamino)-pentanoic acid (4-cyano-1-propyl-piperidin-4-yl)-amide; MS: 453 (M+1)

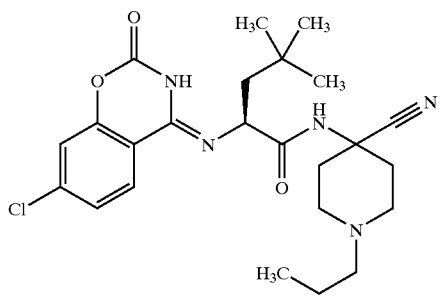

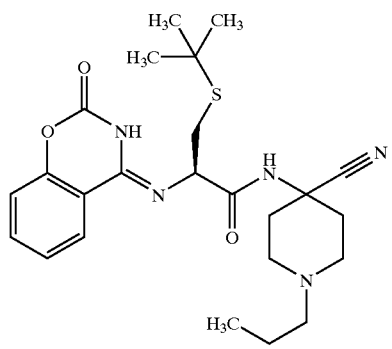

2-(7-Chloro-2-oxo-2,3-dihydro-benzo[e][1,3]oxazin-4-ylideneamino)-4,4-dimethyl-pentanoic acid (4-cyano-1-propyl-piperidin-4-yl)-amide; MS: 475 (M+1)

3-tert-Butylsulfanyl-N-(4-cyano-1-propyl-piperidin-4-yl)-2-(2-oxo-2,3-dihydro-benzo[e][1,3]oxazin-4-ylideneamino)-propionamide; MS: 472 (M+1)

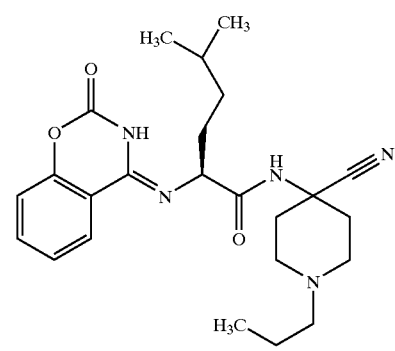

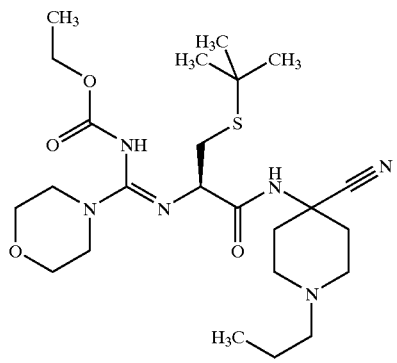

5-Methyl-2-(2-oxo-2,3-dihydro-benzo[e][1,3]oxazin-4-ylideneamino)-hexanoic acid (4-cyano-1-propyl-piperidin-4-yl)-amide; MS: 440 (M+1)

{[2-tert-Butylsulfanyl-1-(4-cyano-1-propyl-piperidin-4-ylcarbamoyl)-ethylimino]-morpholin-4-yl-methyl}-carbamic acid ethyl ester; MS: 511 (M+1)

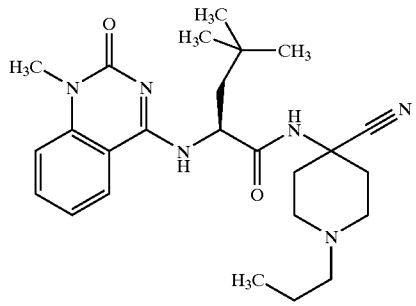

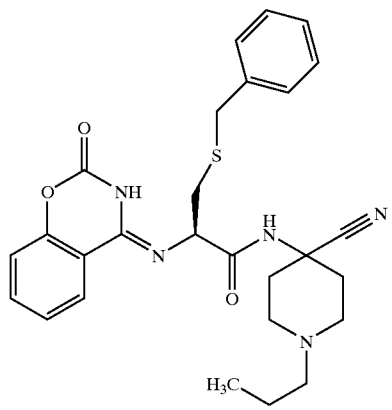

81

3-Benzylsulfanyl-N-(4-cyano-1-propyl-piperidin-4-yl)-2-(2-oxo-2,3-dihydro-benzo[e][1,3]oxazin-4-ylideneamino)-propionamide; MS: 506 (M+1)

82

N-(4-Cyano-1-propyl-piperidin-4-yl)-3-cycloheptyl-2-(2-oxo-2,3-dihydro-benzo[e][1,3]oxazin-4-ylideneamino)-propionamide; MS: 480 (M+1)

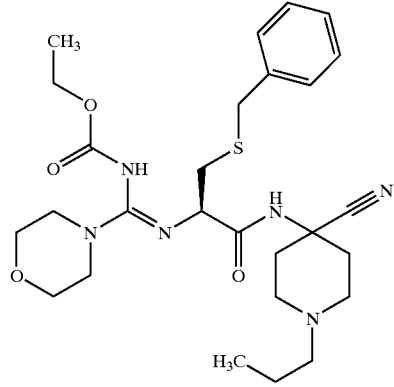

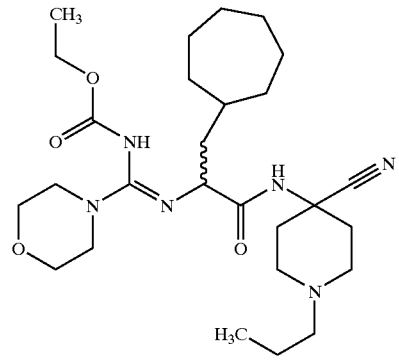

{[2-Benzylsulfanyl-1-(4-cyano-1-propyl-piperidin-4-ylcarbamoyl)-ethylimino]-morpholin-4-yl-methyl}-carbamic acid ethyl ester; MS: 545 (M+1)

{[1-(4-Cyano-1-propyl-piperidin-4-ylcarbamoyl)-2-cycloheptyl-ethylimino]-morpholin-4-yl-methyl}-carbamic acid ethyl ester; MS: 519 (M+1)

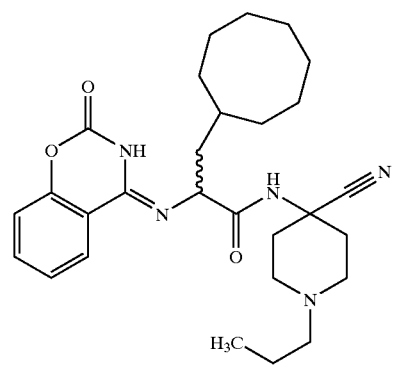

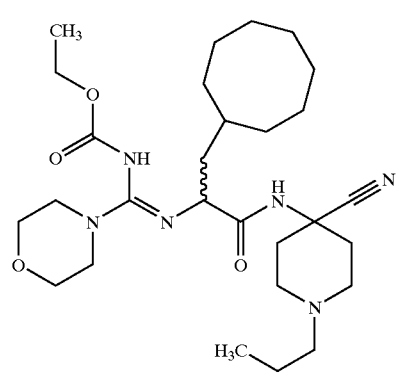

N-(4-Cyano-1-propyl-piperidin-4-yl)-3-cyclooctyl-2-(2-oxo-2,3-dihydro-benzo[e][1,3]oxazin-4-ylideneamino)-propionamide; MS: 494 (M+1)

{[1-(4-Cyano-1-propyl-piperidin-4-ylcarbamoyl)-2-cyclooctyl-ethylimino]-morpholin-4-yl-methyl}-carbamic acid ethyl ester; MS: 533 (M+1)

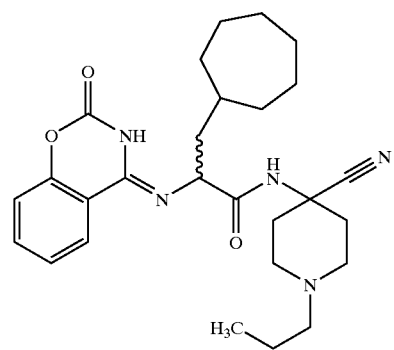

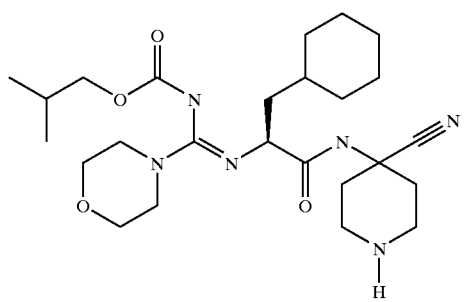

83
{[1-(4-Cyano-piperdin-4-ylcarbamoyl)-2-cyclohexyl-ethylamino]-morpholin-4-yl-methylene}-carbamic acid isobutyl ester; MS: 491 (M+1)

84
[(1-{4-Cyano-1-[2-(2-methoxyl-ethoxy)-ethyl]-piperidin-4-ylcarbamoyl}-2-cyclohexyl-ethylamino)-morpholin-4-yl-methylene]-carbamic acid isobutyl ester; MS: 593 (M+1)

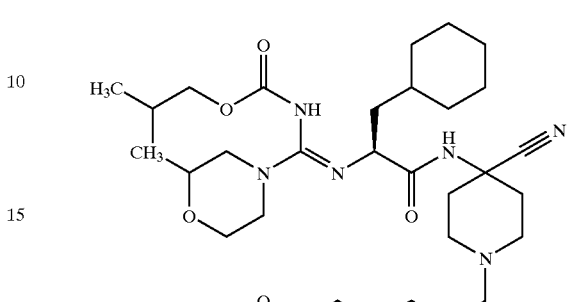

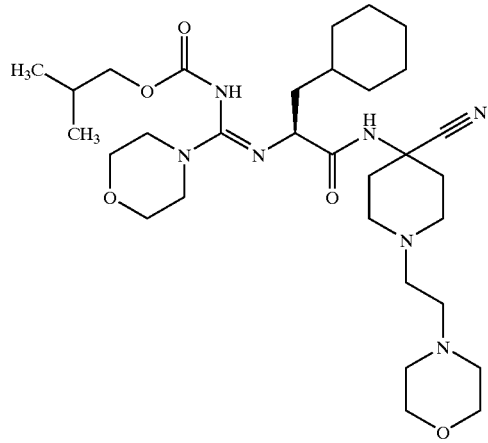

[(1-{4-Cyano-1-[3-(2-methoxyl-ethoxy)-propyl]-piperidin-4-ylcarbamoyl}-2-cyclohexyl-ethylamino)-morpholin-4-yl-methylene]-carbamic acid isobutyl ester; MS: 607 (M+1)

({1-[4-Cyano-1-(2-morpholin-4-yl-ethyl)-piperidin-4-ylcarbamoyl]-2-cyclohexyl-ethylamino}-morpholin-4-yl-methylene)-carbamic acid isobutyl ester; MS: 604 (M+1)

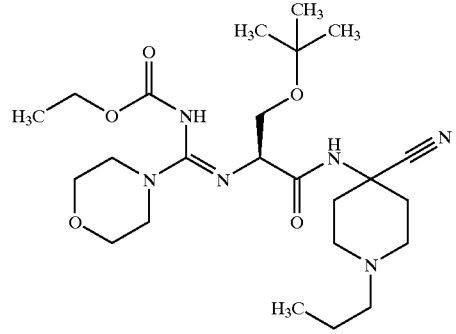

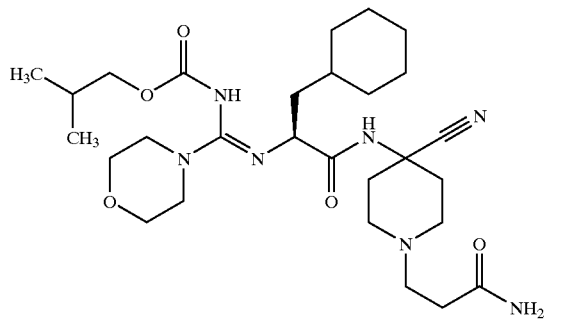

({1-[1-2-Carbamoyl-ethyl)-4-cyano-piperidin-4-ylcarbamoyl]-2-cyclohexyl-ethylamino}-morpholin-4-yl-methylene)-carbamic acid isobutyl ester; MS: 562 (M+1)

{[2-tert-Butoxy-1-(4-cyano-1-propyl-piperidin-4-ylcarbamoly)-ethylamino]-morpholin-4-yl-methylene}-carbamic acid ethyl ester; MS: 495 (M+1)

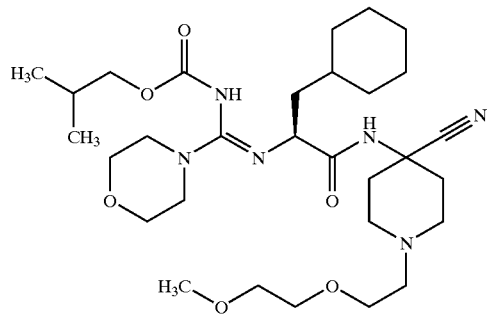

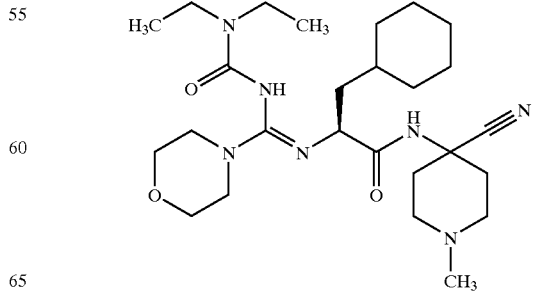

85

N-(4-Cyano-1-methyl-piperidin-4-yl)-3-cyclohexyl-2-{[diethyl-carbamoylimino)-morpholin-4-yl-methyl]-amino}-propionamide; MS: 504 (M+1)

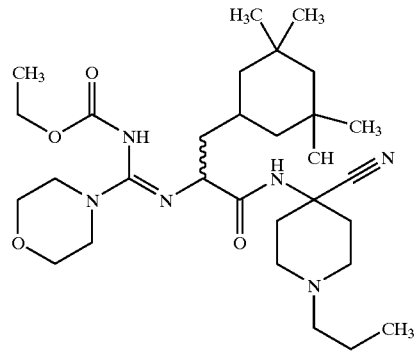

{[1-(4-Cyano-1-propyl-piperidin-4-ylcarbamoyl)-2-(3,3,5,5-tetramethyl-cyclohexyl)-ethylamino]-morpholin-4-yl-methylene}-carbamic acid ethyl ester; MS: 561 (M+1)

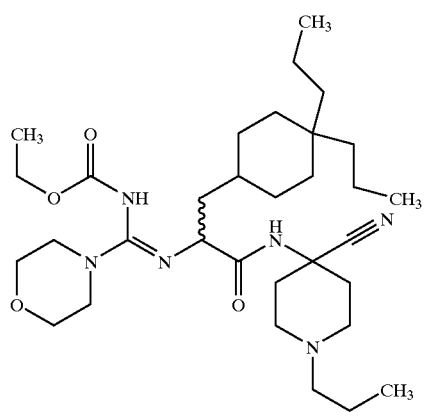

{[1-(4-Cyano-1-propyl-piperidin-4-ylcarbamoyl)-2-(4,4-dipropyl-cyclohexyl)-ethylamino]-morpholin-4-yl-methylene}-carbamic acid ethyl ester; MS: 589 (M+1)

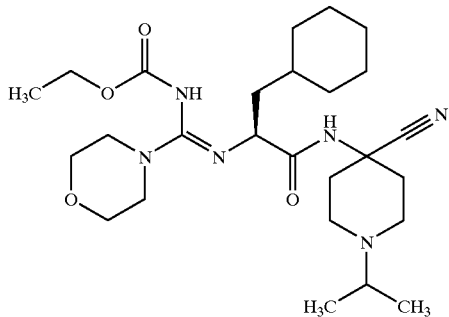

86

{[1-(4-Cyano-1-isopropyl-piperidin-4-ylcarbamoyl)-2-cyclohexyl-ethylamino]-morpholin-4-yl-methylene}-carbamic acid ethyl ester; MS: 505 (M+1)

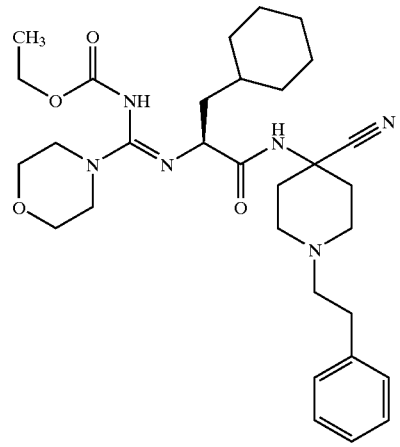

{[1-(4-Cyano-1-phenethyl-piperidin-4-ylcarbamoyl)-2-cyclohexyl-ethylamino]-morpholin-4-yl-methylene}-carbamic acid ethyl ester; MS: 567 (M+1)

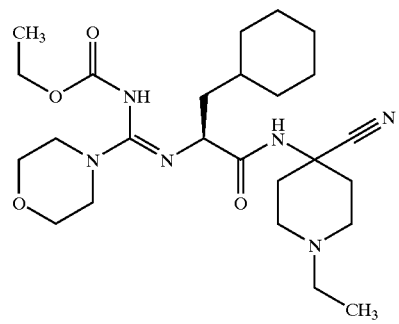

{[1-(4-Cyano-1-ethyl-piperidin-4-ylcarbamoyl)-2-cyclohexyl-ethylamino]-morpholin-4-yl-methylene}-carbamic acid ethyl ester; MS: 491 (M+1)

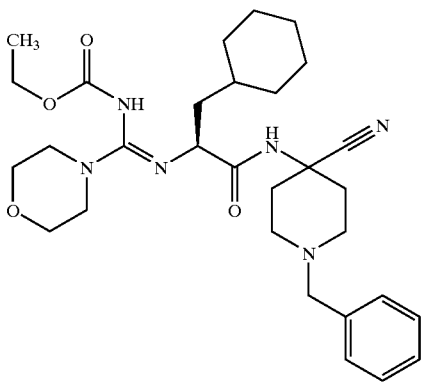

{[1-(1-Benzyl-4-cyano-piperidin-4-ylcarbamoyl)-2-cyclohexyl-ethylamino]-morpholin-4-yl-methylene}-carbamic acid ethyl ester; MS: 553 (M+1)

{[1-(4-cyano-1-phenethyl-piperidin-4-ylcarbamoyl)-3,3-dimethyl-butylamino]-morpholin-4-yl-methylene}-carbamic acid ethyl ester; MS: 541 (M+1)

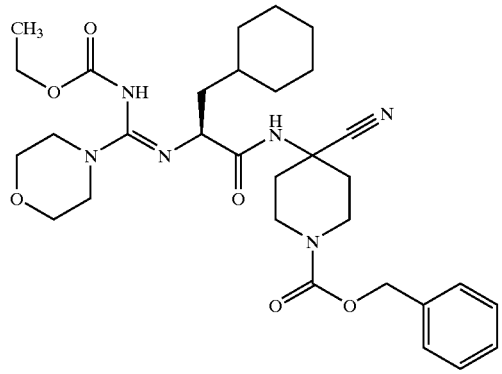

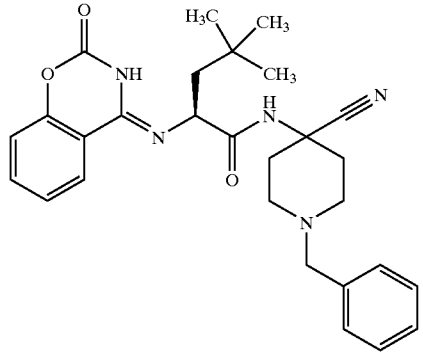

4-Cyano-4-{3-cyclohexyl-2-[(ethoxycarbonylimino-morpholin-4-yl-methyl)-amino]-propionylamino}-piperidine-1-carboxylic acid benzyl ester; MS: 597 (M+1)

4,4-Dimethyl-2-(2-oxo-2H-benzo[e][1,3]oxazin-4-ylamino)-pentanoic acid (1-benzyl-4-cyano-piperidin-4-yl)-amide; MS: 488 (M+1)

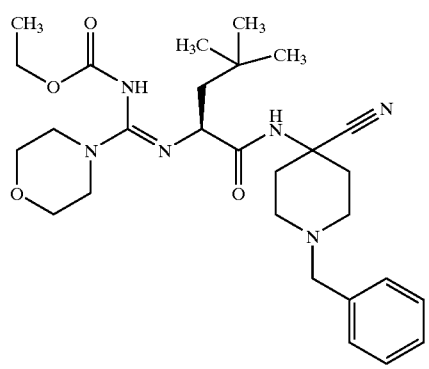

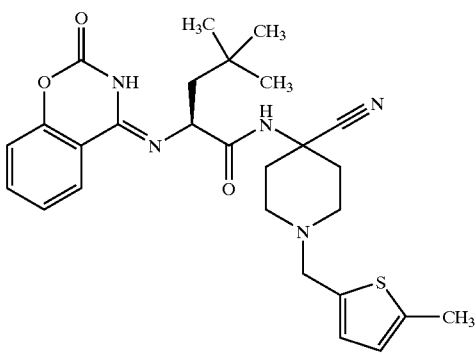

{[-(1-Benzyl-4-cyano-piperidin-4-ylcarbamoyl)-3,3-dimethyl-butylamino]-morpholin-4-yl-methylene}-carbamic acid ethyl ester; MS: 527 (M+1)

4,4-Dimethyl-2-(2-oxo-2H-benzo[e][1,3]oxazin-4-ylamino)-pentanoic acid [4-cyano-1-(5-methyl-thiophen-2-ylmethyl)-piperidin-4-yl]-amide; MS: 508 (M+1)

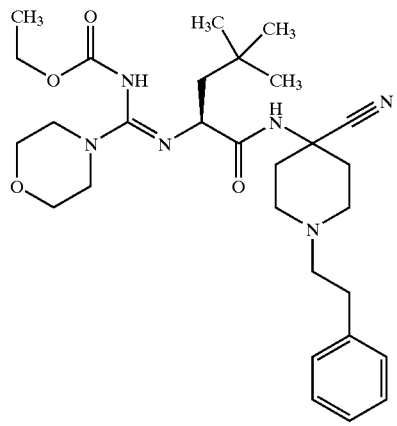

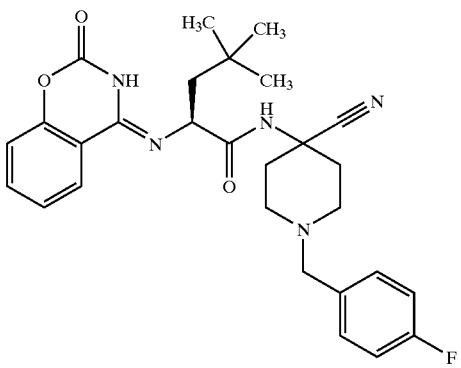

4,4-Dimethyl-2-(2-oxo-2H-benzo[e][1,3]oxazin-4-ylamino)-pentanoic acid [4-cyano-1-(4-fluoro-benzyl)-piperidin-4-yl]-amide; MS: 506 (M+1)

4,4-Dimethyl-2-(2-oxo-2H-benzo[e][1,3]oxazin-4-ylamino)-pentanoic acid (4-cyano-piperidin-4-yl)-amide; MS: 398 (M+1)

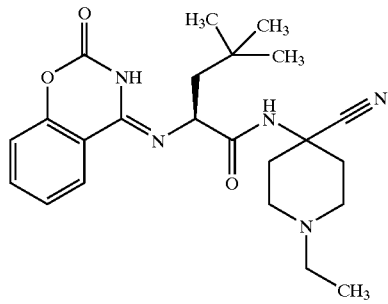

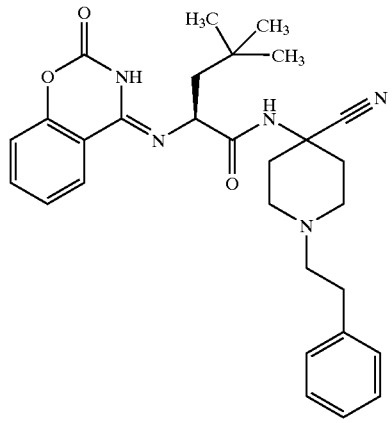

4,4-Dimethyl-2-(2-oxo-2H-benzo[e][1,3]oxazin-4-ylamino)-pentanoic acid (4-cyano-1-ethyl-piperidin-4-yl)-amide; MS: 426 (M+1)

4,4-Dimethyl-2-(2-oxo-2H-benzo[e][1,3]oxazin-4-ylamino)-pentanoic acid (4-cyano-1-phenethyl-piperidin-4-yl)-amide; MS: 502 (M+1)

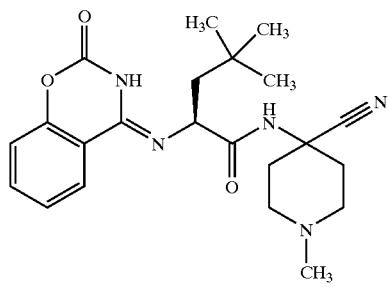

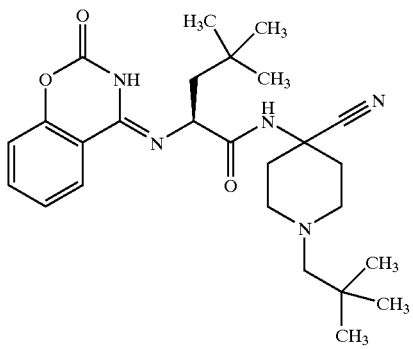

4,4-Dimethyl-2-(2-oxo-2H-benzo[e][1,3]oxazin-4-ylamino)-pentanoic acid (4-cyano-1-methyl-piperidin-4-yl)-amide; MS: 412 (M+1)

4,4-Dimethyl-2-(2-oxo-2H-benzo[e][1,3]oxazin-4-ylamino)-pentanoic acid [4-cyano-1-(2,2-dimethyl-propyl)-piperidin-4-yl]-amide; MS: 468 (M+1)

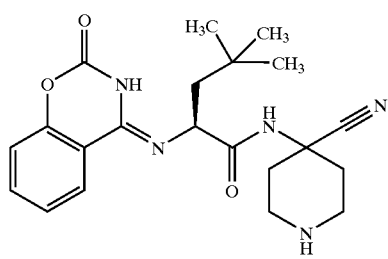

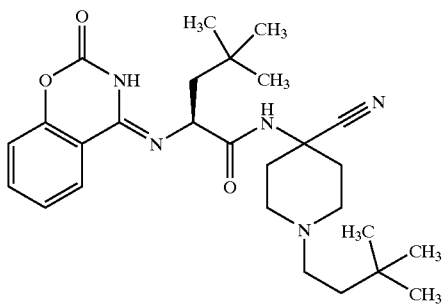

91

4,4-Dimethyl-2-(2-oxo-2H-benzo[e][1,3]oxazin-4-ylamino)-pentanoic acid [4-cyano-1-(3,3-dimethyl-butyl)-piperidin-4-yl]-amide; MS: 482 (M+1)

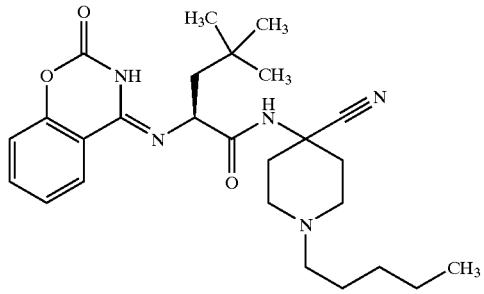

4,4-Dimethyl-2-(2-oxo-2H-benzo[e][1,3]oxazin-4-ylamino)-pentanoic acid (4-cyano-1-pentyl-piperidin-4-yl)-amide; MS: 468 (M+1)

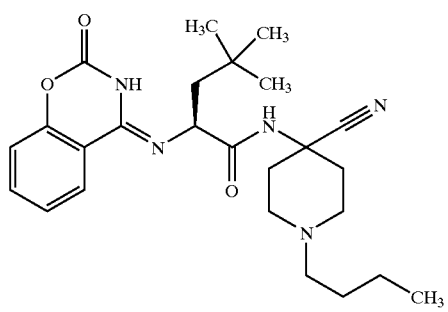

4,4-Dimethyl-2-(2-oxo-2H-benzo[e][1,3]oxazin-4-ylamino)-pentanoic acid (1-butyl-4-cyano-piperidin-4-yl)-amide; MS: 454(M+1)

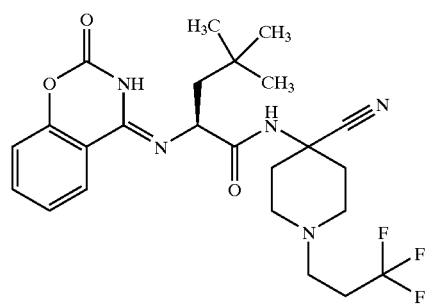

92

4,4-Dimethyl-2-(2-oxo-2H-benzo[e][1,3]oxazin-4-ylamino)-pentanoic acid [4-cyano-1-(3,3,3-trifluoro-propyl)-piperidin-4-yl]-amide; MS: 494 (M+1)

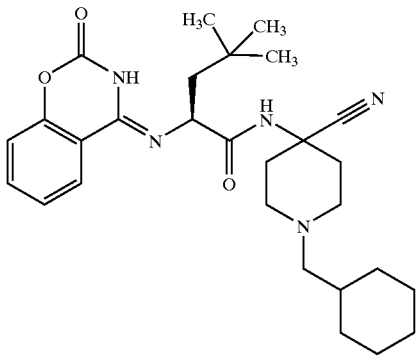

4,4-Dimethyl-2-(2-oxo-2H-benzo[e][1,3]oxazin-4-ylamino)-pentanoic acid (4-cyano-1-cyclohexylmethyl-piperidin-4-yl)-amide; MS: 494 (M+1)

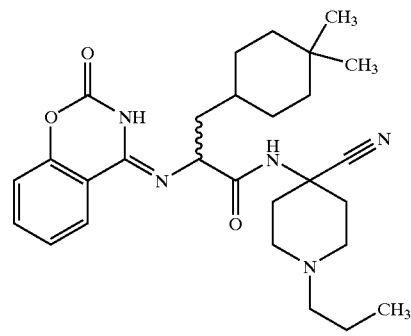

N-(4-Cyano-1-propyl-piperidin-4-yl)-3-(4,4-dimethyl-cyclohexyl)-2-(2-oxo-2H-benzo[e][1,3]oxazin-4-ylamino)-propionamide; MS: 494 (M+1)

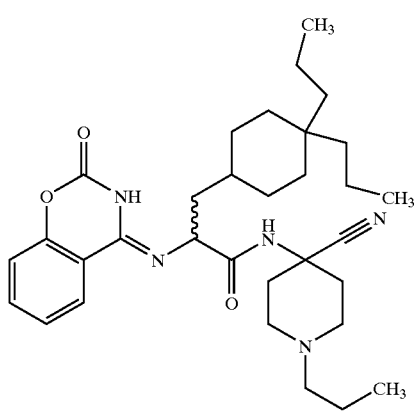

93

N-(4-Cyano-1-propyl-piperidin-4-yl)-3-(4,4-dipropyl-cyclohexyl)-2-(2-oxo-2H-benzo[e][1,3]oxazin-4-ylamino)-propionamide; MS: 550 (M+1)

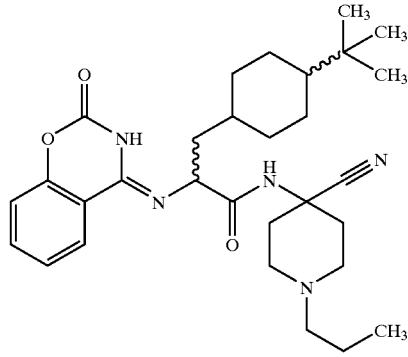

N-(4-Cyano-1-propyl-piperidin-4-yl)-3-(4-tert-butyl-cyclohexyl)-2-(2-oxo-2H-benzo[e][1,3]oxazin-4-ylamino)-propionamide; MS: 522 (M+1)

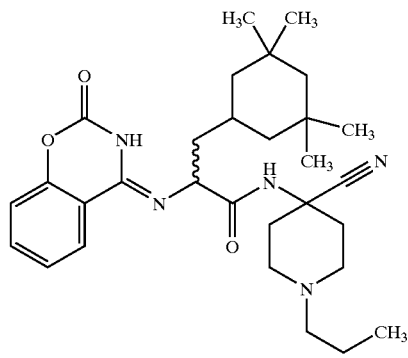

N-(4-Cyano-1-propyl-piperidin-4-yl)-3-(3,3,5,5-tetramethyl-cyclohexyl)-2-(2-oxo-2H-benzo[e][1,3]oxazin-4-ylamino)-propionamide; MS: 522 (M+1)

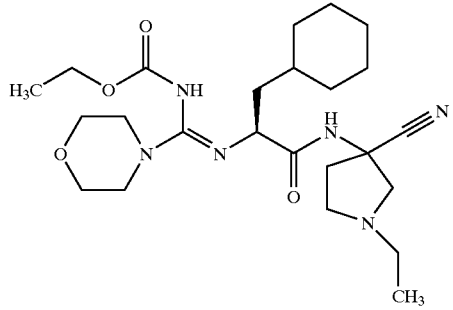

94

{[1-(3-Cyano-1-ethyl-pyrrolidin-3-ylcarbamoyl)-2-cyclohexyl-ethylamino]-morpholin-4-yl-methylene}-carbamic acid ethyl ester. MS: 477 (M+1)

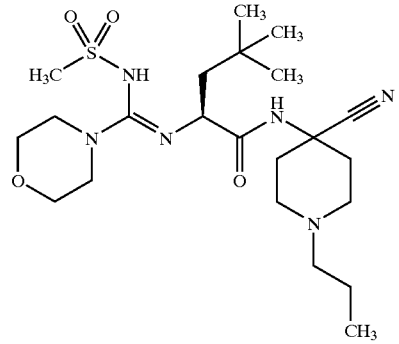

2-[(Methanesulfonylimino-morpholin-4-yl-methyl)-amino]-4,4-dimethyl-pentanoic acid (4-cyano-1-propyl-piperidin-4-yl)-amide. MS: 485 (M+1)

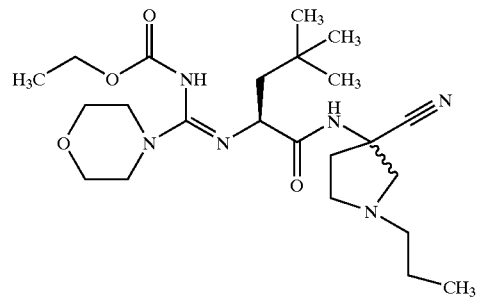

{[1-(3-Cyano-1-propyl-pyrrolidin-3-ylcarbamoyl)-3,3-dimethyl-butylamino]-morpholin-4-yl-methylene}-carbamic acid ethyl ester. MS: 465 (M+1)

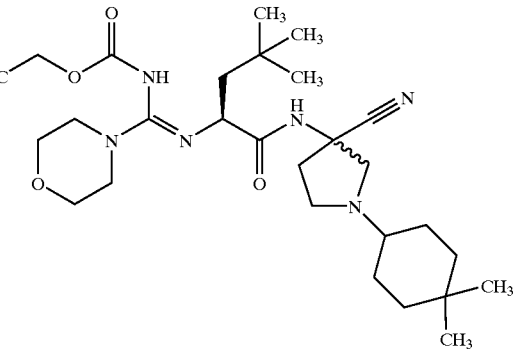

({1-[3-Cyano-1-(4,4-dimethyl-cyclohexyl)-pyrrolidin-3-ylcarbamoyl]-3,3-dimethyl-butylamino}-morpholin-4-yl-methylene)-carbamic acid ethyl ester. MS: 533 (M+1)

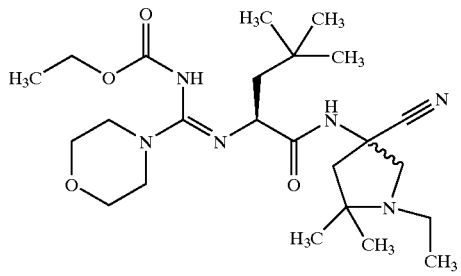

{[1-(3-Cyano-1-ethyl-5,5-dimethyl-pyrrolidin-3-ylcarbamoyl)-3,3-dimethyl-butylamino]-morpholin-4-yl-methylene}-carbamic acid ethyl ester. MS: 479 (M+1)

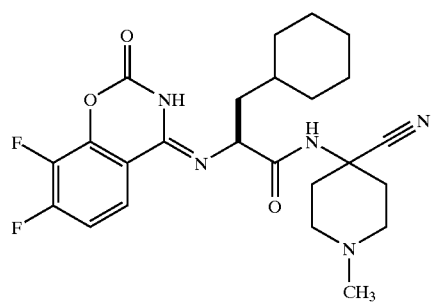

N-(4-Cyano-1-methyl-piperidin-4-yl)-3-cyclohexyl-2-(7,8-difluoro-2-oxo-2H-benzo[e][1,3]oxazin-4-ylamino)-propionamide; MS: 474 (M+1)

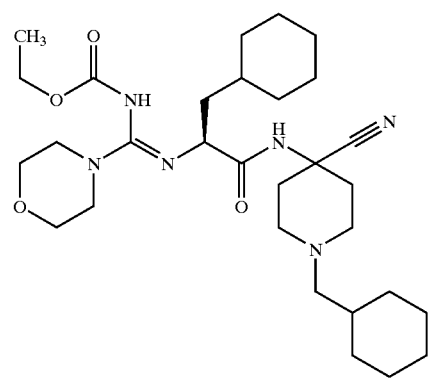

{[1-(4-Cyano-1-cyclohexylmethyl-piperidin-4-ylcarbamoyl)-2-cyclohexyl-ethylamino]-morpholin-4-yl-methylene}-carbamic acid ethyl ester; MS: 559 (M+1)

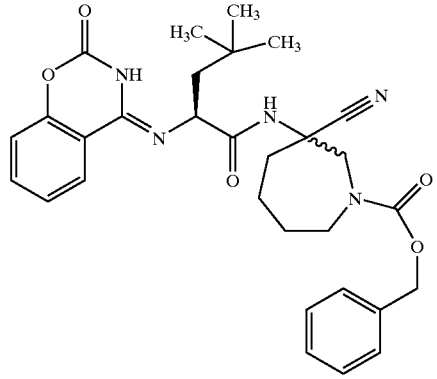

3-Cyano-3-[4,4-dimethyl-2-(2-oxo-2H-benzo[e][1,3]oxazin-4-ylamino)-pentanoylamino]-azepane-1-carboxylic acid benzyl ester; MS: 546 (M+1)

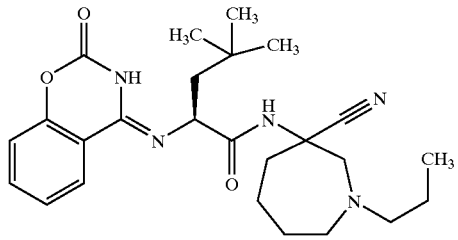

4,4-Dimethyl-2-(2-oxo-2H-benzo[e][1,3]oxazin-4-ylamino)-pentanoic acid (3-cyano-1-propyl-azepan-3-yl)-amide; MS: 454 (M+1)

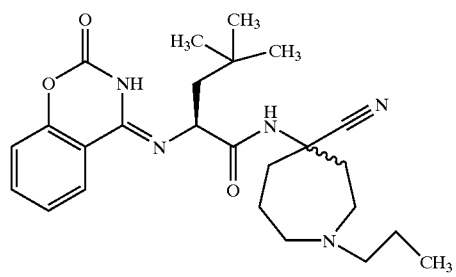

4,4-Dimethyl-2-(2-oxo-2H-benzo[e][1,3]oxazin-4-ylamino)-pentanoic acid (4-cyano-1-propyl-azepan-4-yl)-amide; MS: 454 (M+1)

{[1-(4-Cyano-1-propyl-piperidin-4-ylcarbamoyl)-3,3-dimethyl-butylamino]-phenyl-methylene}-carbamic acid ethyl ester; MS: 470 (M+1)

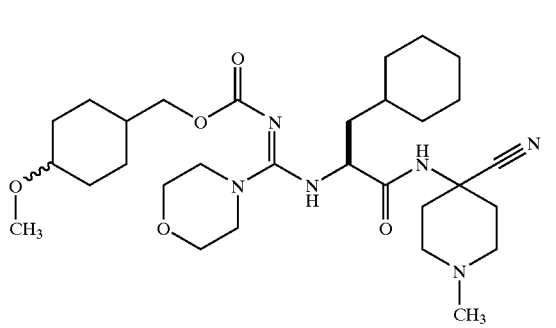

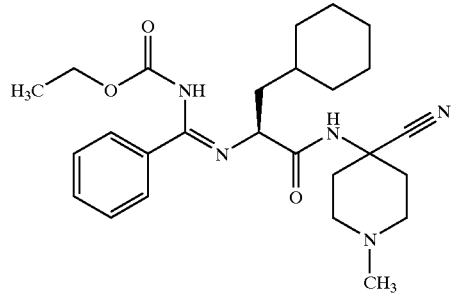

{[1-(4-Cyano-1-methyl-piperidin-4-ylcarbamoyl)-2-cyclohexyl-ethylamino]-phenyl-methylene}-carbamic acid ethyl ester; MS: 468 (M+1)

{[1-(4-Cyano-1-methyl-piperdin-4-ylcarbamoyl)-2-cyclohexyl-ethylamino]-morpholin-4-yl-methylene}-carbamic acid 4-methoxy-cyclohexylmethyl ester; MS: 575 (M+1)

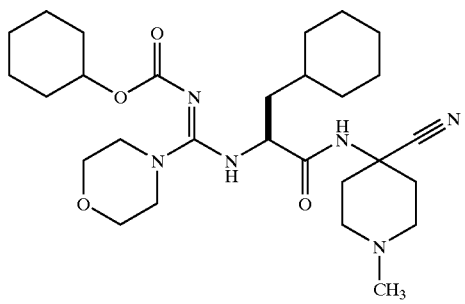

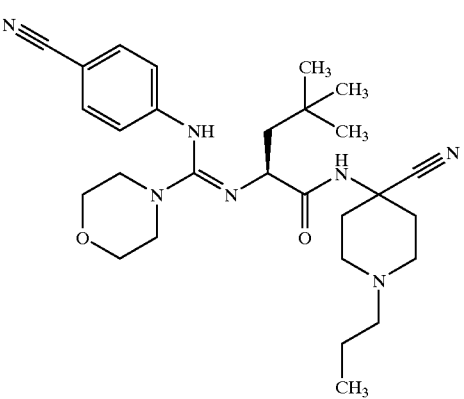

{[1-(4-Cyano-1-methyl-piperidin-4-ylcarbamoyl)-2-cyclohexyl-ethylamino]-morpholin-4-yl-methylene}-carbamic acid cyclohexyl ester; MS: 531 (M+1)

2-{[N-(4-Cyano-phenyl)-morpholine-4-carboximidoyl]-amino}-4,4-dimethyl-pentanoic acid (4-cyano-1-propyl-piperidin-4-yl)-amide; MS: 508 (M+1)

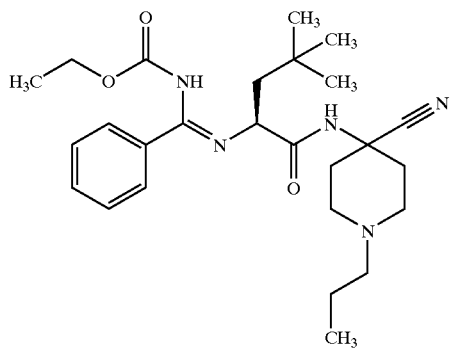

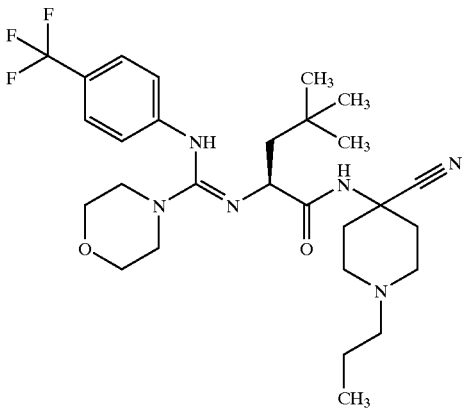

4,4-Dimethyl-2-{[N-(4-trifluoromethyl-phenyl)-morpholine-4-carboximidoyl]-amino}-pentanoic acid (4-cyano-1-propyl-piperidin-4-yl)-amide; MS: 551 (M+1)

{[1-(4-cyano-1-methyl-piperidin-4-ylcarbamoyl)-2-cyclohexyl-ethylamino]-morpholin-4-yl-methylene}-carbamic acid cyclohexylmethyl ester; MS: 545 (M+1)

The following are preferred compounds of the Formulas (Ia) and (Ib):

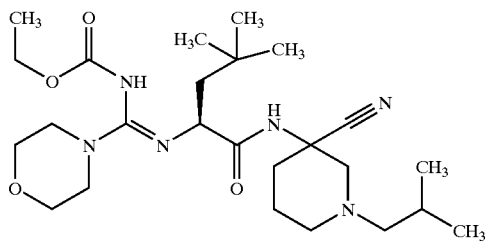

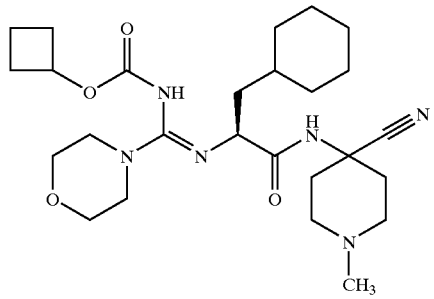

{[1-(3-cyano-1-isobutyl-piperdin-3-yl carbamoyl)-3,3-dimethyl-butylamino]-morpholin-4-yl-methylene}-carbamic acid ethyl ester; MS: 493 (M+1)

{[-1-(4-cyano-1-methyl-piperidin-4-ylcarbamoyl)-2-cyclohexyl-ethylamino]-morpholin-4-yl-methylene}-carbamic acid cyclobutyl ester; MS: 503 (M+1)

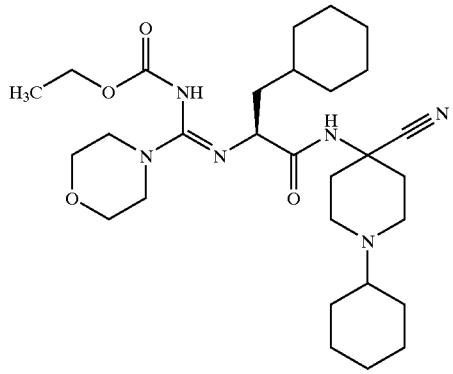

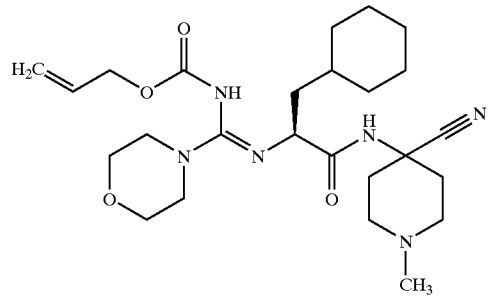

{[1-(4-cyano-1-methyl-piperidin-4-ylcarbamoyl)-2-cyclohexyl-ethylamino]-morpholin-4-yl-methylene}-carbamic acid allyl ester; MS: 489 (M+1)

{[1-(4-cyano-1-cyclohexyl-piperidin-4-ylcarbamoyl)-2-cyclohexyl-ethylamino]-morpholin-4-yl-methylene}-carbamic acid ethyl ester; MS: 545 (M+1)

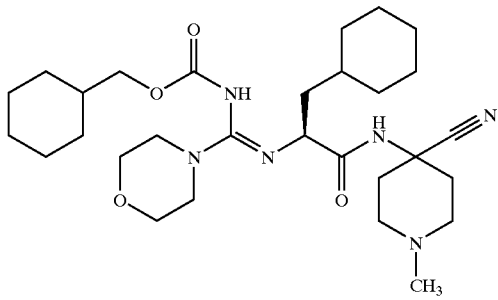

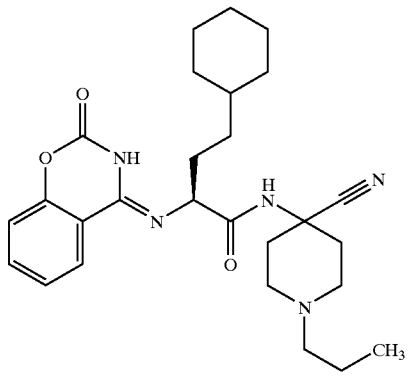

101

N-(4-Cyano-1-propyl-piperidin-4-yl)-4-cyclohexyl-2-(2-oxo-2,3-dihydro-benzo[e][1,3]oxazin-4-ylideneamino)-butyramide; MS: 480 (M+1)

102

N-(4-Cyano-1-methyl-piperidin-4-yl)-3-cyclohexyl-2-(5,6-difluoro-3-oxo-2,3-dihydro-isoindol-1-ylideneamino)-propionamide; MS: 458 (M+1)

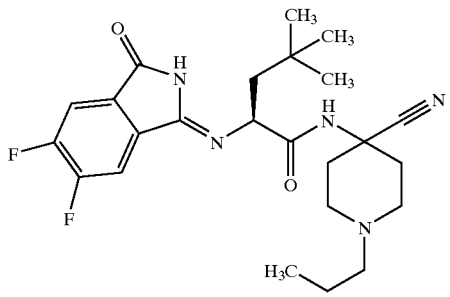

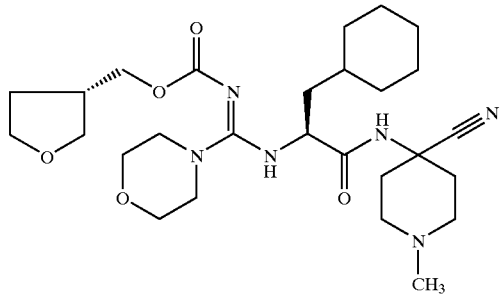

2-(5,6-Difluoro-3-oxo-2,3-dihydro-isoindol-1-ylideneamino)-4,4-dimethyl-pentanoic acid (4-cyano-1-propyl-piperidin-4-yl)-amide; MS: 460 (M+1)

{[1-(4-cyano-1-methyl-piperidin-4-ylcarbamoyl)-2-cyclohexyl-ethylamino]-morpholin-4-yl-methylene}-carbamic acid tetrahydro-furan-3ylmethyl ester; MS: 533 (M+1)

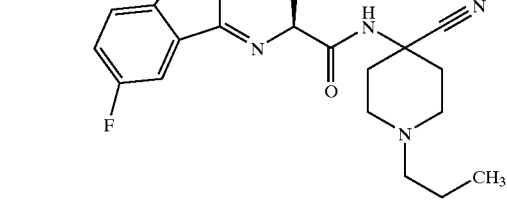

2-(6-Fluoro-3-oxo-2,3-dihydro-isoindol-1-ylideneamino)-4,4-dimethyl-pentanoic acid (4-cyano-1-propyl-piperidin-4-yl)-amide; MS: 442 (M+1)

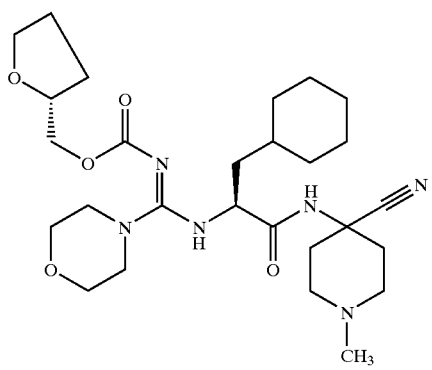

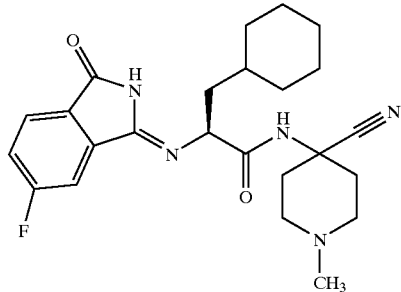

{[1-(4-cyano-1-methy-piperidin-4-ylcarbamoyl)-2-cyclohexyl-ethyl amino]-morpholin-4-yl-methylene}-carbamic acid tetrahydro-furan-2-ylmethyl ester; MS: 533 (M+1)

N-(4-Cyano-1-methyl-piperidin-4-yl)-3-cyclohexyl-2-(6-fluoro-3-oxo-2,3-dihydro-isoindol-1-ylideneamino)-propionamide; MS: 440 (M+1)

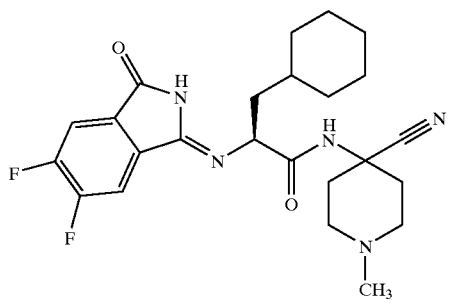

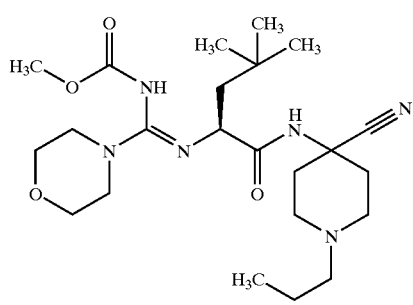

103

{[1-(4-Cyano-1-propyl-piperidin-4-ylcarbamoyl)-3,3-dimethyl-butylimino]-morpholin-4-yl-methyl}-carbamic acid methyl ester; MS: 465 (M+1)

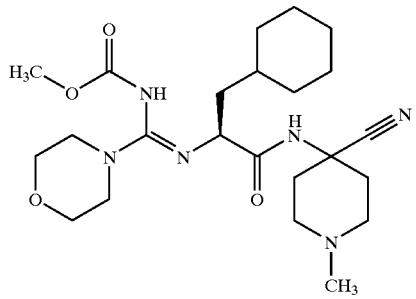

{[1-(4-Cyano-1-methyl-piperidin-4-ylcarbamoyl)-2-cyclohexyl-ethylimino]-morpholin-4-yl-methyl}-carbamic acid methyl ester; MS: 463 (M+1)

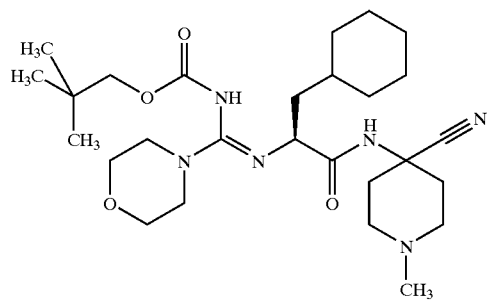

{[1-(4-Cyano-1-methyl-piperidin-4-ylcarbamoyl)-2-cyclohexyl-ethylimino]-morpholin-4-yl-methyl}-carbamic acid 2,2-dimethyl-propyl ester; MS: 519 (M+1)

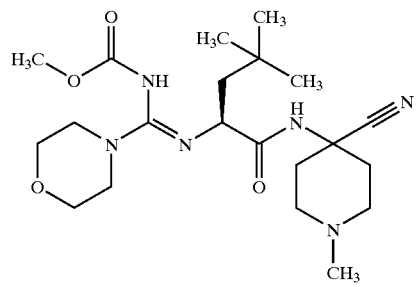

{[1-(4-Cyano-1-methyl-piperidin-4-ylcarbamoyl)-3,3-dimethyl-butylimino]-morpholin-4-yl-methyl}-carbamic acid methyl ester; MS: 437 (M+1)

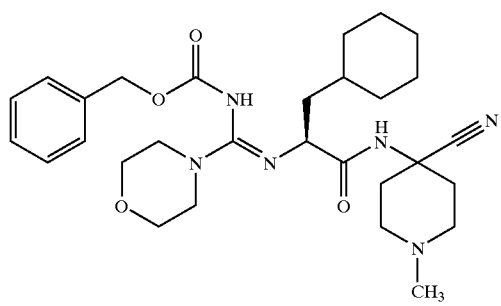

104

{[1-(4-Cyano-1-methyl-piperidin-4-ylcarbamoyl)-2-cyclohexyl-ethylimino]-morpholin-4-yl-methyl}-carbamic acid benzyl ester; MS: 539 (M+1)

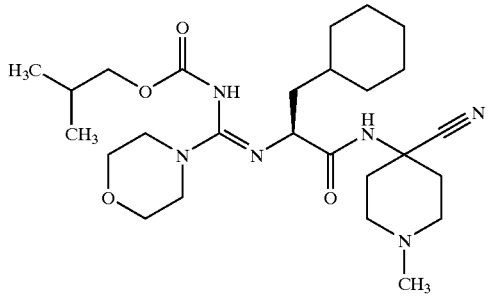

{[1-(4-Cyano-1-methyl-piperidin-4-ylcarbamoyl)-2-cyclohexyl-ethylimino]-morpholin-4-yl-methyl}-carbamic acid isobutyl ester; MS: 505 (M+1)

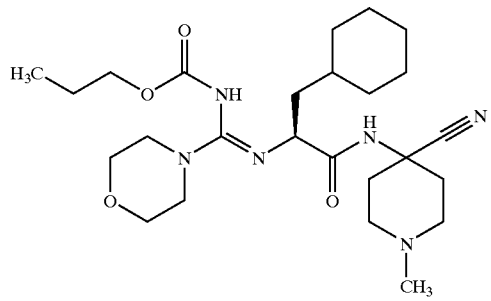

{[1-(4-Cyano-1-methyl-piperidin-4-ylcarbamoyl)-2-cyclohexyl-ethylimino]-morpholin-4-yl-methyl}-carbamic acid propyl ester; MS: 491 (M+1)

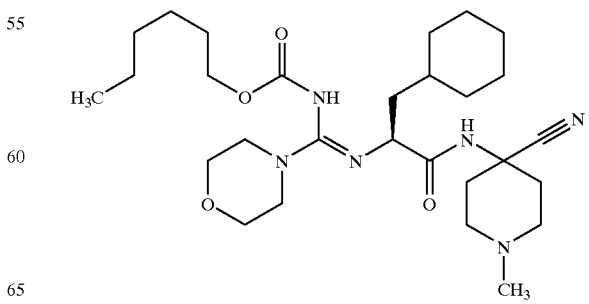

105

{[1-(4-Cyano-1-methyl-piperidin-4-ylcarbamoyl)-2-cyclohexyl-ethylimino]-morpholin-4-yl-methyl}-carbamic acid hexyl ester; MS: 533 (M+1)

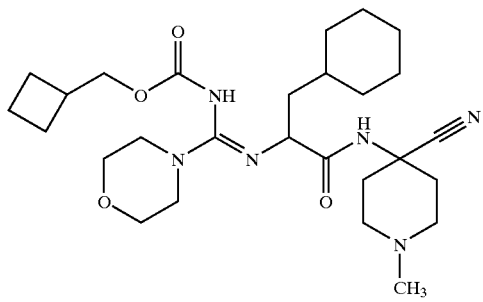

{[1-(4-Cyano-1-methyl-piperidin-4-ylcarbamoyl)-2-cyclohexyl-ethylimino]-morpholin-4-yl-methyl}-carbamic acid cyclobutylmethyl ester; MS: 517 (M+1)

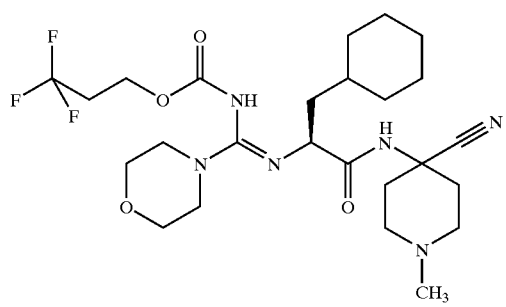

{[1-(4-Cyano-1-methyl-piperidin-4-ylcarbamoyl)-2-cyclohexyl-ethylimino]-morpholin-4-yl-methyl}-carbamic acid 3,3,3-trifluoro-propyl ester; MS: 545 (M+1)

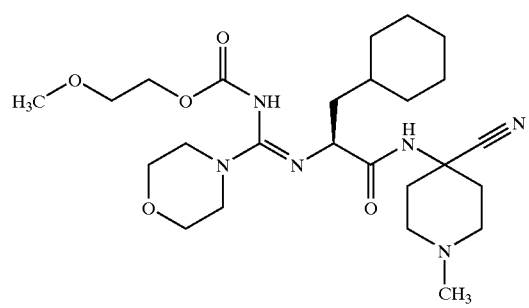

106

{[1-(4-Cyano-1-methyl-piperidin-4-ylcarbamoyl)-2-cyclohexyl-ethylimino]-morpholin-4-yl-methyl}-carbamic acid 2-methoxy-ethyl ester; MS: 507 (M+1)

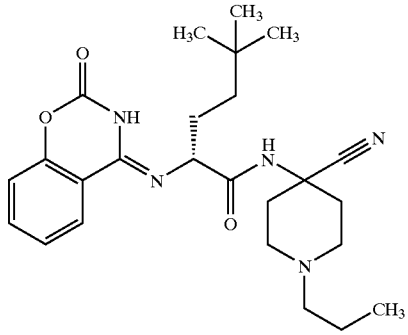

5,5-Dimethyl-2-(2-oxo-2,3-dihydro-benzo[e][1,3]oxazin-4-ylideneamino)-hexanoic acid (4-cyano-1-propyl-piperidin-4-yl)-amide; MS: 454 (M+1)

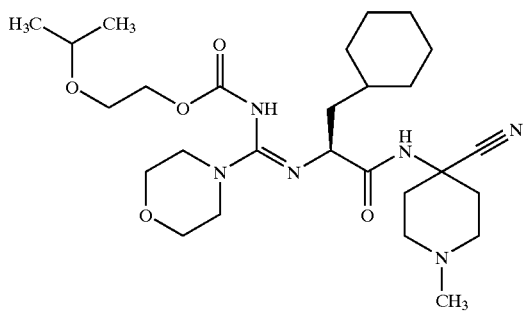

{[1-(4-Cyano-1-methyl-piperidin-4-ylcarbamoyl)-2-cyclohexyl-ethylimino]-morpholin-4-yl-methyl}-carbamic acid 2-isopropoxy-ethyl ester; MS: 534 (M+1)

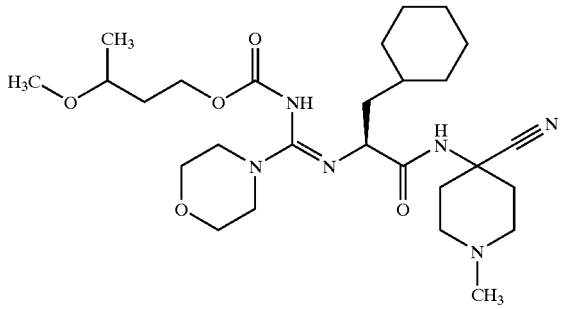

107

{[1-(4-Cyano-1-methyl-piperidin-4-ylcarbamoyl)-2-cyclohexyl-ethylimino]-morpholin-4-yl-methyl}-carbamic acid 3-methoxy-butyl ester; MS: 534 (M+1)

108

N-(4-Cyano-1-methyl-piperidin-4-yl)-4-cyclohexyl-2-(6-methoxy-2-oxo-2,3-dihydro-benzo[e][1,3]oxazin-4-ylideneamino)-butyramide; MS: 468 (M+1)

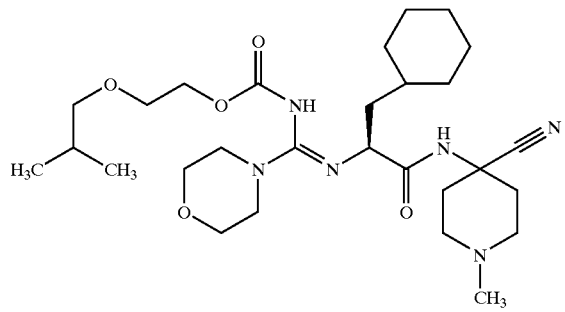

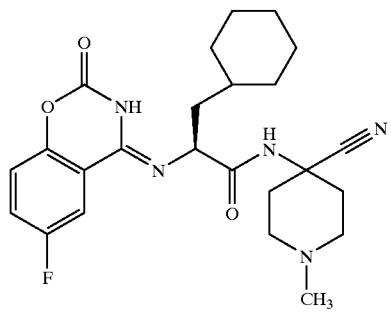

{[1-(4-Cyano-1-methyl-piperidin-4-ylcarbamoyl)-2-cyclohexyl-ethylimino]-morpholin-4-yl-methyl}-carbamic acid 2-isobutoxy-ethyl ester; MS: 549 (M+1)

N-(4-Cyano-1-methyl-piperidin-4-yl)-4-cyclohexyl-2-(6-fluoro-2-oxo-2,3-dihydro-benzo[e][1,3]oxazin-4-ylideneamino)-butyramide; MS: 456 (M+1)

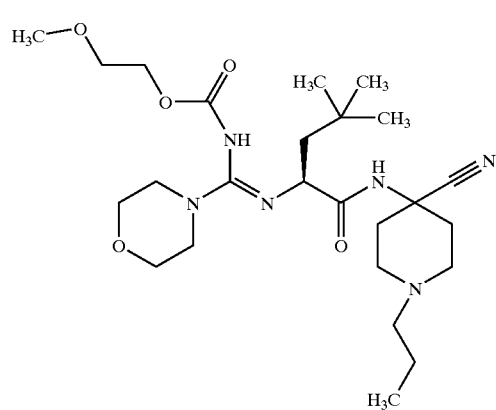

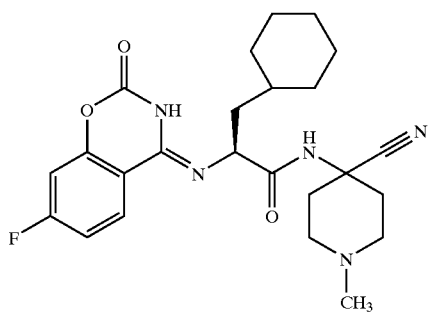

{[1-(4-Cyano-1-propyl-piperidin-4-ylcarbamoyl)-3,3-dimethyl-butylimino]-morpholin-4-yl-methyl}-carbamic acid 2-methoxy-ethyl ester; MS: 509 (M+1)

N-(4-Cyano-1-methyl-piperidin-4-yl)-4-cyclohexyl-2-(7-fluoro-2-oxo-2,3-dihydro-benzo[e][1,3]oxazin-4-ylideneamino)-butyramide; MS: 456 (M+1)

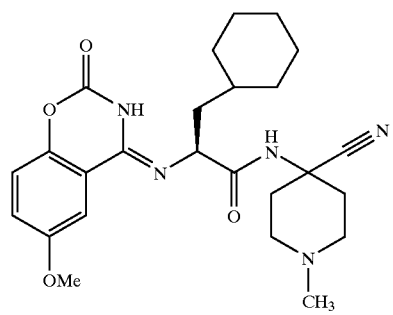

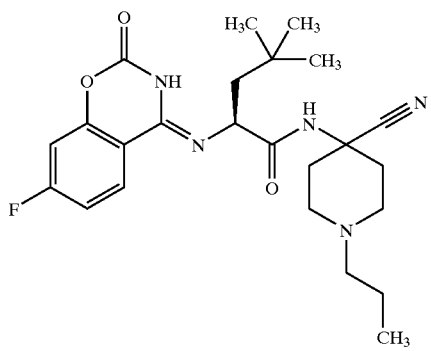

2-(7-Fluoro-2-oxo-2,3-dihydro-benzo[e][1,3]oxazin-4-ylideneamino)-5,5-dimethyl-hexanoic acid(4-cyano-1-propyl-piperidin-4-yl)-amide; MS: 458 (M+1)

N-(4-Cyano-1-methyl-piperidin-4-yl)-3-cyclohexyl-2-(2-oxo-2,3-dihydro-benzo[e][1,3]oxazin-4-ylideneamino)-propionamide; MS: 438 (M+1).

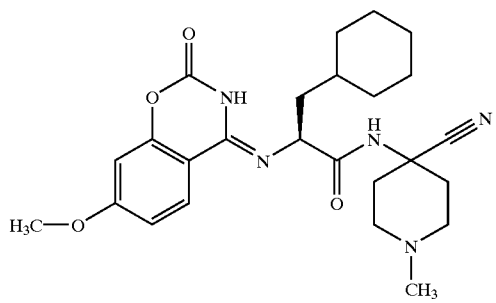

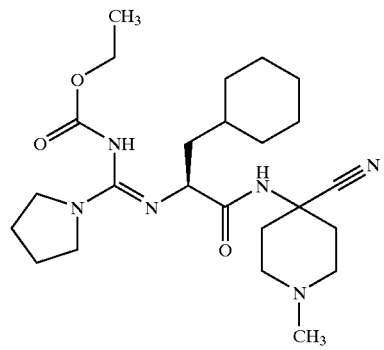

N-(4-Cyano-1-methyl-piperidin-4-yl)-4-cyclohexyl-2-(7-methoxy-2-oxo-2,3-dihydro-benzo[e][1,3]oxazin-4-ylideneamino)-butyramide; MS: 468 (M+1)

{[1-(4-Cyano-1-methyl-piperidin-4-ylcarbamoyl)-2-cyclohexyl-ethylimino]-pyrrolidin-1-yl-methyl}-carbamic acid ethyl ester; MS: 461 (M+1).

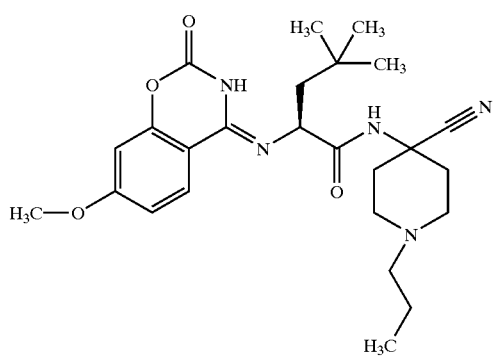

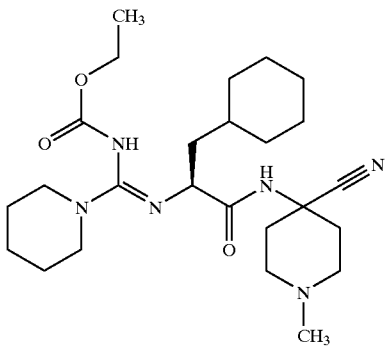

2-(7-Methoxy-2-oxo-2,3-dihydro-benzo[e][1,3]oxazin-4-ylideneamino)-5,5-dimethyl-hexanoic acid(4-cyano-1-propyl-piperidin-4-yl)-amide; MS: 470 (M+1)

{[1-(4-Cyano-1-methyl-piperidin-4-ylcarbamoyl)-2-cyclohexyl-ethylimino]-piperidin-1-yl-methyl}-carbamic acid ethyl ester; MS: 475 (M+1).

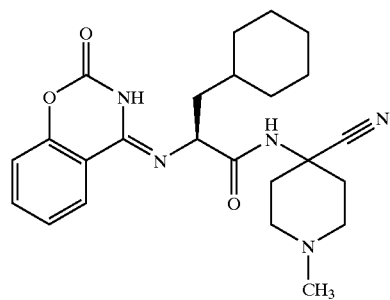

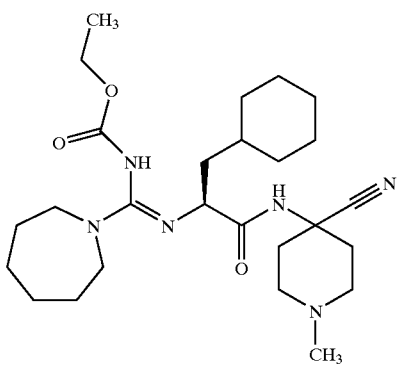

111

{Azepan-1-yl-[1-(4-cyano-1-methyl-piperidin-4-ylcarbamoyl)-2-cyclohexyl-ethylimino]-methyl}-carbamic acid ethyl ester; MS: 489 (M+1).

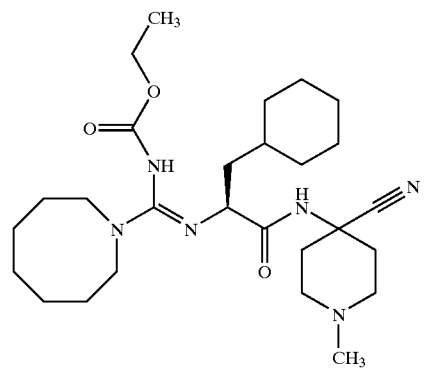

{Azocan-1-yl-[1-(4-cyano-1-methyl-piperidin-4-ylcarbamoyl)-2-cyclohexyl-ethylimino]-methyl}-carbamic acid ethyl ester; MS: 503 (M+1).

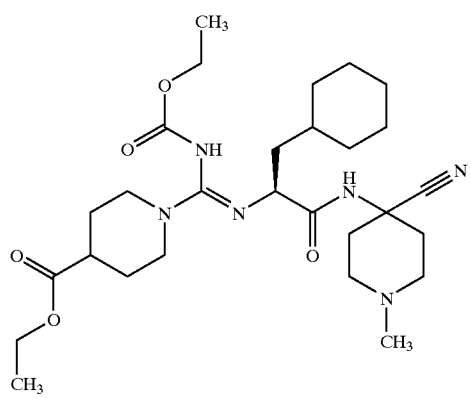

1-{[1-(4-Cyano-1-methyl-piperidin-4-ylcarbamoyl)-2-cyclohexyl-ethylimino]-ethoxycarbonylamino-methyl}-piperidine-4-carboxylic acid ethyl ester; MS: 547 (M+1).

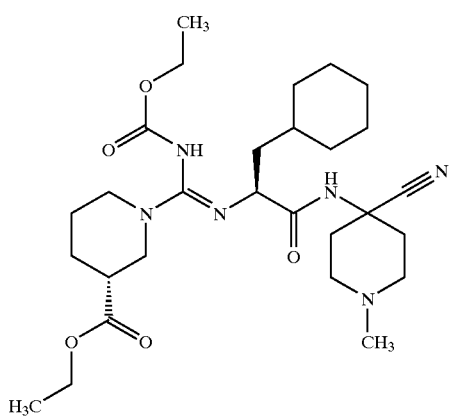

112

1-{[1-(4-Cyano-1-methyl-piperidin-4-ylcarbamoyl)-2-cyclohexyl-ethylimino]-ethoxycarbonylamino-methyl}-piperidine-3-carboxylic acid ethyl ester; MS: 547 (M+1).

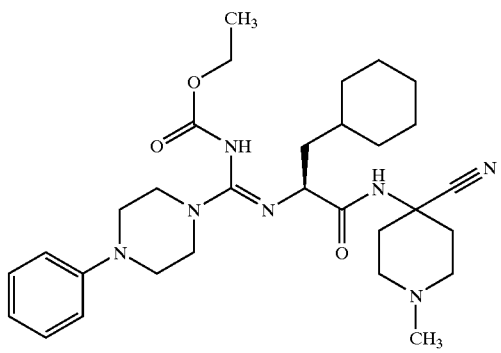

[[1-(4-Cyano-1-methyl-piperidin-4-ylcarbamoyl)-2-cyclohexyl-ethylimino]-(4-phenyl-piperazin-1-yl)-methyl]-carbamic acid ethyl ester; MS: 552 (M+1).

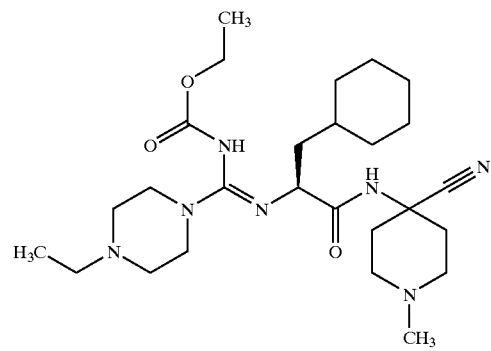

[[1-(4-Cyano-1-methyl-piperidin-4-ylcarbamoyl)-2-cyclohexyl-ethylimino]-(4-ethyl-piperazin-1-yl)-methyl]-carbamic acid ethyl ester; MS: 504 (M+1).

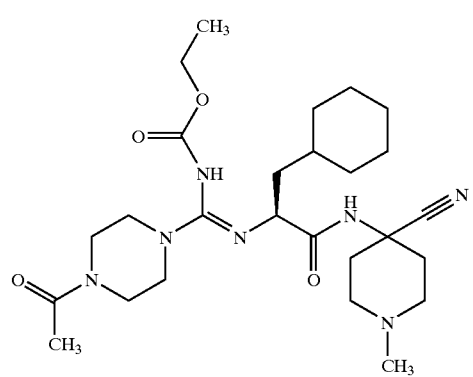

113

{(4-Acetyl-piperazin-1-yl)-[1-(4-cyano-1-methyl-piperidin-4-ylcarbamoyl)-2-cyclohexyl-ethylimino]-methyl}-carbamic acid ethyl ester; MS: 518 (M+1).

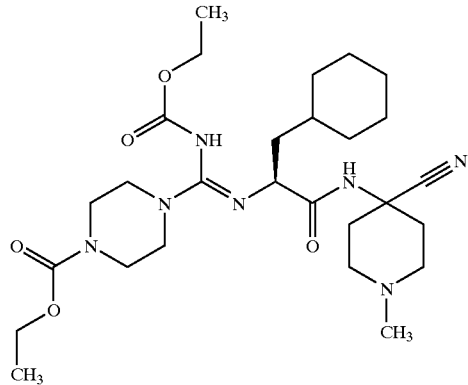

4-{[1-(4-Cyano-1-methyl-piperidin-4-ylcarbamoyl)-2-cyclohexyl-ethylimino]-ethoxycarbonylamino-methyl}-piperazine-1-carboxylic acid ethyl ester; MS: 548 (M+1).

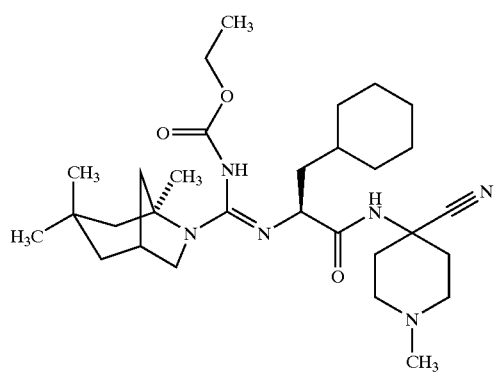

[[1-(4-Cyano-1-methyl-piperidin-4-ylcarbamoyl)-2-cyclohexyl-ethylimino]-(3,3,5-trimethyl-6-aza-bicyclo[3.2.1]oct-6-yl)-methyl]-carbamic acid ethyl ester; MS: 543 (M+1).

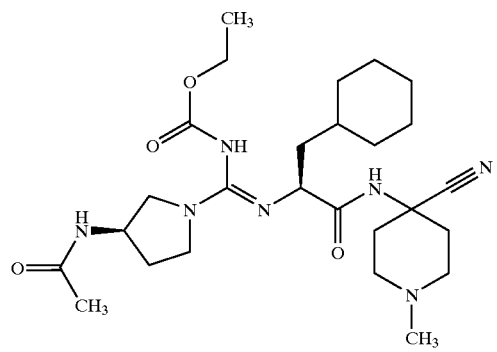

114

{(3-Acetylamino-pyrrolidin-1-yl)-[1-(4-cyano-1-methyl-piperidin-4-ylcarbamoyl)-2-cyclohexyl-ethylimino]-methyl}-carbamic acid ethyl ester; MS: 518 (M+1).

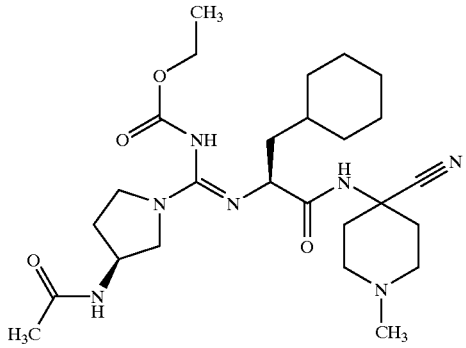

{(3-Acetylamino-pyrrolidin-1-yl)-[1-(4-cyano-1-methyl-piperidin-4-ylcarbamoyl)-2-cyclohexyl-ethylimino]-methyl}-carbamic acid ethyl ester; MS: 518 (M+1).

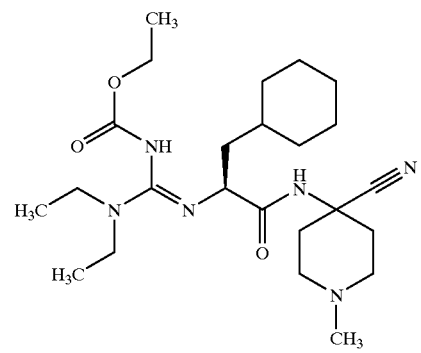

{(3-Azapent-3-yl)-[1-(4-cyano-1-methyl-piperidin-4-ylcarbamoyl)-2-cyclohexyl-ethylimino]-methyl}-carbamic acid ethyl ester; MS: 463 (M+1).

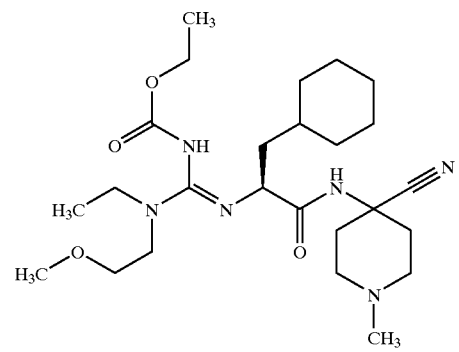

{(1-Methoxy-3-azapent-3-yl)-[1-(4-cyano-1-methyl-piperidin-4-ylcarbamoyl)-2-cyclohexyl-ethylimino]-methyl}-carbamic acid ethyl ester; MS: 493 (M+1).

4,4-Dimethyl-2-(2-oxo-2,3-dihydro-benzo[e][1,3]oxazin-4-ylideneamino)-pentanoic acid (4-cyano-1-propyl-piperidin-4-yl)-amide; MS: 440 (M+1)

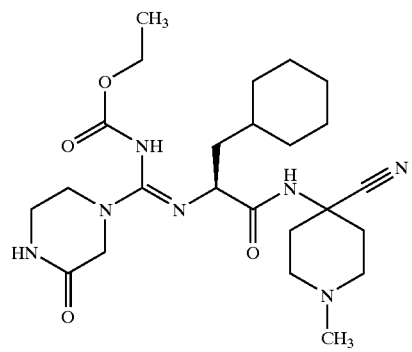

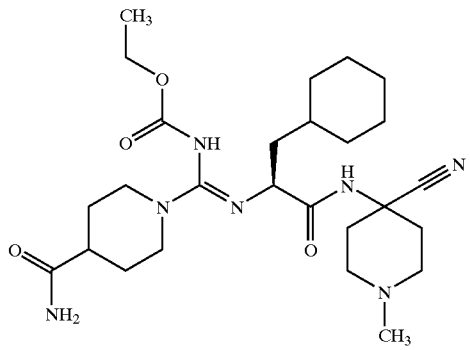

[[1-(4-Cyano-1-methyl-piperidin-4-ylcarbamoyl)-2-cyclohexyl-ethylimino]-(3-oxo-piperazin-1-yl)-methyl]-carbamic acid ethyl ester; MS: 490 (M+1).

{(4-Carbamoyl-piperidin-1-yl)-[1-(4-cyano-1-methyl-piperidin-4-ylcarbamoyl)-2-cyclohexyl-ethylimino]-methyl}-carbamic acid ethyl ester; MS: 518 (M+1)

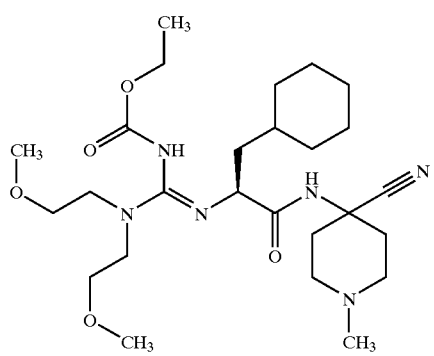

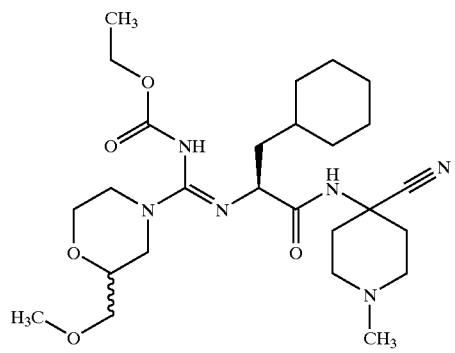

{(1,5-Dimethoxy-3-azapent-3-yl)-[1-(4-cyano-1-methyl-piperidin-4-ylcarbamoyl)2-cyclohexyl-ethylimino]-methyl}-carbamic acid ethyl ester; MS: 523 (M+1).

[[1-(4-Cyano-1-methyl-piperidin-4-ylcarbamoyl)-2-cyclohexyl-ethylimino]-(2-methoxymethyl-morpholin-4-yl)-methyl]-carbamic acid ethyl ester; MS: 521 (M+1)

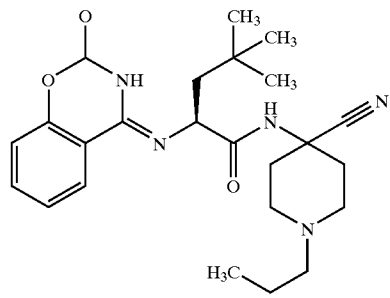

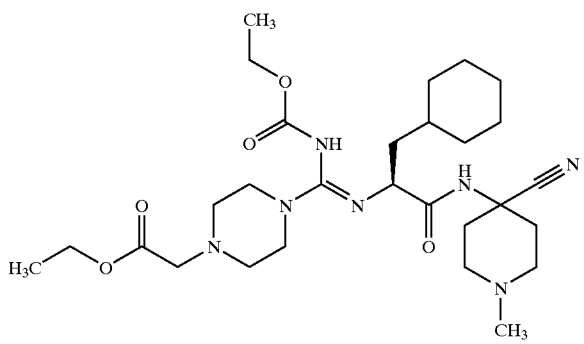

(4-{[1-(4-Cyano-1-methyl-piperidin-4-ylcarbamoyl)-2-cyclohexyl-ethylimino]-ethoxycarbonylamino-methyl}-piperazin-1-yl)-acetic acid ethyl ester; MS: 562 (M+1)

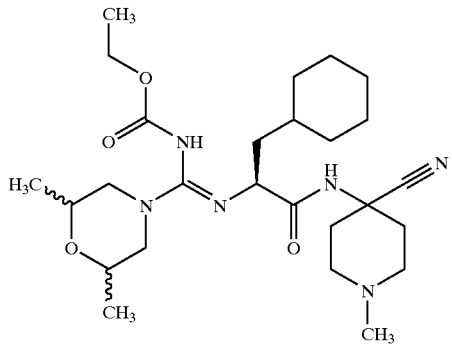

[[1-(4-Cyano-1-methyl-piperidin-4-ylcarbamoyl)-2-cyclohexyl-ethylimino]-(2,6-dimethyl-morpholin-4-yl)-methyl]-carbamic acid ethyl ester; MS: 505 (M+1)

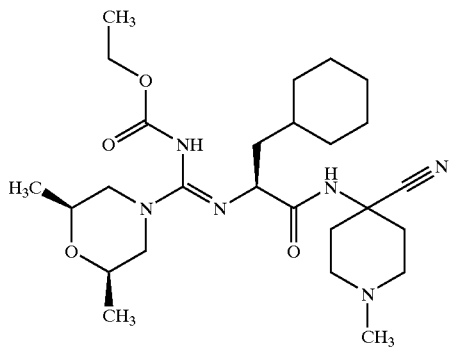

[[1-(4-Cyano-1-methyl-piperidin-4-ylcarbamoyl)-2-cyclohexyl-ethylimino]-(2,6-dimethyl-morpholin-4-yl)-methyl]-carbamic acid ethyl ester; MS: 505 (M+1)

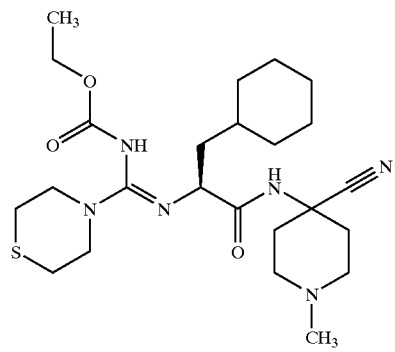

{[1-(4-Cyano-1-methyl-piperidin-4-ylcarbamoyl)-2-cyclohexyl-ethylimino]-thiomorpholin-4-yl-methyl}-carbamic acid ethyl ester; MS: 493 (M+1)

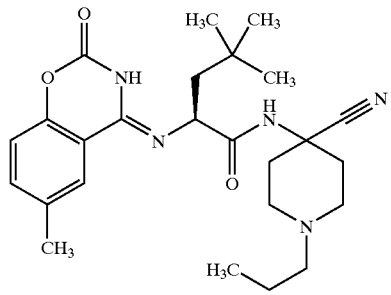

4,4-Dimethyl-2-(6-methyl-2-oxo-2,3-dihydro-benzo[e][1,3]oxazin-4-ylideneamino)-pentanoic acid (4-cyano-1-propyl-piperidin-4-yl)-amide; MS: 454 (M+1)

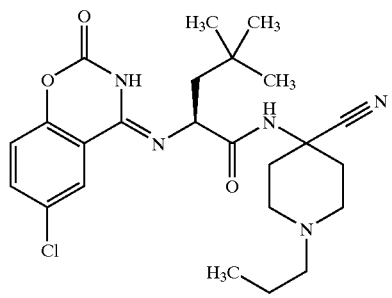

2-(6-Chloro-2-oxo-2,3-dihydro-benzo[e][1,3]oxazin-4-ylideneamino)-4,4-dimethyl-pentanoic acid (4-cyano-1-propyl-piperidin-4-yl)-amide; MS: 475 (M+1)

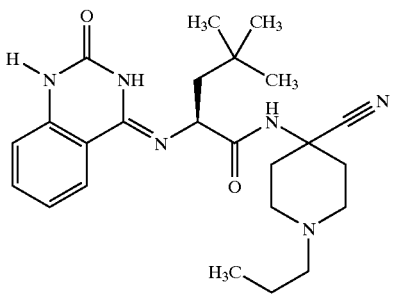

4,4-Dimethyl-2-(2-oxo-2,3-dihydro-1H-quinazolin-4-ylideneamino)-pentanoic acid (4-cyano-1-propyl-piperidin-4-yl)-amide; MS: 439 (M+1)

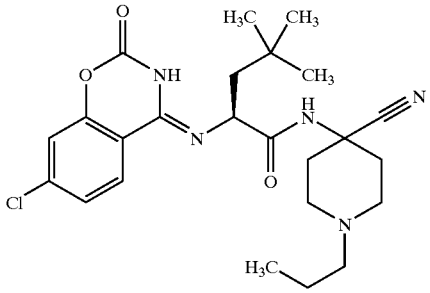

2-(7-Chloro-2-oxo-2,3-dihydro-benzo[e][1,3]oxazin-4-ylideneamino)-4,4-dimethyl-pentanoic acid (4-cyano-1-propyl-piperidin-4-yl)-amide; MS: 475 (M+1)

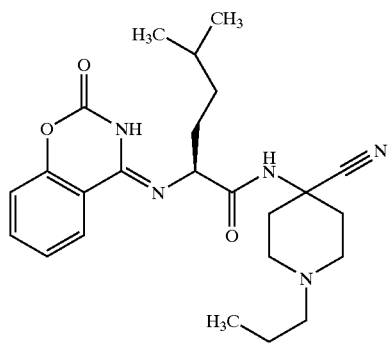

5-Methyl-2-(2-oxo-2,3-dihydro-benzo[e][1,3]oxazin-4-ylideneamino)-hexanoic acid (4-cyano-1-propyl-piperidin-4-yl)-amide; MS: 440 (M+1)

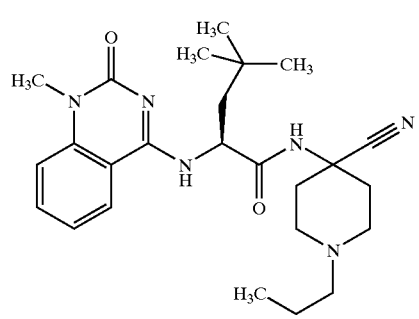

4,4-Dimethyl-2-(1-methyl-2-oxo-1,2-dihydro-quinazolin-4-ylamino)-pentanoic acid (4-cyano-1-propyl-piperidin-4-yl)-amide; MS: 453 (M+1)

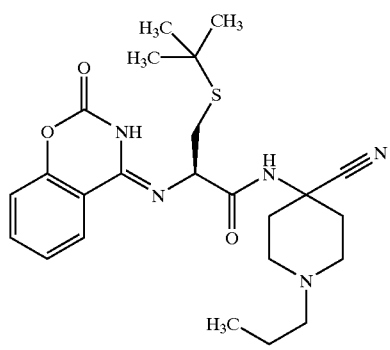

3-tert-Butylsulfanyl-N-(4-cyano-1-propyl-piperidin-4-yl)-2-(2-oxo-2,3-dihydro-benzo[e][1,3]oxazin-4-ylideneamino)-propionamide; MS: 472 (M+1)

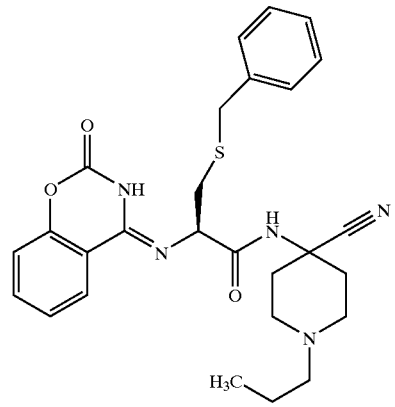

3-Benzylsulfanyl-N-(4-cyano-1-propyl-piperidin-4-yl)-2-(2-oxo-2,3-dihydro-benzo[e][1,3]oxazin-4-ylideneamino)-propionamide; MS: 506 (M+1)

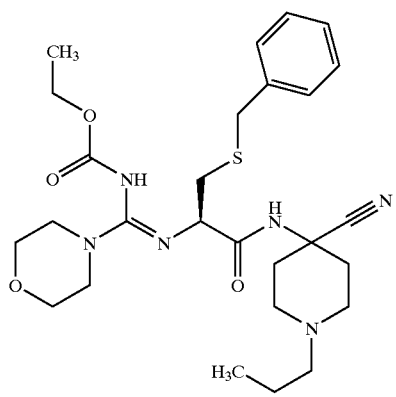

{[2-Benzylsulfanyl-1-(4-cyano-1-propyl-piperidin-4-ylcarbamoyl)-ethylimino]-morpholin-4-yl-methyl}-carbamic acid ethyl ester; MS: 545 (M+1)

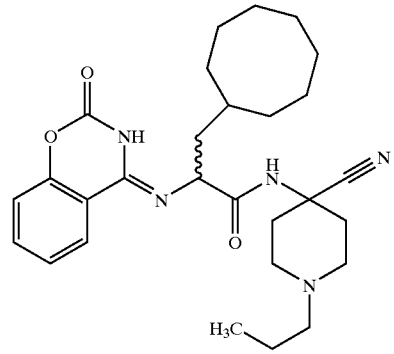

121

N-(4-Cyano-1-propyl-piperidin-4-yl)-3-cyclooctyl-2-(2-oxo-2,3-dihydro-benzo[e][1,3]oxazin-4-ylideneamino)-propionamide; MS: 494 (M+1)

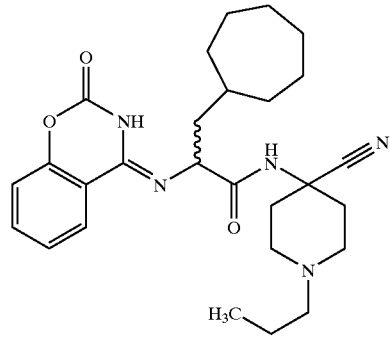

N-(4-Cyano-1-propyl-piperidin-4-yl)-3-cycloheptyl-2-(2-oxo-2,3-dihydro-benzo[e][1,3]oxazin-4-ylideneamino)-propionamide; MS: 480 (M+1)

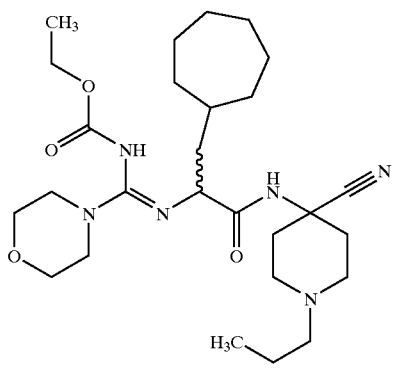

{[1-(4-Cyano-1-propyl-piperidin-4-ylcarbamoyl)-2-cycloheptyl-ethylimino]-morpholin-4-yl-methyl}-carbamic acid ethyl ester; MS: 519 (M+1)

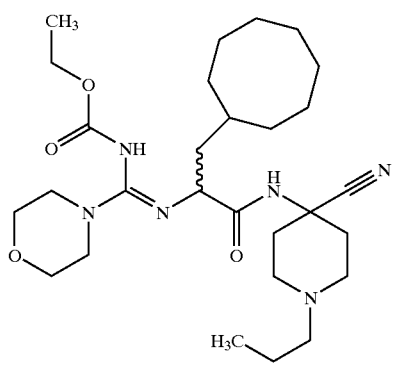

122

{[1-(4-Cyano-1-propyl-piperidin-4-ylcarbamoyl)-2-cyclooctyl-ethylimino]-morpholin-4-yl-methyl}-carbamic acid ethyl ester; MS: 533 (M+1)

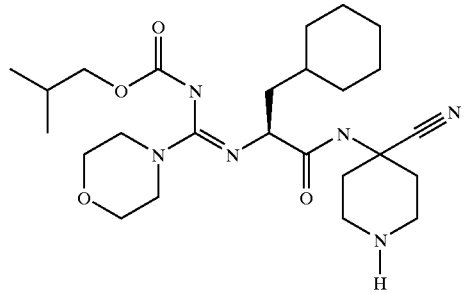

{[1-(4-Cyano-piperidin-4-ylcarbamoyl)-2-cyclohexyl-ethylamino]-morpholin-4-yl-methylene}-carbamic acid isobutyl ester; MS: 491 (M+1)

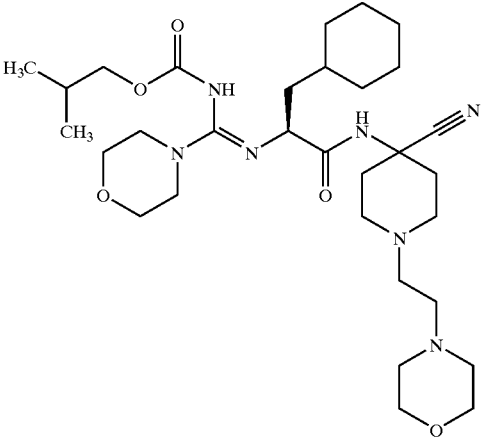

({1-[4-Cyano-1-(2-morpholin-4-yl-ethyl)-piperidin-4-ylcarbamoyl]-2-cyclohexyl-ethylamino}-morpholin-4-yl-methylene)-carbamic acid isobutyl ester; MS: 604 (M+1)

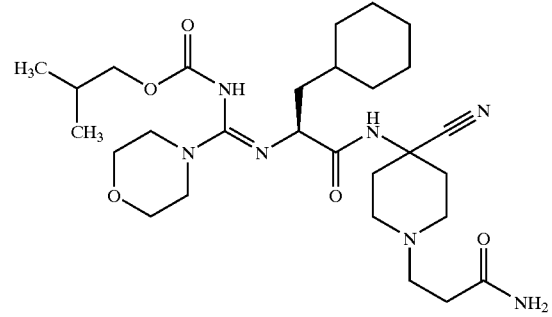

123

({1-[1-2-Carbamoyl-ethyl)-4-cyano-piperidin-4-ylcarbamoyl]-2-cyclohexyl-ethylamino}-morpholin-4-yl-methylene)-carbamic acid isobutyl ester; MS: 562 (M+1)

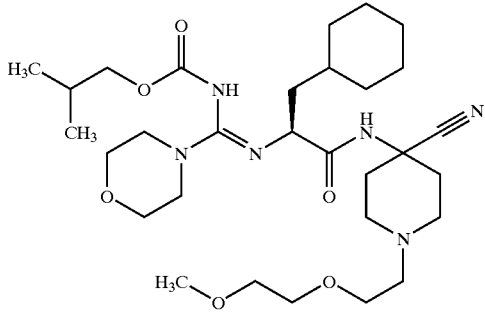

[(1-{4-Cyano-1-[2-(2-methoxyl-ethoxy)-ethyl]-piperidin-4-ylcarbamoyl}-2-cyclohexyl-ethylamino)-morpholin-4-yl-methylene]-carbamic acid isobutyl ester; MS: 593 (M+1)

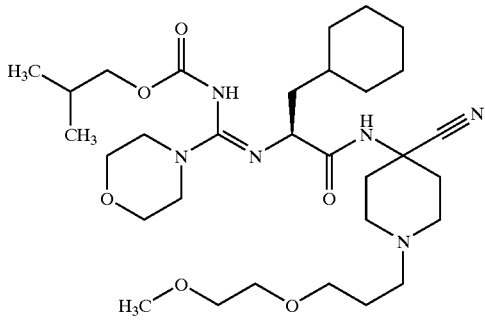

[(1-{4-Cyano-1-[3-(2-methoxyl-ethoxy)-propyl]-piperidin-4-ylcarbamoyl}-2-cyclohexyl-ethylamino)-morpholin-4-yl-methylene]-carbamic acid isobutyl ester; MS: 607 (M+1)

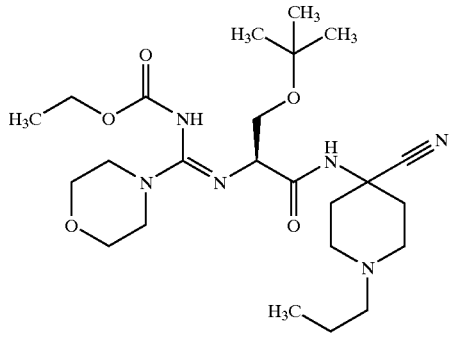

124

{[2-tert-Butoxy-1-(4-cyano-1-propyl-piperidin-4-ylcarbamoly)-ethylamino]-morpholin-4-yl-methylene}-carbamic acid ethyl ester; MS: 495 (M+1)

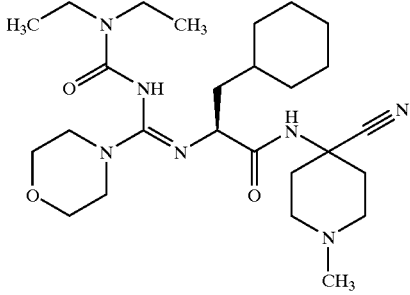

N-(4-Cyano-1-methyl-piperidin-4-yl)-3-cyclohexyl-2-{[diethyl-carbamoylimino)-morpholin-4-yl-methyl]-amino}-propionamide; MS: 504 (M+1)

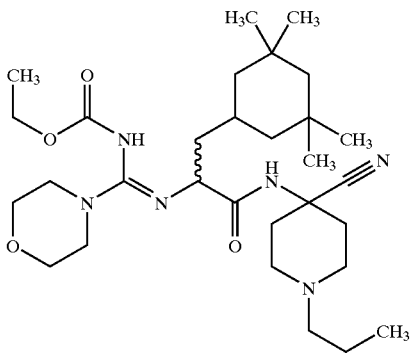

{[1-(4-Cyano-1-propyl-piperidin-4-ylcarbamoyl)-2-(3,3,5,5-tetramethyl-cyclohexyl)-ethylamino]-morpholin-4-yl-methylene}-carbamic acid ethyl ester; MS: 561 (M+1)

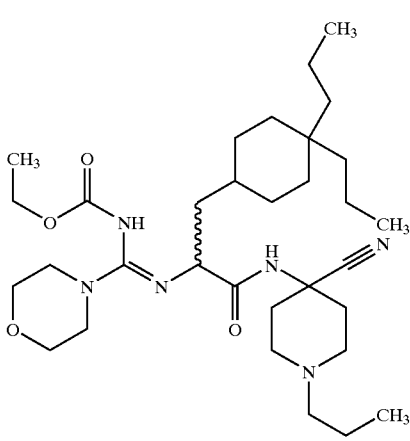

125

{[1-(4-Cyano-1-propyl-piperidin-4-ylcarbamoyl)-2-(4,4-dipropyl-cyclohexyl)-ethylamino]-morpholin-4-yl-methylene}-carbamic acid ethyl ester; MS: 589 (M+1)

126

{[1-(4-Cyano-1-ethyl-piperidin-4-ylcarbamoyl)-2-cyclohexyl-ethylamino]-morpholin-4-yl-methylene}-carbamic acid ethyl ester; MS: 491 (M+1)

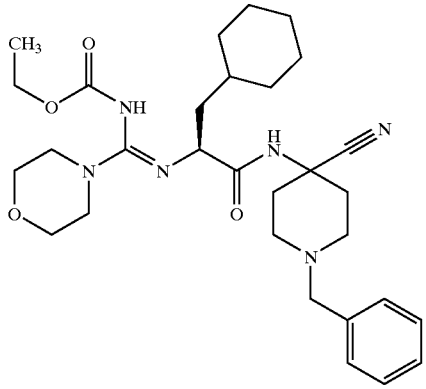

{[1-(4-Cyano-1-isopropyl-piperidin-4-ylcarbamoyl)-2-cyclohexyl-ethylamino]-morpholin-4-yl-methylene}-carbamic acid ethyl ester; MS: 505 (M+1)

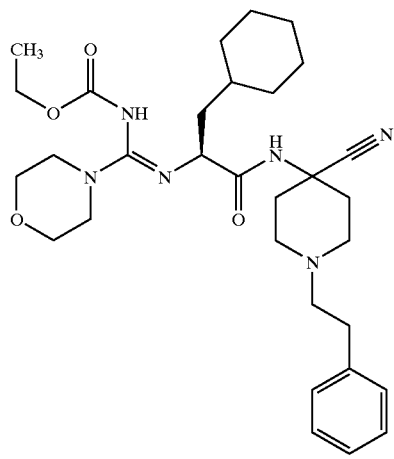

{[1-(1-Benzyl-4-cyano-piperidin-4-ylcarbamoyl)-2-cyclohexyl-ethylamino]-morpholin-4-yl-methylene}-carbamic acid ethyl ester; MS: 553 (M+1)

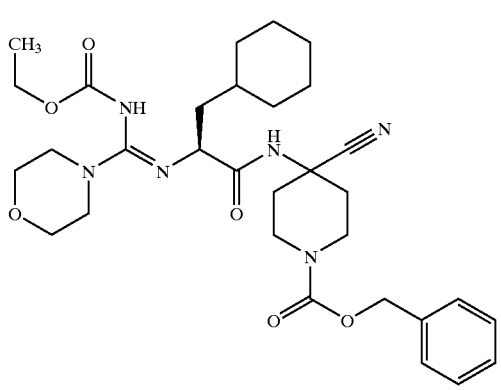

{[1-(4-Cyano-1-phenethyl-piperidin-4-ylcarbamoyl)-2-cyclohexyl-ethylamino]-morpholin-4-yl-methylene}-carbamic acid ethyl ester; MS: 567 (M+1)

4-Cyano-4-{3-cyclohexyl-2-[(ethoxycarbonylimino-morpholin-4-yl-methyl)-amino]-propionylamino}-piperidine-1-carboxylic acid benzyl ester; MS: 597 (M+1)

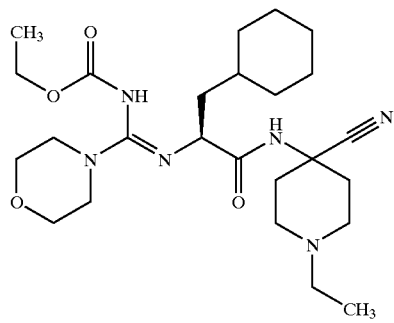

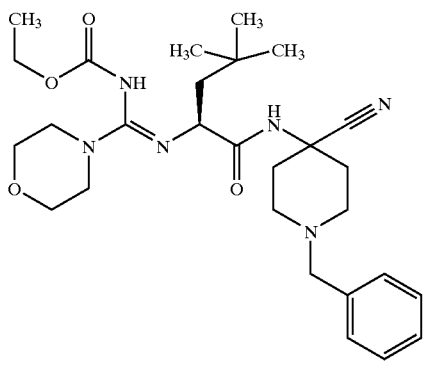

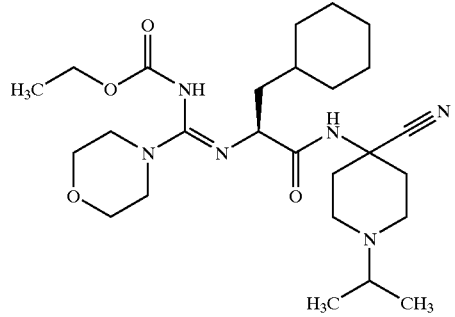

127

{[1-(1-Benzyl-4-cyano-piperidin-4-ylcarbamoyl)-3,3-dimethyl-butylamino]-morpholin-4-yl-methylene}-carbamic acid ethyl ester; MS: 527 (M+1)

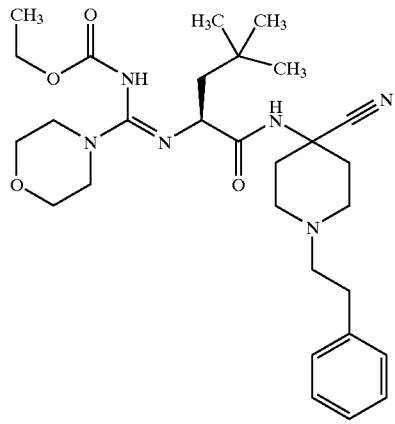

{[1-(4-cyano-1-phenethyl-piperidin-4-ylcarbamoyl)-3,3-dimethyl-butylamino]-morpholin-4-yl-methylene}-carbamic acid ethyl ester; MS: 541 (M+1)

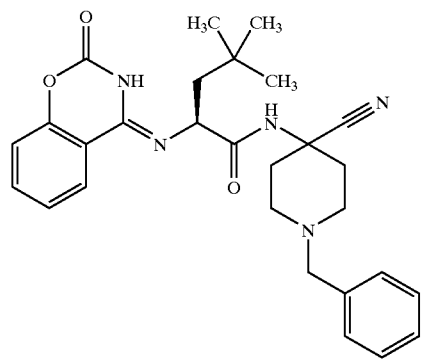

4,4-Dimethyl-2-(2-oxo-2H-benzo[e][1,3]oxazin-4-ylamino)-pentanoic acid (1-benzyl-4-cyano-piperidin-4-yl)-amide; MS: 488 (M+1)

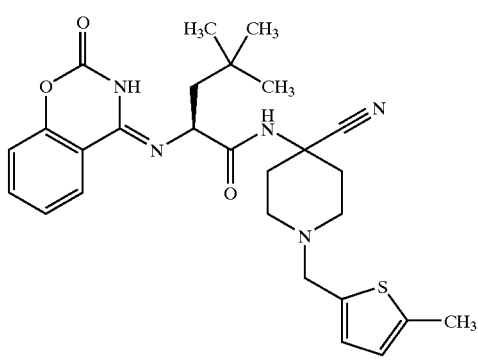

128

4,4-Dimethyl-2-(2-oxo-2H-benzo[e][1,3]oxazin-4-ylamino)-pentanoic acid [4-cyano-1-(5-methyl-thiophen-2-ylmethyl)-piperidin-4-yl]-amide; MS: 508 (M+1)

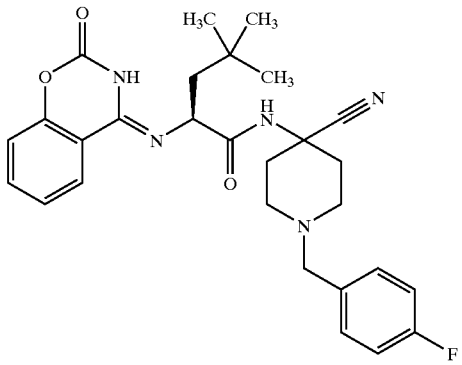

4,4-Dimethyl-2-(2-oxo-2H-benzo[e][1,3]oxazin-4-ylamino)-pentanoic acid [4-cyano-1-(4-fluoro-benzyl)-piperidin-4-yl]-amide; MS: 506 (M+1)

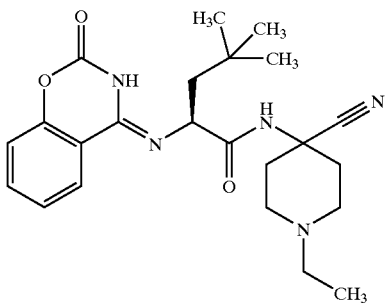

4,4-Dimethyl-2-(2-oxo-2H-benzo[e][1,3]oxazin-4-ylamino)-pentanoic acid (4-cyano-1-ethyl-piperidin-4-yl)-amide; MS: 426 (M+1)

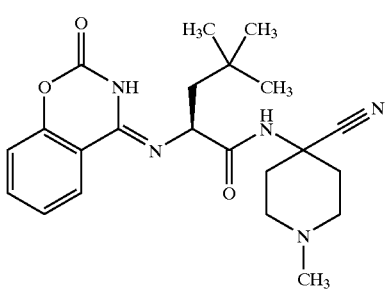

4,4-Dimethyl-2-(2-oxo-2H-benzo[e][1,3]oxazin-4-ylamino)-pentanoic acid (4-cyano-1-methyl-piperidin-4-yl)-amide; MS: 412 (M+1)

4,4-Dimethyl-2-(2-oxo-2H-benzo[e][1,3]oxazin-4-ylamino)-pentanoic acid [4-cyano-1-(2,2-dimethyl-propyl)-piperidin-4-yl]-amide; MS: 468 (M+1)

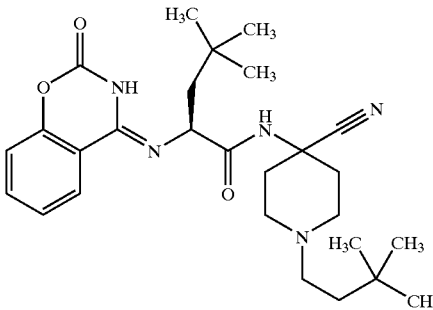

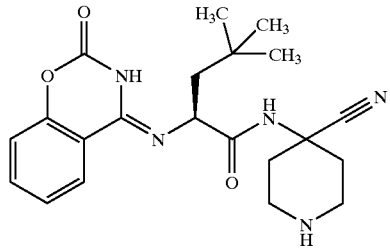

4,4-Dimethyl-2-(2-oxo-2H-benzo[e][1,3]oxazin-4-ylamino)-pentanoic acid (4-cyano-piperidin-4-yl)-amide; MS: 398 (M+1)

4,4-Dimethyl-2-(2-oxo-2H-benzo[e][1,3]oxazin-4-ylamino)-pentanoic acid [4-cyano-1-(3,3-dimethyl-butyl)-piperidin-4-yl]-amide; MS: 482 (M+1)

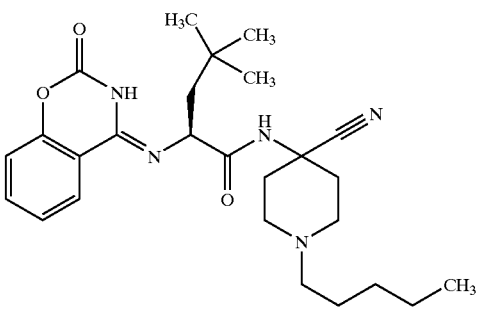

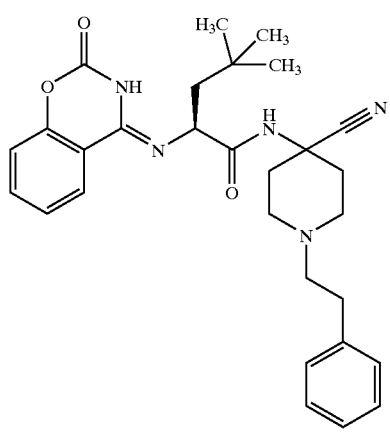

4,4-Dimethyl-2-(2-oxo-2H-benzo[e][1,3]oxazin-4-ylamino)-pentanoic acid (4-cyano-1-pentyl-piperidin-4-yl)-amide; MS: 468 (M+1)

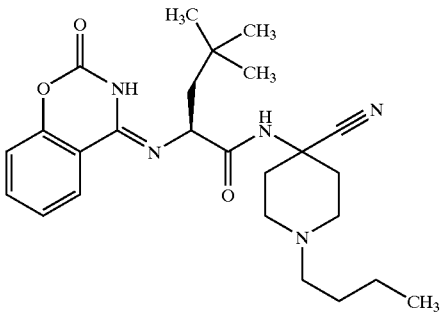

4,4-Dimethyl-2-(2-oxo-2H-benzo[e][1,3]oxazin-4-ylamino)-pentanoic acid (4-cyano-1-phenethyl-piperdin-4-yl)-amide; MS: 502 (M+1)

4,4-Dimethyl-2-(2-oxo-2H-benzo[e][1,3]oxazin-4-ylamino)-pentanoic acid (1-butyl-4-cyano-piperidin-4-yl)-amide; MS: 454(M+1)

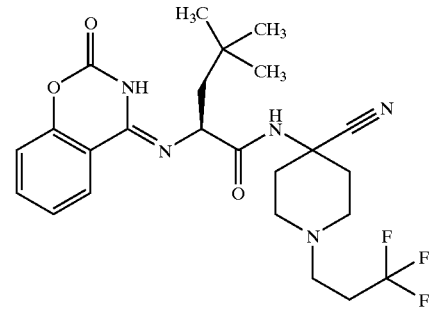

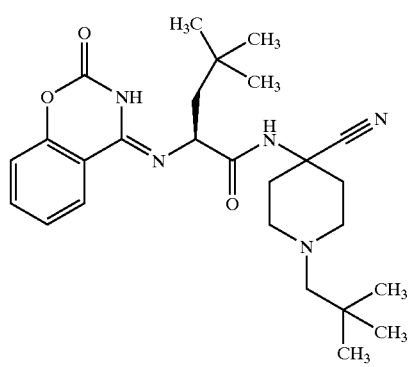

131

4,4-Dimethyl-2-(2-oxo-2H-benzo[e][1,3]oxazin-4-ylamino)-pentanoic acid [4-cyano-1-(3,3,3-trifluoro-propyl)-piperidin-4-yl]-amide; MS: 494 (M+1)

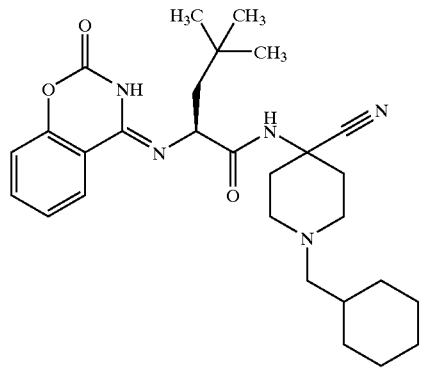

4,4-Dimethyl-2-(2-oxo-2H-benzo[e][1,3]oxazin-4-ylamino)-pentanoic acid (4-cyano-1-cyclohexylmethyl-piperidin-4-yl)-amide; MS: 494 (M+1)

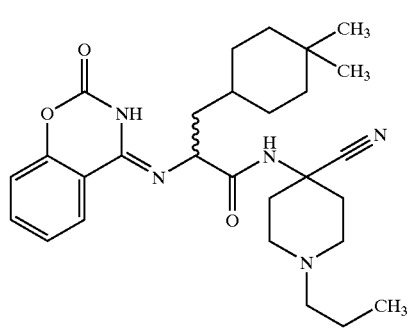

N-(4-Cyano-1-propyl-piperidin-4-yl)-3-(4,4-dimethyl-cyclohexyl)-2-(2-oxo-2H-benzo[e][1,3]oxazin-4-ylamino)-propionamide; MS: 494 (M+1)

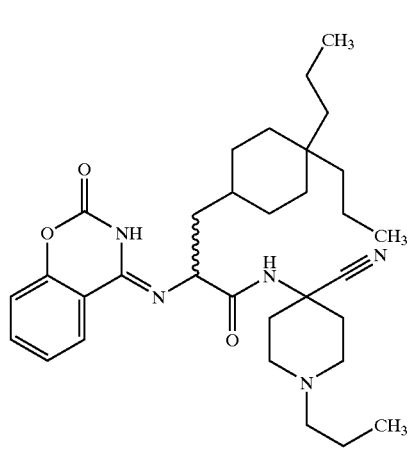

132

N-(4-Cyano-1-propyl-piperidin-4-yl)-3-(4,4-dipropyl-cyclohexyl)-2-(2-oxo-2H-benzo[e][1,3]oxazin-4-ylamino)-propionamide; MS: 550 (M+1)

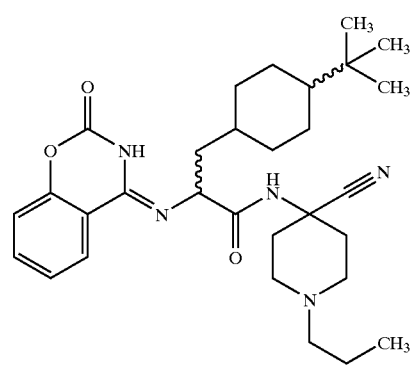

N-(4-Cyano-1-propyl-piperidin-4-yl)-3-(4-tert-butyl-cyclohexyl)-2-(2-oxo-2H-benzo[e][1,3]oxazin-4-ylamino)-propionamide; MS: 522 (M+1)

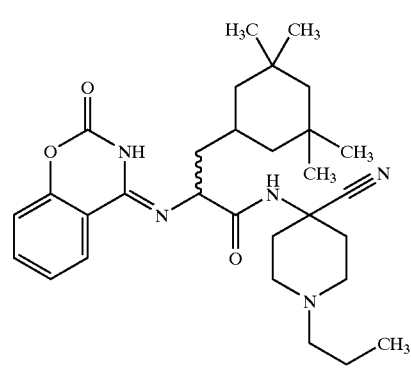

N-(4-Cyano-1-propyl-piperidin-4-yl)-3-(3,3,5,5-tetramethyl-cyclohexyl)-2-(2-oxo-2H-benzo[e][1,3]oxazin-4-ylamino)-propionamide; MS: 522 (M+1)

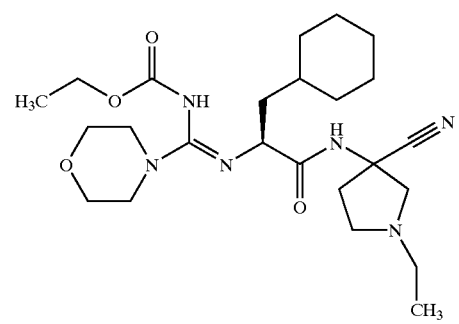

{[1-(3-Cyano-1-ethyl-pyrrolidin-3-ylcarbamoyl)-2-cyclohexyl-ethylamino]-morpholin-4-yl-methylene}-carbamic acid ethyl ester. MS: 477 (M+1).

N-(4-Cyano-1-methyl-piperidin-4-yl)-3-cyclohexyl-2-(7,8-difluoro-2-oxo-2H-benzo[e][1,3]oxazin-4-ylamino)-propionamide; MS: 474 (M+1)

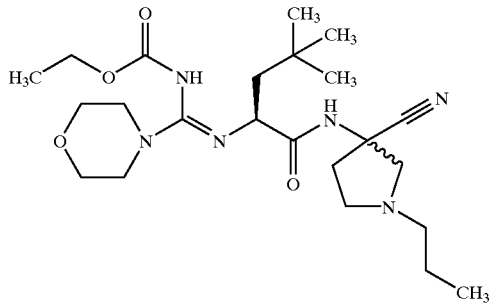

{[1-(3-Cyano-1-propyl-pyrrolidin-3-ylcarbamoyl)-3,3-dimethyl-butylamino]-morpholin-4-yl-methylene}-carbamic acid ethyl ester. MS: 465 (M+1).

{[1-(4-Cyano-1-cyclohexylmethyl-piperidin-4-ylcarbamoyl)-2-cyclohexyl-ethylamino]-morpholin-4-yl-methylene}-carbamic acid ethyl ester; MS: 559 (M+1)

({1-[3-Cyano-1-(4,4-dimethyl-cyclohexyl)-pyrrolidin-3-ylcarbamoyl]-3,3-dimethyl-butylamino}-morpholin-4-yl-methylene)-carbamic acid ethyl ester. MS: 533 (M+1).

3-Cyano-3-[4,4-dimethyl-2-(2-oxo-2H-benzo[e][1,3]oxazin-4-ylamino)-pentanoylamino]-azepane-1-carboxylic acid benzyl ester; MS: 546 (M+1)

4,4-Dimethyl-2-(2-oxo-2H-benzo[e][1,3]oxazin-4-ylamino)-pentanoic acid (3-cyano-1-propyl-azepan-3-yl)-amide; MS: 454 (M+1)

{[1-(4-Cyano-1-methyl-piperidin-4-ylcarbamoyl)-2-cyclohexyl-ethylamino]-morpholin-4-yl-methylene}-carbamic acid cyclohexyl ester; MS: 531 (M+1)

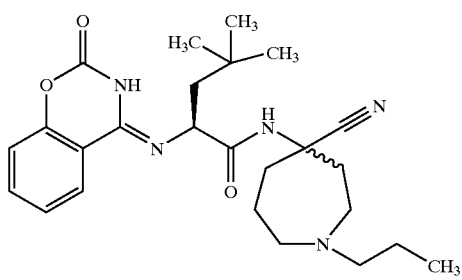
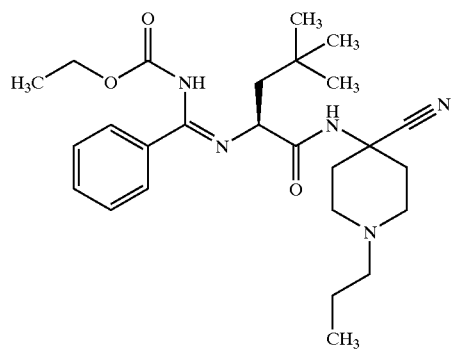

4,4-Dimethyl-2-(2-oxo-2H-benzo[e][1,3]oxazin-4-ylamino)-pentanoic acid (4-cyano-1-propyl-azepan-4-yl)-amide; MS: 454 (M+1)

{[1-(4-Cyano-1-propyl-piperidin-4-ylcarbamoyl)-3,3-dimethyl-butylamino]-phenyl-methylene}-carbamic acid ethyl ester; MS: 470 (M+1)

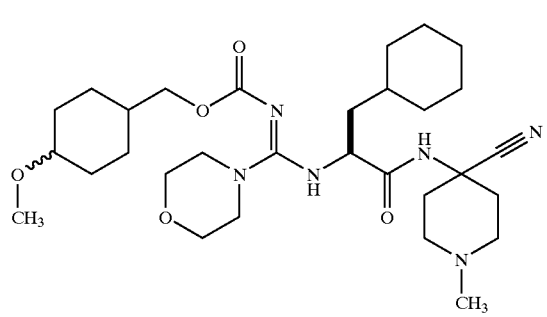
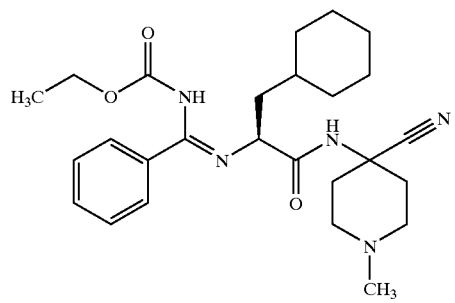

{[1-(4-Cyano-1-methyl-piperidin-4-ylcarbamoyl)-2-cyclohexyl-ethylamino]-morpholin-4-yl-methylene}-carbamic acid 4-methoxy-cyclohexylmethyl ester; MS: 575 (M+1)

{[1-(4-Cyano-1-methyl-piperidin-4-ylcarbamoyl)-2-cyclohexyl-ethylamino]-phenyl-methylene}-carbamic acid ethyl ester; MS: 468 (M+1)

More preferred compounds of the formulas (Ia) and (Ib) are chosen from the following:

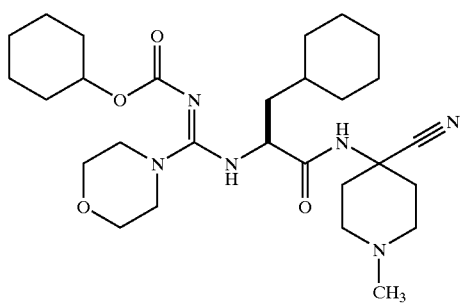
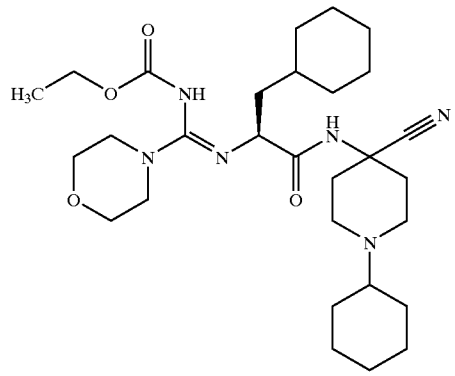

137

{[1-(4-cyano-1-cyclohexyl-piperidin-4-ylcarbamoyl)-2-cyclohexyl-ethylamino]-morpholin-4-yl-methylene}-carbamic acid ethyl ester; MS: 545 (M+1)

138

{[1-(4-cyano-1-methyl-piperidin-4-ylcarbamoyl)-2-cyclohexyl-ethylamino]-morpholin-4-yl-methylene}-carbamic acid allyl ester; MS: 489 (M+1)

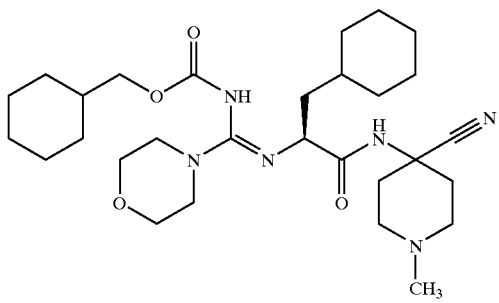

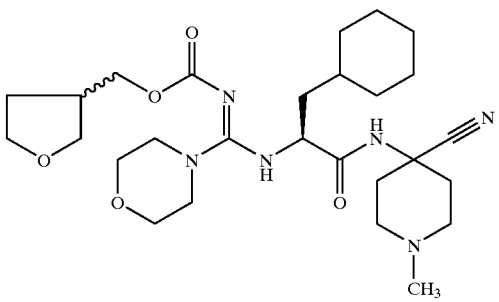

{[1-(4-cyano-1-methyl-piperidin-4-ylcarbamoyl)-2-cyclohexyl-ethylamino]-morpholin-4-yl-methylene}-carbamic acid cyclohexylmethyl ester; MS: 545 (M+1)

{[1-(4-cyano-1-methyl-piperidin-4-ylcarbamoyl)-2-cyclohexyl-ethylamino]-morpholin-4-yl-methylene}-carbamic acid tetrahydro-furan-3ylmethyl ester; MS: 533 (M+1)

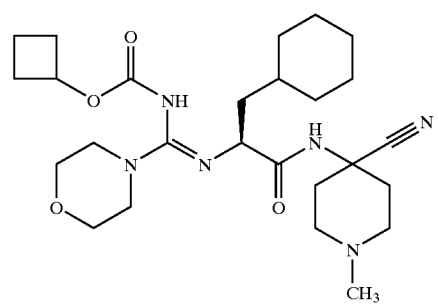

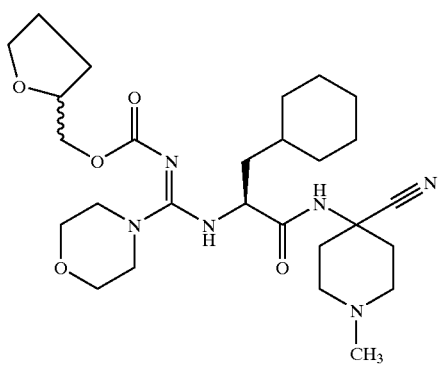

{[-1-(4-cyano-1-methyl-piperidin-4-ylcarbamoyl)-2-cyclohexyl-ethylamino]-morpholin-4-yl-methylene}-carbamic acid cyclobutyl ester; MS: 503 (M+1)

{[1-(4-cyano-1-methy-piperidin-4-ylcarbamoyl)-2-cyclohexyl-ethyl amino]-morpholin-4-yl-methylene}-carbamic acid tetrahydro-furan-2-ylmethyl ester; MS: 533 (M+1)

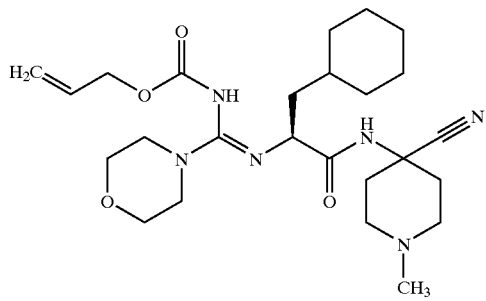

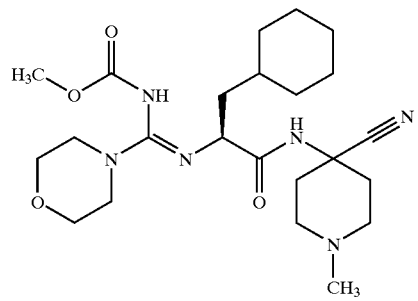

{[1-(4-Cyano-1-methyl-piperidin-4-ylcarbamoyl)-2-cyclohexyl-ethylimino]-morpholin-4-yl-methyl}-carbamic acid methyl ester; MS: 463 (M+1)

{[1-(4-Cyano-1-methyl-piperidin-4-ylcarbamoyl)-2-cyclohexyl-ethylimino]-morpholin-4-yl-methyl}-carbamic acid isobutyl ester; MS: 505 (M+1)

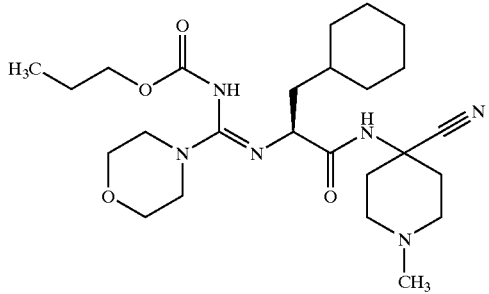

{[1-(4-Cyano-1-methyl-piperidin-4-ylcarbamoyl)-2-cyclohexyl-ethylimino]-morpholin-4-yl-methyl}-carbamic acid propyl ester; MS: 491 (M+1)

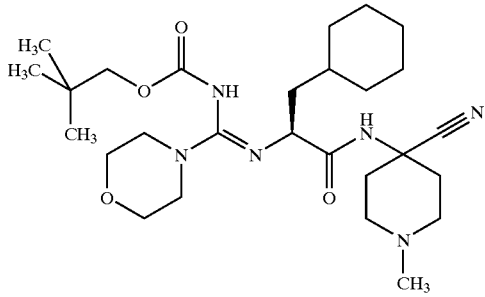

{[1-(4-Cyano-1-methyl-piperidin-4-ylcarbamoyl)-2-cyclohexyl-ethylimino]-morpholin-4-yl-methyl}-carbamic acid 2,2-dimethyl-propyl ester; MS: 519 (M+1)

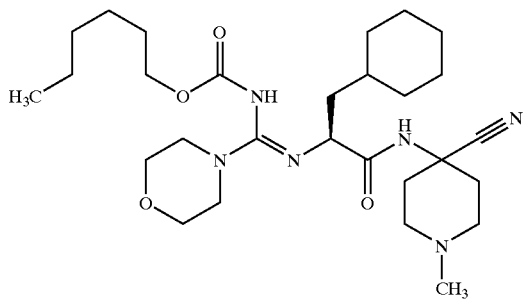

{[1-(4-Cyano-1-methyl-piperidin-4-ylcarbamoyl)-2-cyclohexyl-ethylimino]-morpholin-4-yl-methyl}-carbamic acid hexyl ester; MS: 533 (M+1)

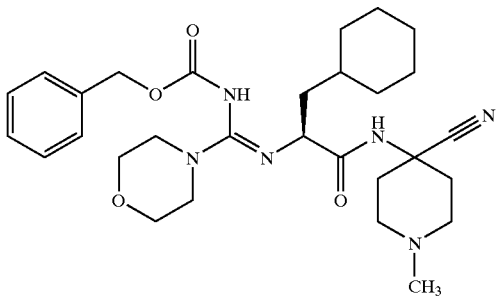

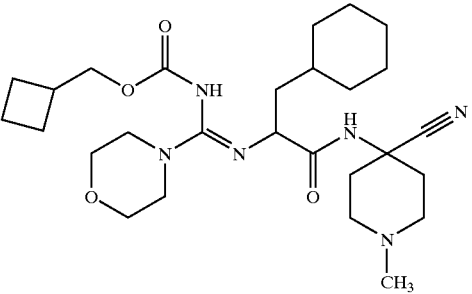

{[1-(4-Cyano-1-methyl-piperidin-4-ylcarbamoyl)-2-cyclohexyl-ethylimino]-morpholin-4-yl-methyl}-carbamic acid benzyl ester; MS: 539 (M+1)

{[1-(4-Cyano-1-methyl-piperidin-4-ylcarbamoyl)-2-cyclohexyl-ethylimino]-morpholin-4-yl-methyl}-carbamic acid cyclobutylmethyl ester; MS: 517 (M+1)

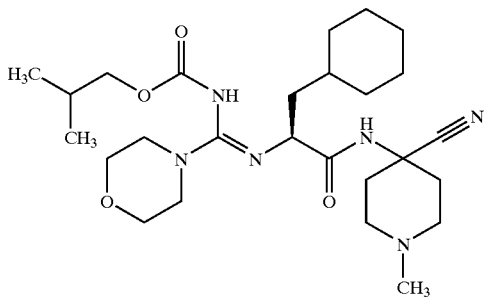

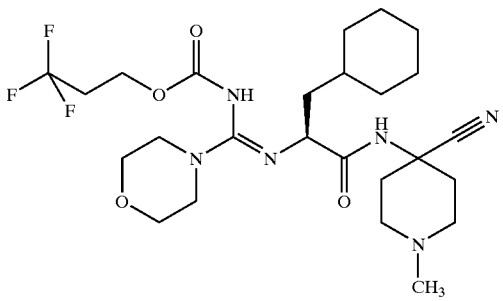

141

{[1-(4-Cyano-1-methyl-piperdin-4-ylcarbamoyl)-2-cyclohexyl-ethylimino]-morpholin-4-yl-methyl}-carbamic acid 3,3,3-trifluoro-propyl ester; MS: 545 (M+1)

142

{[1-(4-Cyano-1-methyl-piperidin-4-ylcarbamoyl)-2-cyclohexyl-ethylimino]-morpholin-4-yl-methyl}-carbamic acid 2-isopropoxy-ethyl ester; MS: 534 (M+1)

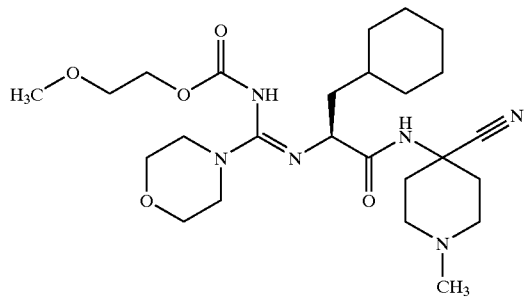

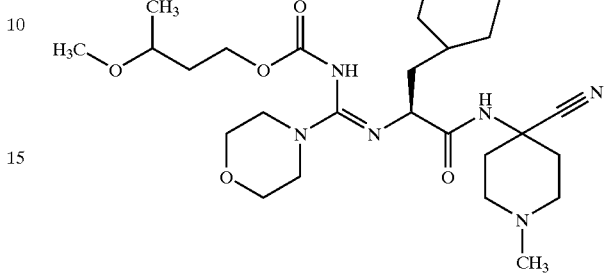

{[1-(4-Cyano-1-methyl-piperidin-4-ylcarbamoyl)-2-cyclohexyl-ethylimino]-morpholin-4-yl-methyl}-carbamic acid 2-methoxy-ethyl ester; MS: 507 (M+1)

{[1-(4-Cyano-1-methyl-piperidin-4-ylcarbamoyl)-2-cyclohexyl-ethylimino]-morpholin-4-yl-methyl}-carbamic acid 3-methoxy-butyl ester; MS: 534 (M+1)

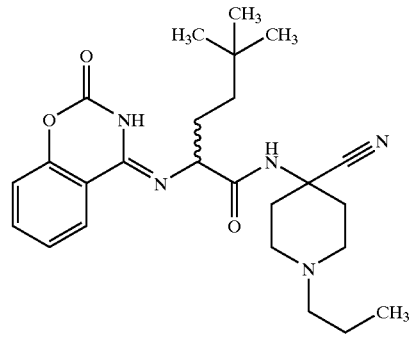

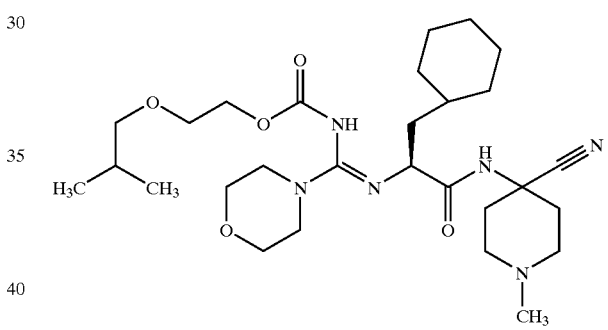

5,5-Dimethyl-2-(2-oxo-2,3-dihydro-benzo[e][1,3]oxazin-4-ylideneamino)-hexanoic acid (4-cyano-1-propyl-piperidin-4-yl)-amide; MS: 454 (M+1)

{[1-(4-Cyano-1-methyl-piperidin-4-ylcarbamoyl)-2-cyclohexyl-ethylimino]-morpholin-4-yl-methyl}-carbamic acid 2-isobutoxy-ethyl ester; MS: 549 (M+1)

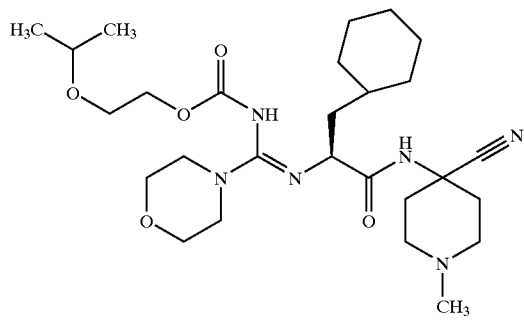

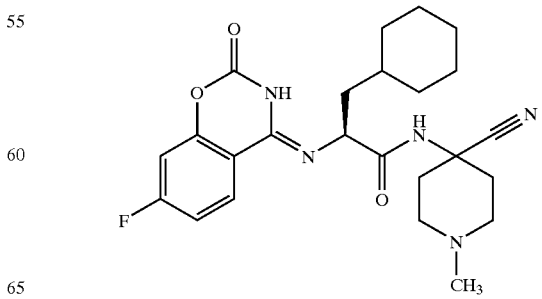

143

N-(4-Cyano-1-methyl-piperidin-4-yl)-4-cyclohexyl-2-(7-fluoro-2-oxo-2,3-dihydro-benzo[e][1,3]oxazin-4-ylideneamino)-butyramide; MS: 456 (M+1)

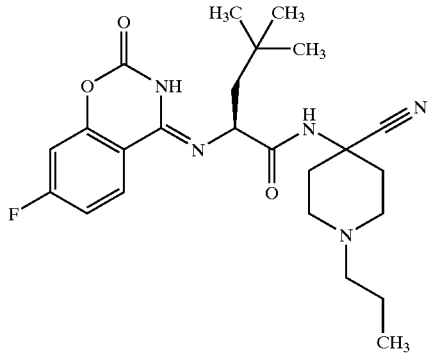

2-(7-Fluoro-2-oxo-2,3-dihydro-benzo[e][1,3]oxazin-4-ylideneamino)-5,5-dimethyl-hexanoic acid(4-cyano-1-propyl-piperidin-4-yl)-amide; MS: 458 (M+1)

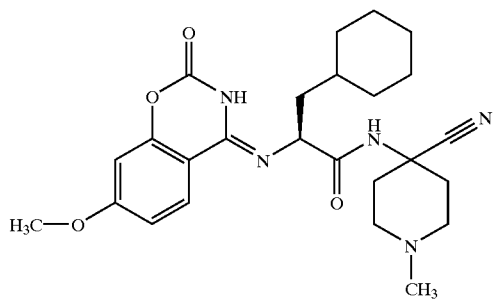

N-(4-Cyano-1-methyl-piperidin-4-yl)-4-cyclohexyl-2-(7-methoxy-2-oxo-2,3-dihydro-benzo[e][1,3]oxazin-4-ylideneamino)-butyramide; MS: 468 (M+1)

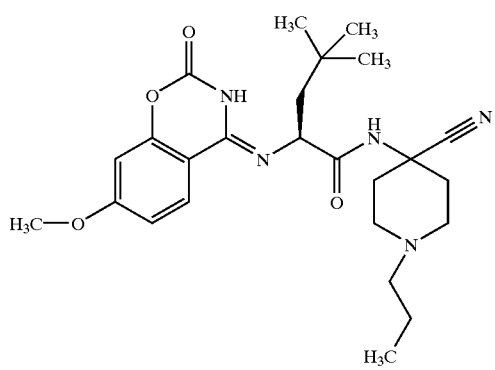

144

2-(7-Methoxy-2-oxo-2,3-dihydro-benzo[e][1,3]oxazin-4-ylideneamino)-5,5-dimethyl-hexanoic acid(4-cyano-1-propyl-piperidin-4-yl)-amide; MS: 470 (M+1)

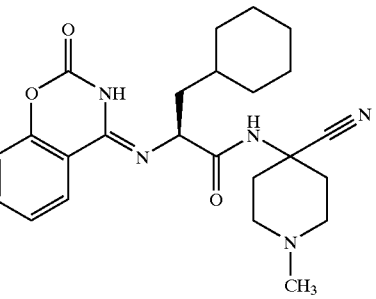

N-(4-Cyano-1-methyl-piperidin-4-yl)-3-cyclohexyl-2-(2-oxo-2,3-dihydro-benzo[e][1,3]oxazin-4-ylideneamino)-propionamide; MS: 438 (M+1).

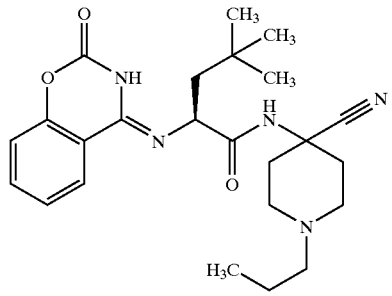

4,4-Dimethyl-2-(2-oxo-2,3-dihydro-benzo[e][1,3]oxazin-4-ylideneamino)-pentanoic acid (4-cyano-1-propyl-piperidin-4-yl)-amide; MS: 440 (M+1)

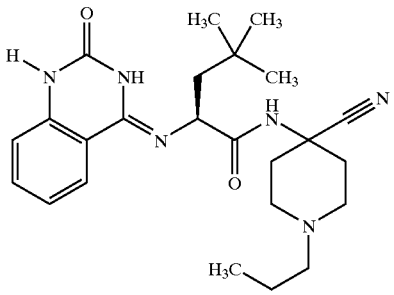

4,4-Dimethyl-2-(2-oxo-2,3-dihydro-1H-quinazolin-4-ylideneamino)-pentanoic acid (4-cyano-1-propyl-piperidin-4-yl)-amide; MS: 439 (M+1)

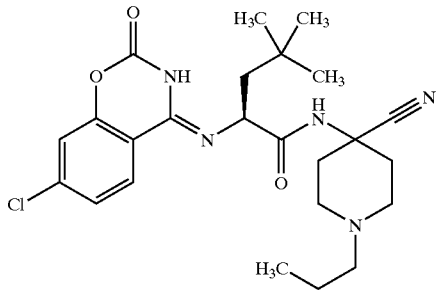

2-(7-Chloro-2-oxo-2,3-dihydro-benzo[e][1,3]oxazin-4-ylideneamino)-4,4-dimethyl-pentanoic acid (4-cyano-1-propyl-piperidin-4-yl)-amide; MS: 475 (M+1)

N-(4-Cyano-1-propyl-piperidin-4-yl)-3-cycloheptyl-2-(2-oxo-2,3-dihydro-benzo[e][1,3]oxazin-4-ylideneamino)-propionamide; MS: 480 (M+1)

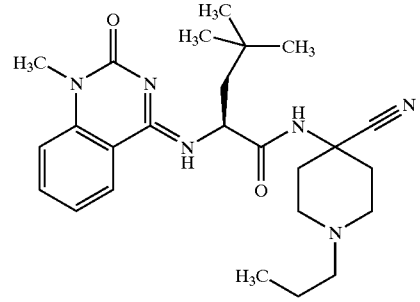

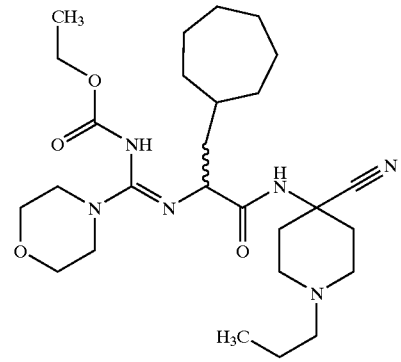

4,4-Dimethyl-2-(1-methyl-2-oxo-1,2-dihydro-quinazolin-4-ylamino)-pentanoic acid (4-cyano-1-propyl-piperidin-4-yl)-amide; MS: 453 (M+1)

{[1-(4-Cyano-1-propyl-piperidin-4-ylcarbamoyl)-2-cycloheptyl-ethylimino]-morpholin-4-yl-methyl}-carbamic acid ethyl ester; MS: 519 (M+1)

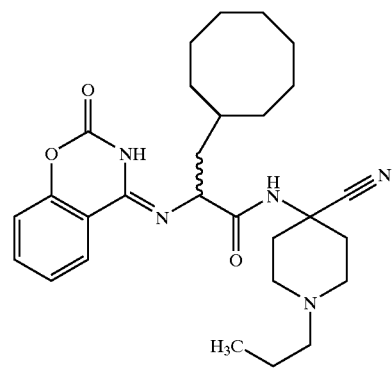

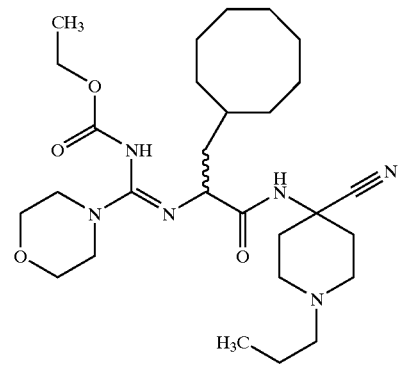

N-(4-Cyano-1-propyl-piperidin-4-yl)-3-cyclooctyl-2-(2-oxo-2,3-dihydro-benzo[e][1,3]oxazin-4-ylideneamino)-propionamide; MS: 494 (M+1)

{[1-(4-Cyano-1-propyl-piperidin-4-ylcarbamoyl)-2-cyclooctyl-ethylimino]-morpholin-4-yl-methyl}-carbamic acid ethyl ester; MS: 533 (M+1)

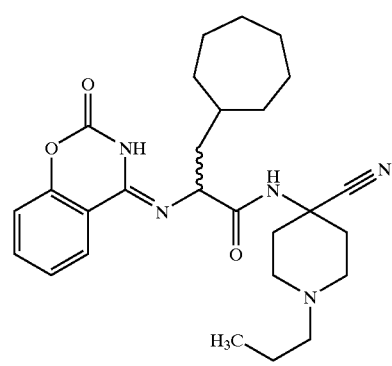

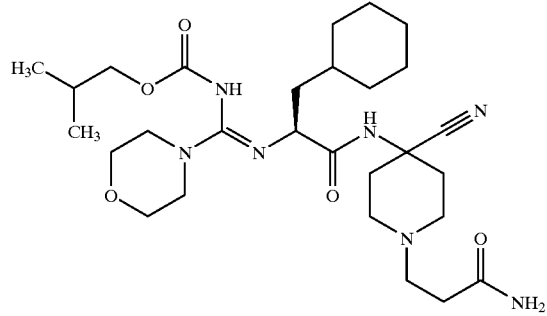

147

({1-[1-2-Carbamoyl-ethyl)-4-cyano-piperidin-4-ylcarbamoyl]-2-cyclohexyl-ethylamino}-morpholin-4-yl-methylene)-carbamic acid isobutyl ester; MS: 562 (M+1)

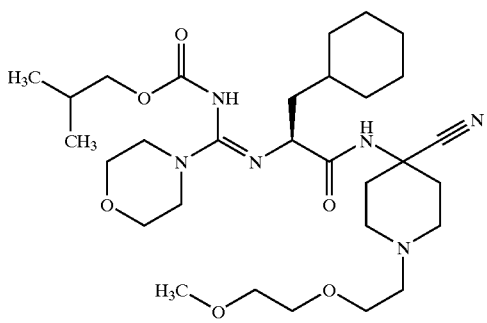

[(1-{4-Cyano-1-[2-(2-methoxyl-ethoxy)-ethyl]-piperidin-4-ylcarbamoyl}-2-cyclohexyl-ethylamino)-morpholin-4-yl-methylene]-carbamic acid isobutyl ester; MS: 593 (M+1)

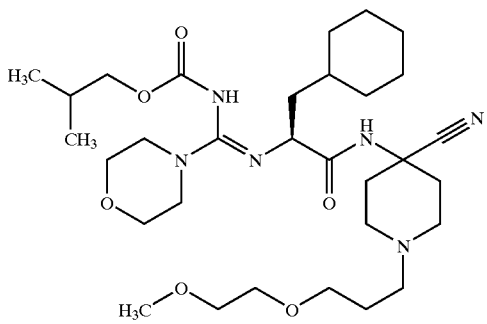

[(1-{4-Cyano-1-[3-(2-methoxyl-ethoxy)-propyl]-piperidin-4-ylcarbamoyl}-2-cyclohexyl-ethylamino)-morpholin-4-yl-methylene]-carbamic acid isobutyl ester; MS: 607 (M+1)

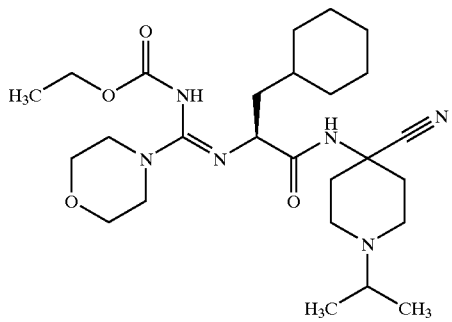

148

{[1-(4-Cyano-1-isopropyl-piperidin-4-ylcarbamoyl)-2-cyclohexyl-ethylamino]-morpholin-4-yl-methylene}-carbamic acid ethyl ester; MS: 505 (M+1)

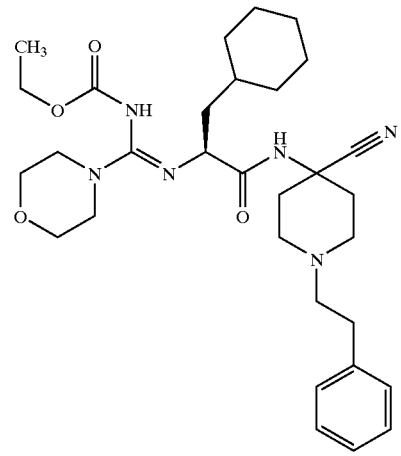

{[1-(4-Cyano-1-phenethyl-piperidin-4-ylcarbamoyl)-2-cyclohexyl-ethylamino]-morpholin-4-yl-methylene}-carbamic acid ethyl ester; MS: 567 (M+1)

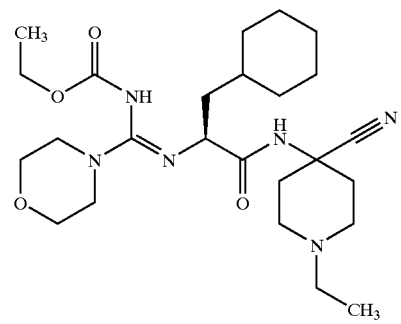

{[1-(4-Cyano-1-ethyl-piperidin-4-ylcarbamoyl)-2-cyclohexyl-ethylamino]-morpholin-4-yl-methylene}-carbamic acid ethyl ester; MS: 491 (M+1)

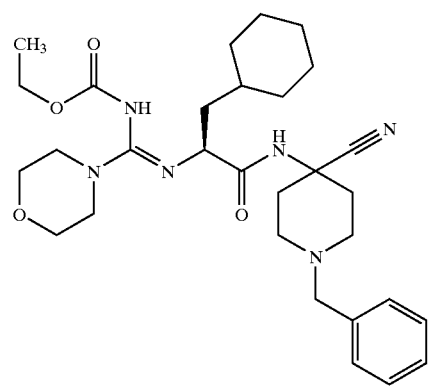

{[1-(1-Benzyl-4-cyano-piperidin-4-ylcarbamoyl)-2-cyclohexyl-ethylamino]-morpholin-4-yl-methylene}-carbamic acid ethyl ester; MS: 553 (M+1)

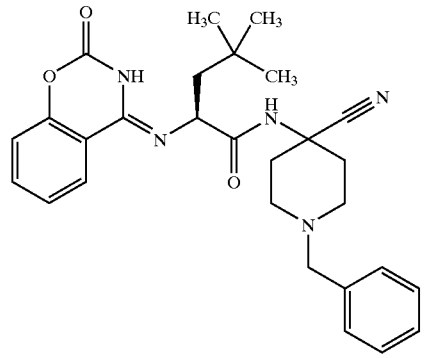

4,4-Dimethyl-2-(2-oxo-2H-benzo[e][1,3]oxazin-4-ylamino)-pentanoic acid (1-benzyl-4-cyano-piperidin-4-yl)-amide; MS: 488 (M+1)

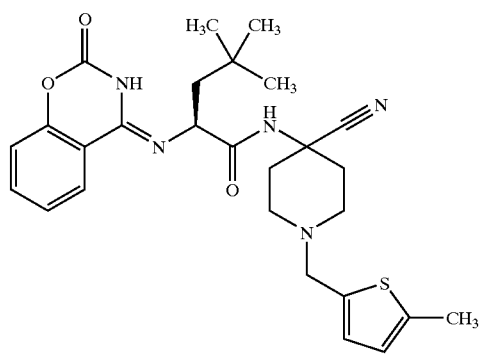

4,4-Dimethyl-2-(2-oxo-2H-benzo[e][1,3]oxazin-4-ylamino)-pentanoic acid [4-cyano-1-(5-methyl-thiophen-2-ylmethyl)-piperidin-4-yl]-amide; MS: 508 (M+1)

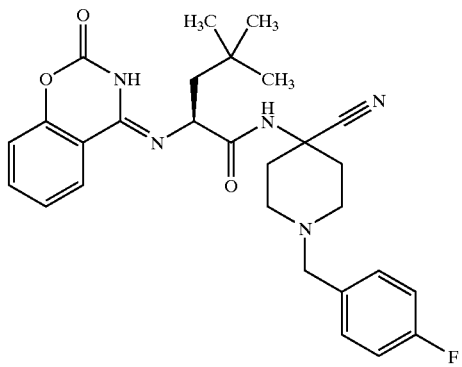

4,4-Dimethyl-2-(2-oxo-2H-benzo[e][1,3]oxazin-4-ylamino)-pentanoic acid [4-cyano-1-(4-fluoro-benzyl)-piperidin-4-yl]-amide; MS: 506 (M+1)

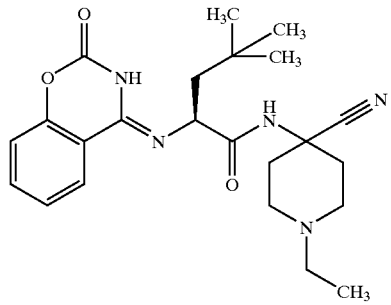

4,4-Dimethyl-2-(2-oxo-2H-benzo[e][1,3]oxazin-4-ylamino)-pentanoic acid (4-cyano-1-ethyl-piperidin-4-yl)-amide; MS: 426 (M+1)

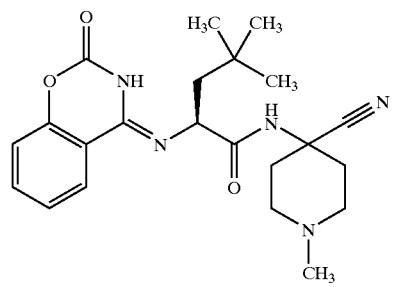

4,4-Dimethyl-2-(2-oxo-2H-benzo[e][1,3]oxazin-4-ylamino)-pentanoic acid (4-cyano-1-methyl-piperidin-4-yl)-amide; MS: 412 (M+1)

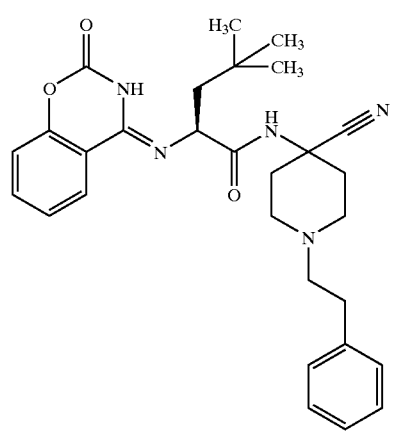

151

4,4-Dimethyl-2-(2-oxo-2H-benzo[e][1,3]oxazin-4-ylamino)-pentanoic acid (4-cyano-1-phenethyl-piperidin-4-yl)-amide; MS: 502 (M+1)

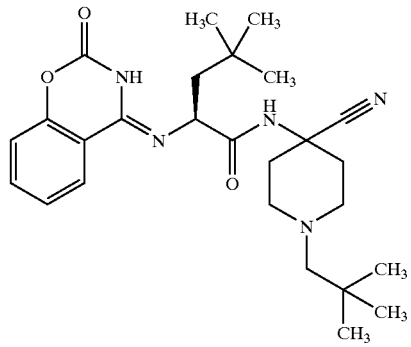

4,4-Dimethyl-2-(2-oxo-2H-benzo[e][1,3]oxazin-4-ylamino)-pentanoic acid [4-cyano-1-(2,2-dimethyl-propyl)-piperidin-4-yl]-amide; MS: 468 (M+1)

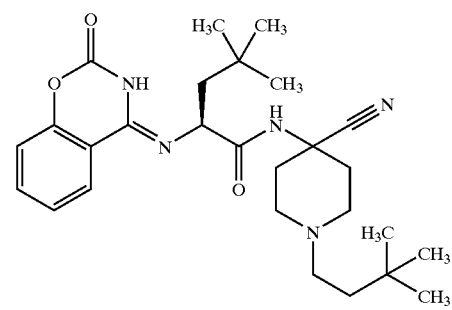

4,4-Dimethyl-2-(2-oxo-2H-benzo[c][1,3]oxazin-4-ylamino)-pentanoic acid [4-cyano-1-(3,3-dimethyl-butyl)-piperidin-4-yl]-amide; MS: 482 (M+1)

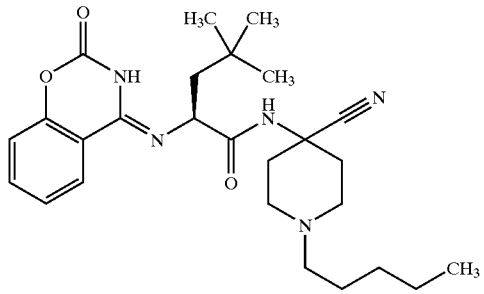

152

4,4-Dimethyl-2-(2-oxo-2H-benzo[e][1,3]oxazin-4-ylamino)-pentanoic acid (4-cyano-1-pentyl-piperidin-4-yl)-amide; MS: 468 (M+1)

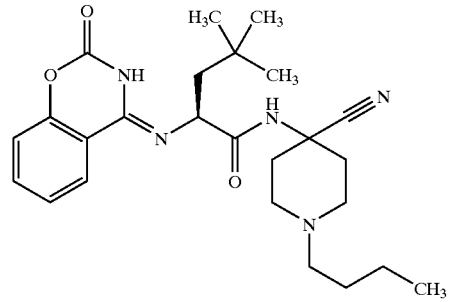

4,4-Dimethyl-2-(2-oxo-2H-benzo[e][1,3]oxazin-4-ylamino)-pentanoic acid (1-butyl-4-cyano-piperidin-4-yl)-amide; MS: 454(M+1)

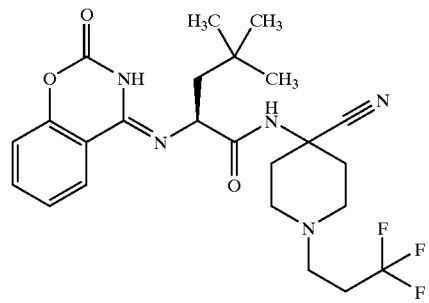

4,4-Dimethyl-2-(2-oxo-2H-benzo[e][1,3]oxazin-4-ylamino)-pentanoic acid [4-cyano-1-(3,3,3-trifluoro-propyl)-piperidin-4-yl]-amide; MS: 494 (M+1)

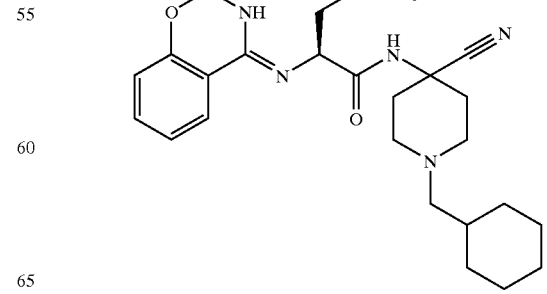

153

4,4-Dimethyl-2-(2-oxo-2H-benzo[e][1,3]oxazin-4-ylamino)-pentanoic acid (4-cyano-1-cyclohexylmethyl-piperidin-4-yl)-amide; MS: 494 (M+1)

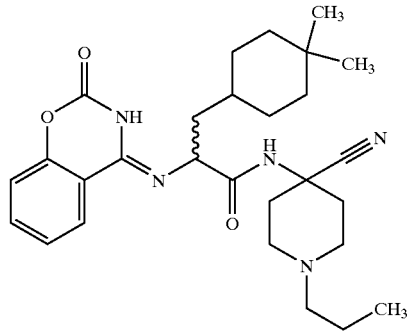

N-(4-Cyano-1-propyl-piperidin-4-yl)-3-(4,4-dimethyl-cyclohexyl)-2-(2-oxo-2H-benzo[e][1,3]oxazin-4-ylamino)-propionamide; MS: 494 (M+1)

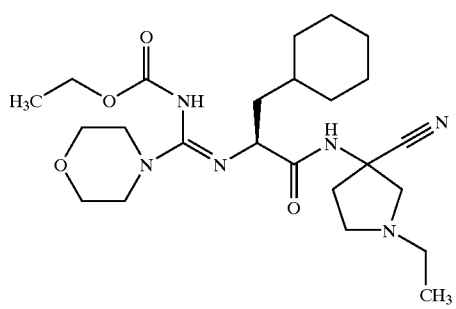

{[1-(3-Cyano-1-ethyl-pyrrolidin-3-ylcarbamoyl)-2-cyclohexyl-ethylamino]-morpholin-4-yl-methylene}-carbamic acid ethyl ester. MS: 477 (M+1)

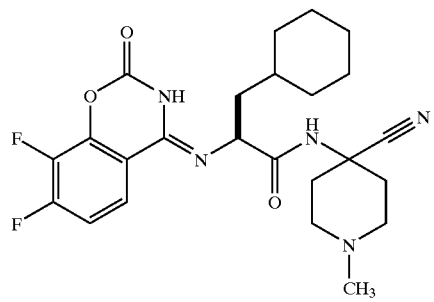

154

N-(4-Cyano-1-methyl-piperidin-4-yl)-3-cyclohexyl-2-(7,8-difluoro-2-oxo-2H-benzo[e][1,3]oxazin-4-ylamino)-propionamide; MS: 474 (M+1)

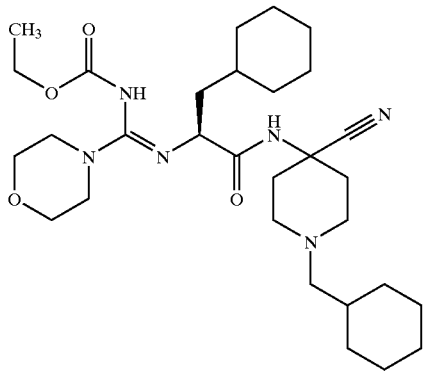

{[1-(4-Cyano-1-cyclohexylmethyl-piperidin-4-ylcarbamoyl)-2-cyclohexyl-ethylamino]-morpholin-4-yl-methylene}-carbamic acid ethyl ester; MS: 559 (M+1)

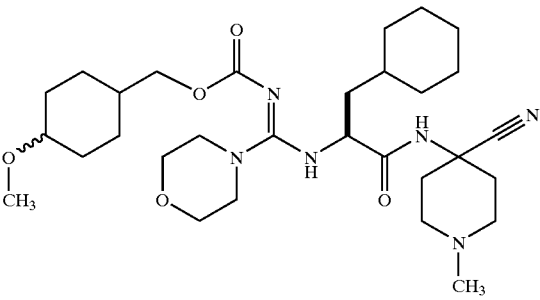

{[1-(4-Cyano-1-methyl-piperidin-4-ylcarbamoyl)-2-cyclohexyl-ethylamino]-morpholin-4-yl-methylene}-carbamic acid 4-methoxy-cyclohexylmethyl ester; MS: 575 (M+1)

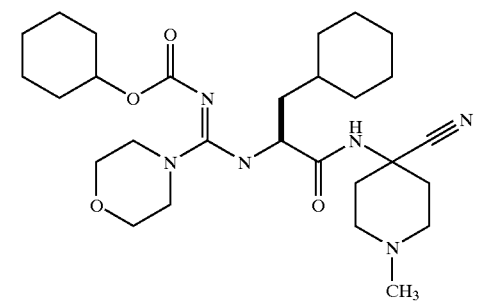

155

{[1-(4-Cyano-1-methyl-piperidin-4-ylcarbamoyl)-2-cyclohexyl-ethylamino]-morpholin-4-yl-methylene}-carbamic acid cyclohexyl ester; MS: 531 (M+1)

156

{[1-(3-cyano-1-isobutyl-piperdin-3-yl carbamoyl)-3,3-dimethyl-butylamino]-morpholin-4-yl-methylene}-carbamic acid ethyl ester; MS: 493 (M+1)

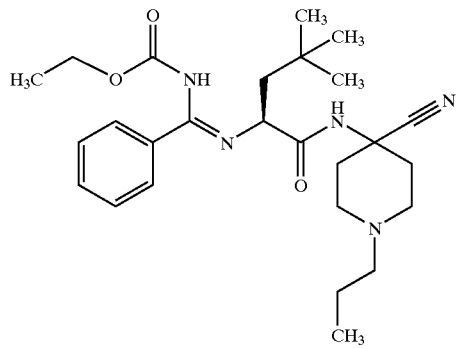
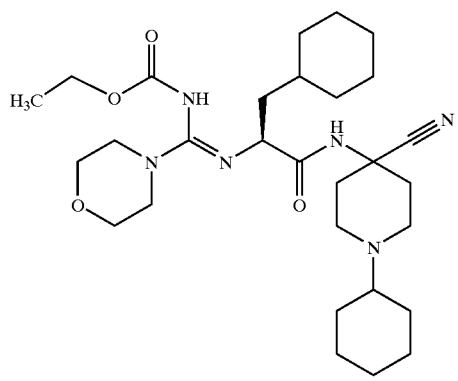

{[1-(4-Cyano-1-propyl-piperidin-4-ylcarbamoyl)-3,3-dimethyl-butylamino]-phenyl-methylene}-carbamic acid ethyl ester; MS: 470 (M+1)

{[1-(4-cyano-1-cyclohexyl-piperidin-4-ylcarbamoyl)-2-cyclohexyl-ethylamino]-morpholin-4-yl-methylene}-carbamic acid ethyl ester; MS: 545 (M+1)

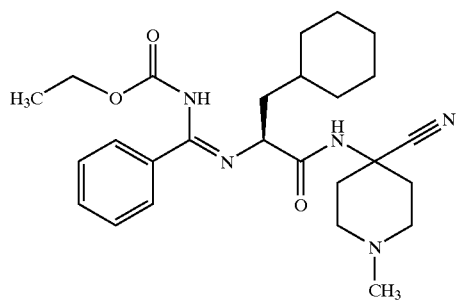
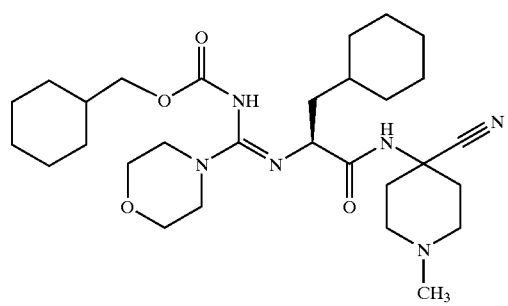

{[1-(4-Cyano-1-methyl-piperidin-4-ylcarbamoyl)-2-cyclohexyl-ethylamino]-phenyl-methylene}-carbamic acid ethyl ester; MS: 468 (M+1)

{[1-(4-cyano-1-methyl-piperdin-4-ylcarbamoyl)-2-cyclohexyl-ethylamino]-morpholin-4-yl-methylene}-carbamic acid cyclohexylmethyl ester; MS: 545 (M+1)

Most preferred compounds of the formulas (Ia) and (Ib) are those chosen from the following:

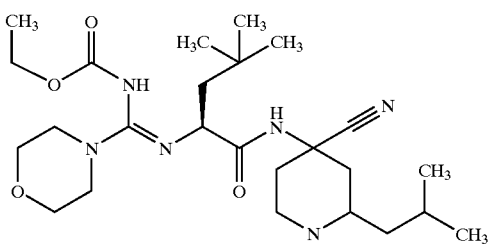
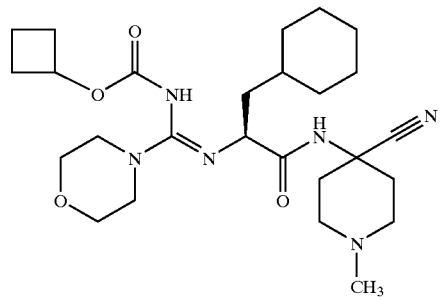

157

{[-1-(4-cyano-1-methyl-piperidin-4-ylcarbamoyl)-2-cyclohexyl-ethylamino]-morpholin-4-yl-methylene}-carbamic acid cyclobutyl ester; MS: 503 (M+1)

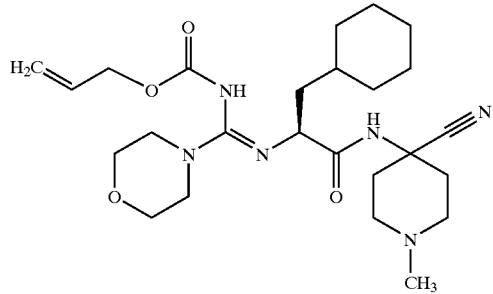

{[1-(4-cyano-1-methyl-piperidin-4-ylcarbamoyl)-2-cyclohexyl-ethylamino]-morpholin-4-yl-methylene}-carbamic acid allyl ester; MS: 489 (M+1)

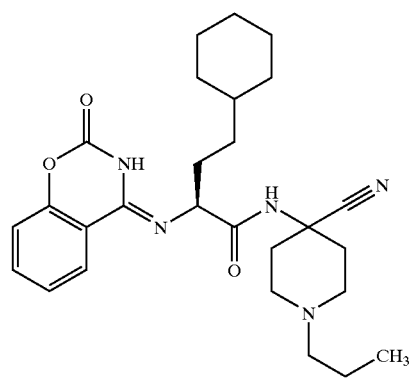

N-(4-Cyano-1-propyl-piperidin-4-yl)-4-cyclohexyl-2-(2-oxo-2,3-dihydro-benzo[e][1,3]oxazin-4-ylideneamino)-butyramide; MS: 480 (M+1)

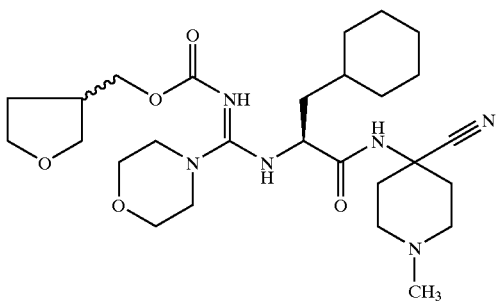

158

{[1-(4-cyano-1-methy-piperdin-4-ylcarbamoyl)-2-cyclohexyl-ethylamino]-morpholin-4-yl-methylene}-carbamic acid tetrahydro-furan-3ylmethyl ester; MS: 533 (M+1)

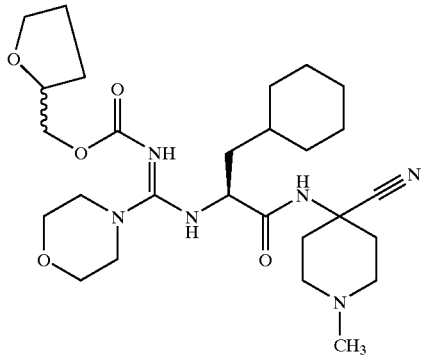

{[1-(4-cyano-1-methy-piperidin-4-ylcarbamoyl)-2-cyclohexyl-ethyl amino]-morpholin-4-yl-methylene}-carbamic acid tetrahydro-furan-2-ylmethyl ester; MS: 533 (M+1)

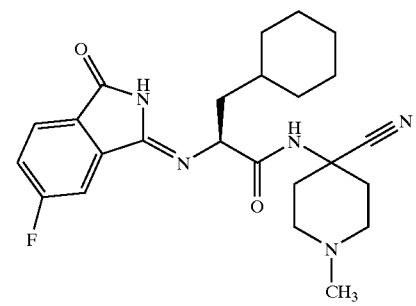

N-(4-Cyano-1-methyl-piperidin-4-yl)-3-cyclohexyl-2-(6-fluoro-3-oxo-2,3-dihydro-isoindol-1-ylideneamino)-propionamide; MS: 440 (M+1)

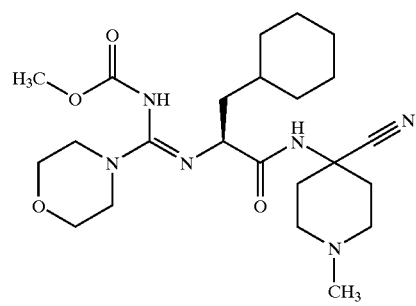

{[1-(4-Cyano-1-methyl-piperidin-4-ylcarbamoyl)-2-cyclohexyl-ethylimino]-morpholin-4-yl-methyl}-carbamic acid methyl ester; MS: 463 (M+1)

{[1-(4-Cyano-1-methyl-piperidin-4-ylcarbamoyl)-2-cyclohexyl-ethylimino]-morpholin-4-yl-methyl}-carbamic acid isobutyl ester; MS: 505 (M+1)

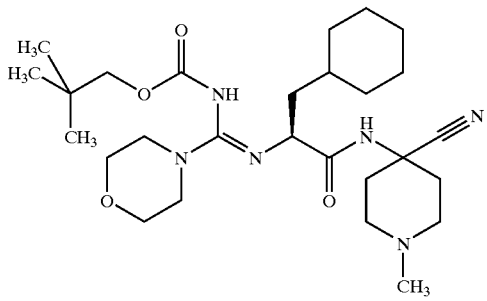

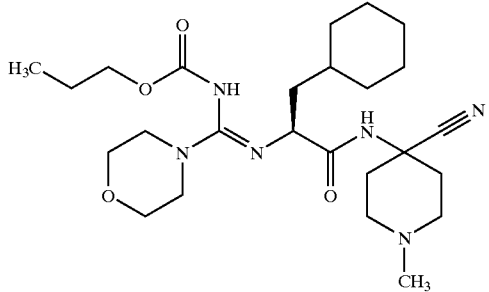

{[1-(4-Cyano-1-methyl-piperidin-4-ylcarbamoyl)-2-cyclohexyl-ethylimino]-morpholin-4-yl-methyl}-carbamic acid 2,2-dimethyl-propyl ester; MS: 519 (M+1)

{[1-(4-Cyano-1-methyl-piperidin-4-ylcarbamoyl)-2-cyclohexyl-ethylimino]-morpholin-4-yl-methyl}-carbamic acid propyl ester; MS: 491 (M+1)

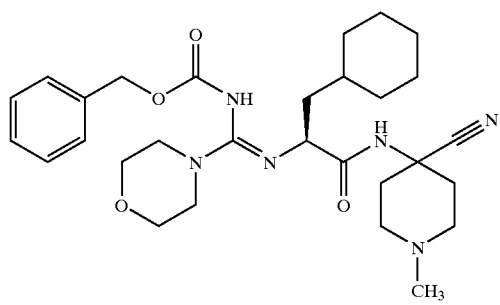

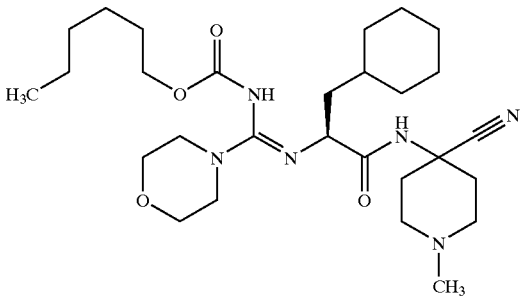

{[1-(4-Cyano-1-methyl-piperidin-4-ylcarbamoyl)-2-cyclohexyl-ethylimino]-morpholin-4-yl-methyl}-carbamic acid benzyl ester; MS: 539 (M+1)

{[1-(4-Cyano-1-methyl-piperidin-4-ylcarbamoyl)-2-cyclohexyl-ethylimino]-morpholin-4-yl-methyl}-carbamic acid hexyl ester; MS: 533 (M+1)

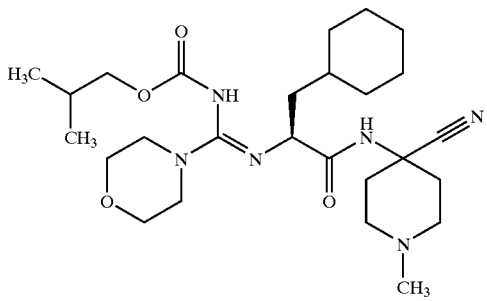

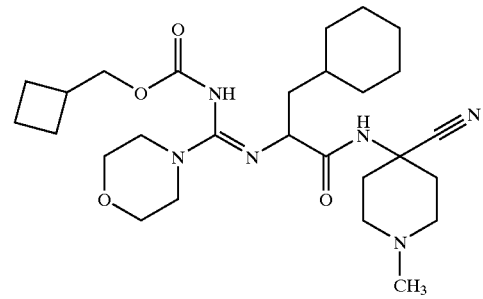

{[1-(4-Cyano-1-methyl-piperidin-4-ylcarbamoyl)-2-cyclohexyl-ethylimino]-morpholin-4-yl-methyl}-carbamic acid cyclobutylmethyl ester; MS: 517 (M+1)

5,5-Dimethyl-2-(2-oxo-2,3-dihydro-benzo[e][1,3]oxazin-4-ylideneamino)-hexanoic acid (4-cyano-1-propyl-piperidin-4-yl)-amide; MS: 454 (M+1)

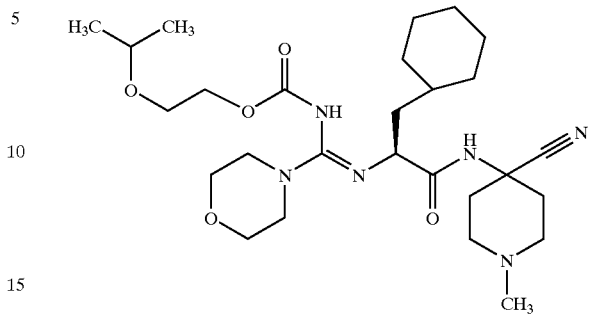

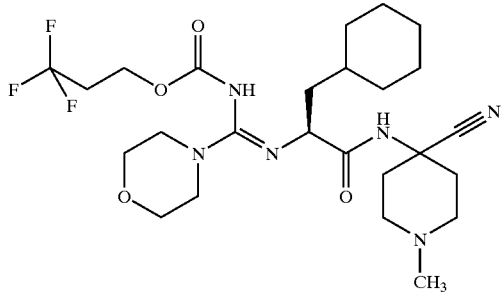

{[1-(4-Cyano-1-methyl-piperidin-4-ylcarbamoyl)-2-cyclohexyl-ethylimino]-morpholin-4-yl-methyl}-carbamic acid 2-isopropoxy-ethyl ester; MS: 534 (M+1)

{[1-(4-Cyano-1-methyl-piperidin-4-ylcarbamoyl)-2-cyclohexyl-ethylimino]-morpholin-4-yl-methyl}-carbamic acid 3,3,3-trifluoro-propyl ester; MS: 545 (M+1)

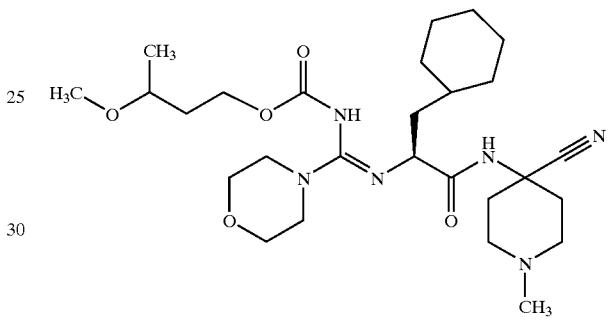

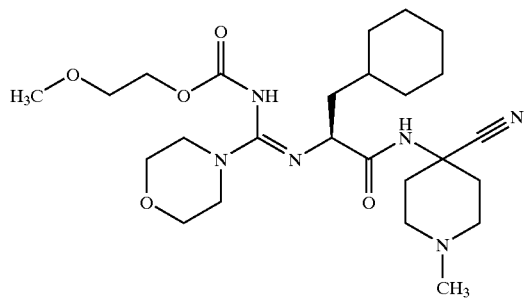

{[1-(4-Cyano-1-methyl-piperidin-4-ylcarbamoyl)-2-cyclohexyl-ethylimino]-morpholin-4-yl-methyl}-carbamic acid 3-methoxy-butyl ester; MS: 534 (M+1)

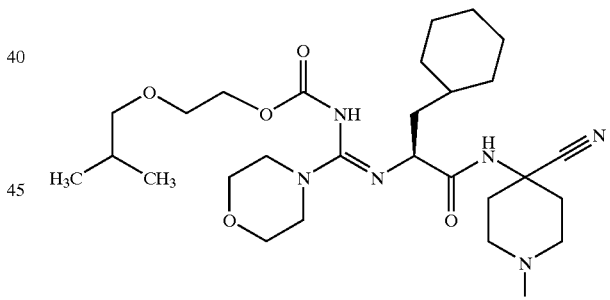

{[1-(4-Cyano-1-methyl-piperidin-4-ylcarbamoyl)-2-cyclohexyl-ethylimino]-morpholin-4-yl-methyl}-carbamic acid 2-methoxy-ethyl ester; MS: 507 (M+1)

{[1-(4-Cyano-1-methyl-piperidin-4-ylcarbamoyl)-2-cyclohexyl-ethylimino]-morpholin-4-yl-methyl}-carbamic acid 2-isobutoxy-ethyl ester; MS: 549 (M+1)

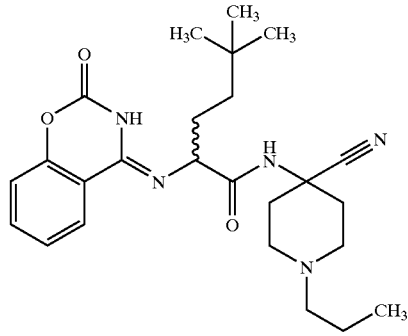

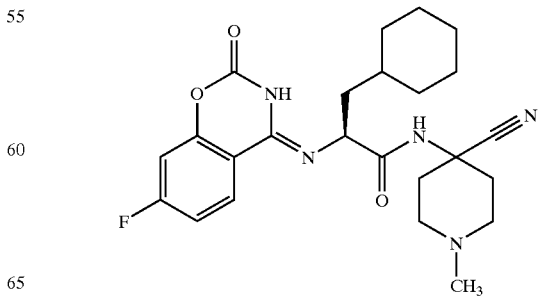

163

N-(4-Cyano-1-methyl-piperidin-4-yl)-4-cyclohexyl-2-(7-fluoro-2-oxo-2,3-dihydro-benzo[e][1,3]oxazin-4-ylideneamino)-butyramide; MS: 456 (M+1)

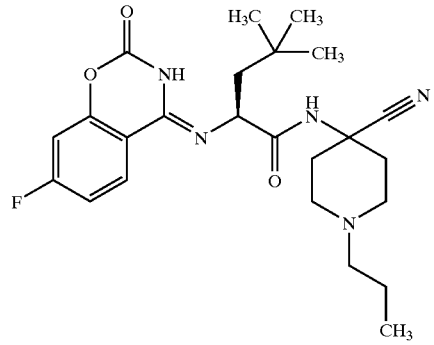

2-(7-Fluoro-2-oxo-2,3-dihydro-benzo[e][1,3]oxazin-4-ylideneamino)-5,5-dimethyl-hexanoic acid(4-cyano-1-propyl-piperidin-4-yl)-amide; MS: 458 (M+1)

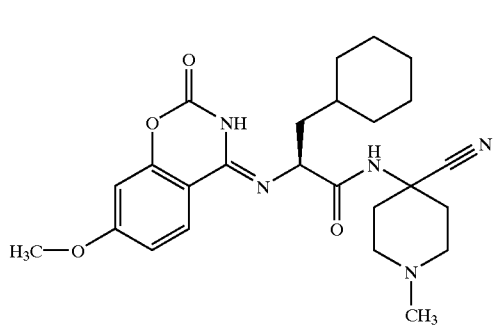

N-(4-Cyano-1-methyl-piperidin-4-yl)-4-cyclohexyl-2-(7-methoxy-2-oxo-2,3-dihydro-benzo[e][1,3]oxazin-4-ylideneamino)-butyramide; MS: 468 (M+1)

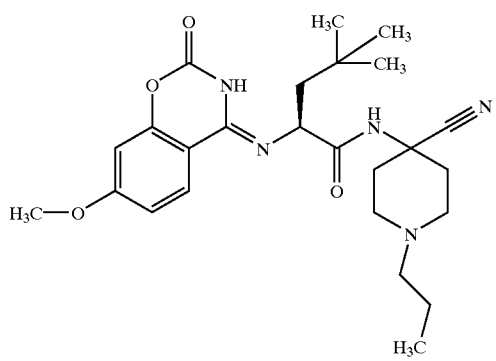

164

2-(7-Methoxy-2-oxo-2,3-dihydro-benzo[e][1,3]oxazin-4-ylideneamino)-5,5-dimethyl-hexanoic acid(4-cyano-1-propyl-piperidin-4-yl)-amide; MS: 470 (M+1)

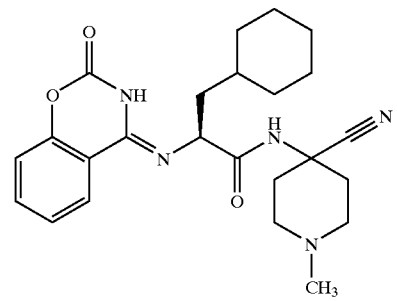

N-(4-Cyano-1-methyl-piperidin-4-yl)-3-cyclohexyl-2-(2-oxo-2,3-dihydro-benzo[e][1,3]oxazin-4-ylideneamino)-propionamide; MS: 438 (M+1).

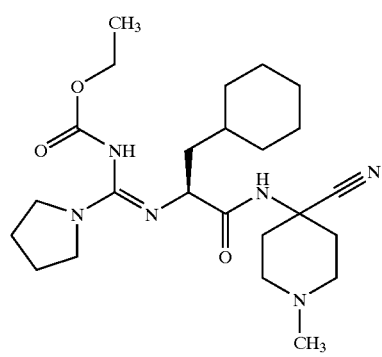

{[1-(4-Cyano-1-methyl-piperidin-4-ylcarbamoyl)-2-cyclohexyl-ethylimino]-pyrrolidin-1-yl-methyl}-carbamic acid ethyl ester; MS: 461 (M+1).

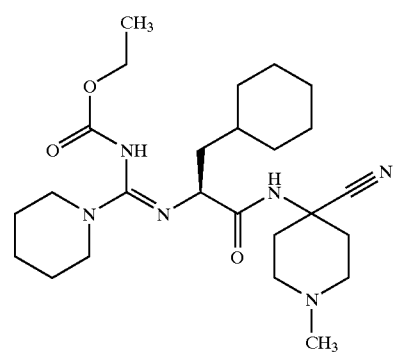

{[1-(4-Cyano-1-methyl-piperidin-4-ylcarbamoyl)-2-cyclohexyl-ethylimino]-piperidin-1-yl-methyl}-carbamic acid ethyl ester; MS: 475 (M+1).

[[1-(4-Cyano-1-methyl-piperidin-4-ylcarbamoyl)-2-cyclohexyl-ethylimino]-(4-phenyl-piperazin-1-yl)-methyl]-carbamic acid ethyl ester; MS: 552 (M+1).

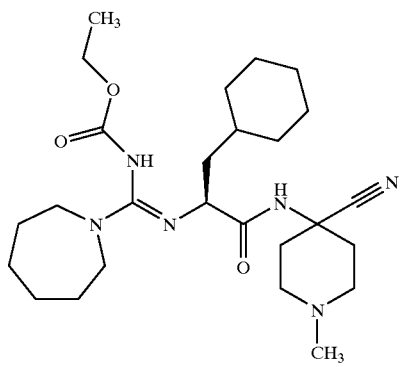

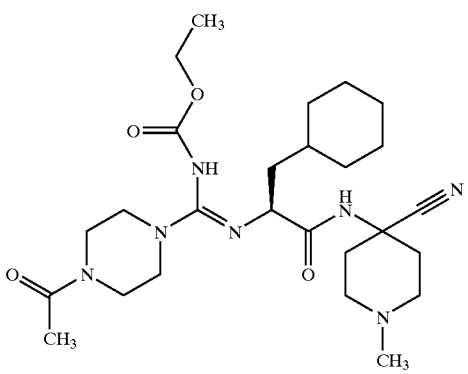

{Azepan-1-yl-[1-(4-cyano-1-methyl-piperidin-4-ylcarbamoyl)-2-cyclohexyl-ethylimino]-methyl}-carbamic acid ethyl ester; MS: 489 (M+1).

{(4-Acetyl-piperazin-1-yl)-[1-(4-cyano-1-methyl-piperidin-4-ylcarbamoyl)-2-cyclohexyl-ethylimino]-methyl}-carbamic acid ethyl ester; MS: 518 (M+1).

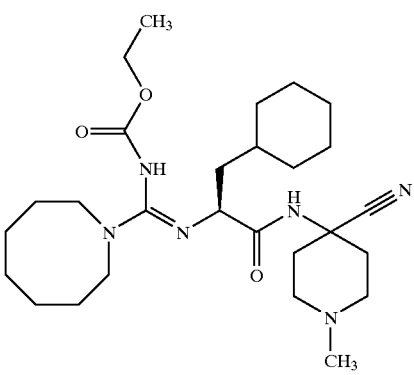

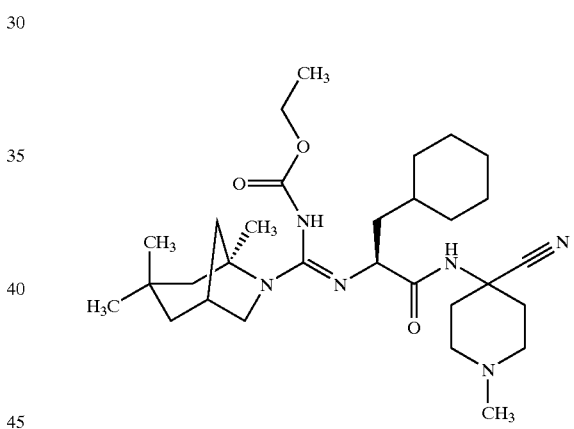

{Azocan-1-yl-[1-(4-cyano-1-methyl-piperidin-4-ylcarbamoyl)-2-cyclohexyl-ethylimino]-methyl}-carbamic acid ethyl ester; MS: 503 (M+1).

[[1-(4-Cyano-1-methyl-piperidin-4-ylcarbamoyl)-2-cyclohexyl-ethylimino]-(3,3,5-trimethyl-6-aza-bicyclo[3.2.1]oct-6-yl)-methyl]-carbamic acid ethyl ester; MS: 543 (M+1).

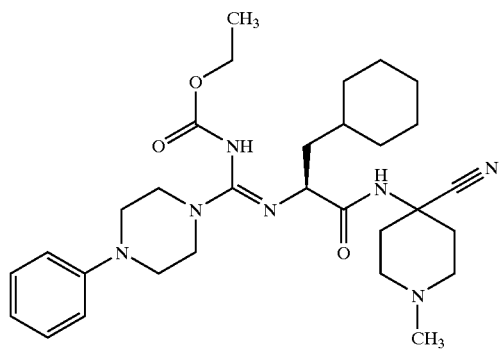

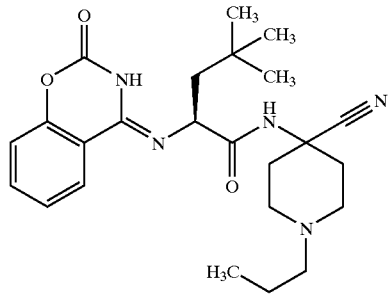

4,4-Dimethyl-2-(2-oxo-2,3-dihydro-benzo[e][1,3]oxazin-4-ylideneamino)-pentanoic acid (4-cyano-1-propyl-piperidin-4-yl)-amide; MS: 440 (M+1)

[[1-(4-Cyano-1-methyl-piperidin-4-ylcarbamoyl)-2-cyclohexyl-ethylimino]-(2,6-dimethyl-morpholin-4-yl)-methyl]-carbamic acid ethyl ester; MS: 505 (M+1)

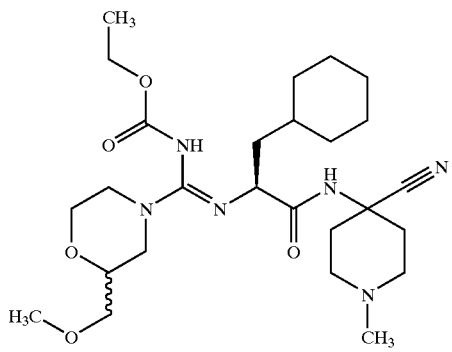

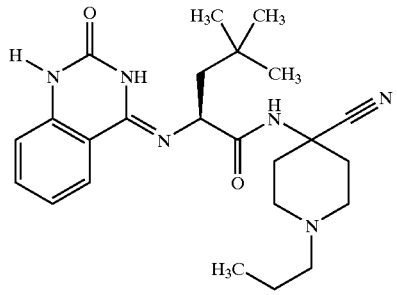

[[1-(4-Cyano-1-methyl-piperidin-4-ylcarbamoyl)-2-cyclohexyl-ethylimino]-(2-methoxymethyl-morpholin-4-yl)-methyl]-carbamic acid ethyl ester; MS: 521 (M+1)

4,4-Dimethyl-2-(2-oxo-2,3-dihydro-1H-quinazolin-4-ylideneamino)-pentanoic acid (4-cyano-1-propyl-piperidin-4-yl)-amide; MS: 439 (M+1)

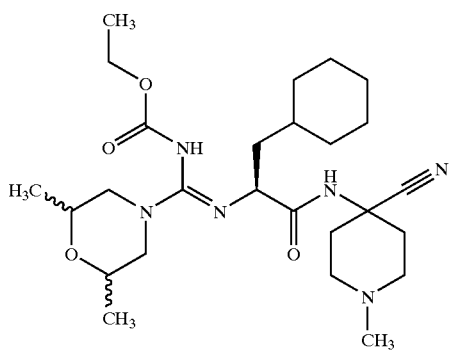

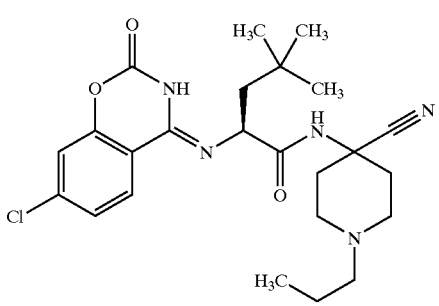

[[1-(4-Cyano-1-methyl-piperidin-4-ylcarbamoyl)-2-cyclohexyl-ethylimino]-(2,6-dimethyl-morpholin-4-yl)-methyl]-carbamic acid ethyl ester; MS: 505 (M+1)

2-(7-Chloro-2-oxo-2,3-dihydro-benzo[e][1,3]oxazin-4-ylideneamino)-4,4-dimethyl-pentanoic acid (4-cyano-1-propyl-piperidin-4-yl)-amide; MS: 475 (M+1)

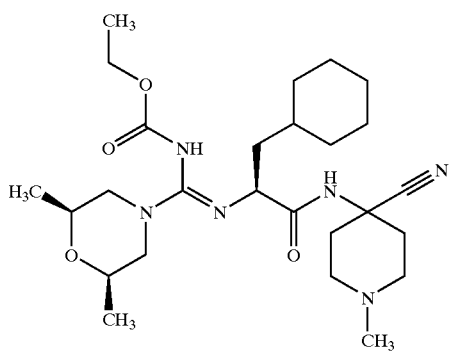

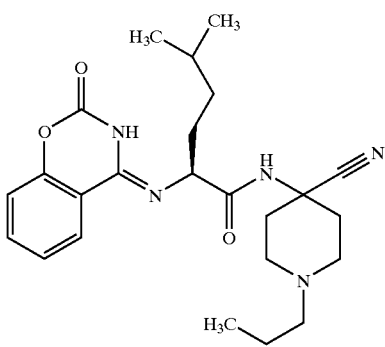

5-Methyl-2-(2-oxo-2,3-dihydro-benzo[e][1,3]oxazin-4-ylideneamino)-hexanoic acid (4-cyano-1-propyl-piperidin-4-yl)-amide; MS: 440 (M+1)

N-(4-Cyano-1-propyl-piperidin-4-yl)-3-cycloheptyl-2-(2-oxo-2,3-dihydro-benzo[e][1,3]oxazin-4-ylideneamino)-propionamide; MS: 480 (M+1)

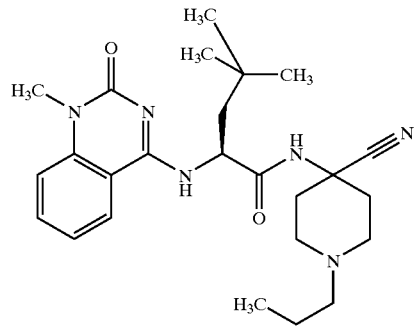

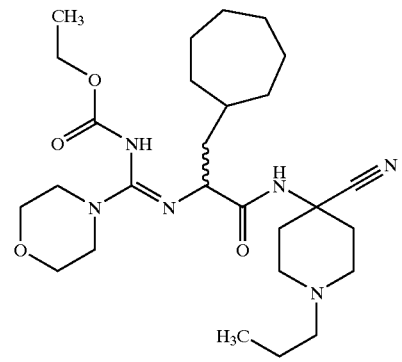

4,4-Dimethyl-2-(1-methyl-2-oxo-1,2-dihydro-quinazolin-4-ylamino)-pentanoic acid (4-cyano-1-propyl-piperidin-4-yl)-amide; MS: 453 (M+1)

{[1-(4-Cyano-1-propyl-piperidin-4-ylcarbamoyl)-2-cycloheptyl-ethylimino]-morpholin-4-yl-methyl}-carbamic acid ethyl ester; MS: 519 (M+1)

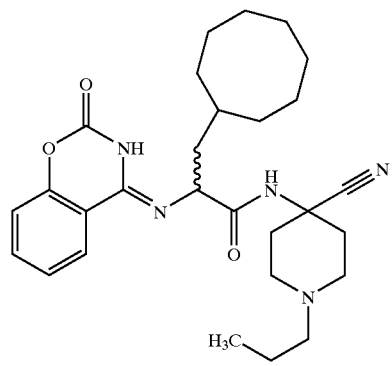

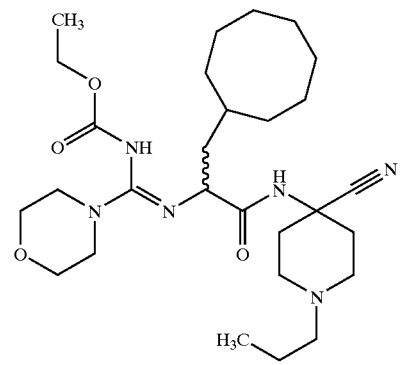

N-(4-Cyano-1-propyl-piperidin-4-yl)-3-cyclooctyl-2-(2-oxo-2,3-dihydro-benzo[e][1,3]oxazin-4-ylideneamino)-propionamide; MS: 494 (M+1)

{[1-(4-Cyano-1-propyl-piperidin-4-ylcarbamoyl)-2-cyclooctyl-ethylimino]-morpholin-4-yl-methyl}-carbamic acid ethyl ester; MS: 533 (M+1)

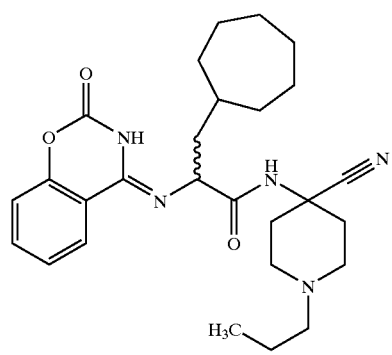

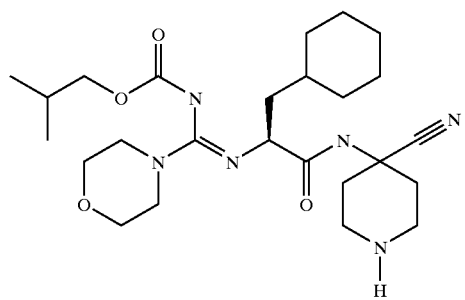

171

{[1-(4-Cyano-piperidin-4-ylcarbamoyl)-2-cyclohexyl-ethylamino]-morpholin-4-yl-methylene}-carbamic acid isobutyl ester; MS: 491 (M+1)

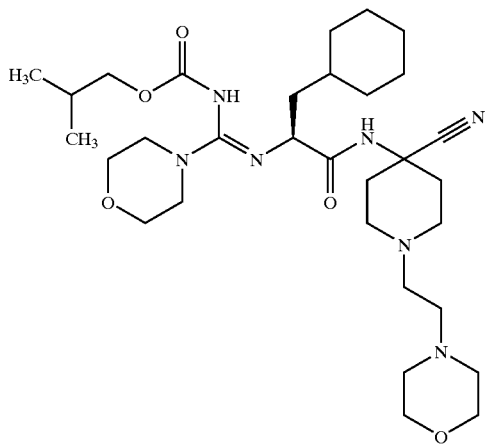

({1-[4-Cyano-1-(2-morpholin-4-yl-ethyl)-piperidin-4-ylcarbamoyl]-2-cyclohexyl-ethylamino}-morpholin-4-yl-methylene)-carbamic acid isobutyl ester; MS: 604 (M+1)

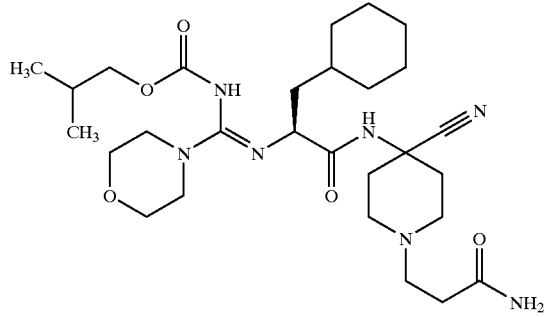

({1-[1-2-Carbamoyl-ethyl)-4-cyano-piperidin-4-ylcarbamoyl]-2-cyclohexyl-ethylamino}-morpholin-4-yl-methylene)-carbamic acid isobutyl ester; MS: 562 (M+1)

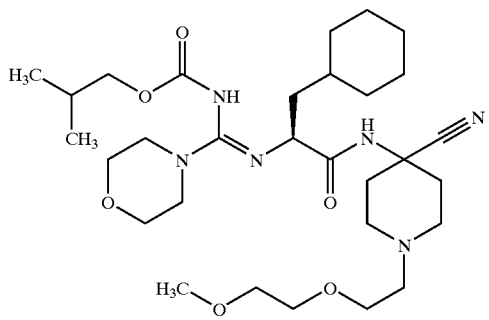

172

[(1-{4-Cyano-1-[2-(2-methoxyl-ethoxy)-ethyl]-piperidin-4-ylcarbamoyl}-2-cyclohexyl-ethylamino)-morpholin-4-yl-methylene]-carbamic acid isobutyl ester; MS: 593 (M+1)

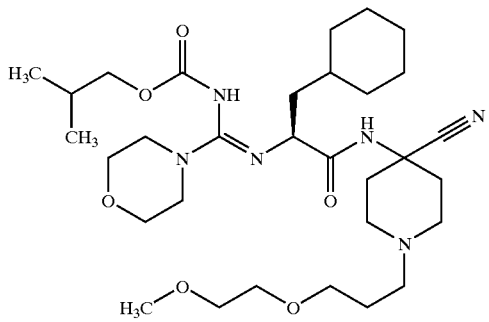

[(1-{4-Cyano-1-[3-(2-methoxyl-ethoxy)-propyl]-piperidin-4-ylcarbamoyl}-2-cyclohexyl-ethylamino)-morpholin-4-yl-methylene]-carbamic acid isobutyl ester; MS: 607 (M+1)

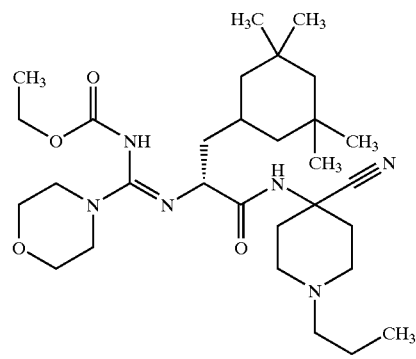

{[1-(4-Cyano-1-propyl-piperidin-4-ylcarbamoyl)-2-(3,3,5,5-tetramethyl-cyclohexyl)-ethylamino-]-morpholin-4-yl-methylene}-carbamic acid ethyl ester; MS: 561 (M+1)

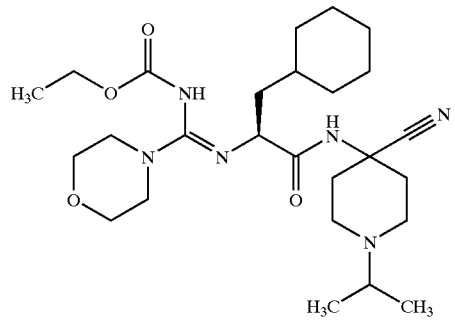

173

{[1-(4-Cyano-1-isopropyl-piperidin-4-ylcarbamoyl)-2-cyclohexyl-ethylamino]-morpholin-4-yl-methylene}-carbamic acid ethyl ester; MS: 505 (M+1)

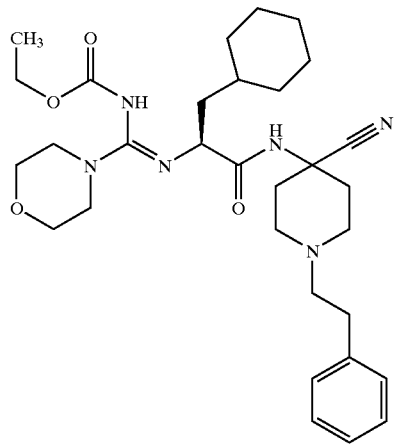

{[1-(4-Cyano-1-phenethyl-piperidin-4-ylcarbamoyl)-2-cyclohexyl-ethylamino]-morpholin-4-yl-methylene}-carbamic acid ethyl ester; MS: 567 (M+1)

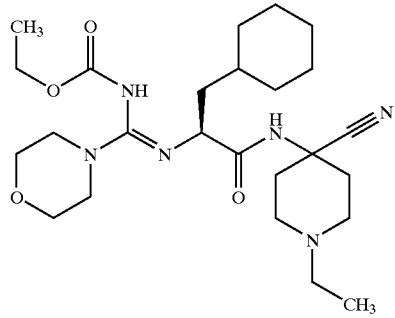

{[1-(4-Cyano-1-ethyl-piperidin-4-ylcarbamoyl)-2-cyclohexyl-ethylamino]-morpholin-4-yl-methylene}-carbamic acid ethyl ester; MS: 491 (M+1)

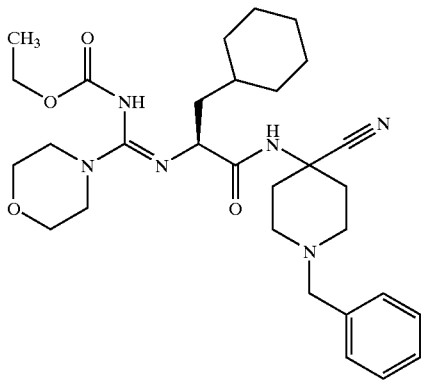

174

{[1-(1-Benzyl-4-cyano-piperidin-4-ylcarbamoyl)-2-cyclohexyl-ethylamino]-morpholin-4-yl-methylene}-carbamic acid ethyl ester; MS: 553 (M+1)

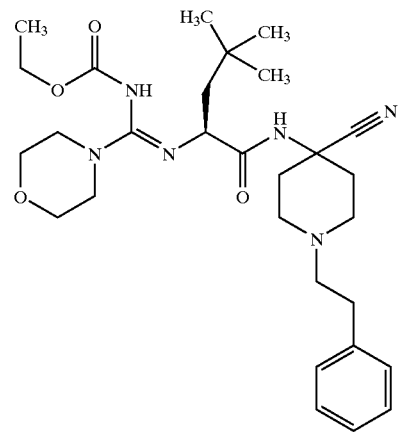

{[1-(4-cyano-1-phenethyl-piperidin-4-ylcarbamoyl)-3,3-dimethyl-butylamino]-morpholin-4-yl-methylene}-carbamic acid ethyl ester; MS: 541 (M+1)

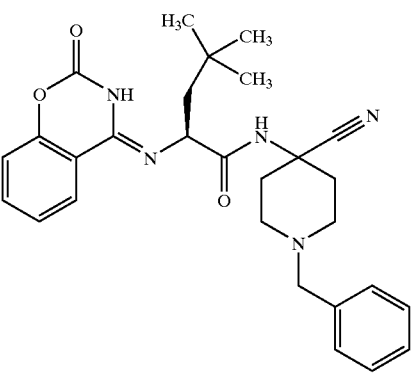

4,4-Dimethyl-2-(2-oxo-2H-benzo[e][1,3]oxazin-4-ylamino)-pentanoic acid (1-benzyl-4-cyano-piperidin-4-yl)-amide; MS: 488 (M+1)

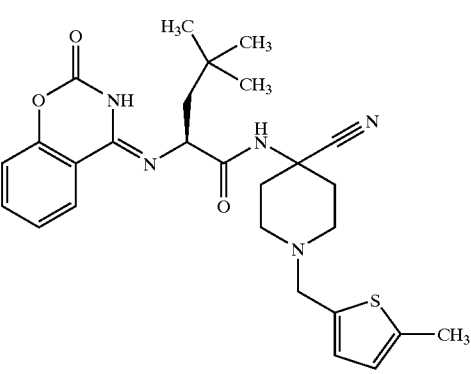

4,4-Dimethyl-2-(2-oxo-2H-benzo[e][1,3]oxazin-4-ylamino)-pentanoic acid [4-cyano-1-(5-methyl-thiophen-2-ylmethyl)-piperidin-4-yl]-amide; MS: 508 (M+1)

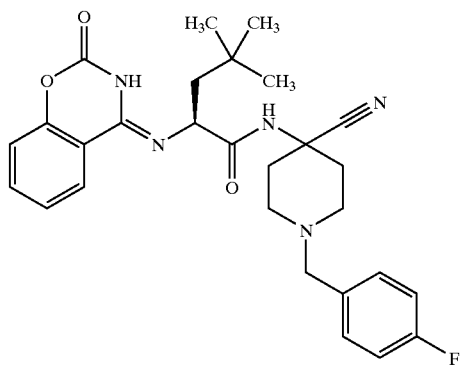

4,4-Dimethyl-2-(2-oxo-2H-benzo[e][1,3]oxazin-4-ylamino)-pentanoic acid [4-cyano-1-(4-fluoro-benzyl)-piperidin-4-yl]-amide; MS: 506 (M+1)

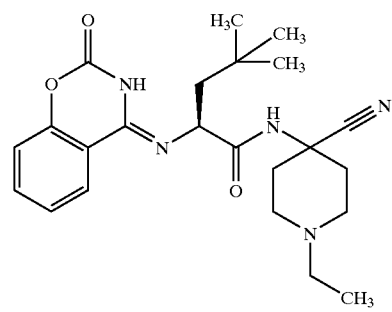

4,4-Dimethyl-2-(2-oxo-2H-benzo[e][1,3]oxazin-4-ylamino)-pentanoic acid (4-cyano-1-ethyl-piperidin-4-yl)-amide; MS: 426 (M+1)

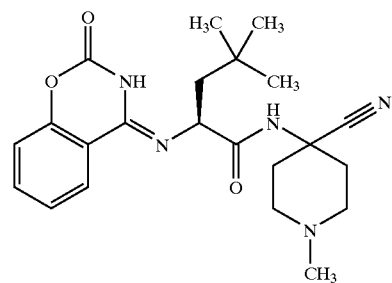

4,4-Dimethyl-2-(2-oxo-2H-benzo[e][1,3]oxazin-4-ylamino)-pentanoic acid (4-cyano-1-methyl-piperidin-4-yl)-amide; MS: 412 (M+1)

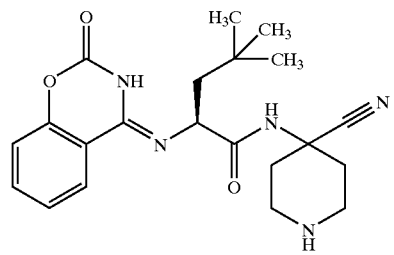

4,4-Dimethyl-2-(2-oxo-2H-benzo[e][1,3]oxazin-4-ylamino)-pentanoic acid (4-cyano-piperidin-4-yl)-amide; MS: 398 (M+1)

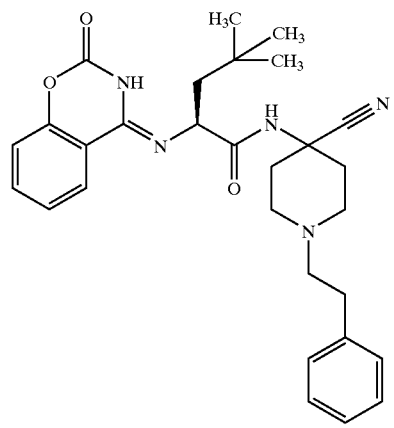

4,4-Dimethyl-2-(2-oxo-2H-benzo[e][1,3]oxazin-4-ylamino)-pentanoic acid (4-cyano-1-phenethyl-piperidin-4-yl)-amide; MS: 502 (M+1)

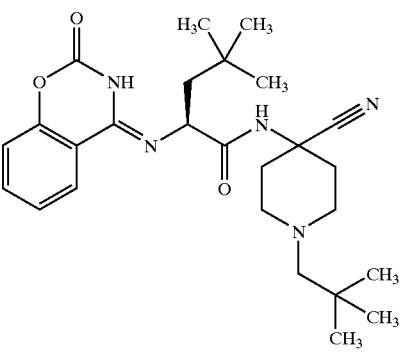

4,4-Dimethyl-2-(2-oxo-2H-benzo[c][1,3]oxazin-4-ylamino)-pentanoic acid [4-cyano-1-(2,2-dimethyl-propyl)-piperidin-4-yl]-amide; MS: 468 (M+1)

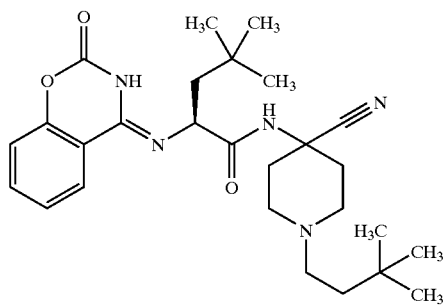

4,4-Dimethyl-2-(2-oxo-2H-benzo[e][1,3]oxazin-4-ylamino)-pentanoic acid [4-cyano-1-(3,3-dimethyl-butyl)-piperidin-4-yl]-amide; MS: 482 (M+1)

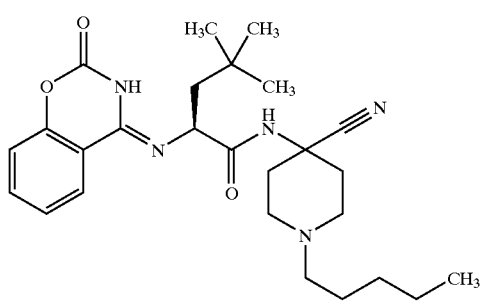

4,4-Dimethyl-2-(2-oxo-2H-benzo[e][1,3]oxazin-4-ylamino)-pentanoic acid (4-cyano-1-pentyl-piperidin-4-yl)-amide; MS: 468 (M+1)

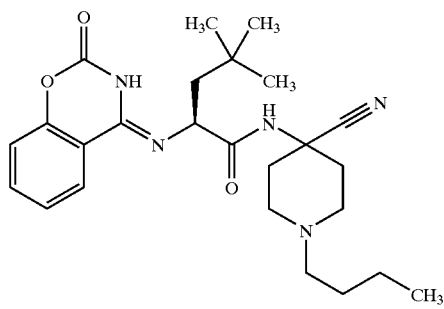

4,4-Dimethyl-2-(2-oxo-2H-benzo[e][1,3]oxazin-4-ylamino)-pentanoic acid (1-butyl-4-cyano-piperidin-4-yl)-amide; MS: 454(M+1)

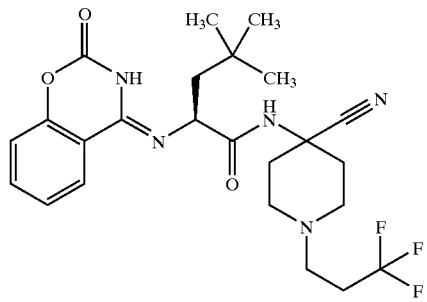

4,4-Dimethyl-2-(2-oxo-2H-benzo[e][1,3]oxazin-4-ylamino)-pentanoic acid [4-cyano-1-(3,3,3-trifluoro-propyl)-piperidin-4-yl]-amide; MS: 494 (M+1)

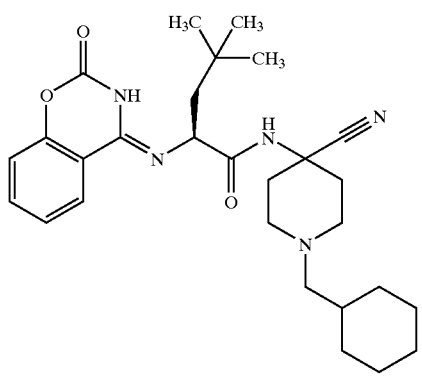

4,4-Dimethyl-2-(2-oxo-2H-benzo[e][1,3]oxazin-4-ylamino)-pentanoic acid (4-cyano-1-cyclohexylmethyl-piperidin-4-yl)-amide; MS: 494 (M+1)

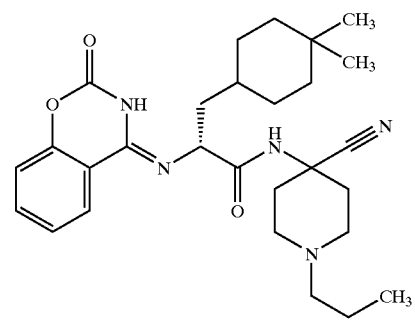

N-(4-Cyano-1-propyl-piperidin-4-yl)-3-(4,4-dimethyl-cyclohexyl)-2-(2-oxo-2H-benzo[e][1,3]oxazin-4-ylamino)-propionamide; MS: 494 (M+1)

({1-[3-Cyano-1-(4,4-dimethyl-cyclohexyl)-pyrrolidin-3-ylcarbamoyl]-3,3-dimethyl-butylamino}-morpholin-4-yl-methylene)-carbamic acid ethyl ester. MS: 533 (M+1).

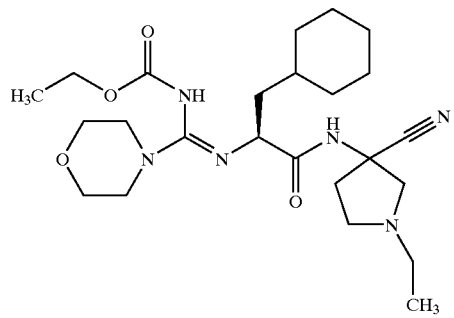

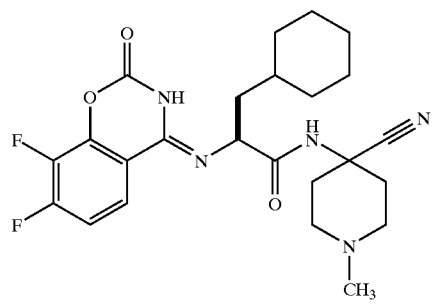

{[1-(3-Cyano-1-ethyl-pyrrolidin-3-ylcarbamoyl)-2-cyclohexyl-ethylamino]-morpholin-4-yl-methylene}-carbamic acid ethyl ester. MS: 477 (M+1).

N-(4-Cyano-1-methyl-piperidin-4-yl)-3-cyclohexyl-2-(7,8-difluoro-2-oxo-2H-benzo[e][1,3]oxazin-4-ylamino)-propionamide; MS: 474 (M+1)

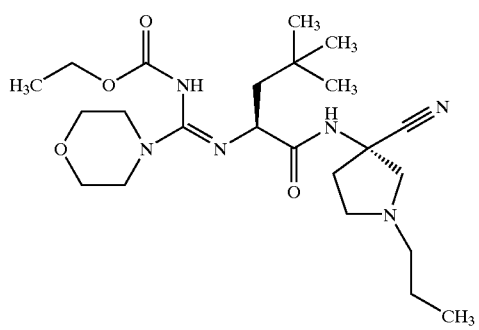

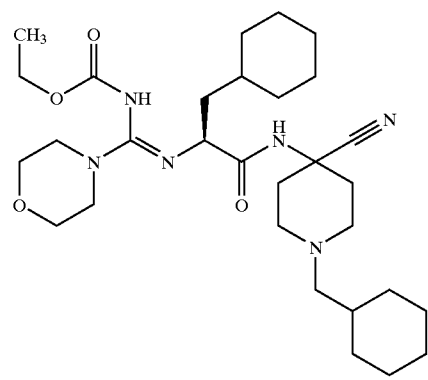

{[1-(3-Cyano-1-propyl-pyrrolidin-3-ylcarbamoyl)-3,3-dimethyl-butylamino]-morpholin-4-yl-methylene}-carbamic acid ethyl ester. MS: 465 (M+1).

{[1-(4-Cyano-1-cyclohexylmethyl-piperidin-4-ylcarbamoyl)-2-cyclohexyl-ethylamino]-morpholin-4-yl-methylene}-carbamic acid ethyl ester; MS: 559 (M+1)

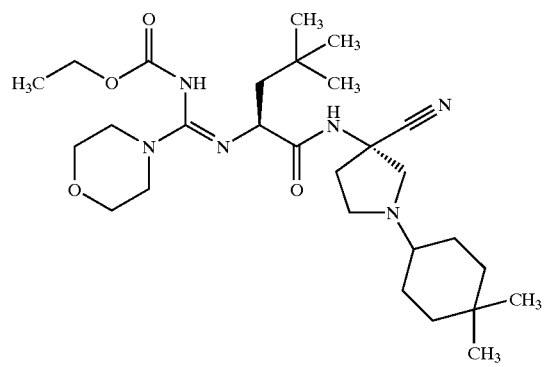

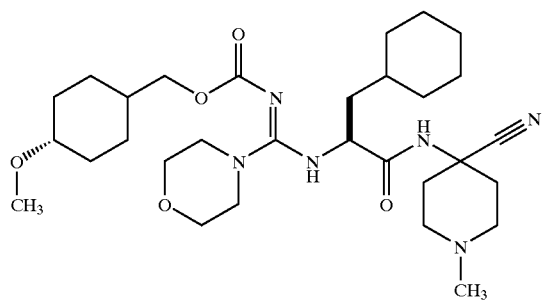

{[1-(4-Cyano-1-methyl-piperidin-4-ylcarbamoyl)-2-cyclohexyl-ethylamino]-morpholin-4-yl-methylene}-carbamic acid 4-methoxy-cyclohexylmethyl ester; MS: 575 (M+1)

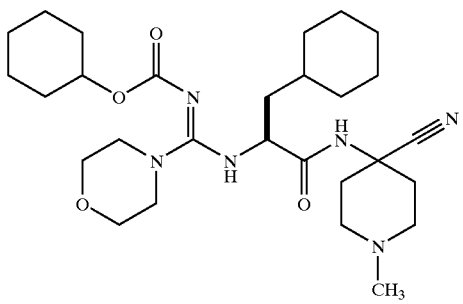

{[1-(4-Cyano-1-methyl-piperidin-4-ylcarbamoyl)-2-cyclohexyl-ethylamino]-morpholin-4-yl-methylene}-carbamic acid cyclohexyl ester; MS: 531 (M+1)

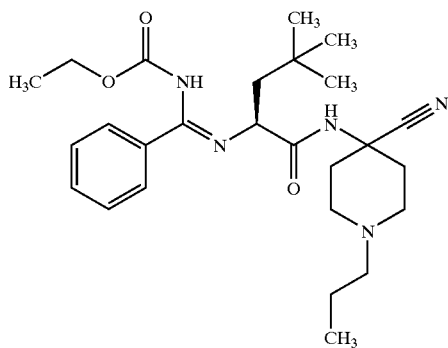

{[1-(4-Cyano-1-propyl-piperidin-4-ylcarbamoyl)-3,3-dimethyl-butylamino]-phenyl-methylene}-carbamic acid ethyl ester; MS: 470 (M+1)

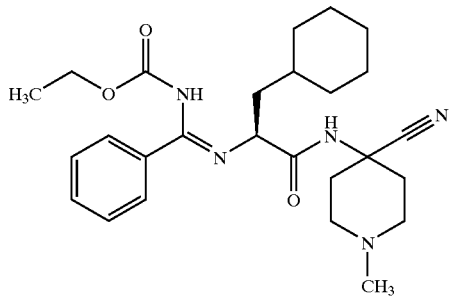

{[1-(4-Cyano-1-methyl-piperidin-4-ylcarbamoyl)-2-cyclohexyl-ethylamino]-phenyl-methylene}-carbamic acid ethyl ester; MS: 468 (M+1).

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration unless otherwise specified, or a combination of configurations.

Some of the compounds of formulas (Ia) and (Ib) can exist in more than one tautomeric form. The invention includes all such tautomers.

It shall be understood by one of ordinary skill in the art that all compounds of the invention are those which are chemically stable.

The invention includes pharmaceutically acceptable derivatives of compounds of formula (Ia) and (Ib). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

In addition, the compounds of this invention include prodrugs of compounds of the formulas (Ia) and (Ib). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (Ia) and (Ib), thereby imparting the desired pharmacological effect.

In order that the invention herein described may be more fully understood, the following detailed description is set forth. As used herein, the following abbreviations are used:

BOC or t-BOC is tertiary-butoxycarbonyl;
t-Bu is tertiary-butyl;
DMF is dimethylformamide;
EtOAc is ethyl acetate;
THF is tetrahydrofuran;
Ar is argon;
EDC is 1-(3-dimethylaminopropyl)-3-ethylcarbodimide hydrochloride and
HOBT is 1-hydroxybenzotriazole.

Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to eight carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms. Each cycloalkyl described herein shall be understood to be optionally partially or fully halogenated.

The term "aryl" refers to phenyl and naphthyl.

The term "halo" refers to a halogen radical selected from fluoro, chloro, bromo or iodo. Representative halo groups of the invention are fluoro, chloro and bromo.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, The term "heterocycle" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The terms "heterocycle", "heteroaryl" or "aryl", when associated with another moiety, unless otherwise specified shall have the same meaning as given above. For example, "aroyl" refers to phenyl or naphthyl linked to a carbonyl group (C=O).

Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

The term heterocycle as it pertains to "Het" shall to be understood to mean a stable non-aromatic spiroheterocycle, 4–8 membered (but preferably, 5 or 6 membered) monocyclic, 8–11 membered bicyclic heterocycle radical which may be either saturated or unsaturated or a C6–C10 bridged bicyclo wherein one or more carbon atoms are optionally replaced by a heteroatom. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "Het" include the following heterocycles: azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydro-oxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydroquinolinyl, decahydro-isoquinolinyl, 1,2,3,4-tetrahydroquinolinyl, indolinyl, octahydro-quinolizinyl, dihydroindolizinyl, octahydro-indolizinyl, octahydro-indolyl, decahydroquinazolinyl, decahydroquinoxalinyl, 1,2,3,4-tetrahydroquinazolinyl or 1,2,3,4-tetrahydroquinoxalinyl, aza-bicyclo[3.2.1]octane, aza-bicyclo[2.2.1]heptane, aza-bicyclo[2.2.2]octane, aza-bicyclo[3.2.2]nonane, aza-bicyclo[2.1.1]hexane, aza-bicyclo[3.1.1]heptane, aza-bicyclo[3.3.2]decane and 2-oxa or 2-thia-5-aza-bicyclo[2.2.1]heptaneeach; heterocyclic ring being substituted with one or more $R_5$. The substituent $R_5$ is defined above.

As used herein above and throughout this application, "nitrogen" and "sulfur" include any oxidized form of nitrogen and sulfur and the quaternized form of any basic nitrogen.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

General Synthetic Methods

The invention also provides processes of making the present novel compounds of formula (Ia) and (Ib). Compounds of the invention may be prepared by methods described below, those found in U.S. application Ser. No. 09/655,351, incorporated herein be reference in it's entirety, and by methods known to those of ordinary skill in the art.

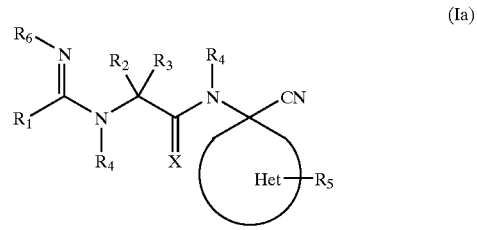

(Ia)

(Ib)

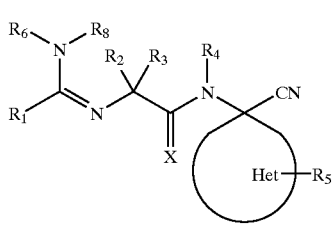

A key intermediate in the preparation of compounds of formula (Ia) and (Ib) is the dipeptide nitrile intermediate (III).

(III)

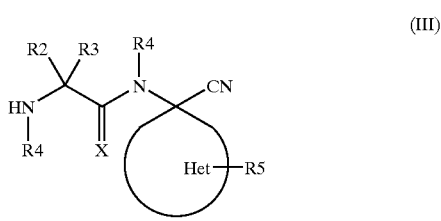

The synthesis of intermediates of formula (III) is described in U.S. provisional patent application No. 60/222,900 and outlined below in Schemes I and II.

Scheme I

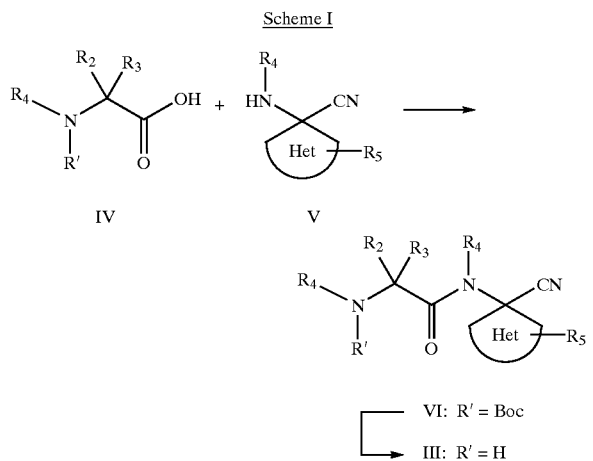

VI: R' = Boc
III: R' = H

As illustrated in Scheme I, an amino acid bearing a suitable protecting group R' (IV), is reacted with an amino nitrile (V) under suitable coupling conditions. An example of a suitable protecting group is the t-butoxycarbonyl (BOC) group. An example of standard coupling conditions would be combining the starting materials in the presence of a coupling reagent such as 1-(3-dimethylaminopropyl)-3-ethylcarbodiimide (EDC) with 1-hydroxybenzotriazole (HOBT), in a suitable solvent such as DMF or methylene chloride. A base such as N-methylmorpholine may be added. This is followed by deprotection to give amino acid nitrile III.

The intermediate aminonitrile (V) used in Scheme I above may be prepared as outlined in Scheme II.

Scheme II

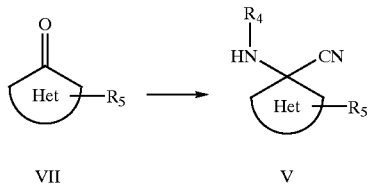

VII    V

In this method, a ketone bearing "Het" (VII) is reacted with an a primary amine or an ammonium salt, such as ammonium chloride, and a cyanide salt, such as potassium cyanide or sodium cyanide, in a suitable solvent, such as water or a solution of ammonia in methanol, at about room temperature to reflux temperature.

Compounds having formula (Ia/Ib) may be prepared by Methods A–D, as illustrated in Schemes III–VI.

Scheme III (Method A)

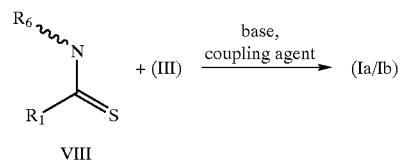

VIII

According to Method A, a dipeptide nitrile intermediate (III), or a basic salt thereof, is allowed to react with (VIII) in the presence of a suitable coupling agent to provide the desired product (Ia/Ib). Suitable reaction conditions are known to those skilled in the art and some examples of suitable coupling agents include 2-chloro-1-methylpyridinium iodide (Yong, Y. F. et al., J. Org. Chem. 1997, 62, 1540), phosgene or triphosgene (Barton, D. H. et al., J. Chem. Soc. Perkin Trans. I, 1982, 2085), alkyl halides (Brand, E. and Brand, F. C., Org. Synth., 1955, 3, 440) carbodiimides (Poss, M. A. et al., Tetrahedron Lett., 1992, 40, 5933) and mercury salts (Su, W., Synthetic Comm., 1996, 26, 407 and Wiggall, K. J. and Richardson, S. K. J., Heterocyclic Chem., 1995, 32, 867).

Compounds having formulas (Ia) and (Ib) may also be prepared by Method B as illustrated in Scheme IV, where R is an alkyl or aryl group.

Scheme IV (Method B)

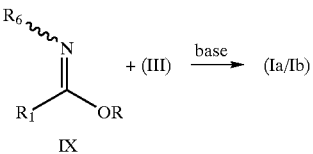

IX

According to Method B a dipeptide nitrile intermediate (III), or a basic salt thereof, is allowed to react with IX, with or without an added base such as triethylamine, to provide the desired product (Ia/Ib). Suitable reaction conditions are known to those skilled in the art and examples of such amine additions may be found in the chemical literature, for example Haake, M. and Schummelfeder, B., Synthesis, 1991, 9, 753; Dauwe, C. and Buddrus, J., Synthesis 1995, 2, 171; Ried, W. and Piechaczek, D., Justus Liebigs Ann. Chem. 1966, 97, 696 and Dean, W. D. and Papadopoulos, E. P., J. Heterocyclic Chem., 1982, 19, 1117.

The intermediate IX is either commercially available or can be synthesized by methods known to those skilled in the art and described in the literature, for example Francesconi, I. et. al., J. Med. Chem. 1999, 42, 2260; Kurzer, F., Lawson, A., Org. Synth. 1963, 645, and Gutman, A. D. U.S. Pat. No. 3,984,410, 1976.

In a similar reaction, intermediate X having a halogen or other suitable leaving group (X') may be used in place of intermediate IX, as illustrated in Method C, Scheme V.

Scheme V (Method C)

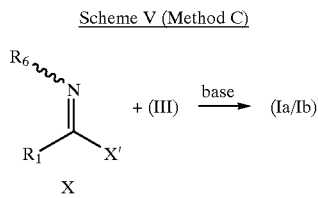

According to Method C, a dipeptide nitrile intermediate, or a basic salt thereof, is allowed to react with intermediate X, with or without an added base such as triethylamine, to provide the desired product (Ia/Ib). Procedures for accomplishing this reaction are known to those skilled in the art and described in the chemical literature (for example, Dunn, A. D., Org. Prep. Proceed. Int., 1998, 30, 709; Lindstroem, S. et al., Heterocycles, 1994, 38, 529; Katritzky, A. R. and Saczewski, F., Synthesis, 1990, 561; Hontz, A. C. and Wagner, E. C., Org Synth., 1963, IV, 383; Stephen, E. and Stephen, H., J. Chem. Soc., 1957, 490).

Compounds having formula (Ia/Ib) in which $R_1$ is an amine may also be prepared by Method D as illustrated in Scheme VI.

Scheme VI (Method D)

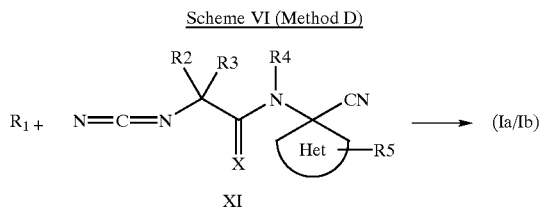

According to Method D, a carbodiimide (XI) derivative of (III) is allowed to react with an amine ($R_1$) to provide the desired guanidine (Ia/Ib) product. The conversion of amines to carbodiimides is known to those in the art and described in the literature (for example, Pri-Bar, I. and Schwartz, J., J. Chem. Soc. Chem. Commun., 1997, 347; Hirao, T. and Saegusa, T., J. Org. Chem., 1975, 40, 298). The reaction of carbodiimides with amine nucleophiles is also described in the literature (for example, Yoshiizumi, K. et al., Chem. Pharm. Bull., 1997, 45, 2005; Thomas, E. W. et al., J. Med. Chem., 1989, 32, 228; Lawson, A. and Tinkler, R. B., J. Chem. Soc. C, 1971, 1429.

In a modification of Method D, one may start with the thiourea XII (formed by reaction of the corresponding amine with an isothiocyanate $R_6N=C=S$) and then form the corresponding carbodiimide (XI) in situ by reaction with a suitable desulfurizing agent, such as $HgCl_2$, in a suitable solvent such as DMF or acetonitrile.

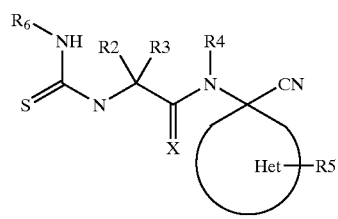

Compounds of formula (Ib), where $R_1$ is an amine may be prepared using a general procedure described by M. Haake and B. Schummfelder (Synthesis, 1991, 753). According to this procedure (Method E, Scheme VII), intermediate XIII bearing two suitable leaving groups Z, such as phenoxy groups, is reacted sequentially with amines $R_1$ and $R_6R_8NH$ in a suitable solvent such as methanol or isopropanol to provide the desired product. Reaction of the first amine may be carried out at about room temperature and reaction of the second amine is preferentially carried out with heating at the reflux temperature of the solvent. If XIII is allowed to react with a bifunctional nucleophile intermediate XIV, where Y is a nucleophilic heteroatom such as N, O or S, one may obtain the product of formula (Ib) where $R_1$ and $R_6$ form a heterocyclic ring. Intermediate XIII may be prepared by reaction of III ($R_4=H$) with dichlorodiphenoxymethane, which in turn, may be prepared by heating diphenyl carbonate with $PCl_5$ (R. L. Webb and C. S. Labow, J. Het. Chem., 1982, 1205).

Scheme VII (Method E)

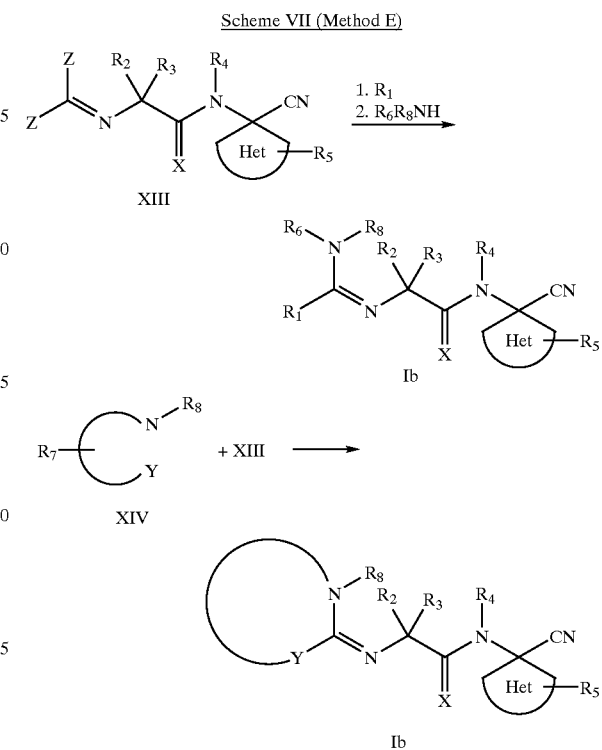

In order that this invention be more fully understood, the following examples are set forth. These examples are for the purpose of illustrating embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

SYNTHETIC EXAMPLES

Example 1

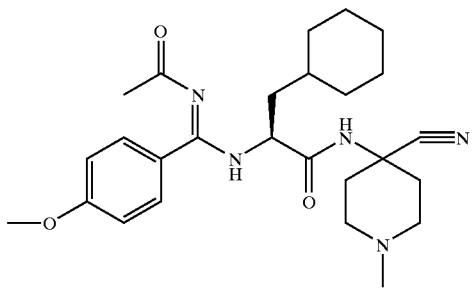

2-{[Acetylimino-(4-methoxy-phenyl)-methyl]-amino}-N-(4-cyano-1-methyl-piperidin-4-yl)-3-cyclohexyl-propionamide (Method A).

(a) N-(4-methoxy-thiobenzoyl)acetamide.

A solution of acetyl chloride (4.69 g, 59.8 mmol) in acetone (20 mL) was added dropwise to a solution of 4-methoxythiobenzamide (5.00 g, 29.9 mmol) and pyridine (4.76 g, 60.1 mmol) in acetone (30 mL). The reaction mixture was heated to reflux for 30 min then poured onto ice water. The resulting precipitate was isolated via filtration and dried under vacuum overnight to provide a light yellow/orange solid (4.52 g, 72%).

$^1$H NMR (400 MHz, CDCl$_3$) δ 2.56 (s, 3H), 3.87 (s, 3H), 6.89 (dd, J=6.9, 2.0 Hz, 2H), 7.77 (dd, J=6.9, 2.0 Hz, 2H).

(b) 2-{[Acetylimino-(4-methoxy-phenyl)-methyl]-amino}-N-(4-cyano-1-methyl-piperidin-4-yl)-3-cyclohexyl-propionamide.

2-Chloro-N-methylpyridinium iodide (660 mg, 2.58 mmol), was added to a solution of N-(4-methoxy-thiobenzoyl)acetamide (420 mg, 2.01 mmol), 2-amino-N-(4-cyano-1-methyl-piperidin-4-yl)-3-cyclohexyl-propionamide bis hydrochloride salt (730 mg, 2.00 mmol), and N,N-diisopropylethylamine (1.05 mL, 6.02 mmol) in dichloromethane (8.0 mL). The reaction mixture was stirred at room temperature for 2 h, then diluted with dichloromethane (100 mL) and washed with 2×150 mL of saturated sodium bicarbonate. The organic phase was dried (MgSO$_4$) and concentrated. The resulting residue was chromatographed over 100 g of flash silica first using EtOAc, then dichloromethane/methanol 9:1 as the eluant to provide the desired product as an off white solid (377 mg, 40%). $^1$H NMR (400 MHz, DMSO-d6) δ 0.70–0.90 (m, 2H), 1.00–1.30 (m, 4H), 1.35–1.65 (m, 8H), 1.72 (s, 3H), 1.85–2.20 (m, 6H), 2.48–2.60 (m, 1H), 3.78 (s, 3H), 4.20–4.35 (m, 1H), 6.95–6.99 (m, 2 H), 7.33 (d, J=8.4 Hz, 1H), 7.72 (d, J=8.4 Hz, 1H). MS, m/z 468=M+1.

Example 2

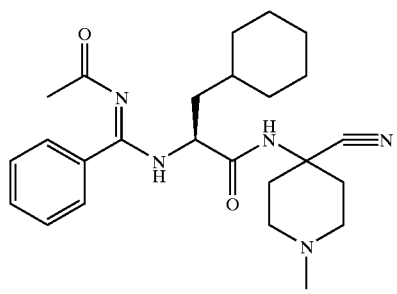

2-[(Acetylimino-phenyl-methyl)-amino]-N-(4-cyano-1-methyl-piperidin-4-yl)-3-cyclohexyl-propionamide.

(a) Thiobenzoyl acetamide was prepared according to the procedure from Example 1, step a, starting with thiobenzamide.

(b) The title compound was prepared starting from thiobenzoyl acetamide and 2-amino-N-(4-cyano-1-methyl-piperidin-4-yl)-3-cyclohexyl-propionamide bis hydrochloride salt according to the procedure from Example 1, step b. MS, m/z 438=M+1.

Example 3

2-{[Acetylimino-(4-fluoro-phenyl)-methyl]-amino}-N-(4-cyano-1-methyl-piperidin-4-yl)-3-cyclohexyl-propionamide.

(a) N-(4-Fluoro-thiobenzoyl)acetamide was prepared according to the procedure from Example 1, step a, starting with 4-fluorothiobenzamide.

(b) The title compound was prepared starting from N-(4-fluoro-thiobenzoyl) acetamide and 2-amino-N-(4-cyano-1-methyl-piperidin-4-yl)-3-cyclohexyl-propionamide bis hydrochloride salt according to the procedure from Example 1, step b. MS, m/z 456=M+1.

Example 4

2-[(Acetylimino-phenyl-methyl)]-amino-N-[3-cyano-1-(1-ethyl-propyl)-pyrrolidin-3-yl]-3-cyclohexyl-propionamide.

(a) The title compound was prepared starting from thiobenzoyl acetamide and 2-amino-N-[3-cyano-1-(1-ethylpropyl)-pyrrolidin-3-yl]-3-cyclohexyl-propionamide bis hydrochloride salt according to the procedure from Example 1, step b, except that the compound was purified by HPLC using a 20×250 mm C18 reverse phase column with the method being 20% acetonitrile in water to 90% acetonitrile in water. MS, m/z 480=M+1.

Example 5

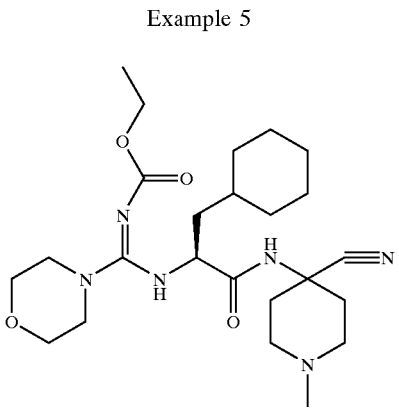

{[1-(4-Cyano-1-methyl-piperidin-4-ylcarbamoyl)-2-cyclohexyl-ethylamino]-morpholin-4-yl-methylen}-carbamic acid ethyl ester (Method A).

(a) (Morpholine-4-carbothioyl)-carbamic Acid Ethyl Ester.

Morpholine (7.5 mL, 86.0 mmol) was added dropwise to a solution of ethyl isothiocyanato formate (10.0 mL, 84.8 mmol) in tetrahydrofuran (200 mL). The reaction mixture was stirred at room temperature for 2.5 h, then concentrated and dried under vacuum to provide the desired product as a white solid (16.5 g, 89%). This material was used without further purification. $^1$H NMR (400 MHz, CDCl$_3$) δ 1.28 (t, J=7.1 Hz, 3H), 3.61–3.97 (m, 8H), 4.16 (q, 7.1 Hz, 2H), 7.44 (br s, 1H).

(a) {[1-(4-Cyano-1-methyl-piperidin-4-ylcarbamoyl)-2-cyclohexyl-ethylamino]-morpholin-4-yl-methylen}-carbamic Acid Ethyl Ester.

2-Chloro-N-methylpyridinium iodide (680 mg, 2.66 mmol), was added to a solution of (morpholine-4-carbothioyl)-carbamic acid ethyl ester (450 mg, 2.06 mmol), 2-amino-N-(4-cyano-1-methyl-piperidin-4-yl)-3-cyclohexyl-propionamide bis hydrochloride salt (745 mg, 2.04 mmol), and N,N-diisopropylethylamine (1.10 mL, 6.3 mmol) in dichloromethane (8.0 mL). The reaction was stirred at room temperature for 2.5 h then taken up in 10% citric acid solution and washed with EtOAc. The aqueous phase was then basified with saturated sodium carbonate and extracted with EtOAc. The organic extract was dried (MgSO$_4$) and concentrated to provide the desired product as a white solid (250 mg, 26%). This material was further purified by HPLC using a 20×250 mm C$_{18}$ reverse phase column with the method being 20% acetonitrile in water to 90% acetonitrile in water. MS, m/z 477=M+1.

Example 6

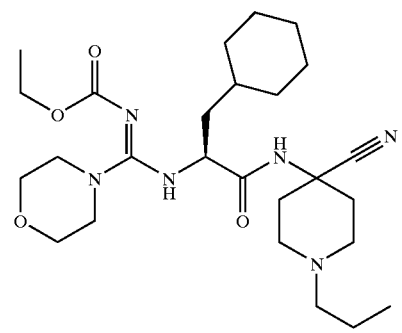

{[1-(4-Cyano-1-propyl-piperidin-4-ylcarbamoyl)-2-cyclohexyl-ethylimino]-morpholin-4-yl-methyl}-carbamic acid ethyl ester.

The title compound was prepared starting from (morpholine-4-carbothioyl)-carbamic acid ethyl ester and 2-amino-N-(-4-cyano-1-propyl-piperidin-4-yl)-3-cyclohexylpropionamide bis hydrochloride salt according to the procedure from Example 5, step b, except that the compound was first purified by chromatography over silica gel using 9:1 methylene chloride:methanol as the eluant prior to reverse phase HPLC purification. MS, m/z 505=M+1.

Example 7

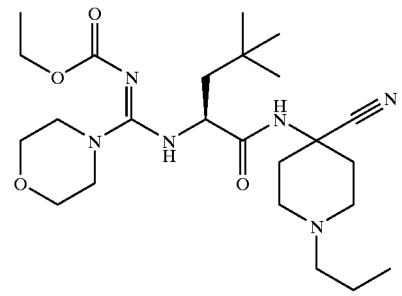

{[1-(4-Cyano-1-propyl-piperidin-4-ylcarbamoyl)-3,3-dimethyl-butylimino]-morpholin-4-yl-methyl}-carbamic acid ethyl ester.

The title compound was prepared starting from (morpholine-4-carbothioyl)-carbamic acid ethyl ester and 2-amino-4,4-dimethyl-pentanoic acid (4-cyano-1-propyl-piperidin-4-yl)amide bis hydrochloride salt according to the procedure from Example 5. MS, m/z 460=M+1.

Example 8

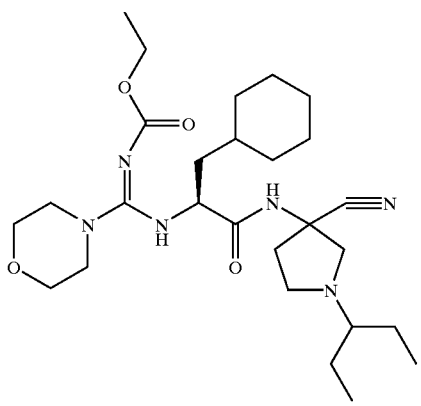

({1-[3-Cyano-1-(1-ethyl-propyl)-pyrrolidin-3-ylcarbamoyl]-2-cyclohexyl-ethylamino}-morpholin-4-yl-methylene)-carbamic acid ethyl ester.

The title compound was prepared starting from (morpholine-4-carbothioyl)-carbamic acid ethyl ester and 2-amino-N-[3-cyano-1-(1-ethyl-propyl)-pyrrolidin-3-yl]-3-cyclohexyl-propionamide bis hydrochloride salt according to the procedure from Example 5, step b. MS, m/z 519=M+1.

Example 9

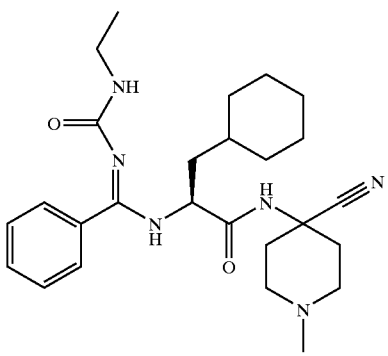

N-(4-Cyano-1-methyl-piperidin-4-yl)-3-cyclohexyl-2-[(ethylcarbamoylimino-phenyl-methyl)-amino]-propionamide (Method B).

(a) Benzimidic Acid Methyl Ester.

Benzimidic acid methyl ester hydrochloride (5 g, 29.1 mmol) was partitioned between saturated sodium carbonate solution (200 mL) and diethyl ether (100 mL). The organic layer was dried (MgSO$_4$) and concentrated to provide the desired product as a colorless liquid (3.20 g, 81%). This material was used without further purification. $^1$H NMR (400 MHz, CDCl$_3$) δ 3.93 (s, 3H), 7.39–7.46 (m, 3H), 7.75 (d, J=1.1 Hz, 2H).

(a) 1-Ethyl-3-(methoxy-phenyl-methylene)-urea.

A neat mixture of benzimidic acid methyl ester (750 mg, 5.56 mmol) and ethyl isocyanate (808 mg, 11.3 mmol) was stirred at 50° C. for 24 h. Excess isocyanate was removed under vacuum to provide the desired product as a colorless viscous oil (1.09 g, 95%). This material was used without further purification. $^1$H NMR (400 MHz, CDCl$_3$) δ 1.07 (t, J=7.3 Hz, 3 H), 3.25 (q, J=7.3 Hz, 2 H), 3.87 (s, 3H), 4.97 (br s, 1H), 7.26–7.40 (m, 2H), 7.45 (d, J=7.4 Hz, 1H), 7.69–7.71 (m, 2H). MS, m/z 207=M+1.

(a) N-(4-Cyano-1-methyl-piperidin-4-yl)-3-cyclohexyl-2-[(ethylcarbamoylimino-phenyl-methyl)-amino]-propionamide.

A solution of 1-ethyl-3-(methoxy-phenyl-methylene)-urea (350 mg, 1.70 mmol), 2-amino-N-(4-cyano-1-methyl-piperidin-4-yl)-3-cyclohexyl-propionamide bis hydrochloride salt (512 mg, 1.40 mmol) and N,N-diisopropylethylamine (352 mg, 2.73 mmol) in dry methanol (5.0 mL) was stirred at room temperature for 60 h. The reaction mixture was concentrated and the resulting residue was chromatographed over 50 g of flash silica gel using dichloromethane to 5% methanol in dichloromethane as the eluant. This provided the desired product as a light yellow solid (280 mg, 43%) which was further purified by HPLC using a 20×250 mm C$_{18}$ reverse phase column with the method being 20% acetonitrile in water to 90% acetonitrile in water. MS, m/z 467=M+1.

Example 10

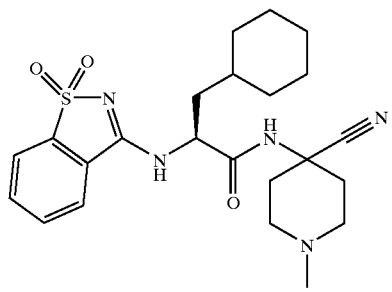

N-(4-Cyano-1-methyl-piperidin-4-yl)-3-cyclohexyl-2-(1,1-dioxo-1H-1λ$^6$-benzo[d]isothiazol-3-ylamino)-propionamide (Method C).

A suspension of 3-chloro-benzo[d]isothiazole 1,1-dioxide (300 mg, 1.49 mmol) and 2-amino-N-(-4-cyano-1-methyl-piperidin-4-yl)-3-cyclohexylpropionamide bis hydrochloride salt (500 mg, 1.37 mmol) was prepared in 5.5 mL of acetonitrile. Triethylamine (575 μL, 4.10 mmol) was added and the reaction mixture was stirred at room temperature for 1 day. The suspension was filtered to remove triethylamine hydrochloride and the filtrate was concentrated. The resulting residue was chromatographed over 50 g of flash silica using dichloromethane/methanol 9:1 as the eluant to provide the desired product as a light yellow solid (310 mg, 49%). $^1$H NMR (400 MHz, CDCl$_3$) δ 0.25–0.45 (m, 1H), 0.65–0.85 (m, 2H), 0.95–1.10 (m, 2H), 1.30–1.60 (m, 7H), 1.75–1.85 (m, 2H), 1.85–2.2 (m, 2H), 2.31 (s, 3H), 2.35–2.50 (m, 3H), 2.65–2.80 (m, 2H), 4.60–4.70 (m, 1H), 7.35–7.50 (m, 2H), 7.58 (t, J=7.3, 1H), 7.78 (d, J=7.7 Hz, 1H), 7.81 (br s, 1H), 8.91 (br s, 1H). MS, m/z 458=M+1.

Example 11

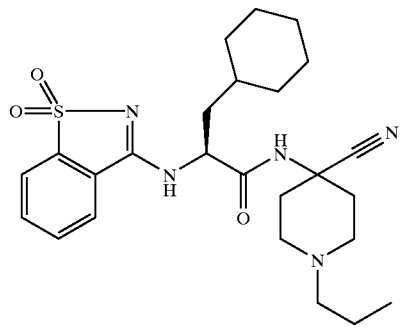

N-(4-Cyano-1-propyl-piperidin-4-yl)-3-cyclohexyl-2-(1,1-dioxo-1H-1λ$^6$-benzo[d]isothiazol-3-ylamino)-propionamide.

The title compound was prepared starting from 3-chloro-benzo[d]isothiazole 1,1-dioxide and 2-amino-N-(-4-cyano- 1-propyl-piperidin-4-yl)-3-cyclohexylpropionamide bis hydrochloride salt according to the procedure from Example 10, except that the compound was further purified by HPLC using a 20×250 mm $C_{18}$ reverse phase column with the method being 20% acetonitrile in water to acetonitrile. MS, m/z 486=M+1.

Example 12

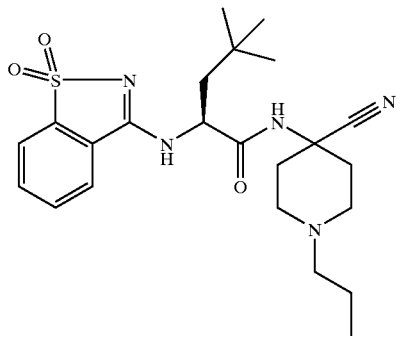

2-(1,1-dioxo-1H-1$\lambda^6$-benzo[d]isothiazol-3-ylamino)-4,4-dimethyl-pentanoic acid(4-cyano-1-propylpiperidin-4-yl)-amide.

The title compound was prepared starting from 3-chloro-benzo[d]isothiazole 1,1-dioxide and 2-amino-4,4-dimethyl-pentanoic acid (4-cyano-1-propyl-piperidin-4-yl)amide bis hydrochloride salt according to the procedure from Example 10, except that the compound was further purified by HPLC using a 20×250 mm $C_{18}$ reverse phase column with the method being 20% acetonitrile in water to acetonitrile. MS, m/z 460=M+1.

Example 13

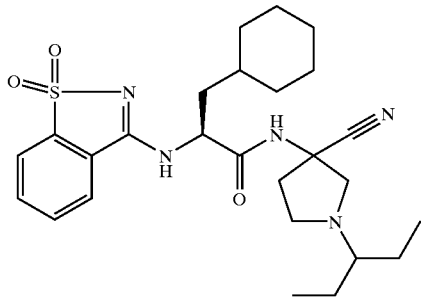

N-[3-Cyano-1-(1-ethyl-propyl)-pyrrolidin-3-yl]-3-cyclohexyl-2-(1,1-dioxo-1H-1$\lambda^6$-benzo[d]isothiazol-3-ylamino)-propionamide.

The title compound was prepared starting from 3-chloro benzo[d]isothiazole 1,1-dioxide and 2-amino-N-[3-cyano-1-(1-ethyl-propyl)-pyrrolidin-3-yl]-3-cyclohexyl-propionamide bis hydrochloride salt according to the procedure from Example 10, except that the compound was further purified by HPLC using a 20×250 mm $C_{18}$ reverse phase column with the method being 40% acetonitrile in water to acetonitrile. MS, m/z 500=M+1.

Example 14

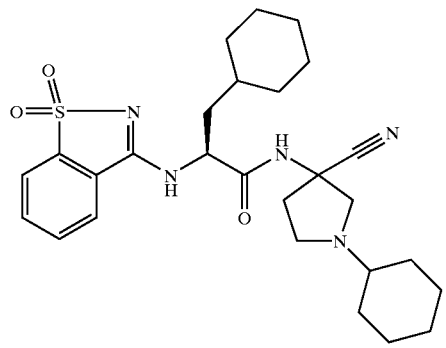

N-(3-Cyano-1-cyclohexyl-pyrrolidin-3-yl)-3-cyclohexyl-2-(1,1-dioxo-1H-1$\lambda^6$-benzo[d]isothiazol-3-ylamino)-propionamide.

The title compound was prepared starting from 3-chloro benzo[d]isothiazole 1,1-dioxide and 2-amino-N-(3-cyano-1-cyclohexyl-pyrrolidin-3-yl)-3-cyclohexyl-propionamide bis hydrochloride salt according to the procedure from Example 10, except that the compound was further purified by HPLC using a 20×250 mm $C_{18}$ reverse phase column with the method being 40% acetonitrile in water to acetonitrile. MS, m/z 512=M+1.

Example 15

N-(4-Cyano-methyl-piperidin-4-yl)-3-cyclohexyl-2-(3-oxo-3H-isoindol-1-ylamino)-propionamide.

The title compound was prepared starting from 3-imino-2,3-dihydro-isoindol-1-one and 2-amino-N-(4-cyano-1-methyl-piperidin-4-yl)-3-cyclohexyl-propionamide bis hydrochloride salt according to the procedure from Example 10, except that refluxing THF was used as the solvent. The compound was further purified by HPLC using a 20×250 mm $C_{18}$ reverse phase column with the method being 20% acetonitrile in water to acetonitrile. MS, m/z 422.5=M+1.

Example 16

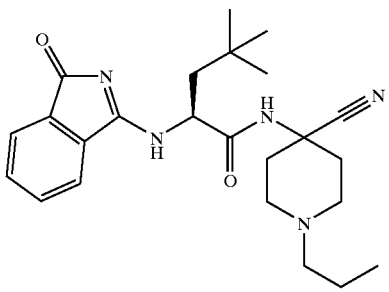

4,4-Dimethyl-2-(3-oxo-3H-isoindol-1-ylamino)-pentanoicacid-(4-cyano-1-propyl-piperidin-4-yl)-amide.

The title compound was prepared from 3-imino-2,3-dihydro-isoindol-1-one and 2-amino-4,4-dimethyl-pentanoic acid (4-cyano-1-propyl-piperidin-4-yl)amide bis hydrochloride salt according to the procedure from Example 15. MS, m/z 424.5=M+1.

Example 17

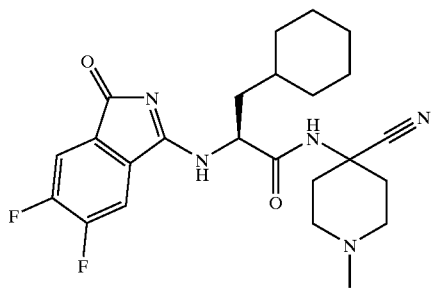

N-(4-cyano-1-methyl-piperidin-4-yl)-3-cyclohexyl-2-(5,6-difluoro-3-oxo-3H-isoindol-1-ylamino)propionamide.

(a) 2-Chloro-4,5-difluorobenzoic Acid Methyl Ester.

2-Chloro-4,5-difluorobenzoic acid (1.93 g, 10 mmol) was dissolved in 20 mL of acetone. Cesium carbonate (5.29 g, 15 mmol) was added followed by iodomethane (1.0 mL, 15 mmol). This reaction mixture was heated under reflux for 1 h and then cooled to room temperature. This suspension was then diluted with 40 mL of ethyl ether. The solid was removed by filtration and washed with ethyl ether. The filtrate was evaporated in vacuo to give the title compound in quantitative yield as a clear oil.

(b) 2-Cyano-4,5-difluorobenzoic Acid Methyl Ester.

The above oil (2.06 g, 10 mmol) was dissolved in 10 mL of N-methyl pyrrolidinone. Copper (I) cyanide (1.79 g, 20 mmol) was added. This mixture was heated at 195° C. under nitrogen for 1 h. After cooling to room temperature, this solution was diluted with 100 mL of water. The resulting solid was collected by filtration. This solid was then suspended in a rapidly stirred solution of potassium cyanide (0.5 g) in 30 mL of water for 1 h. EtOAc (30 mL) was added. The mixture was filtered through diatomaceous earth. The organic phase was separated and the aqueous phase was extracted with EtOAc (20 mL×2). The combined organic phase was washed with brine and dried over magnesium sulfate. The solvent was removed in vacuo. The residue was crystallized from ethyl ether and petroleum ether to give the title compound as a yellow solid (1.26 g, 64%).

(c) 5,6-Difluoro-2,3-dihydro-3-imino-1H-isoindol-1-one.

The above solid (0.493 g, 2.5 mmol) was dissolved in 20 mL of MeOH. This solution was saturated with ammonia at 0° C. and then stirred in a pressure tube at room temperature for 3 days. The solid was collected by filtration and washed with ethyl ether to give the title compound as a yellow solid (0.363 g, 80%).

The title compound was prepared from 5,6-difluoro-2,3-dihydro-3-imino-1H-isoindol-1-one and 2-amino-N-(4-cyano-1-methyl-piperidin-4-yl)-3-cyclohexyl-propionamide bis hydrochloride salt according to the procedure from Example 15. MS, m/z 458.3=M+1.

Example 18

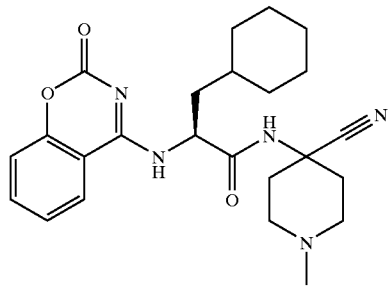

N-(4-cyano-1-methyl-piperidin-4-yl)-3-cyclohexyl-2-(2-oxo-2H-benzo[e][1,3]oxazin-4-ylamino)-propionamide.

The title compound was prepared starting from 4-chloro-benzo[e][1,3]oxazin-2-one (prepared from benzo[e][1,3]oxazin-2,4-dione and $PCl_5$ in refluxing toluene) and 2-amino-N-(4-cyano-1-methyl-piperidin-4-yl)-3-cyclohexyl-propionamide bis hydrochloride salt according to the procedure from Example 10. MS, m/z 438=M+1.

Example 19

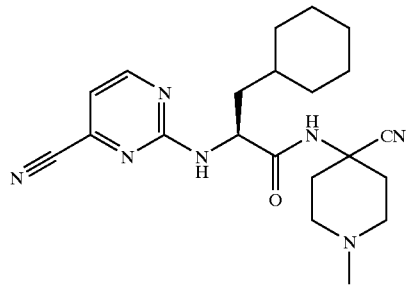

N-(4-cyano-1-methyl-piperidin-4-yl)-2-(4-cyano-pyrimidin-2-ylamino)-3-cyclohexyl-propionamide (Method C).

2-Chloro-4-pyrimidinecarbonitrile (0.3 mmol, Daves, G. D. Jr., O'Brien, D. E., Cheng, C. C. *J. Het. Chem,* 1964, 1, 130) and 2-amino-N-(4-cyano-1-methyl-piperidin-4-yl)-3-cyclohexyl-propionamide (0.7 mmol) were dissolved in acetonitrile (10 mL) containing N,N-diisopropylethylamine (0.6 mmol). The solution was heated to a gentle reflux for 17 h. The volatiles were evaporated and the residue was subjected to chromatography (silica gel, eluant=EtOAc then MeOH). The methanolic fraction was concentrated to a colorless solid which was rechromatographed (10% MeOH/EtOAc) to afford the title compound as a colorless solid (52%). The material was recrystallized from dichloromethane/petroleum ether.

Example 20

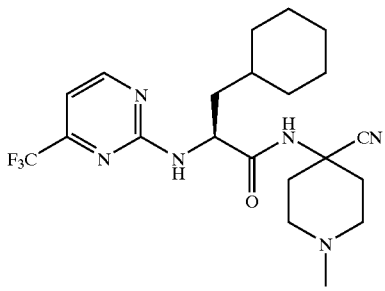

N-(4-cyano-1-methyl-piperidin-4-yl)-2-(4-trifluoromethyl-pyrimidin-2-ylamino)-3-cyclohexyl-propionamide.

The title compound was prepared from 2-chloro-4-trifluoromethyl pyrimidine and 2-amino-N-(4-cyano-1-methyl-piperidin-4-yl)-3-cyclohexyl-propionamide according to the procedure from Example 19. MS, m/z 439.5=M+1.

Example 21

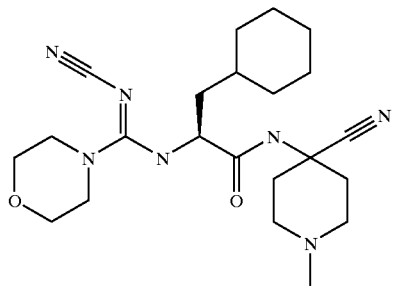

N-(4-cyano-1-methyl-piperidine-4-yl)-3-cyclohexyl-2[N-cyano-morpholine-4-carboximidoyl)-amino]-propionamide (Method D).

(a) 2-(N-Cyano-iminomethylene-amino)-N-(4-cyano-1-methyl-piperidine-4-yl)-3-cyclohexyl-propionamide.

A solution of diphenylcyanocarbonimidate (455 mg, 1.91 mmol), 2-amino-N-(4-cyano-1-methyl-piperidin-4-yl)-3-cyclohexyl-propionamide bis hydrochloride salt (680 mg, 1.86 mmol) and N,N-diisopropylethylamine (482 mg, 3.73 mmol) in isopropanol (5.0 mL) was stirred overnight at room temperature. The reaction mixture was then filtered to provide the desired carbodiimide as a white powder (140 mg, 22%). This material was used without further purification. $^1$H NMR (400 MHz, CDCl$_3$) δ 0.80–1.00 (m, 2H), 1.05–1.20 (m, 1H), 1.20–1.40 (2H), 1.50–1.85 (m, 8H), 2.32 (s, 3H), 2.40–2.50 (m, 2H), 2.55–2.70 (m, 4H), 2.85–2.95 (m, 2H), 4.10–4.20 (m, 1H), 8.77 (br s, 1H). MS, m/z 343=M+1.

(b) 2-(N-Cyano-benzimidoyl-amino)-N-(4-cyano-1-methyl-piperidine-4-yl)-3-cyclohexyl-propionamide.

A suspension of 2-(N-cyano-iminomethylene-amino)-N-(4-cyano-1-methyl-piperidine-4-yl)-3-cyclohexyl-propionamide (120 mg, 0.35 mmol) in tetrahydrofuran (1 mL) was treated with morpholine (4 mL, 45.9 mmol). The reaction mixture was stirred at room temperature for 3 days then concentrated to dryness. The residue was purified by HPLC using a 20×250 mm C$_{18}$ reverse phase column with the method being 20% acetonitrile in water to 90% acetonitrile in water. MS, m/z 430=M+1.

Example 22

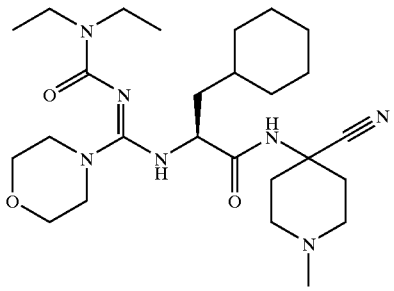

N-(4-Cyano-1-methyl-piperidin-4-yl)-3-cyclohexyl-2-{[(diethyl-carbamoylimino)-morpholin-4-yl-methyl]-amino}-propionamide (Method D).

(a) N,N-Diethyl Carbamoyl Thiocyanate.

A suspension of sodium thiocyanate (3.30 g, 40.7 mmol) in dry acetonitrile (25 mL) at 80° C. was treated dropwise with a solution of N,N-diethyl carbamoyl chloride (5.0 g, 36.9 mmol) in dry acetonitrile (15 mL). The reaction mixture was stirred at 80° C. for 50 min, cooled to room temperature, then filtered through a fine glass frit. The resulting filtrate was used as a 0.9 M solution of N,N-diethyl carbamoyl thiocyanate in acetonitrile.

(b) N-(4-Cyano-1-methyl-piperidin-4-yl)-3-cyclohexyl-2-(3-diethylamino-carbonyl-thioureido)-propionamide A solution of 2-amino-N-(-4-cyano-1-propyl-piperidin-4-yl)-3-cyclohexylpropionamide bis hydrochloride salt (560 mg, 1.53 mmol) and triethylamine (500 μL, 3.59 mmol) in acetonitrile (4 mL) was treated with a solution of N,N-diethyl carbamoyl thiocyanate in acetonitrile (3.0 mL, 2.7 mmol). The reaction mixture was stirred overnight at room temperature and concentrated on a rotary evaporator. The resulting residue was chromatographed (ethyl acetate:hexanes 1:1 then ethyl acetate and finally methanol:methylene chloride 1:9 as the eluant) to provide the desired product as a light yellow solid (340 mg, 49%). MS, m/z 451.3=M+1.

The title compound was prepared by treating a solution of the resulting thiourea (340 mg, 0.75 mmol) and triethylamine (230 μL, 1.65 mmol) in dry acetonitrile (4 mL) with mercury (II) chloride (225 mg, 0.83 mmol) and morpholine (200 μL, 2.23 mmol). The reaction mixture was stirred at room temperature for 4 h then filtered through a 0.45 μm filter disc. The resulting filtrate was filtered through a column of silica (5% methanol/methylene chloride as the eluant) and the resulting crude product was further purified by HPLC using a 20×250 mm C$_{18}$ reverse phase column with the method being 20% acetonitrile in water to acetonitrile. MS, m/z 504.6=M+1.

The following examples were prepared by Method D in a parallel fashion:

Example 23

{[1-(4-Cyano-1-methyl-piperidin-4-ylcarbamoyl)-2-cyclohexyl-ethylamino]-pyrrolidin-1-yl-methyl}-carbamic acid ethyl ester. MS, m/z 461=M+1.

Example 24

{[1-(4-Cyano-1-methyl-piperidin-4-ylcarbamoyl)-2-cyclohexyl-ethylamino]-piperidin-1-yl-methyl}-carbamic acid ethyl ester. MS, m/z 477=M+1.

Example 25

{Azepan-1-yl-[1-(4-cyano-1-methyl-piperidin-4-ylcarbamoyl)-2-cyclohexyl-ethylamino]-methylene}-carbamic acid ethyl ester. MS, m/z 490=M+1.

Example 26
{Azocan-1-yl-[1-(4-cyano-1-methyl-piperidin-4-ylcarbamoyl)-2-cyclohexyl-ethylamino]-methylene}-carbamic acid ethyl ester. MS, m/z 504=M+1.

Example 27
1-{[1-(4-Cyano-1-methyl-piperidin-4-ylcarbamoyl)-2-cyclohexyl-ethylamino]-ethoxycarbonylimino-methyl}-piperidine-4-carboxylic acid ethyl ester. MS, m/z 548=M+1.

Example 28
1-{[1-(4-Cyano-1-methyl-piperidin-4-ylcarbamoyl)-2-cyclohexyl-ethylamino]-ethoxycarbonylimino-methyl}-piperidine-3-carboxylic acid ethyl ester. MS, m/z 548=M+1.

Example 29
[[1-(4-Cyano-1-methyl-piperidin-4-ylcarbamoyl)-2-cyclohexyl-ethylamino]-(4-pyrrolidin-1-yl-piperidin-1-yl)-methylene]-carbamic acid ethyl ester. MS, m/z 545=M+1.

Example 30
{[1,4']Bipiperidinyl-1'-yl-[1-(4-cyano-1-methyl-piperidin-4-ylcarbamoyl)-2-cyclohexyl-ethylamino]-methylene}-carbamic acid ethyl ester. MS, m/z 559=M+1.

Example 31
[[1-(4-Cyano-1-methyl-piperidin-4-ylcarbamoyl)-2-cyclohexyl-ethylamino]-(4-phenyl-piperazin-1-yl)-methylene]-carbamic acid ethyl ester. MS, m/z 553=M+1.

Example 32
[[1-(4-Cyano-1-methyl-piperidin-4-ylcarbamoyl)-2-cyclohexyl-ethylamino]-(4-ethyl-piperazin-1-yl)-methylene]-carbamic acid ethyl ester. MS, m/z 505=M+1.

Example 33
{(4-Acetyl-piperazin-1-yl)-[1-(4-cyano-1-methyl-piperidin-4-ylcarbamoyl)-2-cyclohexyl-ethylamino]-methylene}-carbamic acid ethyl ester. MS, m/z 519=M+1.

Example 34
4-{[1-(4-Cyano-1-methyl-piperidin-4-ylcarbamoyl)-2-cyclohexyl-ethylamino]-ethoxycarbonylimino-methyl}-piperazine-1-carboxylic acid ethyl ester. MS, m/z 549=M+1.

Example 35
[[1-(4-Cyano-1-methyl-piperidin-4-ylcarbamoyl)-2-cyclohexyl-ethylamino]-(3,3,5-trimethyl-6-aza-bicyclo[3.2.1]oct-6-yl)-methylene]-carbamic acid ethyl ester. MS, m/z 544=M+1.

Example 36
2-(7-Fluoro-2-oxo-2,3-dihydro-benzo[e][1,3]oxazin-4-yldeneamino)-5,5-dimethyl-hexanoic acid(4-cyano-1-propyl-piperidin-4-yl)-amide.

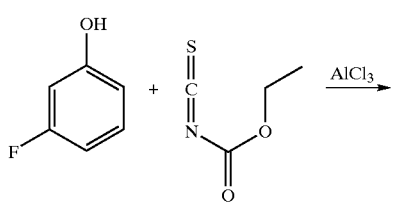

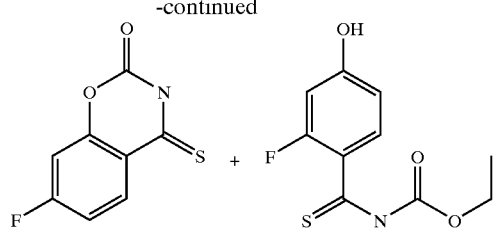

-continued

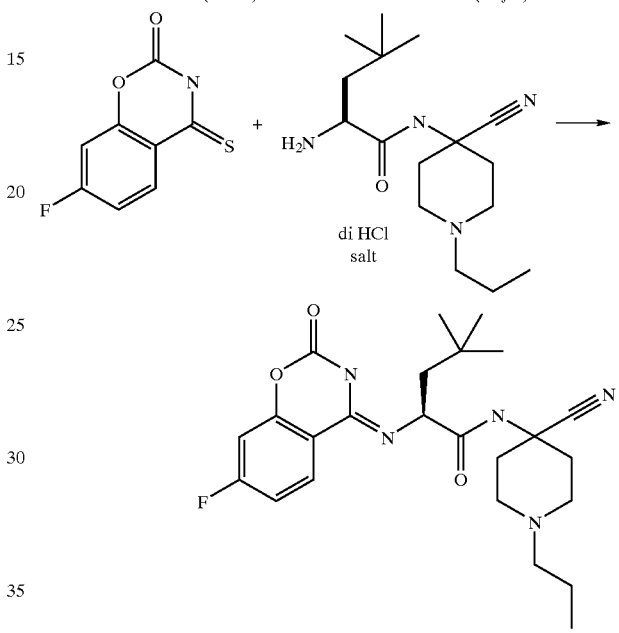

To a stirred solution of aluminum chloride (7.13 g, 53.5 mmol) in nitromethane (40 mL) at 0° C. was added ethyl isothiocyanato formate (3.5 g, 26.8 mmol). The reaction was stirred at 0° C. for 1 h and then at room temperature for 48 h. The reaction mixture was then poured over crushed ice and filtered to give 2.0 g of an orange solid. The solid was dissolved in pyridine (20 mL) and heated at reflux for 4 h. The reaction was diluted with methylene chloride and washed with water. The organic fraction was dried over anhydrous sodium sulfate and evaporated on a rotary evaporator. The crude product was purified by flash column chromatography over silica gel using 25% EtOAc and hexane to give 0.27 g of 7-fluoro-4-thioxo-3,4-dihydro-benzo[e][1,3]oxazin-2-one (5.1%).

To the above intermediate (0.135 g, 0.685 mmol) and 2-amino-5,5-dimethyl-hexanoic acid (4-cyano-1-propyl-piperidin-4-yl)-amide (0.251 g, 0.685 mmol) in dry THF (10 mL) was added diisopropylethyl amine (0.36 mL, 2.06 mmol) and 2-chloro-1-methylpyridinium iodide (0.288 g, 0.89 mmol). The reaction was stirred at room temperature for 48 h. Solvent was evaporated and the residue dissolved in methylene chloride, washed with water, dried over anhydrous sodium sulfate and evaporated. The crude product was purified initially by flash column chromatography over silica gel using 10% MeOH/methylene chloride (0.25 g, 79.8%). Final purification by HPLC afforded the title compound, 1HNMR and MS were consistent with the desired product; MS: 458 (M+1).

Example 37

N-(4-Cyano-1-propyl-piperidin-4-yl)-3-(4,4-dimethyl-cyclohexyl)-2-(2-oxo-2H-benzo[e][1,3]oxazin-4-ylamino)-propionamide.

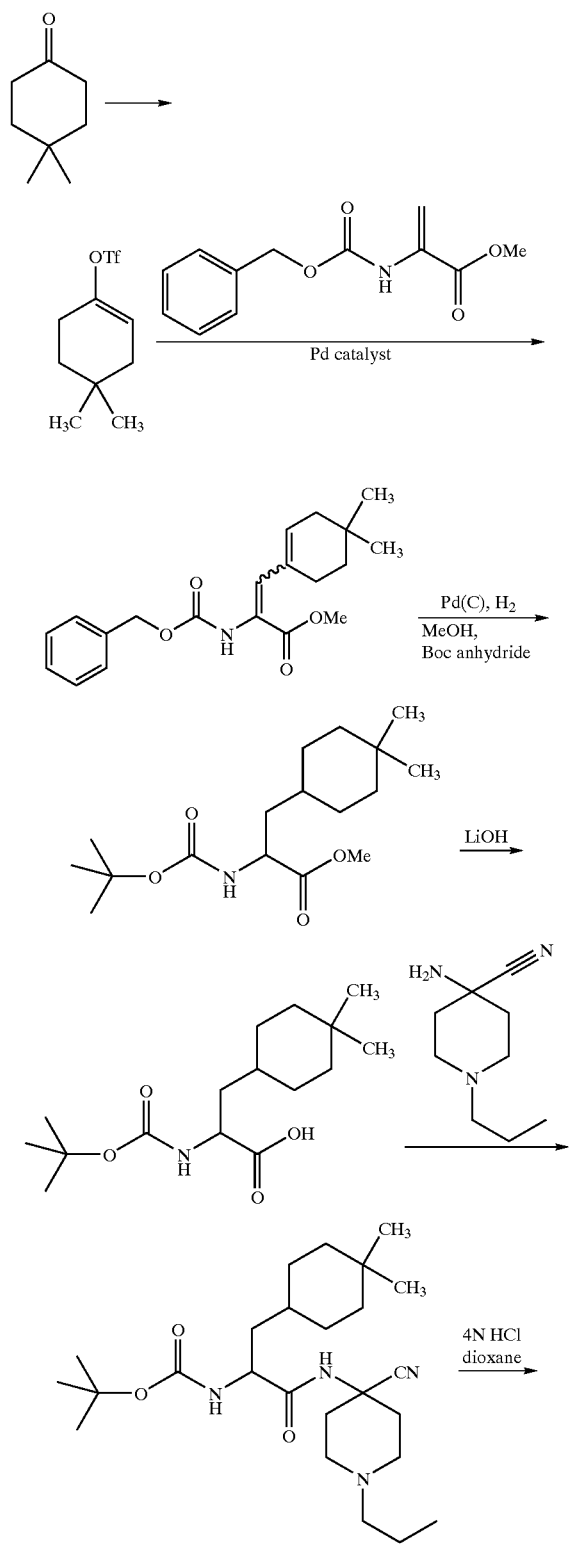

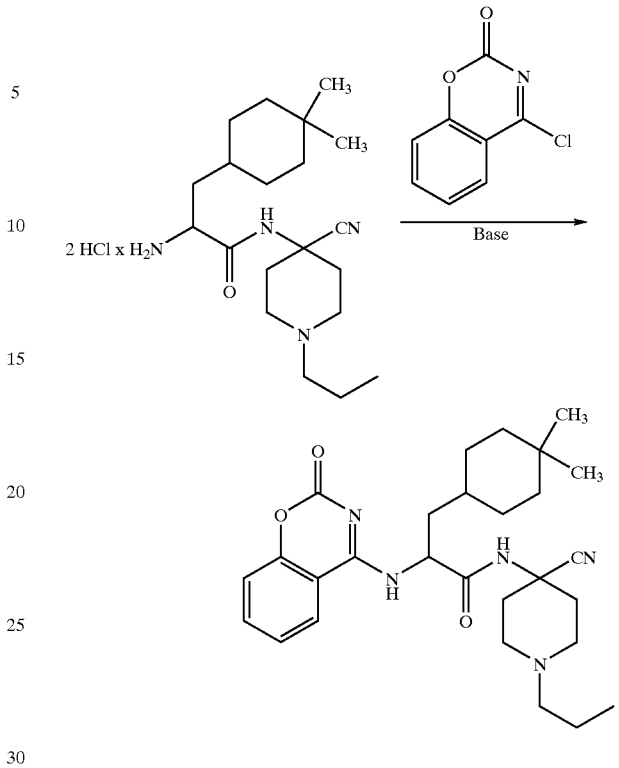

To a solution of 4,4-dimethyl cyclohexanone (4.60 g, 36.5 mmol) in dry THF (82 mL) cooled in a dry ice/acetone bath, was added sodium bis (trimethylsilyl)amide (38 mL of a 1.0 M solution in THF, 38 mmol). The reaction mixture was stirred under an argon atmosphere at −78° C. for 30 min. A solution of 2-(N,N-bis trifluoromethanesulfonyl)amino-5-chloropyridine (15 g, 37.7 mmol) in dry THF (20 mL) was introduced via syringe and the resulting solution was warmed to room temperature and stirred overnight. The reaction mixture was washed with half saturated brine (60 mL) and the aqueous phase was extracted with diethyl ether. The combined organic extracts were dried ($MgSO_4$) and concentrated to provide a dark brown oil (23 g). Chromatography over silica gel using petroleum ether as the eluant provided trifluoro-methane sulfonic acid 4,4-dimethyl-cyclohexyl-1-enyl ester as a colorless liquid (5.2 g, 56%). $^1$H NMR (400 MHz, $CDCl_3$) δ 0.98 (s, 6H), 1.53 (t, J=6.5 Hz, 2H), 1.95–1.99 (m, 2H), 2.30–2.40 (m, 2H), 5.65–5.70 (m, 1H).

A mixture of the above triflate ester (2.26 g, 8.75 mmol), Cbz dehydroalanine methyl ester (2.10 g, 8.93 mmol), Pd$(OAc)_2$ (160 mg, 0.71 mmol), and KOAc (3.42 g, 34.8 mmol) in dry DMF was stirred at room temperature for 24 h. The reaction mixture was diluted with water (400 mL) and extracted with EtOAc (2×150 mL). The combined organic extracts were dried ($MgSO_4$) and concentrated. Chromatography of the resulting residue over silica gel using 1:20 EtOAc/hexanes then 3:17 EtOAc/hexanes provided 2-benzyloxycarbonylamino-3-(4,4-dimethyl-cyclohex-1-enyl)-acrylic acid methyl ester as a yellow oil (1.38 g, 46%). $^1$H NMR (400 MHz, $CDCl_3$) δ 0.88 (s, 6H), 1.34 (t, J=6.4

Hz, 2H), 1.95–2.00 (m, 2H), 2.23–2.30 (m, 2H), 3.74 (s, 3H), 5.15 (s, 2H), 5.90–6.10 (m, 1H), 6.10–6.15 (m, 1H), 7.0 (s, 1H), 7.25–7.36 (m, 5H). m/z 382.4 (MK$^+$).

A suspension of the above acrylic acid ester (2.18 g, 6.35 mmol), Boc anhydride (1.52 g, 6.96 mmol), and 10% Pd/C (300 mg) in MeOH was shaken on a Parr apparatus under 40 psi of hydrogen gas for 17 h. The reaction mixture was filtered through a pad of diatomaceous earth and concentrated to provide 2-tert-butoxycarbonylamino-3-(4,4-dimethyl-cyclohexyl)-propionic acid methyl ester as a yellow oil (1.87 g, 94%). $^1$H NMR (400 MHz, CDCl$_3$) δ 0.85 (s, 3H), 0.88 (s, 3H), 1.05–1.20 (m, 5H), 1.21–1.40 (m, 2H), 1.44 (s, 9H), 1.45–1.59 (m, m, 2H), 1.60–1.78 (m, 2H), 3.72 (broad s, 3H), 4.27–4.40 (m, 1H), 4.82–4.96 (m, 1H).

A suspension of the above methyl ester (1.87 g, 5.97 mmol) and lithium hydroxide monohydrate (1.76 g, 41.9 mmol) in THF (18 mL), MeOH (6 mL), and water (6 mL) was stirred at room temperature for 4 h. The reaction mixture was acidified with 10% citric acid (aqueous) and extracted with diethyl ether (3×100 mL). The combined organic layers were dried (MgSO$_4$) and concentrated to provide a the corresponding carboxylic acid as a white foam (1.21 g, 68%). $^1$H NMR (400 MHz, DMSO d$_6$) δ 0.83 (s, 3H), 0.85 (s, 3H), 0.87–1.10 (m, 4H), 1.10–1.46 (m, 3H), 1.35 (s, 9H), 1.46–1.60 (m, 4H), 3.88–3.94 (m, 1H), 7.0 (d, 8.2 Hz, 1H), 11.7–12.9 (broad s, 1H).

Isobutyl chloroformate (0.55 mL, 4.24 mmol) was added dropwise to a solution of the above carboxylic acid (1.21 g, 4.04 mmol) and N-methyl morpholine (0.89 mL, 8.10 mmol) in dry THF cooled to 0° C. The reaction mixture was stirred at 0° C. for 1 h. A solution of 4-amino-1-propyl-piperidine-4-carbonitrile (780 mg, 4.65 mmol) in dry THF (5 mL) was added and the reaction mixture was allowed to warm to room temperature and stirred overnight. Volatiles were removed on a rotary evaporator and the resulting residue was dissolved in EtOAc (50 mL) and washed with saturated Na$_2$CO$_3$ (50 mL). The organic phase was dried (MgSO$_4$) and concentrated. Chromatography of this crude material over silica gel using a gradient of dichloromethane to 5% MeOH in dichloromethane provided [1-(4-cyano-1-propyl-piperidin-4-ylcarbamoyl)-2-(4,4-dimethyl-cyclohexyl)-ethyl]-carbamic acid tert-butyl ester as a white foam (1.17 g, 65%). $^1$H NMR (400 MHz, CDCl$_3$) δ 0.85 (s, 3H), 0.88 (s, 3H), 0.89 (t, J=7.3 Hz, 3H), 1.05–1.30 (m, 6H), 1.30–1.40 (m, 2H), 1.45 (s, 9H), 1.40–1.60 (m, 5H), 1.70–1.83 (m, 1H), 1.87–2.02 (m, 2H), 2.32–2.54 (m, 6H), 2.68–2.90 (m, 2H), 4.00–4.10 (m, 1H), 4.80–5.00 (m, 1H), 6.70–6.90 (m, 1H); m/z 449.5 (M+H)$^+$, 447.4 (M−H)$^-$.

The above tert-butyl ester (1.17 g, 2.6 mmol) was dissolved in a solution of HCl in 1,4-dioxane (10.0 mL of a 4.0 M solution, 40 mmol) and stirred under an active sweep of argon gas for 10 min. The solution was concentrated on a rotary evaporator then taken up in CHCl$_3$ (50 mL) and concentrated again to provide the amine dihydrochloride as a white powder (1.05 g, 95%). m/z=349.5 (M+H)$^+$.

A suspension of 4-chloro benzoxazin-2-one (500 mg, 2.69 mmol), the above amine salt (400 mg, 0.95 mmol), and polystyrene supported diisopropylamine (2.40 g, 8.40 mmol) in dry acetonitrile was heated at 50° C. for 5 h. The reaction mixture was filtered through a pad of diatomaceous earth and the filtrate was concentrated. The resulting residue was chromatographed over silica gel using methylene chloride then 2.5% MeOH in methylene chloride and finally 10% MeOH in methylene chloride as the eluant to provide the title compound as a white solid (45 mg, 10%). $^1$H NMR (400 MHz, DMSO d$_6$) δ 0.82 (t, J=7.5 Hz, 3H), 0.83 (s, 3H), 0.84 (s, 3H), 1.00–1.20 (m, 5H), 1.25–1.42 (m, 5H), 1.48–1.58 (m, 2H), 1.60–1.70 (m, 1H), 1.80–1.92 (m, 2H), 2.10–2.30 (m, 6H), 2.55–2.68 (m, 2H), 4.83–4.92 (m, 1H), 7.29 (d, J=8.3 Hz, 1H), 7.36 (t, J=7.7 Hz, 1H), 7.73 (t, J=7.3 Hz, 1H), 8.36 (d, J=8.1 Hz, 1H), 8.73 (s, 1H), 8.98–9.10 (m, 1H); m/z=494.5 (M+H)$^+$, 492.4 (M−H)$^-$.

Example 38

4,4-Dimethyl-2-(1-methyl-2-oxo-1,2-dihydro-quinazolin-4-ylamino)-pentanoic acid (4-cyano-1-propyl-piperidin-4-yl)-amide.

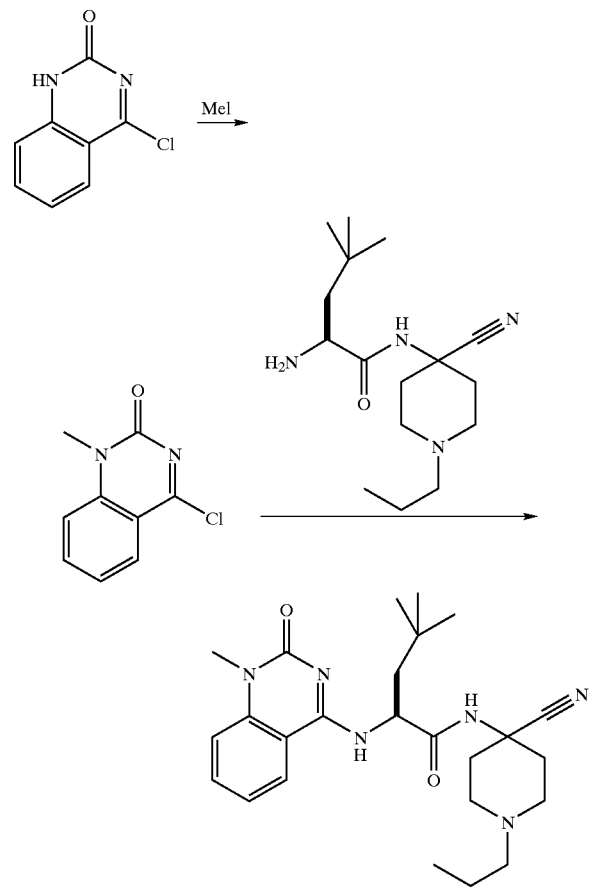

A mixture of 4-chloro-1,2-dihydro-2-oxo-quinazoline (1.0 g, 5.5 mmol), iodomethane (0.86 mL, 2.5 equiv.) and potassium carbonate (1.91 g, 2.5 equiv.) in DMF (15 mL) was heated at 80° C. for 90 min before the solvent was removed at reduced pressure at 80° C. The residue was taken up in dichloromethane and filtered. The filtrate was concentrated and column chromatography on silica gel (eluent: EtOAc) gave the N-methyl analog (0.21 g, 19.5%).

A mixture of the above intermediate (100 mg, 0.5 mmol), 2-amino-4,4-dimethylpentanoic acid (4-cyano-1-propyl-piperidin-4-yl)amide (151 mg, 0.5 mmol), Cu (powder, 66 mg, 1 mmol) and potassium carbonate (285 mg, 2 mmol) in NMP (3 mL) was heated at 150° C. for 16 h. After it was cooled to room temperature, it was filtered. The filtrate was diluted with water and extracted with dichloromethane. The organic phase was washed with brine, dried (sodium sulfate), concentrated and chromatographed on silica gel affording the title compound (101 mg, 44.6%); MS: 453 (M+1).

Example 39

{[1-(4-Cyano-1-methyl-piperidin-4-ylcarbamoyl)-2-cyclohexyl-ethylimino]-morpholin-4-yl-methyl}-carbamic acid 2,2-dimethyl-propyl ester.

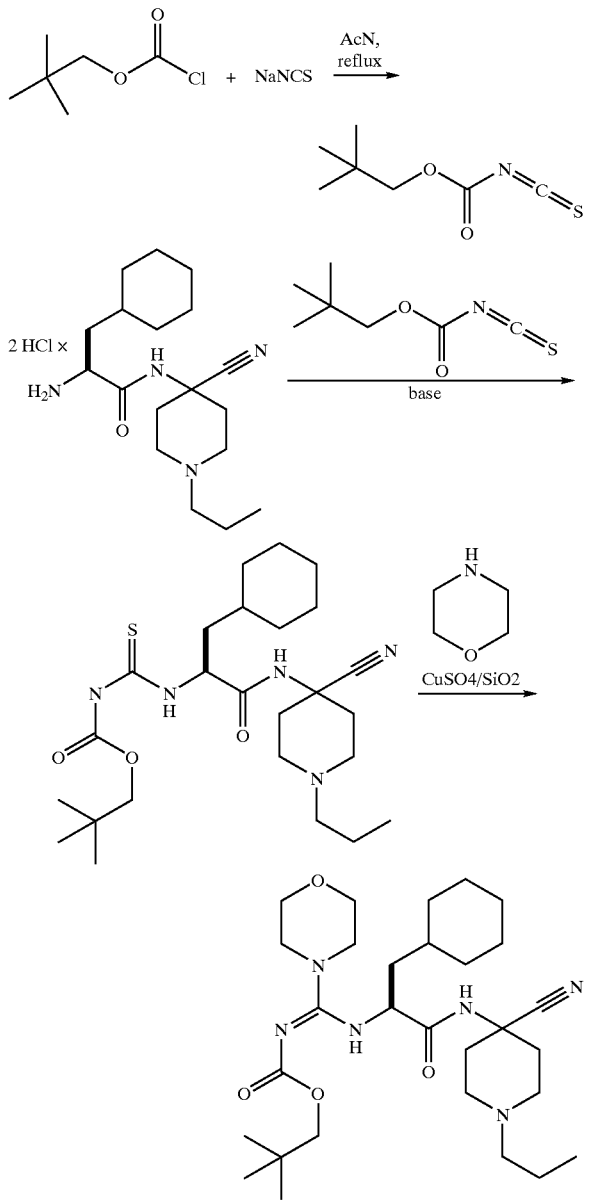

To a solution of sodium thiocyanate (4.46 g, 55 mmol) in 50 mL of acetonitrile was added neopentyl chloroformate (6.15 mL, 50 mmol). This mixture was heated at 80° C. for 2 h. After cooling to room temperature, the solid was removed by filtration and the filtrate was used as a 1 M stock solution of neopentyl isothiocyanatoformate.

2-Amino-N-(4-cyano-1-methyl-piperidin-4-yl)-3-cyclohexyl-propionamide dihydrochloride salt (6.33 g, 17.32 mmol) was suspended in 50 mL of methylene chloride. Triethylamine (5.00 mL, 35.9 mL) was added. To this solution at 0° C. was added the above solution (20 mL, 20 mmol). This mixture was stirred at 0° C. for 1 h. The solvent was removed in vacuo. The residue was purified by flash chromatography on silica gel eluting with 5% MeOH in ethyl ether (Rf=0.2) to give the thiourea (4.76 g, 59%) as a yellow oil; MS: M+1=466.

The thiourea (4.67 g, 10.0 mmol) was dissolved in 30 mL of THF. Copper sulfate on silica gel (4.00 g, 10.0 mmol) was added followed by 1 mL of triethylamine. This mixture was stirred at room temperature for 30 min. Morpholine (1.25 mL, 20 mmol) was added. The reaction mixture was heated under reflux for 2 h. Another 4 g of copper sulfate on silica gel and 1.25 mL of morpholine were added. The reaction mixture was heated for an additional 2 h. After cooling to room temperature, solids were removed by filtration and washed with acetonitrile. The filtrate was concentrated under reduced pressure and then purified by flash chromatography on silica gel, eluting with a mixture of ethyl ether, methylene chloride and MeOH (2:1:0.1) to give a yellow oil. This oil was crystalized from ethyl ether and hexane to give the title compound (1.81 g, 35%) as a white solid; M+1=519.

Example 40

2-Amino-4,4,5-trimethyl-hexanoic acid (4-cyano-1-propyl-piperidin-4-yl)-amide bis-hydrochloride.

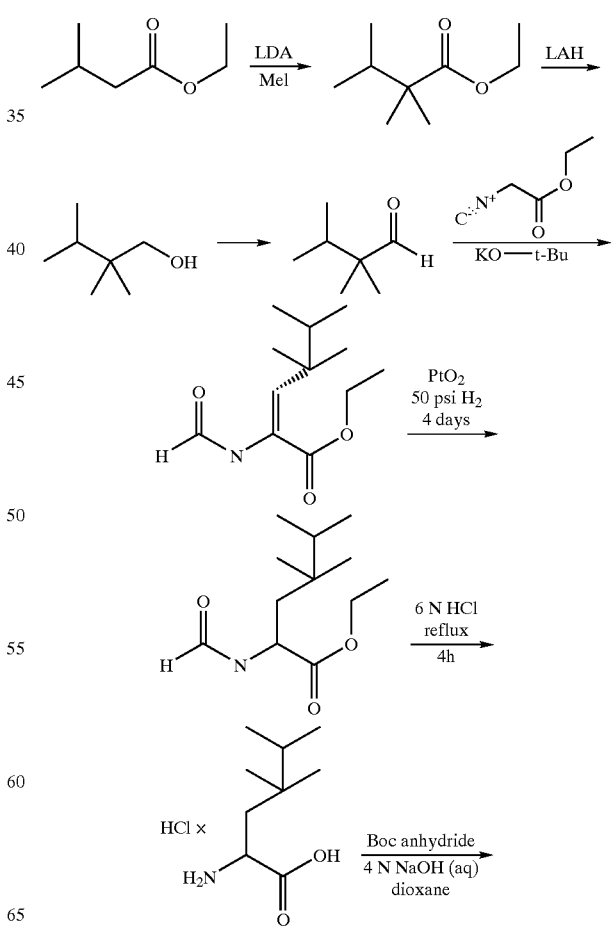

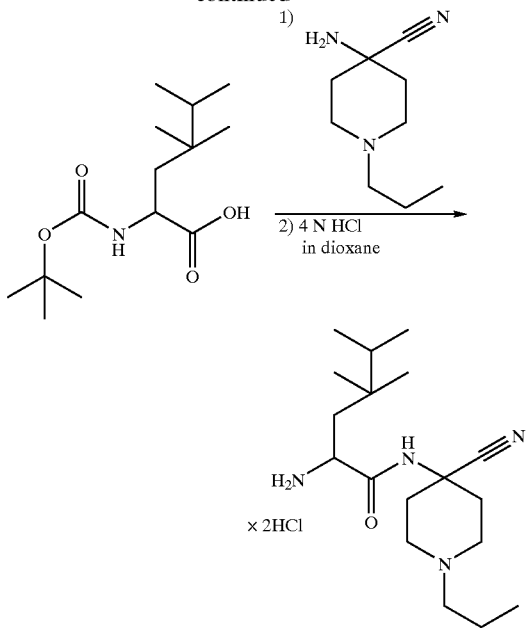

Lithium diisopropylamide (1.5 M solution in cyclohexane/THF/ethylbenzene) (113 mL, 169 mmol, 1.1 equiv) was syringed into a 1000 mL round-bottom flask under a blanket of Ar. Dry THF (150 mL) was added and the mixture was cooled to −78° C. with a dry-ice/acetone bath. 3-Methyl-butanoic acid ethyl ester (20 g, 23 mL, 154 mmol, 1.0 equiv) was added dropwise from a syringe over a 10 min period followed by stirring at −78° C. for 1 h. Methyl iodide (10.5 mL, 169 mmol, 1.1 equiv) was added dropwise from a syringe over a 10 min period and the creamy mixture was stirred for 1 h at −78° C., resulting in a very thick mixture. The dry-ice bath was removed and replaced with an ice bath at 0° C. Another 150 mL of dry THF was added followed by another addition of LDA (113 mL, 169 mmol, 1.1 equiv). The resulting mixture was stirred for 10 min and then the flask was re-immersed in a dry-ice/acetone bath. Stirring was continued for another 50 min and then methyl iodide was added dropwise (10.5 mL, 169 mmol, 1.1 equiv) and the dry-ice/acetone bath was removed and the resulting mixture was stirred at ambient temperature for 14 h. The reaction mixture was quenched with 3 mL of conc. HCl and 2 N HCl was added until the pH was adjusted to <1. The mixture was further diluted with 150 mL water and 500 mL Et$_2$O. The layers were separated and the organic layer was washed with 1×100 mL 2 N HCl, 1×100 mL saturated NaHCO$_3$, and 1×200 mL brine. The organic layer was dried over Na$_2$SO$_4$ and then concentrated in vacuo to provide 2,2,3-trimethylbutanoic acid ethyl ester as an orange oil mixed with ethyl benzene (36.4 g of which 22.1 g was product by NMR). The mixture was used without further purification.

A 500 mL round-bottom-flask equipped with a stir bar was flushed with Ar and charged with 50 mL dry THF and a 1 M solution of LAH in Et$_2$O (87.5 mL, 87.5 mmol, 0.625 equiv). The solution was cooled to 0° C. with an ice bath and the above ethyl ester (22.1 g, 140 mmol, 1.0 equiv) (approximately a 50% solution in ethylbenzene) was added dropwise at such a rate that the solution did not reflux (required 50 min). After addition of the ester, the reaction was stirred at 0° C. for 2 h and then at ambient temperature for 14 h. The reaction solution was re-cooled to 0° C. and carefully quenched by addition of EtOAc. 1 N NaOH was added until a granular precipitate formed (7.5 mL). The mixture was filtered on a pad of diatomaceous earth which was then washed 3×100 mL Et$_2$O. The organics were combined and dried over Na$_2$SO$_4$. The solution was decanted and concentrated in vacuo to yield 2,2,3-trimethyl-butanol 2,2,3-trimethyl-butanol as a nearly colorless oil (11.7 g of alcohol in 15.4 g of a mix with ethylbenzene). The crude product was used without further purification.

A 1000 mL round-bottom-flask was equipped with a stir bar, flushed with Ar and charged with 300 mL dry CH$_2$Cl$_2$ and oxalyl chloride (13.2 mL, 151 mmol, 1.5 equiv). The solution was cooled to −78° C. with a dry-ice/acetone bath. Dry DMSO (21.5 mL, 302 mmol, 3.0 equiv) was added dropwise over a 30 min period (vigorous gas evolution). The above alcohol (11.7 g, 100 mmol, 1.0 equiv) was added (with residual ethylbenzene) over a 10 min period. The resulting solution was stirred for 90 min. Triethylamine (56 mL, 403 mmol, 4.0 equiv) was added over 5 min and the cold-bath was removed. The resulting creamy white mixture was stirred at room temperature over 1.5 h. The reaction mixture was carefully diluted with 200 mL water (more gas evolution). Layers were separated and the organic phase was washed with 1×100 mL 2 N HCl and 1×100 mL brine. The organic layer was dried over Na$_2$SO$_4$, decanted and concentrated in vacuo. The crude aldehyde was distilled fractionally through a 4 inch Vigoreux column at 57–67° C. at 15 mm Hg to provide the 2,2,3-trimethyl-butanal (9.1 g) as a colorless oil.

A clean and dry 250 mL round-bottom flask was equipped with a stir bar and flushed with Ar. Dry THF was added (40 mL) followed by addition of a 1.0 M solution of KO-t-Bu (32.2 mL, 32.2 mmol, 1.05 equiv). The solution was cooled to −78° C. in a dry-ice/acetone bath. Ethyl isocyanoacetate (3.35 mL, 30.7 mmol, 1.0 equiv) was added dropwise over a 10 min period. The resulting mixture was stirred an additional 5 min followed by addition, via syringe, of 2,2,3-trimethyl-butanal (3.5 g, 30.7 mmol, 1.0 equiv). The cold-bath was removed and resulting mixture was stirred at room temperature for 1 h. The reaction mixture was diluted by addition of a mix of 125 mL Et$_2$O, 20 g ice, 2 mL AcOH. After the ice melted, 50 mL of water was added and the layers were mixed and separated. The organic layer was washed with 1×50 mL sat. NaHCO$_3$ and dried over Na$_2$SO$_4$. The organic layer was decanted and concentrated. The crude enamide was purified by flash chromatography on silica gel using CH$_2$Cl$_2$ to 4% MeOH in CH$_2$Cl$_2$ to provide 2-formylamino-4,4,5-trimethyl-hex-2-enoic acid ethyl ester as a thick oil (4.54 g); MS: 228 (M+1).

The above ethyl ester (4.54 g, 20 mmol, 1.0 equiv) was dissolved in 35 mL of MeOH in a Parr bottle followed by addition of PtO$_2$ (1 g, 4.4 mmol, 0.22 equiv). The mixture was shaken on a Parr hydrogenation apparatus for 4 days at which time MS showed consumption of the starting material; MS: 230 (M+1), 216 (M+1 of methyl ester). The liquid was carefully decanted and the Pt was washed 3×20 mL MeOH followed each time by decantation, being careful not to allow the Pt to dry (if allowed to dry, the Pt may ignite). The MeOH solutions were combined and concentrated to a thick oil that was suspended in 25 mL of 6 N HCl and the mixture was refluxed for 4 h during which time 5 mL of conc. HCl was added at the end of each of the first 3 h. The mixture was cooled and the water and excess HCl were removed on a rotovap at a bath temperature of 70° C. After about 50% concentration, a flaky crystalline solid formed. The mixture was cooled to 0° C. and the precipitate was collected by filtration. The filtrate was again concentrated by about 50% and cooled again to 0° C. to provide a second crop of crystals. The crystals were combined and dried under high vacuum to provide 2-amino-4,4,5-trimethyl-hexanoic acid hydrochloride as an off-white crystalline solid (2.32 g); MS: 174 (M−Cl+1).

The above amino acid salt (2.32 g, 11.1 mmol, 1.0 equiv) was dissolved in 100 mL of 50/50 dioxane/4 N NaOH. The solution was cooled to 0° C. and Boc anhydride (3.6 g, 16.6 mmol, 1.5 equiv) was added. The cold-bath was removed and the reaction stirred at ambient temperature for 16 h. The pH was carefully adjusted to 2 with conc. HCl, and the product was extracted with 3×100 mL CH$_2$Cl$_2$. The organic layers were combined and dried over Na$_2$SO$_4$. The solution was decanted and concentrated using 100 mL of hexane as a chaser to provide a thick glass, which was triturated with 100 mL of hexane. After vigorous stirring for 4 h, a waxy solid resulted which was filtered and dried in air to provide 2-tert-butoxycarbonylamino-4,4,5-trimethyl-hexanoic acid (1.42 g).

The above carboxylic acid (0.400 g, 1.46 mmol, 1.0 equiv) was dissolved in 15 mL of THF and cooled to 0° C. N-Methylmorpholine (0.338 mL, 3.07 mmol, 2.1 equiv) was added followed by dropwise addition, over 1 min, of isobutylchloroformate (0.19 mL, 1.0 equiv). A white precipitate immediately formed. The mixture was stirred for 30 min at which time a solution of 4-amino-4-cyano-1-propyl-piperidine (0.257 g, 1.54 mmol, 1.05 equiv) in 5 mL of THF was added. The resulting mixture was stirred for 16 h at room temperature. The volatiles were removed on a rotovap and the resulting paste was triturated with 100 mL water with vigorous stirring to give a fluffy white solid which was collected by filtration. The solid was washed with 100 mL of water and dried under vacuum to yield the desired product as an off-white powder (0.521 g); MS: 423 (M+1). The Boc protecting group was removed by treatment of the solid under Ar with 20 mL of 4N HCl in dioxane for 1 h. The resulting paste was diluted with 40 mL of Et$_2$O and the solid was filtered under Ar. The resulting paste was washed 1×25 mL Et$_2$O and dried in vacuo to yield the title compound as the dihydrochloride salt; MS: 323 (M+1).

Example 41

2-tert-Butoxycarbonylamino-5,5-dimethyl-hexanoic acid

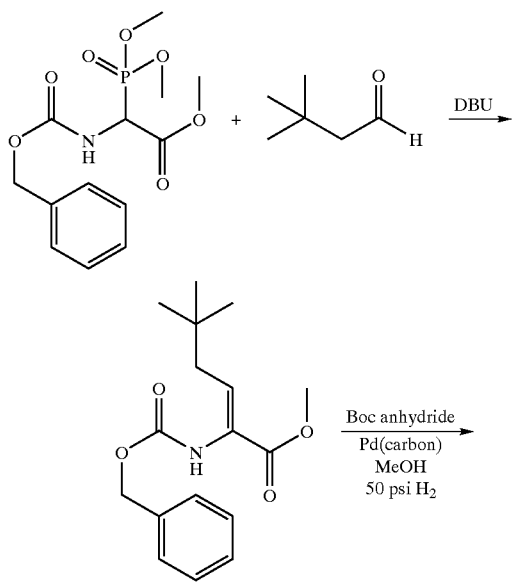

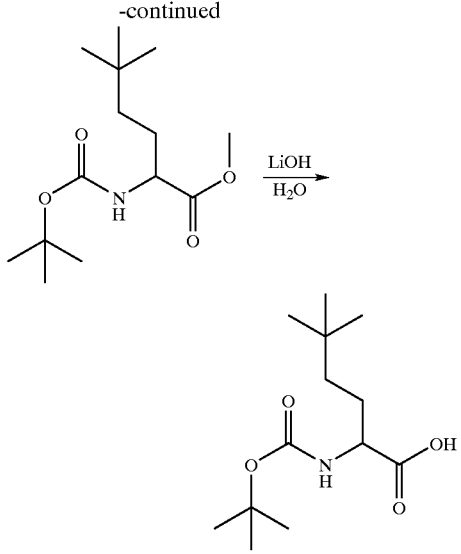

N-(Benzyloxycarbonyl)-α-phosphonoglycine trimethyl ester (2 g, 6.0 mmol, 1.0 equiv) was dissolved in dry THF (20 mL). tert-Butylacetaldehyde (0.758 mL, 6.0 mmol, 1.0 equiv) and DBU (0.903 mL, 6.0 mmol, 1.0 equiv) were added and the reaction mixture was stirred for 16 h. The solution was diluted with 100 mL of CH$_2$Cl$_2$ and washed with 1×50 mL water, and 1×50 mL brine. The organic layer was dried over Na$_2$SO$_4$, decanted and concentrated in vacuo to provide 2-benzyloxycarbonylamino-5,5-dimethyl-hex-2-enoic acid methyl ester as a thick oil (1.73 g, 94%) which was used without further purification; MS: 306 (M+1).

The above ester (1.73 g, 5.67 mmol, 1.0 equiv) was dissolved in a Parr bottle with Boc anhydride (1.36 g, 6.23 mmol, 1.0 equiv) and MeOH (35 mL). Pd on carbon (Degussa type) (0.5 g) was added. The mixture was shaken under 50 psi H$_2$ for 16 h. The mixture was filtered on diatomaceous earth followed by washing of the diatomaceous earth with 3×50 mL MeOH. The organics were combined and concentrated to provide 2-tert-butoxycarbonylamino-5,5-dimethyl-hexanoic acid methyl ester as a very thick oil which was used without further purification.

The above ester (1.31 g, 4.79 mmol, 1.0 equiv) was dissolved in 50 mL of MeOH. 1 N LiOH (50 mL) was added and the mixture was stirred 16 h. Concentrated HCl was added carefully until the pH approached 2 at which time a bright white solid precipitated. The solid was collected by filtration and washed 2×20 mL water and dried under vacuum to provide the title compound (1.05 g, 85%); MS: 258 (M−1).

METHODS OF THERAPEUTIC USE

The compounds of the invention are useful in inhibiting the activity of cathepsin S, K, F, L and B. In doing so, these compounds are useful in blocking disease processes mediated by these cysteine proteases.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis including contact and atopic dermatitis, insulin-dependent diabetes mellitus, endometriosis and asthma including allergic asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

Compounds of the invention also inhibit cathepsin K. In doing so, they may block inappropriate degradation of bone collagen and other bone matrix proteases. Thus, there is provided a method for treating diseases where these processes play a role such as osteoporosis. Inhibition of cathepsins F, L, and B are also within the scope of the invention due to similarity of the active sites in cysteine proteases as described above.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

ASSESSMENT OF BIOLOGICAL PROPERTIES

Expression and Purification of Recombinant Human Cathepsin S

Cloning of Human Cathepsin S:

U937 RNA was subjected to reverse transcriptase/polymerase chain reaction with primer A (5'cacaatgaaacggctggtttg 3') and primer B (5'ctagatttctgggtaagaggg 3') designed to specifically amplify the cathepsin S cDNA. The resulting 900 bp DNA fragment was subcloned into pGEM-T (Promega) and sequenced to confirm its identity. This construct was used for all subsequent manipulations. This procedure is typical for cloning of known genes and is established in its field.

Human Pre-Pro-Cat S was removed from pGem-T vector (Promega, 2800 Woods Hollow Rd, Madison, Wis. 53711) by digestion with restriction enzyme SacII, followed by treatment with T4 DNA polymerase to generate a blunt end, and a second restriction enzyme digest with SalI. It was subcloned into pFastBac1 donor plasmid (GibcoBRL, 8717 Grovemont Cr., Gaithersburg, Md. 20884) which had been cut with restriction enzyme BamH1 and blunt-ended and then cut with restriction enzyme SalI. The ligation mixture was used to transform DH5a competent cells (GibcoBRL) and plated on LB plates containing 100 ug/ml ampicillin. Colonies were grown in overnight cultures of LB media containing 50 ug/ml Ampicillin, plasmid DNA isolated and correct insert confirmed by restriction enzyme digestion. Recombinant pFastBac donor plasmid was transformed into DH10Bac competent cells (GibcoBRL). Large white colonies were picked from LB plates containing 50 ug/ml kanamycin, 7 ug/ml gentamicin, 10 ug/ml tetracycline, 100 ug/ml Bluo-gal, and 40 ug/ml IPTG. DNA was isolated and used to transfect Sf9 insect cells using CellFECTIN reagent (GibcoBRL). Cells and supernatant were harvested after 72 hours. Viral supernatant was passaged twice and presence of Cat S confirmed by PCR of the supernatant.

SF9 cells were infected with recombinant baculovirus at a MOI of 5 for 48–72 hrs. Cell pellet was lysed and incubated in buffer at pH 4.5 at 37 for 2 hours to activate Cat S from pro-form to active mature form (Bromme, D & McGrath, M., *Protein Science,* 1996, 5:789–791.) Presence of Cat S was confirmed by SDS-PAGE and Western blot using rabbit anti-human proCat S.

Inhibition of Cathepsin S

Human recombinant cathepsin S expressed in Baculovirus is used at a final concentration of 10 nM in buffer. Buffer is 50 mM Na acetate, pH 6.5, 2.5 mM EDTA, 2.5 mM TCEP. Enzyme is incubated with either compound or DMSO for 10 min at 37° C. Substrate 7-amino-4-methylcoumarin, CBZ- L-valyl-L-valyl-L-arginineamide (custom synthesis by Molecular Probes) is diluted to 20 uM in water (final concentration of 5 M), added to assay and incubated for additional 10 minutes at 37° C. Compound activity is measured by diminished fluorescence compared to DMSO control when read at 360 nm excitation and 460 nm emission.

Examples listed above were evaluated for inhibition of cathepsin S in the above assay. All had $IC_{50}$ values of 100 micromolar or below.

Inhibition of Cathepsin K, F, L and B:

Inhibition of these enzymes by particular compounds of the invention may be determined without undue experimentation by using art recognized methods as provided hereinbelow each of which is incorporated herein by reference:

Cathepsin B, and L Assays are to be Found in the Following References:

1. Methods in Enzymology, Vol.244, Proteolytic Enzymes: Serine and Cysteine Peptidases, Alan J. Barrett, ed.

Cathepsin K Assay is to be Found in the Following Reference:

2. Bromme, D., Okamoto, K., Wang, B. B., and Biroc, S. (1996) *J. Biol. Chem.* 271, 2126–2132.

Cathepsin F Assays are to be Found in the Following References:

3. Wang, B., Shi, G. P., Yao, P. M., Li, Z., Chapman, H. A., and Bromme, D. (1998) *J. Biol. Chem.* 273, 32000–32008.
4. Santamaria, I., Velasco, G., Pendas, A. M., Paz, A., and Lopez-Otin, C (1999) *J. Biol. Chem.* 274, 13800–13809.

Preferred compounds to be evaluated for inhibition of Cathepsin K, F, L and B in the above assays desirably have $IC_{50}$ values of 100 micromolar or below.

What is claimed is:

1. A compound of the formula (Ia):

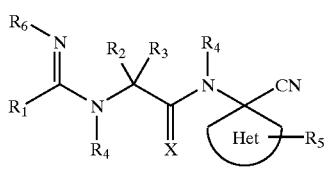

(Ia)

wherein for the Formula (Ia), the components

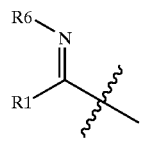

is chosen from A1–A21 in the table below;

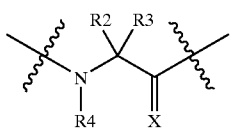

is chosen from B1–B35 in the table below and

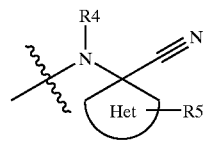

is chosen from C1–C9 in the table below;

| | |
|---|---|
| A | 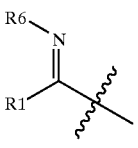 |
| A1 | 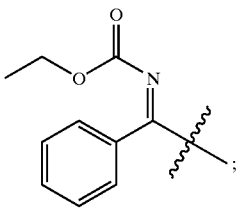 |
| A2 | 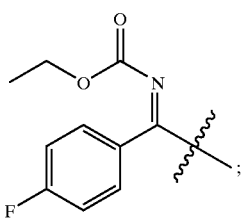 |
| A3 | 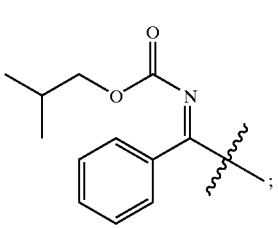 |
| A4 | 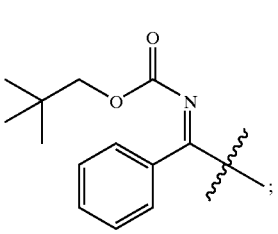 |
| A5 | 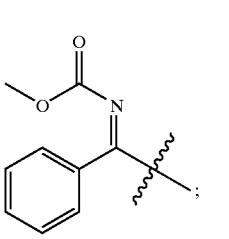 |

-continued
A6 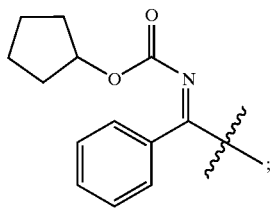
A7 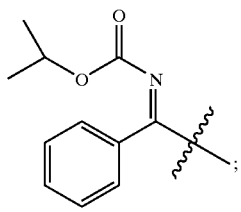
A8 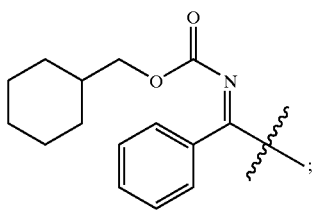
A9 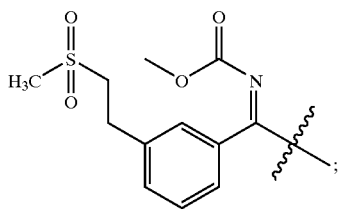
A10 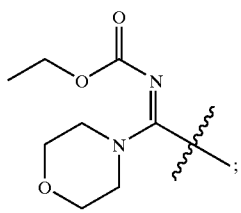
A11 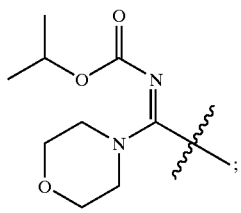
A12 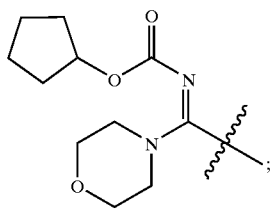
-continued
A13 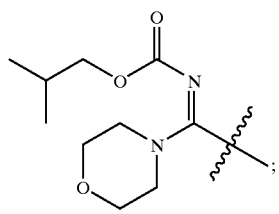
A14 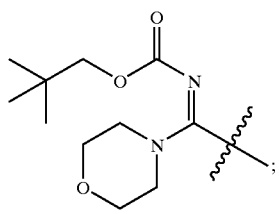
A15 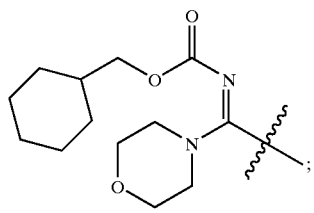
A16 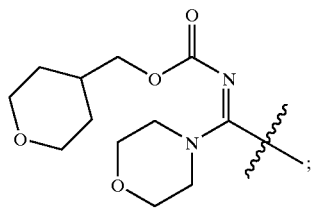
A17 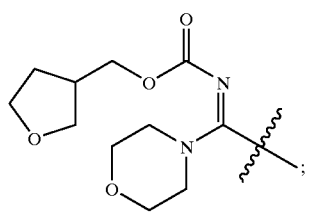
A18 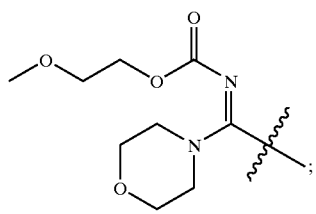
A19 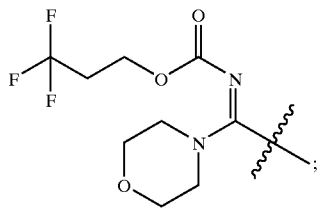

| | |
|---|---|
| A20 | 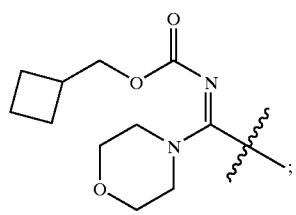 |
| A21 | 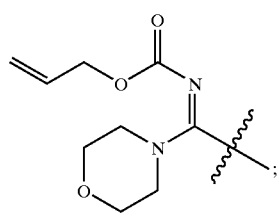 |
| B | 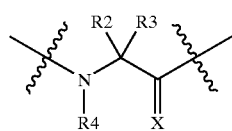 |
| B1 | 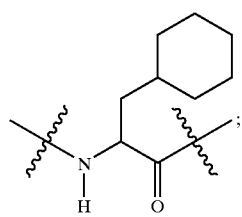 |
| B2 | 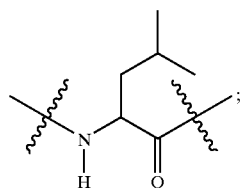 |
| B3 | 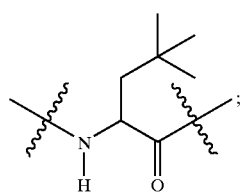 |
| B4 | 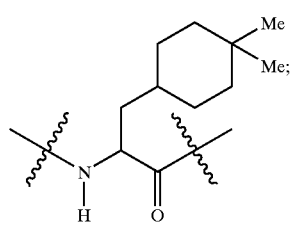 |
| | |
|---|---|
| B5 | 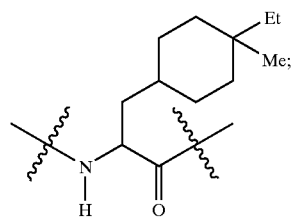 |
| B6 | 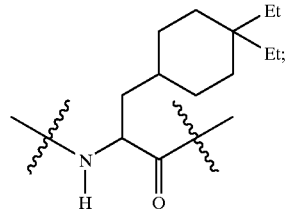 |
| B7 | 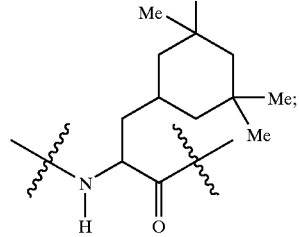 |
| B8 | 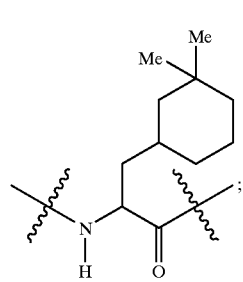 |
| B9 | 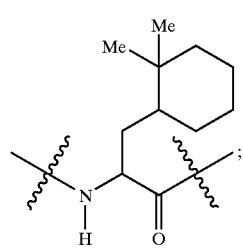 |
| B10 | 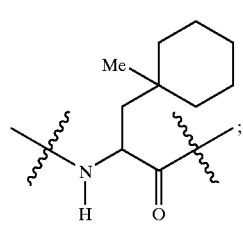 |

| 221 | 222 |
|---|---|
| B11 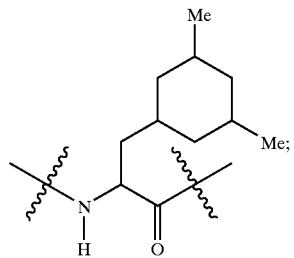 | B17 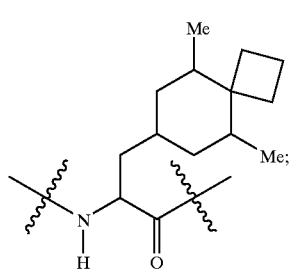 |
| B12 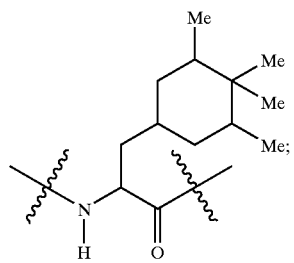 | B18 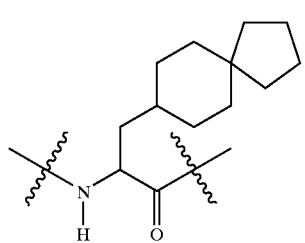 |
| B13 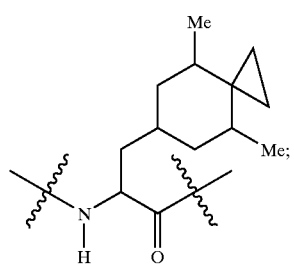 | B19 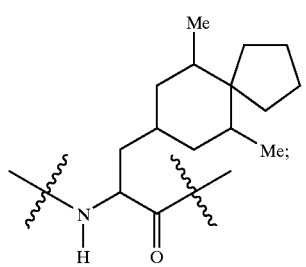 |
| B14 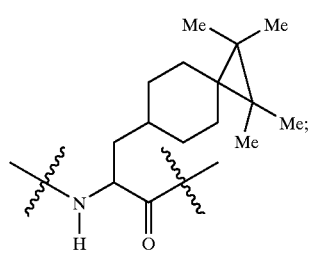 | B20 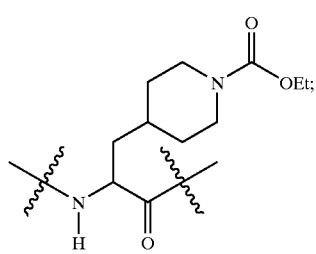 |
| B15 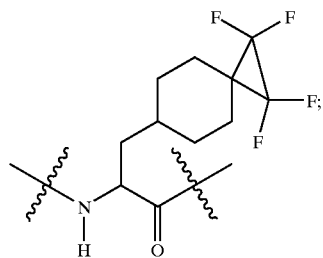 | B21 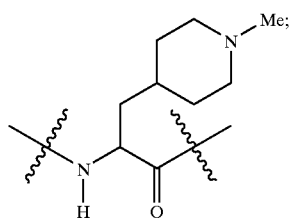 |
| B16 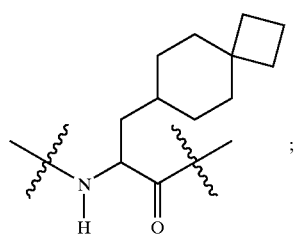 | B22 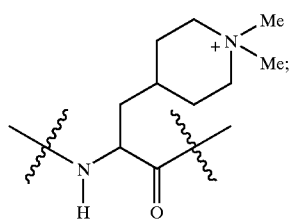 |

-continued
B23 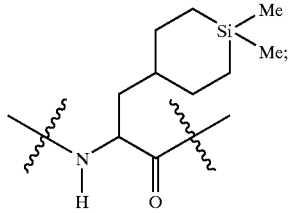
B24 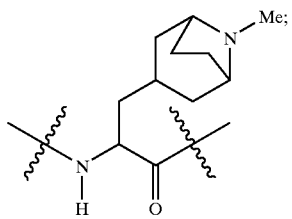
B25 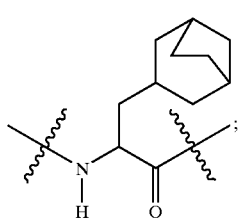
B26 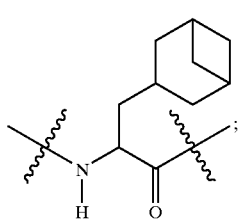
B27 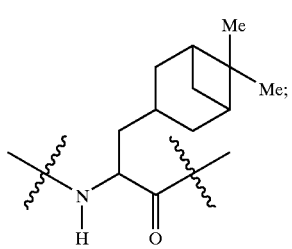
B28 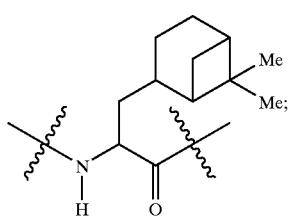
B29 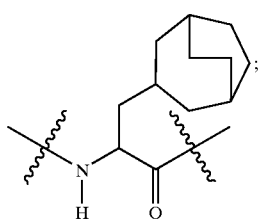
-continued
B30 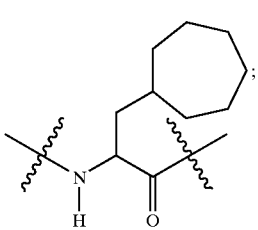
B31 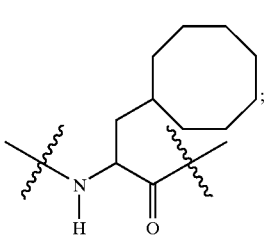
B32 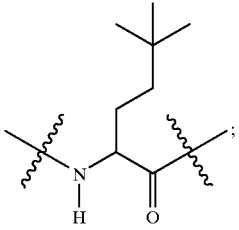
B33 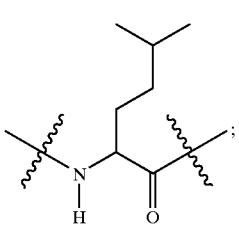
B34 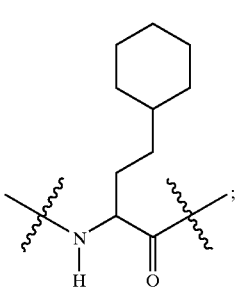
B35 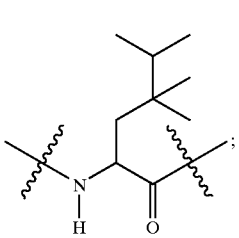

-continued

B35 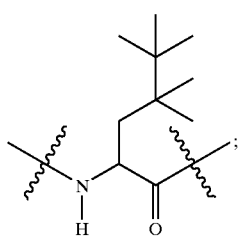

C 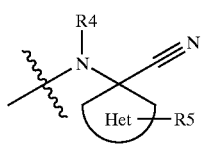

C1 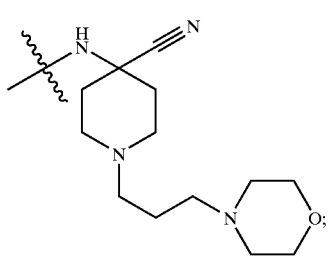

C2 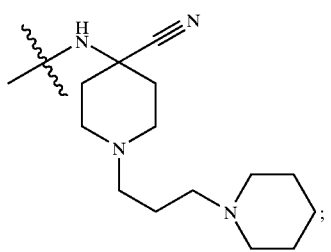

C3 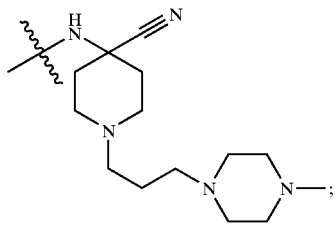

C4 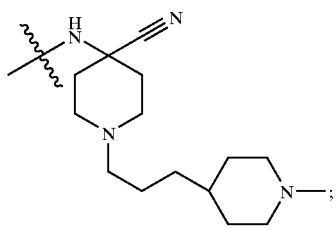

C5 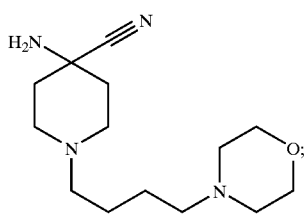

-continued

C6 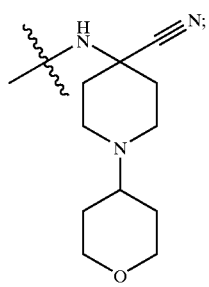

C7 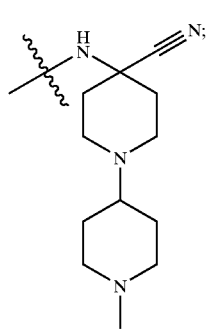

C8 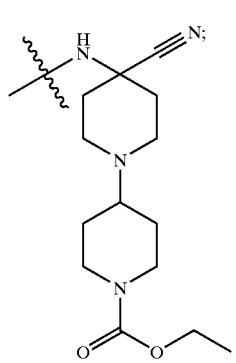

C9 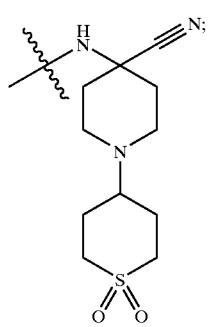

or the pharmaceutically acceptable salts, esters, tautomers, individual isomers and mixtures of isomers thereof.

2. A compound where the compound is:
({1-[4-Cyano-1-(2-morpholin-4-yl-ethyl)-piperidin-4-ylcarbamoyl]-2-cyclohexyl-ethylamino}-morpholin-4-yl-methylene)-carbamic acid isobutyl ester;
or the pharmaceutically acceptable salts, esters, tautomers, individual isomers and mixtures of isomers thereof.

3. A pharmaceutical composition comprising a pharmaceutically effective amount of a compound according to claim 1.

4. A pharmaceutical composition comprising a pharmaceutically effective amount of a compound according to claim 2.

5. A method of treating an autoimmune disease, said method comprising administering to a patient in need of such treatment a pharmaceutically effective amount of a compound according to claim 1.

6. A method of treating an autoimmune disease, said method comprising administering to a patient in need of such treatment a pharmaceutically effective amount of a compound according to claim 2.

7. The method according to claim 5 wherein the autoimmune disease is rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis, endometriosis or insulin-dependent diabetes mellitus.

8. The method according to claim 6 wherein the autoimmune disease is rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, dermatitis, endometriosis or insulin-dependent diabetes mellitus.

9. A method of treating Alzheimer's disease comprising administering to a patient in need of such treatment a pharmaceutically effective amount of a compound according to claim 1.

10. A method of treating Alzheimer's disease comprising administering to a patient in need of such treatment a pharmaceutically effective amount of a compound according to claim 2.

11. A method of treating atherosclerosis comprising administering to a patient in need of such treatment a pharmaceutically effective amount of a compound according to claim 1.

12. A method of treating atherosclerosis comprising administering to a patient in need of such treatment a pharmaceutically effective amount of a compound according to claim 2.

13. A method of treating osteoporosis comprising administering to a patient in need of such treatment a pharmaceutically effective amount of a compound according to claim 1.

14. A method of treating osteoporosis comprising administering to a patient in need of such treatment a pharmaceutically effective amount of a compound according to claim 2.

15. A method of treating asthma comprising administering to a patient in need of such treatment a pharmaceutically effective amount of a compound according to claim 1.

16. A method of treating asthma comprising administering to a patient in need of such treatment a pharmaceutically effective amount of a compound according to claim 2.

* * * * *